United States Patent
Yoon et al.

(10) Patent No.: US 10,399,988 B2
(45) Date of Patent: Sep. 3, 2019

(54) 4-AMINOPYRAZOLO[3,4-D] PYRIMIDINYLAZABICYCLO DERIVATIVES AND PHARMACEUTICAL COMPOSITION COMPRISING THE SAME

(71) Applicant: Daewoong Pharmaceutical Co., Ltd., Gyeonggi-do (KR)

(72) Inventors: Youn-Jung Yoon, Gyeonggi-do (KR); Jung-Eun Park, Gyeonggi-do (KR); Yeon-Jung Park, Gyeonggi-do (KR); Min-June Shim, Gyeonggi-do (KR); Keuk-Chan Bang, Gyeonggi-do (KR); Joon-Seok Park, Gyeonggi-do (KR)

(73) Assignee: Daewoong Pharmaceutical Co., Ltd., Gyeonggi-do (KR)

( * ) Notice: Subject to any disclaimer, the term of this patent is extended or adjusted under 35 U.S.C. 154(b) by 0 days.

(21) Appl. No.: 16/097,646

(22) PCT Filed: Jul. 7, 2017

(86) PCT No.: PCT/KR2017/007281
§ 371 (c)(1),
(2) Date: Oct. 30, 2018

(87) PCT Pub. No.: WO2018/009017
PCT Pub. Date: Jan. 11, 2018

(65) Prior Publication Data
US 2019/0161488 A1    May 30, 2019

(30) Foreign Application Priority Data
Jul. 7, 2016    (KR) .................. 10-2016-0086257

(51) Int. Cl.
C07D 487/04    (2006.01)
A61K 31/519    (2006.01)
C07D 519/00    (2006.01)
A61P 35/00    (2006.01)

(52) U.S. Cl.
CPC ............ *C07D 487/04* (2013.01); *A61P 35/00* (2018.01); *C07D 519/00* (2013.01)

(58) Field of Classification Search
CPC .................................................. C07D 487/04
See application file for complete search history.

(56) References Cited

U.S. PATENT DOCUMENTS

| | | |
|---|---|---|
| 7,514,444 B2 | 4/2009 | Honigberg et al. |
| 8,735,403 B2 | 5/2014 | Honigberg et al. |
| 2006/0025383 A1 | 2/2006 | Wishart et al. |

FOREIGN PATENT DOCUMENTS

| | | |
|---|---|---|
| CN | 105732638 A | 7/2016 |
| WO | WO-2008/039218 A2 | 4/2008 |
| WO | WO-2014/055934 A2 | 4/2014 |
| WO | WO-2014/152114 A1 | 9/2014 |
| WO | WO-2015/061247 A2 | 4/2015 |
| WO | WO-2015/189620 A1 | 12/2015 |

OTHER PUBLICATIONS

Search Report and Written Opinion in International Application No. PCT/KR2017/007281 dated Oct. 19, 2017, 17 pages.
Byrd et al., "Ibrutinib in Relapsed Chronic Lymphocytic Leukemia", The New England Journal of Medicine, 369:13, Sep. 26, 2013, pp. 1277-1279.
Byrd et al., "Ibrutinib Versus Ofatumumab in Previously Treated Chronic Lymphoid Leukemia", the New England Journal of Medicine, 371:3, Jul. 17, 2014, pp. 213-223.
Horwood et al., "Bruton's Tyrosine Kinase is Required for Lipopolysaccharide-induced Tumor Necrosis Factor α Production", J. Exp. Med, vol. 197, No. 12, Jun. 16, 2003, pp. 1603-1611.
Iwaki et al., "Btk Plays a Crucial Role in the Amplification of FcεRI-mediated Mast Cell Activation by Kit", The Journal of Biological Chemistry, vol. 280, No. 48, Dec. 2, 2005, pp. 40261-40270.
O'Brien et al., "Ibrutinib as Initial Therapy for Elderly Patients with Chronic Lymphocytic Leukaemia or Small Lymphocytic Lymphoma: an Open-label, Multicentre, Phase 1b/2 Trial", Lancet Oncology, vol. 15, Jan. 2014, pp. 48-58.

*Primary Examiner* — Emily A Bernhardt
(74) *Attorney, Agent, or Firm* — Marshall, Gerstein & Borun LLP

(57) ABSTRACT

The present invention relates to 4-aminopyrazolo[3,4-d] pyrimidinylazabicyclo derivatives and pharmaceutical compositions containing the same, wherein the 4-aminopyrazolo [3,4-d]pyrimidinylazabicyclo derivatives and pharmaceutical compositions containing them not only have BTK inhibitory activity but also has remarkably high selectivity for the inhibitory activity of BTK vs. ITK, and thereby can be usefully used for the prevention or treatment of autoimmune diseases or cancers as BTK inhibitors.

16 Claims, No Drawings

4-AMINOPYRAZOLO[3,4-D] PYRIMIDINYLAZABICYCLO DERIVATIVES AND PHARMACEUTICAL COMPOSITION COMPRISING THE SAME

TECHNICAL FIELD

The present invention relates to a novel 4-aminopyrazolo [3,4-d]pyrimidinylazabicyclo derivative useful as Bruton's Tyrosince Kinase (BTK) inhibitor and to a pharmaceutical composition comprising the same.

BACKGROUND OF ART

BTK (Bruton's Tyrosine Kinase) is a type of TEC-family tyrosine kinase together with ITK (Interleukin-2 Tyrosine Kinase), RLK (Resting Lymphocyte Kinase) and BMX (Bone-Marrow tyrosine kinase gene on chromosome X), and BTK acts as a regulator of early B-cell development as well as of mature B-cell activation, signaling and survival.

The B-cell is signaled by a B cell receptor (BCR) that recognizes an antigen attached to the surface of an antigen-presenting cell and is activated into a mature antibody-producing cell. However, aberrant signaling via BCR leads to abnormal B-cell proliferation and the formation of pathologic autoantibodies, and thereby can induce cancer, autoimmune and/or inflammatory diseases.

Thus, in the abnormal B-cell proliferation, signaling via BCR may be blocked when BTK is deficient. Thus, inhibition of BTK can block B-cell mediated disease processes, and the use of BTK inhibitors may be a useful approach for the treatment of B-cell mediated diseases.

Furthermore, BTK can be expressed by other cells that may be associated with disease besides B-cells. For example, BTK is important components for Fc-gamma signaling in bone marrow cells, and is expressed by mast cells. Specifically, BTK-deficient bone marrow-induced mast cells exhibit impaired antigen-induced degranulation, and inhibition of BTK activity is known to be useful for treating pathological mast cell responses such as allergy and asthma (Iwaki et al. J. Biol Chem. 2005 280: 40261). In addition, it is known that monocytes from XLA patients, in which BTK activity is absent, show decreased TNF alpha production following stimulation and thus TNF alpha-mediated inflammation could be inhibited by BTF inhibitors (see, Horwood et al., J. Exp. Med. 197: 1603, 2003).

Therefore, there is a need in the art to develop BTK inhibitors capable of inhibiting the activity of BTK. As these BTK inhibitors, WO 2008/039218 discloses 4-aminopyrazolo[3,4-d]pyrimidinylpiperidine derivatives, and WO 2015/061247 discloses hetero compounds such as pyridine, pyrimidine, pyrazine and pyridazine, and WO 2014/055934 discloses pyrimidinyl phenyl acrylamide derivatives.

However, the developed BTK inhibitors show inhibitory activity against BTK as well as various other tyrosine kinases such as EGFR (Epidermal Growth Factor Receptor) and ITK, whereby they show side effects such as rash, diarrhea, arthralgias, myalgias, atrial fibrillation, ecchymosis, and major hemorrhage (see, Byrd J C et al. N Engl J Med 2013; 369:1278-9, Byrd J C et al. N Engl J Med 2014; 371:213-23 and O'brien S et al. Lancet Oncol 2014; 15:48-58). Therefore, selective inhibition of BTK activity is very important.

In view of the above, as a result of studying novel compounds, the present inventors has found that a compound having a chemical structure different from BTK inhibitors reported so far not only has excellent BTK activity inhibitory effect, but also has remarkably high selectivity for the inhibitory activity of BTK vs. ITK, thereby completing the present invention. The compounds belonging to the present invention mainly have BTK inhibitory activity on their own, but do not exclude a possibility of exhibiting a pharmacological action as an efficacious agent by a special body environment or by products of metabolic process, after absorption into the body.

DETAILED DESCRIPTION OF THE INVENTION

Technical Problem

It is an object of the present invention to provide a novel 4-aminopyrazolo[3,4-d]pyrimidinylazabicyclo derivative useful as BTK inhibitor and to a pharmaceutical composition comprising the same.

Technical Solution

In order to achieve the above objects, the present invention provides a compound represented by the following Chemical Formula 1, or a pharmaceutically acceptable salt thereof:

[Chemical Formula 1]

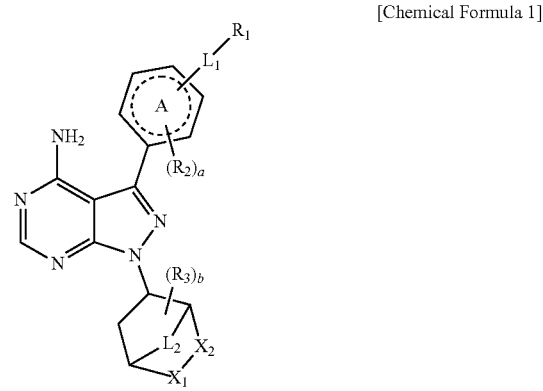

in Chemical Formula 1,

A is a benzene ring, or a 6-membered heteroaromatic ring containing one to three nitrogen atoms, $R_1$ is $C_{1-10}$ alkyl; $C_{6-10}$ aryl; $C_{1-10}$ heteroaryl containing one to four heteroatoms each independently selected from the group consisting of nitrogen, oxygen, and sulfur; or $C_{3-10}$ heterocycloalkyl containing one to four heteroatoms each independently selected from the group consisting of nitrogen, oxygen, and sulfur, wherein $R_1$ is unsubstituted or substituted with one to three substituents each independently selected from the group consisting of halogen, cyano, hydroxy, amino, $NH(C_{1-4}$ alkyl), $N(C_{1-4}$ alkyl$)_2$, $C_{1-4}$ alkyl, $C_{1-4}$ haloalkyl, and $C_{1-4}$ alkoxy, $R_2$ and $R_3$ are each independently hydrogen, halogen, $C_{1-4}$ alkyl, $C_{1-4}$ alkoxy, or $C_{1-4}$ haloalkyl, $L_1$ is a bond, O, S, $SO_2$, NH, $N(C_{1-4}$ alkyl), NHCO, $N(C_{1-4}$ alkyl)CO, NHCONH, $N(C_{1-4}$ alkyl)CONH, NHCON ($C_{1-4}$ alkyl), $N(C_{1-4}$ alkyl)CON($C_{1-4}$ alkyl), CONH, CON ($C_{1-4}$ alkyl), $SO_2NH$, or $SO_2N(C_{1-4}$ akyl), $L_2$ is methylene, or ethylene, one of $X_1$ and $X_2$ is $CH_2$, and the other is N—CO—R', wherein R' is $C_{1-4}$ alkyl; $C_{2-4}$ alkenyl; or $C_{2-4}$ alkynyl, each of which is unsubstituted or substituted by one to three substituents each independently selected from the group consisting of halogen, cyano, hydroxy, amino, $NH(C_{1-4}$ alkyl), $N(C_{1-4}$ alkyl$)_2$, $C_{3-10}$ cycloalkyl, and $C_{3-10}$ heterocycloalkyl containing one or two heteroatoms each independently selected from the group consisting of nitrogen, and oxygen, and a and b are each independently represent an integer of 0 to 4.

Preferably, A is a benzene ring, or a pyridine ring.

Also preferably, $R_1$ is methyl, phenyl, pyridinyl, pyrazinyl, pyrimidinyl, pyridazinyl, pyrrolyl, imidazolyl, pyrazolyl, triazolyl, tetrazolyl, oxazolyl, thiazolyl, oxadiazolyl, piperidinyl, piperazinyl, or pyrrolidinyl, wherein $R_1$ is unsubstituted or substituted by one or two substituents each independently selected from the group consisting of fluoro, chloro, bromo, cyano, hydroxy, $NHCH_3$, $N(CH_3)_2$, methyl, ethyl, propyl, isopropyl, fluoromethyl, difluoromethyl, trifluoromethyl, and methoxy.

Further, preferably, $R_2$ and $R_3$ is each independently hydrogen, fluoro, chloro, bromo, methyl, ethyl, propyl, isopropyl, butyl, isobutyl, sec-butyl, tert-butyl, methoxy, fluoromethyl, difluoromethyl, or trifluoromethyl. Here, a and b may be each independently 0 or 1.

Further, preferably, $L_1$ is a bond, O, S, $SO_2$, NH, NHCO, NHCONH, CONH, or $SO_2NH$.

Further, preferably, $X_1$ is $CH_2$, and $X_2$ is N—CO—R', wherein R' is methyl, vinyl, propenyl, ethynyl, propynyl, or butynyl, each of which is unsubstituted or substituted by halogen, cyano, hydroxy, amino, $NH(CH_3)$, $N(CH_3)_2$, cyclopropyl, piperidinyl, piperazinyl, morpholino, or pyrrolidinyl.

Alternatively, $X_1$ is N—CO—R', and $X_2$ is $CH_2$, wherein R' is methyl, vinyl, propenyl, ethynyl, propynyl, or butynyl, each of which is unsubstituted or substituted by halogen, cyano, hydroxy, amino, $NH(CH_3)$, $N(CH_3)_2$, cyclopropyl, piperidinyl, piperazinyl, morpholino, or pyrrolidinyl.

According to one embodiment, the above-described compound may be represented by the following Chemical Formula 1-1:

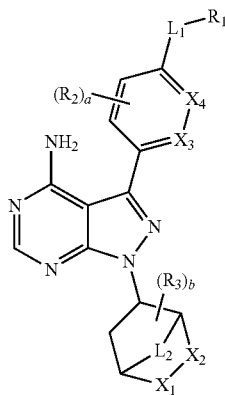

[Chemical Formula 1-1]

in Chemical Formula 1-1, $X_3$ and $X_4$ are each independently N, or CH, and $R_1$ to $R_3$, $L_1$, $L_2$, $X_1$, $X_2$, a and b are as previously defined in Chemical Formula 1.

Preferably, in Chemical Formula 1-1, $R_1$ is methyl, phenyl, pyridinyl, pyrazinyl, pyrazolyl, or piperidinyl, wherein $R_1$ is unsubstituted or substituted by one or two substituents each independently selected from the group consisting of fluoro, chloro, bromo, cyano, hydroxy, methyl, ethyl, propyl, isopropyl, fluoromethyl, difluoromethyl, trifluoromethyl, $NH_3$ and $N(CH_3)_2$, $R_2$ and $R_3$ are each independently hydrogen, fluoro, chloro, bromo, methyl, ethyl, propyl, isopropyl, butyl, isobutyl, sec-butyl, tert-butyl, fluoromethyl, difluoromethyl, or trifluoromethyl, a and b are each independently 0 or 1, $L_1$ is a bond, O, S, $SO_2$, NH, NHCO, NHCONH, CONH, or $SO_2NH$, $L_2$ is methylene, or ethylene, $X_1$ is $CH_2$, and $X_2$ is N—CO—R', wherein R' is methyl, vinyl, propenyl, ethynyl, propynyl, or butynyl, each of which is unsubstituted or substituted by halogen, cyano, hydroxy, amino, $NH(CH_3)$, $N(CH_3)_2$, cyclopropyl, piperidinyl, or pyrrolidinyl, and $X_3$ and $X_4$ is CH.

Further, preferably, in Chemical Formula 1-1, $R_1$ is phenyl, pyridinyl, or piperidinyl, wherein $R_1$ is unsubstituted or substituted by one or two substituents each independently selected from the group consisting of fluoro, chloro, bromo, cyano, hydroxy, methyl, ethyl, propyl, isopropyl, fluoromethyl, difluoromethyl and trifluoromethyl, $R_2$ and $R_3$ are each independently hydrogen, fluoro, chloro, bromo, methyl, ethyl, propyl, isopropyl, butyl, isobutyl, sec-butyl, tert-butyl, fluoromethyl, difluoromethyl, or trifluoromethyl, a and b are each independently 0 or 1, $L_1$ is O, $L_2$ is methylene, $X_1$ is $CH_2$, and $X_2$ is N—CO—R', wherein R' is methyl, vinyl, propenyl, ethynyl, propynyl or butynyl, each of which is unsubstituted or substituted by halogen, cyano, amino, $NH(CH_3)$ or $N(CH_3)_2$, $X_3$ is N, and $X_4$ is CH.

Further, preferably, in Chemical Formula 1-1, $R_1$ is phenyl, pyridinyl, or piperidinyl, wherein $R_1$ is unsubstituted or substituted by one or two substituents each independently selected from the group consisting of fluoro, chloro, bromo, cyano, hydroxy, methyl, ethyl, propyl, isopropyl, fluoromethyl, difluoromethyl and trifluoromethyl, $R_2$ and $R_3$ are each independently hydrogen, fluoro, chloro, bromo, methyl, ethyl, propyl, isopropyl, butyl, isobutyl, sec-butyl, tert-butyl, fluoromethyl, difluoromethyl, or trifluoromethyl, a and b are each independently 0 or 1, $L_1$ is O, NHCO, or CONH, $L_2$ is methylene or ethylene, $X_1$ is N—CO—R' and $X_2$ is $CH_2$, wherein R' is methyl, vinyl, propenyl, ethynyl, propynyl or butynyl, each of which is unsubstituted or substituted by halogen, cyano, amino, $NH(CH_3)$ or $N(CH_3)_2$, and $X_3$ and $X_4$ is CH.

According to another embodiment, the above-described compound may be represented by the following Chemical Formula 1-2:

[Chemical Formula 1-2]

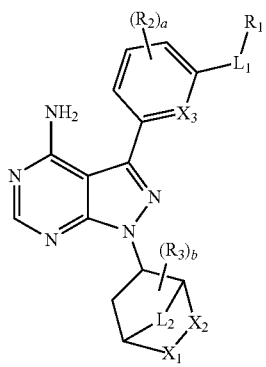

in Chemical Formula 1-2, $X_3$ is N, or CH, and $R_1$ to $R_3$, $L_1$, $L_2$, $X_1$, $X_2$, a and b are as previously defined in Chemical Formula 1.

Preferably, in Chemical Formula 1-2, $R_1$ is phenyl, pyridinyl, or piperidinyl, wherein $R_1$ is unsubstituted or substituted by one or two substituents each independently selected from the group consisting of fluoro, chloro, bromo, cyano, hydroxy, methyl, ethyl, propyl, isopropyl, fluoromethyl, difluoromethyl and trifluoromethyl, $R_2$ and $R_3$ are each independently hydrogen, fluoro, chloro, bromo, methyl, ethyl, propyl, isopropyl, butyl, isobutyl, sec-butyl, tert-butyl, fluoromethyl, difluoromethyl, or trifluoromethyl, a and b are each independently 0 or 1, $L_1$ is O, or CONH, $L_2$ is methylene, $X_1$ is $CH_2$, and $X_2$ is N—CO—R', wherein R' is methyl, vinyl, propenyl, ethynyl, propynyl or butynyl, each of which is unsubstituted or substituted by halogen, cyano, amino, $NH(CH_3)$ or $N(CH_3)_2$, $X_3$ is CH.

Further, preferably, in Chemical Formula 1-2, $R_1$ is phenyl, pyridinyl, or piperidinyl, wherein $R_1$ is unsubstituted or substituted by one or two substituents each independently selected from the group consisting of fluoro, chloro, bromo, cyano, hydroxy, methyl, ethyl, propyl, isopropyl, fluoromethyl, difluoromethyl and trifluoromethyl, $R_2$ and $R_3$ are each independently hydrogen, fluoro, chloro, bromo, methyl, ethyl, propyl, isopropyl, butyl, isobutyl, sec-butyl, tert-butyl, fluoromethyl, difluoromethyl, or trifluoromethyl, a and b are each independently 0 or 1, $L_1$ is O, or CONH, $L_2$ is methylene, $X_1$ is N—CO—R', and $X_2$ is $CH_2$, wherein R' is methyl, vinyl, propenyl, ethynyl, propynyl or butynyl, each of which is unsubstituted or substituted by halogen, cyano, amino, $NH(CH_3)$ or $N(CH_3)_2$, and $X_3$ is CH.

Further, preferably, in Chemical Formula 1,

A is a benzene ring, $R_1$ is $C_{6-10}$ aryl; or $C_{1-10}$ heteroaryl containing one or two nitrogen, wherein $R_1$ is unsubstituted or substituted with halogen, cyano, $N(C_{1-4}$ alkyl$)_2$, $C_{1-4}$ alkyl, $C_{1-4}$ haloalkyl, and $C_{1-4}$ alkoxy, $R_2$ and $R_3$ are each independently hydrogen, halogen, or $C_{1-4}$ alkoxy, $L_1$ is O, S, $SO_2$, CONH, or $SO_2NH$, $L_2$ is methylene, or ethylene, one of X, and $X_2$ is $CH_2$, and the other is N—CO—R', wherein R' is $C_{1-4}$ alkyl; $C_{2-4}$ alkenyl; or $C_{2-4}$ alkynyl, each of which is unsubstituted or substituted by one to three substituents each independently selected from the group consisting of cyano, $C_{3-10}$ cycloalkyl, and $C_{3-10}$ heterocycloalkyl containing two nitrogens, a is 1, and b is 0.

In addition, the compounds of the present invention may exist in the form of salts, especially pharmaceutically acceptable salts. As salts, salts commonly used in the art, such as acid addition salts formed by pharmaceutically acceptable free acids can be used without limitation. The term "pharmaceutically acceptable salt" as used herein refers to any organic or inorganic addition salt of the compound represented by Chemical Formula 1, whose concentration is relatively non-toxic and harmless to a patient and activates effectively and whose side effects do not degrade the beneficial efficacy of the above compound.

As the free acid, an organic acid and an inorganic acid can be used. Examples of the inorganic acids include hydrochloric acid, phosphoric acid, sulfuric acid, nitric acid, tartaric acid and the like. Examples of the organic acids include methanesulfonic acid, p-toluenesulfonic acid, acetic acid, trifluoroacetic acid, maleic acid, succinic acid, oxalic acid, benzoic acid, tartaric acid, fumaric acid, mandelic acid, propionic acid, citric acid, lactic acid, glycollic acid, gluconic acid, galacturonic acid, glutamic acid, glutaric acid, glucuronic acid, aspartic acid, ascorbic acid, carbonic acid, vanillic acid, hydroiodic acid and the like, but are not limited thereto. Preferably, the salt may be a hydrochloride salt.

In addition, a pharmaceutically acceptable metal salt can be obtained by a conventional method using a base. For example, a compound represented by Chemical Formula 1 is dissolved in an excessive amount of an alkali metal hydroxide or an alkaline earth metal hydroxide solution, the non-soluble salt is filtered, and the filtrate is evaporated and dried to obtain a pharmaceutically acceptable metal salt. At this time, it is particularly preferable to prepare a sodium salt, a potassium salt or a calcium salt as the metal salt.

A pharmaceutically unacceptable salt or solvate of the compound of Chemical Formula 1 may be used as an intermediate when preparing the compound of Chemical Formula 1, or the pharmaceutically acceptable salt or the solvate thereof.

The compound of Chemical Formula 1 according to the present invention includes not only pharmaceutically acceptable salts thereof, but also solvates such as hydrates that can be prepared therefrom, and includes all possible stereoisomers, but are not limited thereto. The solvate and the stereoisomer of the compound of Chemical Formula 1 may be prepared from the compound of Chemical Formula 1 using common methods known in the art.

In addition, the compound of Chemical Formula 1 according to the present invention may be prepared either in a crystalline form or in a non-crystalline form, and when the compound of Chemical Formula 1 is prepared in a crystalline form, it may be optionally hydrated or solvated. In the present invention, the compound of Chemical Formula 1 may not only include a stoichiometric hydrate, but also include a compound containing various amounts of water. The solvate of the compound of Chemical Formula 1 according to the present invention includes both stoichiometric solvates and non-stoichiometric solvates.

Representative examples of the compound represented by Chemical Formula 1 or a pharmaceutically acceptable salt thereof are as follows:

1) 1-(6-(4-amino-3-(4-phenoxyphenyl)-1H-pyrazolo[3,4-d]pyrimidin-1-yl)-2-azabicyclo[2.2.1]heptan-2-yl)prop-2-en-1-one,
2) 1-(6-(4-amino-3-(4-phenoxyphenyl)-1H-pyrazolo[3,4-d]pyrimidin-1-yl)-2-azabicyclo[2.2.1]heptan-2-yl)prop-2-yn-1-one,
3) (E)-1-(6-(4-amino-3-(4-phenoxyphenyl)-1H-pyrazolo[3,4-d]pyrimidin-1-yl)-2-azabicyclo[2.2.1]heptan-2-yl)but-2-en-1-one,
4) 4-(4-amino-1-(2-propioloyl-2-azabicyclo[2.2.1]heptan-6-yl)-1H-pyrazolo[3,4-d]pyrimidin-3-yl)-N-(pyridin-2-yl)benzamide,
5) 1-(6-(4-amino-3-(4-phenoxyphenyl)-1H-pyrazolo[3,4-d]pyrimidin-1-yl)-2-azabicyclo[2.2.1]heptan-2-yl)but-2-yn-1-one,
6) 4-(4-amino-1-(2-propioloyl-2-azabicyclo[2.2.1]heptan-6-yl)-1H-pyrazolo[3,4-d]pyrimidin-3-yl)-N-(4-(trifluoromethyl)pyridin-2-yl)benzamide,
7) 3-(4-amino-1-(2-propioloyl-2-azabicyclo[2.2.1]heptan-6-yl)-1H-pyrazolo[3,4-d]pyrimidin-3-yl)-N-(4-isopropylphenyl)benzamide,
8) 3-(1-(2-acryloyl-2-azabicyclo[2.2.1]heptan-6-yl)-4-amino-1H-pyrazolo[3,4-d]pyrimidin-3-yl)-N-(4-isopropylphenyl)benzamide,
9) 3-(4-amino-1-(2-propioloyl-2-azabicyclo[2.2.1]heptan-6-yl)-1H-pyrazolo[3,4-d]pyrimidin-3-yl)-N-(4-isopropyl-3-methylphenyl)benzamide,
10) 3-(1-(2-acryloyl-2-azabicyclo[2.2.1]heptan-6-yl)-4-amino-1H-pyrazolo[3,4-d]pyrimidin-3-yl)-N-(4-isopropyl-3-methylphenyl)benzamide,
11) 1-(5-(4-amino-3-(4-phenoxyphenyl)-1H-pyrazolo[3,4-d]pyrimidin-1-yl)-2-azabicyclo[2.2.1]heptan-2-yl)prop-2-yn-1-one,
12) 1-(5-(4-amino-3-(4-phenoxyphenyl)-1H-pyrazolo[3,4-d]pyrimidin-1-yl)-2-azabicyclo[2.2.1]heptan-2-yl)prop-2-en-1-one,
13) 1-((1S,4S,5R)-5-(4-amino-3-(4-phenoxyphenyl)-1H-pyrazolo[3,4-d]pyrimidin-1-yl)-2-azabicyclo[2.2.1]heptan-2-yl)prop-2-yn-1-one,
14) 1-((1S,4S,5R)-5-(4-amino-3-(4-phenoxyphenyl)-1H-pyrazolo[3,4-d]pyrimidin-1-yl)-2-azabicyclo[2.2.1]heptan-2-yl)prop-2-en-1-one,
15) 1-(6-(4-amino-3-(3-phenoxyphenyl)-1H-pyrazolo[3,4-d]pyrimidin-1-yl)-2-azabicyclo[2.2.1]heptan-2-yl)prop-2-yn-1-one,
16) 1-(6-(4-amino-3-(4-phenoxyphenyl)-1H-pyrazolo[3,4-d]pyrimidin-1-yl)-2-azabicyclo[2.2.1]heptan-2-yl)pent-2-yn-1-one,
17) 4-(4-amino-1-(2-propioloyl-2-azabicyclo[2.2.1]heptan-6-yl)-1H-pyrazolo[3,4-d]pyrimidin-3-yl)-N-phenylbenzamide,
18) 3-(4-amino-1-(2-propioloyl-2-azabicyclo[2.2.1]heptan-6-yl)-1H-pyrazolo[3,4-d]pyrimidin-3-yl)-N-phenylbenzamide,
19) 4-(1-(2-acryloyl-2-azabicyclo[2.2.1]heptan-6-yl)-4-amino-1H-pyrazolo[3,4-d]pyrimidin-3-yl)-N-phenylbenzamide,
20) 4-(4-amino-1-(2-but-2-ynoyl-2-azabicyclo[2.2.1]heptan-6-yl)-1H-pyrazolo[3,4-d]pyrimidin-3-yl)-N-phenylbenzamide,
21) 3-(1-(2-acryloyl-2-azabicyclo[2.2.1]heptan-6-yl)-4-amino-1H-pyrazolo[3,4-d]pyrimidin-3-yl)-N-phenylbenzamide,
22) 3-(4-amino-1-(2-but-2-ynoyl-2-azabicyclo[2.2.1]heptan-6-yl)-1H-pyrazolo[3,4-d]pyrimidin-3-yl)-N-phenylbenzamide,
23) 4-(1-(2-acryloyl-2-azabicyclo[2.2.1]heptan-5-yl)-4-amino-1H-pyrazolo[3,4-d]pyrimidin-3-yl)-N-phenylbenzamide,
24) 3-(1-(2-acryloyl-2-azabicyclo[2.2.1]heptan-5-yl)-4-amino-1H-pyrazolo[3,4-d]pyrimidin-3-yl)-N-phenylbenzamide,
25) 1-(5-(4-amino-3-(3-phenoxyphenyl)-1H-pyrazolo[3,4-d]pyrimidin-1-yl)-2-azabicyclo[2.2.1]heptan-2-yl)prop-2-en-1-one,
26) 3-(1-(2-acryloyl-2-azabicyclo[2.2.1]heptan-6-yl)-4-amino-1H-pyrazolo[3,4-d]pyrimidin-3-yl)-N-(6-(trifluoromethyl)pyridin-3-yl)benzamide,
27) 1-(6-(4-amino-3-(4-(methoxymethyl)phenyl)-1H-pyrazolo[3,4-d]pyrimidin-1-yl)-2-azabicyclo[2.2.1]heptan-2-yl)prop-2-en-1-one,
28) 1-(6-(4-amino-3-(4-phenoxyphenyl)-1H-pyrazolo[3,4-d]pyrimidin-1-yl)-2-azabicyclo[2.2.1]heptan-2-yl)-3-cyclopropylprop-2-yn-1-one,
29) 4-(1-(2-acryloyl-2-azabicyclo[2.2.1]heptan-6-yl)-4-amino-1H-pyrazolo[3,4-d]pyrimidin-3-yl)-N-(4-(trifluoromethyl)pyridin-2-yl)benzamide,
30) 1-(6-(4-amino-3-(biphenyl-4-yl)-1H-pyrazolo[3,4-d]pyrimidin-1-yl)-2-azabicyclo[2.2.1]heptan-2-yl)prop-2-yn-1-one,
31) 1-(6-(4-amino-3-(4-(phenylamino)phenyl)-1H-pyrazolo[3,4-d]pyrimidin-1-yl)-2-azabicyclo[2.2.1]heptan-2-yl)prop-2-yn-1-one,
32) 1-(6-(4-amino-3-(4-(phenylsulfonyl)phenyl)-1H-pyrazolo[3,4-d]pyrimidin-1-yl)-2-azabicyclo[2.2.1]heptan-2-yl)prop-2-en-1-one,
33) 1-(6-(4-amino-3-(4-(phenylthio)phenyl)-1H-pyrazolo[3,4-d]pyrimidin-1-yl)-2-azabicyclo[2.2.1]heptan-2-yl)prop-2-en-1-one,
34) 1-(6-(4-amino-3-(4-(3-fluorophenoxy)phenyl)-1H-pyrazolo[3,4-d]pyrimidin-1-yl)-2-azabicyclo[2.2.1]heptan-2-yl)prop-2-en-1-one,
35) 1-(6-(4-amino-3-(2-fluoro-4-phenoxyphenyl)-1H-pyrazolo[3,4-d]pyrimidin-1-yl)-2-azabicyclo[2.2.1]heptan-2-yl)prop-2-en-1-one,
36) 1-(6-(4-amino-3-(4-(pyridin-4-yloxy)phenyl)-1H-pyrazolo[3,4-d]pyrimidin-1-yl)-2-azabicyclo[2.2.1]heptan-2-yl)prop-2-en-1-one,
37) N-(4-(1-(2-acryloyl-2-azabicyclo[2.2.1]heptan-6-yl)-4-amino-1H-pyrazolo[3,4-d]pyrimidin-3-yl)phenyl)benzamide,
38) N-(4-(1-(2-acryloyl-2-azabicyclo[2.2.1]heptan-6-yl)-4-amino-1H-pyrazolo[3,4-d]pyrimidin-3-yl)phenyl)picolinamide,
39) 1-(4-(1-(2-acryloyl-2-azabicyclo[2.2.1]heptan-6-yl)-4-amino-1H-pyrazolo[3,4-d]pyrimidin-3-yl)phenyl)-3-phenylurea,
40) 1-(6-(4-amino-3-(4-(m-tolyloxy)phenyl)-1H-pyrazolo[3,4-d]pyrimidin-1-yl)-2-azabicyclo[2.2.1]heptan-2-yl)prop-2-en-1-one,
41) 1-(6-(4-amino-3-(4-(3-methoxyphenoxy)phenyl)-1H-pyrazolo[3,4-d]pyrimidin-1-yl)-2-azabicyclo[2.2.1]heptan-2-yl)prop-2-en-1-one,
42) 1-(6-(4-amino-3-(4-(3-(dimethylamino)phenoxy)phenyl)-1H-pyrazolo[3,4-d]pyrimidin-1-yl)-2-azabicyclo[2.2.1]heptan-2-yl)prop-2-en-1-one, 43) 1-(6-(4-amino-3-(4-(3-(trifluoromethyl)phenoxy)phenyl)-1H-pyrazolo[3,4-d]pyrimidin-1-yl)-2-azabicyclo[2.2.1]heptan-2-yl)prop-2-en-1-one,
44) (E)-1-(6-(4-amino-3-(4-phenoxyphenyl)-1H-pyrazolo[3,4-d]pyrimidin-1-yl)-2-azabicyclo[2.2.1]heptan-2-yl)-4-bromobut-2-en-1-one,
45) (E)-1-(6-(4-amino-3-(4-phenoxyphenyl)-1H-pyrazolo[3,4-d]pyrimidin-1-yl)-2-azabicyclo[2.2.1]heptan-2-yl)-4-(dimethylamino)but-2-en-1-one,
46) 4-(1-(2-acryloyl-2-azabicyclo[2.2.1]heptan-6-yl)-4-amino-1H-pyrazolo[3,4-d]pyrimidin-3-yl)-N-(3-ethylphenyl)benzamide,
47) 4-(1-(2-acryloyl-2-azabicyclo[2.2.1]heptan-6-yl)-4-amino-1H-pyrazolo[3,4-d]pyrimidin-3-yl)-N-(3-isopropylphenyl)benzamide,
48) 4-(1-(2-acryloyl-2-azabicyclo[2.2.1]heptan-6-yl)-4-amino-1H-pyrazolo[3,4-d]pyrimidin-3-yl)-N-(3-chlorophenyl)benzamide,
49) 4-(1-(2-acryloyl-2-azabicyclo[2.2.1]heptan-6-yl)-4-amino-1H-pyrazolo[3,4-d]pyrimidin-3-yl)-N-(pyridin-2-yl)benzamide,
50) N-(4-(1-(2-acryloyl-2-azabicyclo[2.2.1]heptan-6-yl)-4-amino-1H-pyrazolo[3,4-d]pyrimidin-3-yl)phenyl)-3-(dimethylamino)benzamide,
51) 1-(6-(4-amino-3-(4-(3-aminophenoxy)phenyl)-1H-pyrazolo[3,4-d]pyrimidin-1-yl)-2-azabicyclo[2.2.1]heptan-2-yl)prop-2-en-1-one hydrochloride,
52) 4-(1-(2-acryloyl-2-azabicyclo[2.2.1]heptan-6-yl)-4-amino-1H-pyrazolo[3,4-d]pyrimidin-3-yl)-3-fluoro-N-phenylbenzamide,
53) 4-(1-(2-acryloyl-2-azabicyclo[2.2.1]heptan-6-yl)-4-amino-1H-pyrazolo[3,4-d]pyrimidin-3-yl)-N-(pyrazin-2-yl)benzamide,
54) 4-(1-(2-acryloyl-2-azabicyclo[2.2.1]heptan-6-yl)-4-amino-1H-pyrazolo[3,4-d]pyrimidin-3-yl)-N-phenylbenzenesulfonamide,
55) 4-(1-(2-acryloyl-2-azabicyclo[2.2.1]heptan-6-yl)-4-amino-1H-pyrazolo[3,4-d]pyrimidin-3-yl)-N-(2-(dimethylamino)phenyl)benzamide,
56) 4-(1-(2-acryloyl-2-azabicyclo[2.2.1]heptan-6-yl)-4-amino-1H-pyrazolo[3,4-d]pyrimidin-3-yl)-N-(1-methyl-1H-pyrazol-4-yl)benzamide,
57) N-(4-(1-(2-acryloyl-2-azabicyclo[2.2.1]heptan-6-yl)-4-amino-1H-pyrazolo[3,4-d]pyrimidin-3-yl)phenyl)-2-(dimethylamino)benzamide,
58) (E)-1-(6-(4-amino-3-(4-phenoxyphenyl)-1H-pyrazolo[3,4-d]pyrimidin-1-yl)-2-azabicyclo[2.2.1]heptan-2-yl)-4-morpholinobut-2-en-1-one,
59) 1-(6-(4-amino-3-(4-phenoxyphenyl)-1H-pyrazolo[3,4-d]pyrimidin-1-yl)-2-azabicyclo[2.2.2]octan-2-yl)prop-2-en-1-one,
60) (E)-4-(4-amino-1-(2-(4-(dimethylamino)but-2-enoyl)-2-azabicyclo[2.2.1]heptan-6-yl)-1H-pyrazolo[3,4-d]pyrimidin-3-yl)-N-(pyridin-2-yl)benzamide,
61) (E)-4-(4-amino-1-(2-(4-(4-methylpiperazin-1-yl)but-2-enoyl)-2-azabicyclo[2.2.1]heptan-6-yl)-1H-pyrazolo[3,4-d]pyrimidin-3-yl)-N-(pyridin-2-yl)benzamide,
62) (E)-1-(6-(4-amino-3-(4-phenoxyphenyl)-1H-pyrazolo[3,4-d]pyrimidin-1-yl)-2-azabicyclo[2.2.1]heptan-2-yl)-4-(4-methylpiperazin-1-yl)but-2-en-1-one,
63) (E)-1-(6-(4-amino-3-(4-phenoxyphenyl)-1H-pyrazolo[3,4-d]pyrimidin-1-yl)-2-azabicyclo[2.2.1]heptan-2-yl)-4-(piperidin-1-yl)but-2-en-1-one,
64) 4-(1-(2-acryloyl-2-azabicyclo[2.2.1]heptan-6-yl)-4-amino-1H-pyrazolo[3,4-d]pyrimidin-3-yl)-3-fluoro-N-(pyridin-2-yl)benzamide,
65) (E)-1-(5-(4-amino-3-(4-phenoxyphenyl)-1H-pyrazolo[3,4-d]pyrimidin-1-yl)-2-azabicyclo[2.2.1]heptan-2-yl)-4-bromobut-2-en-1-one,
66) (E)-1-(5-(4-amino-3-(4-phenoxyphenyl)-1H-pyrazolo[3,4-d]pyrimidin-1-yl)-2-azabicyclo[2.2.1]heptan-2-yl)-4-(piperidin-1-yl)but-2-en-1-one,
67) 4-(1-(2-acryloyl-2-azabicyclo[2.2.1]heptan-6-yl)-4-amino-1H-pyrazolo[3,4-d]pyrimidin-3-yl)-N-(4-fluoropyridin-2-yl)benzamide,
68) 4-(1-(2-acryloyl-2-azabicyclo[2.2.1]heptan-6-yl)-4-amino-1H-pyrazolo[3,4-d]pyrimidin-3-yl)-N-(4-methylpyridin-2-yl)benzamide,
69) 4-(1-((1R,4R,6S)-2-acryloyl-2-azabicyclo[2.2.1]heptan-6-yl)-4-amino-1H-pyrazolo[3,4-d]pyrimidin-3-yl)-N-(pyridin-2-yl)benzamide,
70) 4-(1-(2-acryloyl-2-azabicyclo[2.2.1]heptan-6-yl)-4-amino-1H-pyrazolo[3,4-d]pyrimidin-3-yl)-N-(6-(trifluoromethyl)pyridin-2-yl)benzamide,
71) 4-(1-(2-acryloyl-2-azabicyclo[2.2.1]heptan-6-yl)-4-amino-1H-pyrazolo[3,4-d]pyrimidin-3-yl)-N-(4-cyanopyridin-2-yl)benzamide,
72) 4-(1-((1S,4R,6S)-2-acryloyl-2-azabicyclo[2.2.1]heptan-6-yl)-4-amino-1H-pyrazolo[3,4-d]pyrimidin-3-yl)-N-(4-fluoropyridin-2-yl)benzamide,
73) 4-(1-((1S,4R,6S)-2-acryloyl-2-azabicyclo[2.2.1]heptan-6-yl)-4-amino-1H-pyrazolo[3,4-d]pyrimidin-3-yl)-3-fluoro-N-(4-fluoropyridin-2-yl)benzamide,
74) 4-(4-amino-1-((1R,4R,6S)-2-(2-cyanoacetyl)-2-azabicyclo[2.2.1]heptan-6-yl)-1H-pyrazolo[3,4-d]pyrimidin-3-yl)-N-(pyridin-2-yl)benzamide,
75) 4-(4-amino-1-((1R,4R)-2-(2-cyano-3-cyclopropylacryloyl)-2-azabicyclo[2.2.1]heptan-6-yl)-1H-pyrazolo[3,4-d]pyrimidin-3-yl)-N-(pyridin-2-yl)benzamide,
76) 4-(4-amino-1-((1R,4R)-2-(2-cyano-4-methylpent-2-enoyl)-2-azabicyclo[2.2.1]heptan-6-yl)-1H-pyrazolo[3,4-d]pyrimidin-3-yl)-N-(pyridin-2-yl)benzamide,
77) 4-(1-((1S,4R,6S)-2-acryloyl-2-azabicyclo[2.2.1]heptan-6-yl)-4-amino-1H-pyrazolo[3,4-d]pyrimidin-3-yl)-N-(3-methylpyridin-2-yl)benzamide,
78) 4-(1-((1S,4R,6S)-2-acryloyl-2-azabicyclo[2.2.1]heptan-6-yl)-4-amino-1H-pyrazolo[3,4-d]pyrimidin-3-yl)-N-(3-(trifluoromethyl)pyridin-2-yl)benzamide,
79) 4-(1-((1S,4R,6S)-2-acryloyl-2-azabicyclo[2.2.1]heptan-6-yl)-4-amino-1H-pyrazolo[3,4-d]pyrimidin-3-yl)-3-fluoro-N-methylbenzamide,
80) 4-(1-((1S,4R,6S)-2-acryloyl-2-azabicyclo[2.2.1]heptan-6-yl)-4-amino-1H-pyrazolo[3,4-d]pyrimidin-3-yl)-3-chloro-N-(pyridin-2-yl)benzamide,
81) 4-(1-((1S,4R,6S)-2-acryloyl-2-azabicyclo[2.2.1]heptan-6-yl)-4-amino-1H-pyrazolo[3,4-d]pyrimidin-3-yl)-3-methoxy-N-(pyridin-2-yl)benzamide,
82) 4-(4-amino-1-((1R,4R,6S)-2-(2-cyano-3-cyclopropylacryloyl)-2-azabicyclo[2.2.1]heptan-6-yl)-1H-pyrazolo[3,4-d]pyrimidin-3-yl)-3-fluoro-N-(pyridin-2-yl)benzamide,
83) 4-(4-amino-1-((1R,4R,6S)-2-(2-cyano-3-cyclopropylacryloyl)-2-azabicyclo[2.2.1]heptan-6-yl)-1H-pyrazolo[3,4-d]pyrimidin-3-yl)-3-fluoro-N-(4-fluoropyridin-2-yl)benzamide,
84) 4-(4-amino-1-((1R,4R,6S)-2-methacryloyl-2-azabicyclo[2.2.1]heptan-6-yl)-1H-pyrazolo[3,4-d]pyrimidin-3-yl)-N-(pyridin-2-yl)benzamide, and
85) 4-(1-((1S,4R,6S)-2-acryloyl-2-azabicyclo[2.2.1]heptan-6-yl)-4-amino-1H-pyrazolo[3,4-d]pyrimidin-3-yl)-3-fluoro-N-(pyridin-2-yl)benzamide.

Furthermore, as an example, the present invention can produce the compound represented by Chemical Formula 1 through Reaction Scheme 1 below.

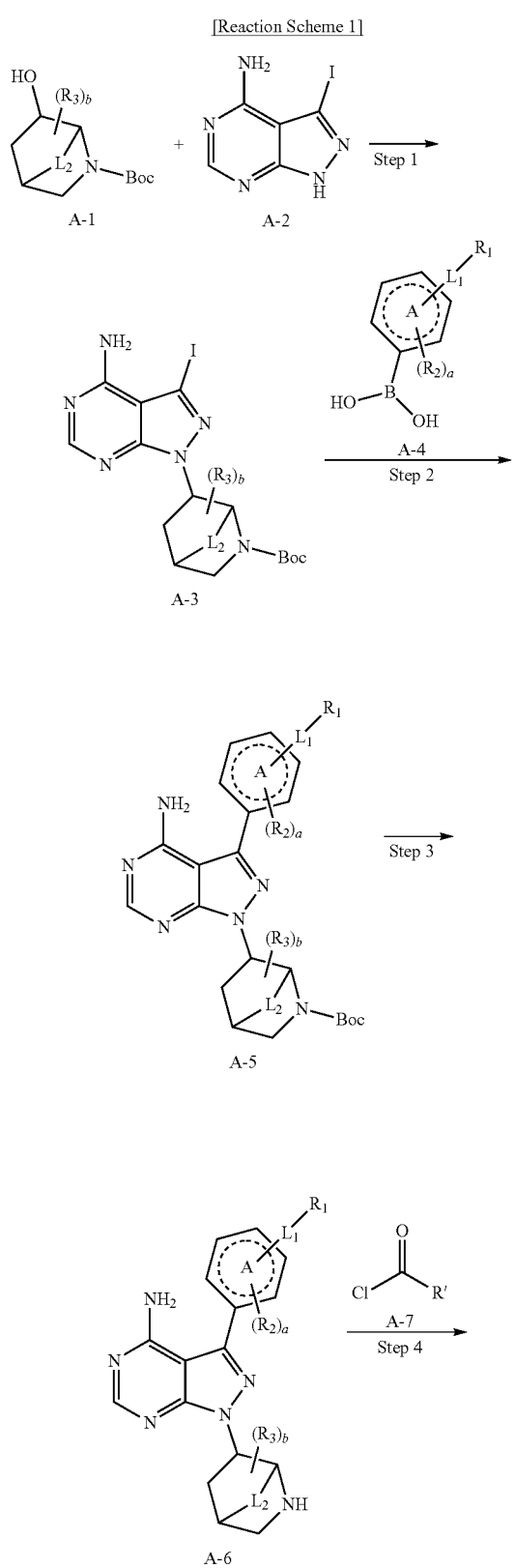

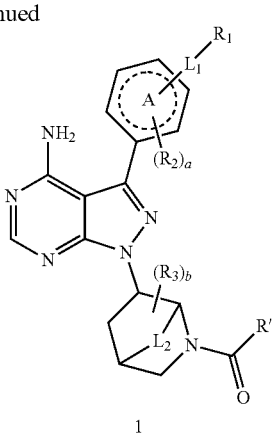

In Reaction Scheme 1, $R_1$ to $R_3$, $L_1$, $L_2$, a and b are as previously defined in Chemical Formula 1, and Boc means tert-butylcarboxyl group.

Step 1 is a step of preparing a compound represented by Chemical Formula A-3 by reacting a compound represented by Chemical Formula A-1 with a compound represented by Chemical Formula A-2 in the presence of triphenylphosphine, which is a step of introducing an azabicyclo compound into the hydrogen position of the 4-aminopyrazolo[3,4-d]pyrimidine derivative. In addition, the reaction can be carried out in a solvent such as tetrahydrofuran.

Step 2 is a step of preparing a compound represented by Chemical Formula A-5 by reacting a compound represented by Chemical Formula A-3 with a compound represented by Chemical Formula A-4 in the presence of a potassium carbonate and a palladium-based catalyst. The reaction is preferably carried out in a mixed solvent of 1,4-dioxane and water at 100° C. to 120° C.

Step 3 is a step of preparing a compound represented by Chemical Formula A-6 by aminating the compound represented by Chemical Formula A-5 in the presence of an aqueous hydrochloric acid solution. The reaction can be carried out in 1,4-dioxane solvent at room temperature.

Step 4 is a step of preparing a compound represented by Chemical Formula 1 by reacting a compound represented by Chemical Formula A-6 with a carbonyl chloride compound represented by Chemical Formula A-7. The reaction is preferably carried out in a mixed solvent of tetrahydrofuran and water after cooling to 0° C.

Further, the present invention provides a pharmaceutical composition for preventing or treating autoimmune diseases or cancer diseases, which is effective for BTK inhibitory actions, comprising the compound represented by Chemical Formula 1, or a pharmaceutically acceptable salt, hydrate, solvate or isomer thereof as an active ingredient.

In this case, the autoimmune diseases include rheumatoid arthritis, systemic lupus erythematosus, childhood diabetes, psoriasis, aphthous stomatitis, chronic thyroiditis, acquired aplastic anemia, primary cirrhosis, ulcerative colitis, Behcet's disease, Crohn's disease, Silicosis, asbestosis, Sjogren's syndrome, Guillain-Barre syndrome, dermatomyositis, polymyositis, multiple sclerosis, autoimmune hemolytic anemia, autoimmune encephalomyelitis, myasthenia gravis, Graves thyroid hyperplasia, nodular polyarteritis, ankylosing spondylitis, fibrositis, temporal arteritis, Wilson's disease, or Fanconi syndrome.

The cancer includes blood cancer, extranodal marginal zone B-cell lymphoma, glioblastoma, lymphoplasmacytic lymphoma, acute myelogenous leukemia, macroglobulinemia, B cell lymphoma, chronic lymphocytic leukemia, follicular lymphoma, non-hodgkin lymphoma, diffuse large B cell lymphoma, hairy cell leukemia, mantle cell lymphoma, glioblastoma, bladder cancer, pancreatic cancer, ovarian cancer, colorectal cancer, renal cancer, gastric cancer, transitional cell carcinoma, carcinoid tumor, breast cancer, non-small cell lung cancer, or multiple myeloma.

As used herein, the term "prevention" refers to any act to delay or inhibit occurrence, spread or recurrence of the above-mentioned diseases by administration of the composition of the present invention, and "treatment" refers to any act to improve or change the symptoms of the above diseases for the better by administration of the composition of the present invention.

The pharmaceutical composition according to the present invention can be formulated in types for oral or parenteral administrations according to a standard pharmaceutical practice. These formulations may contain additives such as pharmaceutically acceptable carrier, adjuvant or diluent in addition to the active ingredient.

Suitable carriers include, for example, physiological saline, polyethylene glycol, ethanol, vegetable oil, and isopropyl myristate and the like. Diluents include, for example, lactose, dextrose, sucrose, mannitol, sorbitol, cellulose and/or glycine and the like but are not limited thereto. Further, the compounds of the present invention can be dissolved in oils, propylene glycol or other solvents commonly used in the preparation of injection solutions. Furthermore, the compounds of the present invention can be formulated in ointments or creams for topical application.

A preferred dose of the compound of the present invention may be varied according to the condition and weight of a patient, the severity of a disease, the type of a drug, and the route and duration of administration, but it may be suitably selected by those skilled in the art. In order to achieve the desirable effects, however, the compound of the present invention may be administrated daily at a dose of 0.0001 to 100 mg/kg (body weight), and preferably 0.001 to 100 mg/kg (body weight). The administration may be performed once a day or in divided doses each day through an oral or parenteral route.

Depending on the method of administration, the Pharmaceutical composition may contain the compound of the present invention in an amount of 0.001 to 99% by weight, preferably 0.01 to 60% by weight.

The pharmaceutical composition according to the present invention may be administered to mammals such as a rat, a mouse, a domestic animal, a human, through various routes. The administration may be carried out through all possible methods, for example, oral, rectal, intravenous, intramuscular, subcutaneous, intra-endometrial, intracerebroventricular injection.

Advantageous Effects

The compound represented by Chemical Formula 1 according to the present invention or a pharmaceutically acceptable salt, hydrate, solvate or isomer thereof not only has BTK inhibitory activity but also has remarkably high selectivity for the inhibitory activity of BTK vs. ITK, and thereby can be usefully used for the prevention or treatment of autoimmune diseases or cancers as BTK inhibitors.

DETAILED DESCRIPTION OF THE EMBODIMENTS

Below, the present invention will be described in more detail by way of examples. However, these examples are provided for illustrative purposes only, and should not be construed as limiting the scope of the present invention to these examples.

Example 1: Preparation of 1-(6-(4-amino-3-(4-phenoxyphenyl)-1H-pyrazolo[3,4-d]pyrimidin-1-yl)-2-azabicyclo[2.2.1]heptan-2-yl)prop-2-en-1-one Step 1-1: Preparation of tert-butyl 6-(4-amino-3-iodo-1H-pyrazolo[3,4-d]pyrimidin-1-yl)-2-azabicyclo[2.2.1]heptane-2-carboxylate

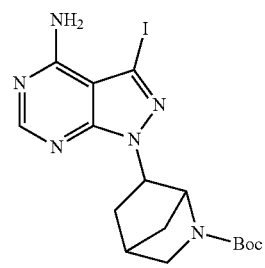 [SMILES: CC(C)(C)OC(=O)N1CC2CC1C(n1nc(I)c3c(N)ncnc31)C2]

After tert-butyl 6-hydroxy-2-azabicyclo[2.2.1]heptane-2-carboxylate (1.0 g, 4.7 mmol) and triphenylphosphine (1.2 g, 4.7 mmol) were dissolved in tetrahydrofuran (18.0 mL), diisopropyl azodicarboxylate (920 uL, 4.7 mmol) was slowly added thereto. After stirring the reaction solution for 5 minutes, 3-iodo-1H-pyrazolo[3,4-d]pyrimidin-4-amine (820 mg, 3.1 mmol) was added, and the mixture was heated for 5 minutes until all of the solids remaining in the reaction dissolved, followed by stirring at room temperature for 1 hour. Upon completion of the reaction, the mixture was concentrated under reduced pressure. The resulting residue was recrystallized from dichloromethane to obtain a title compound (670 mg, yield: 47%).

Step 1-2: Preparation of tert-butyl 6-(4-amino-3-(4-phenoxyphenyl)-1H-pyrazolo[3,4-d]pyrimidin-1-yl)-2-azabicyclo[2.2.1]heptane-2-carboxylate

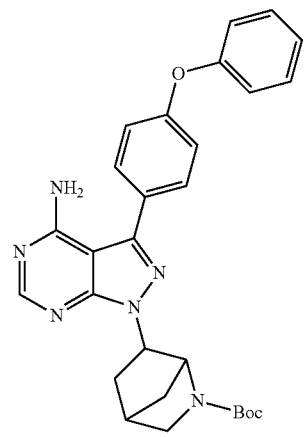 [SMILES: CC(C)(C)OC(=O)N1CC2CC1C(n1nc(-c3ccc(Oc4ccccc4)cc3)c3c(N)ncnc31)C2]

After tert-butyl 6-(4-amino-3-iodo-1H-pyrazolo[3,4-d]pyrimidin-1-yl)-2-azabicyclo[2.2.1]heptane-2-carboxylate (200 mg, 0.44 mmol) obtained in Step 1-1 was dissolved in 1,4-dioxane (4 mL) and water (600 uL), (4-phenoxyphenyl)

boronic acid (120 mg, 0.55 mmol), potassium carbonate (303 mg, 2.2 mmol) and [1,1'-bis(diphenylphosphino)ferrocene]diclopalladium(II) (22 mg, 0.031 mmol) were sequentially added thereto, and the mixture was refluxed and stirred at 110° C. for 90 minutes. Upon completion of the reaction, the mixture was diluted with ethyl acetate and washed with saturated sodium chloride solution. The organic layer was collected, dried over magnesium sulfate, filtered and then concentrated under reduced pressure. The residue was purified by column chromatography (ethyl acetate 100%) to obtain a title compound (180 mg, yield: 92%).

Step 1-3: Preparation of 1-(2-azabicyclo[2.2.1]heptan-6-yl)-3-(4-phenoxyphenyl)-1H-pyrazolo[3,4-d]pyrimidin-4-amine

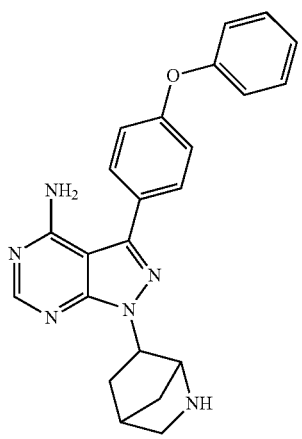 [SMILES: Nc1ncnc2c1c(-c1ccc(Oc3ccccc3)cc1)nn2C1CC2CNC1C2]

After tert-butyl 6-(4-amino-3-(4-phenoxyphenyl)-1H-pyrazolo[3,4-d]pyrimidin-1-yl)-2-azabicyclo[2.2.1]heptane-2-carboxylate (180 mg, 0.36 mmol) obtained in Step 1-2 was dissolved in 1,4-dioxane (5 mL), 4N aqueous hydrochloric acid solution (10 mL) dissolved in dioxane was added thereto, followed by stirring at room temperature for 4 hours. Upon completion of the reaction, the pH was adjusted to 10 by adding sodium bicarbonate solution. The reaction solution was diluted with ethyl acetate and washed with saturated sodium chloride solution. The organic layer was collected, dried over magnesium sulfate, filtered and then concentrated under reduced pressure to obtain a title compound (120 mg, yield: 83%).

Step 1-4: Preparation of 1-(6-(4-amino-3-(4-phenoxyphenyl)-1H-pyrazolo[3,4-d]pyrimidin-1-yl)-2-azabicyclo[2.2.1]heptan-2-yl)prop-2-en-1-one

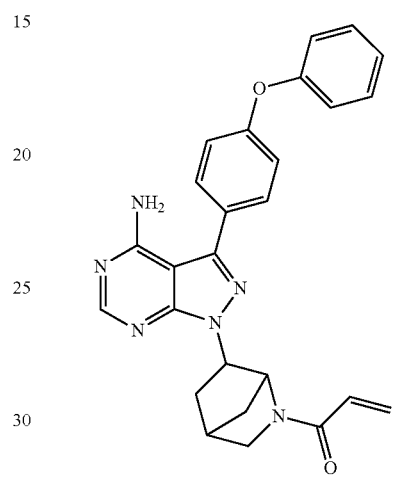

After 1-(2-azabicyclo[2.2.1]heptan-6-yl)-3-(4-phenoxyphenyl)-1H-pyrazolo[3,4-d]pyrimidin-4-amine (60 mg, 0.15 mmol) obtained in Step 1-3 was dissolved in tetrahydrofuran (6 mL) and water (2 mL), and then cooled to 0° C., to which sodium bicarbonate (14 mg, 0.17 mmol) was added. Acryloyl chloride (14 uL, 0.17 mmol) was dissolved in tetrahydrofuran (1 mL), slowly added to the reaction solution, and then stirred at room temperature for 10 minutes. Upon completion of the reaction, the reaction solution was diluted with ethyl acetate and washed with saturated sodium chloride solution. The organic layer was collected, dried over magnesium sulfate, and then concentrated under reduced pressure. The residue was purified by column chromatography (chloromethane:methanol=9:1) to obtain a title compound (39 mg, yield: 57%).

$^1$H NMR (500 MHz, CDCl$_3$): 8.38-8.41 (m, 1H), 7.63-7.64 (m, 2H), 7.38-7.41 (m, 2H), 7.14-7.20 (m, 3H), 7.08-7.10 (m, 2H), 6.78-6.83 (m, 1H), 6.36-6.48 (m, 1H), 5.71-5.77 (m, 1H), 5.56 (s, 2H), 5.08-5.23 (m, 1H), 4.53-4.91 (m, 1H), 3.54-3.56 (m, 1H), 3.26-3.34 (m, 1H), 2.57-2.86 (m, 2H), 2.30-2.51 (m, 1H), 2.12-2.27 (m, 1H), 1.70-1.74 (m, 1H).

Example 2: Preparation of 1-(6-(4-amino-3-(4-phenoxyphenyl)-1H-pyrazolo[3,4-d]pyrimidin-1-yl)-2-azabicyclo[2.2.1]heptan-2-yl)prop-2-yn-1-one

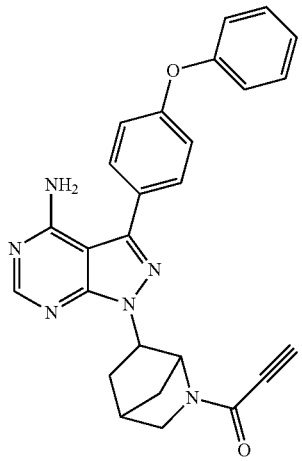 [SMILES: C#CC(=O)N1CC2CC1C(n1nc(-c3ccc(Oc4ccccc4)cc3)c3c(N)ncnc31)C2]

A title compound (45 mg, yield: 66%) was prepared in the same manner as in Step 1-4 of Example 1, except using 1-(2-azabicyclo[2.2.1]heptan-6-yl)-3-(4-phenoxyphenyl)-1H-pyrazolo[3,4-d]pyrimidin-4-amine (60 mg, 0.15 mmol) obtained in Step 1-3 and propionyl chloride (15 uL, 0.17 mmol).

$^1$H NMR (500 MHz, CDCl$_3$): 8.32-8.36 (m, 1H), 7.62-7.64 (m, 2H), 7.37-7.40 (m, 2H), 7.07-7.19 (m, 5H), 5.75 (s, 2H), 5.22-5.24 (m, 1H), 4.71-4.86 (m, 1H), 3.41-3.65 (m, 1H), 3.24-3.38 (m, 1H), 3.01-3.03 (m, 1H), 2.87 (s, 1H), 2.31-2.62 (m, 2H), 2.03-2.20 (m, 1H), 1.72-1.77 (m, 1H).

Example 3: Preparation of (E)-1-(6-(4-amino-3-(4-phenoxyphenyl)-1H-pyrazolo[3,4-d]pyrimidin-1-yl)-2-azabicyclo[2.2.1]heptan-2-yl)but-2-en-1-one

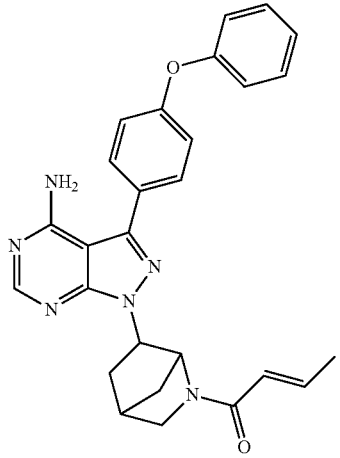 [SMILES: C/C=C/C(=O)N1CC2CC1C(n1nc(-c3ccc(Oc4ccccc4)cc3)c3c(N)ncnc31)C2]

A title compound (45 mg, yield: 70%) was prepared in the same manner as in Step 1-4 of Example 1, except for using 1-(2-azabicyclo[2.2.1]heptan-6-yl)-3-(4-phenoxyphenyl)-1H-pyrazolo[3,4-d]pyrimidin-4-amine (60 mg, 0.15 mmol) obtained in Step 1-3 and but-2-enoyl chloride (16 uL, 0.17 mmol).

$^1$H NMR (500 MHz, CDCl$_3$): 8.30-8.39 (m, 1H), 7.63-7.65 (m, 2H), 7.37-7.40 (m, 2H), 7.13-7.9 (m, 5H), 6.98-7.09 (m, 1H), 6.05-6.56 (m, 1H), 5.77 (s, 2H), 5.03-5.19 (m, 1H), 4.51-4.91 (m, 1H), 3.45-3.51 (m, 1H), 3.20-3.31 (m, 1H), 2.51-2.84 (m, 2H), 2.25-2.47 (m, 1H), 2.15-2.23 (m, 1H), 2.09 (s, 3H), 1.88-1.93 (m, 1H).

Example 4: Preparation of 4-(4-amino-1-(2-propioloyl-2-azabicyclo[2.2.1]heptan-6-yl)-1H-pyrazolo[3,4-d]pyrimidin-3-yl)-N-(pyridin-2-yl)benzamide

Step 4-1: Preparation of 4-(4,4,5,5-tetramethyl-1,3,2-dioxaborolan-2-yl)benzoyl chloride

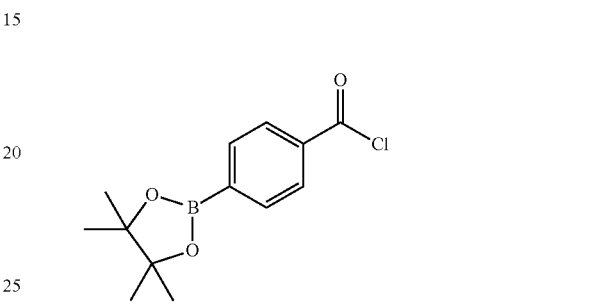

4-(4,4,5,5-tetramethyl-1,3,2-dioxaborolan-2-yl)benzoic acid (100 mg, 0.40 mmol) was dissolved in dichloromethane (2 mL) and then cooled to 0° C. One drop of N,N-dimethylformamide was added and oxalyl chloride (86 uL, 1.01 mmol) was slowly added. After stirring at 0° C. for 30 minutes, the temperature was raised to room temperature and the mixture was then stirred for 3 hours. Upon completion of the reaction, the reaction solution was concentrated under reduced pressure and the subsequent reaction was carried out without purification.

Step 4-2: Preparation of N-(pyridin-2-yl)-4-(4,4,5,5-tetramethyl-1,3,2-dioxaborolan-2-yl)benzamide

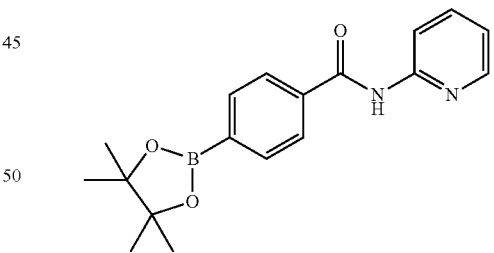

After pyridin-2-amine (42 mg, 0.442 mmol) and N,N-dimethylaminopyridine (49 mg, 0.40 mmol) were dissolved in acetonitrile (1 mL), 4-(4,4,5,5-tetramethyl-1,3,2-dioxaborolan-2-yl)benzoyl chloride obtained in Step 4-1 was dissolved in acetonitrile (1 mL) and then slowly added to the reaction solution, followed by stirring at room temperature for 12 hours. Upon completion of the reaction, the reaction was diluted with chloromethane and washed with 0.2 N aqueous hydrochloric acid solution. The organic layer was collected, dried over magnesium sulfate, and then concentrated under reduced pressure. The residue was purified by column chromatography (hexane:ethyl acetate=1:1) to obtain a title compound (51 mg, yield: 39% over two steps).

Step 4-3: Preparation of tert-butyl 6-(4-amino-3-(4-(pyridin-2-yl)carbamoyl)phenyl)-1H-pyrazolo[3,4-d]pyrimidin-1-yl)-2-azabicyclo[2.2.1]heptane-2-carboxylate

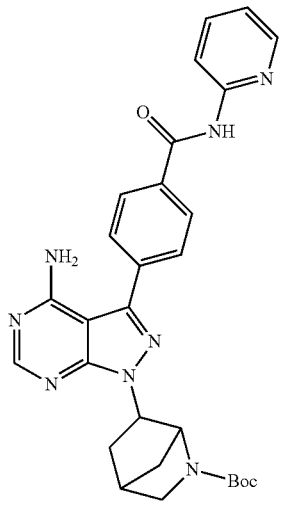

A title compound (58 mg, yield: 25%) was prepared in the same manner as in Step 1-1 of Example 1, except for using tert-butyl 6-(4-amino-3-iodo-1H-pyrazolo[3,4-d]pyrimidin-1-yl)-2-azabicyclo[2.2.1]heptane-2-carboxylate (200 mg, 0.44 mmol) obtained in Step 1-3, 1,4-dioxane (4 mL), water (600 uL), and N-(pyridin-2-yl)-4-(4,4,5,5-tetramethyl-1,3,2-dioxaborolan-2-yl)benzamide (178 mg, 0.55 mmol) obtained in Step 4-2.

Step 4-4: Preparation of 4-(4-amino-1-(2-azabicyclo[2.2.1]heptan-6-yl)-1H-pyrazolo[3,4-d]pyrimidin-3-yl)-N-(pyridin-2-yl)benzamide

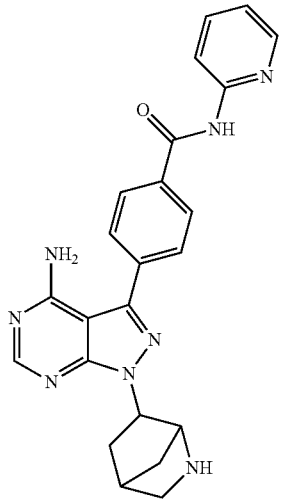 [SMILES: Nc1ncnc2c1c(-c1ccc(C(=O)Nc3ccccn3)cc1)nn2C1CC2CNC1C2]

A title compound (51 mg, yield: 41%) was prepared in the same manner as in Step 1-3 of Example 1, except for using tert-butyl 6-(4-amino-3-(4-(pyridin-2-yl)carbamoyl)phenyl)-1H-pyrazolo[3,4-d]pyrimidin-1-yl)-2-azabicyclo[2.2.1]heptane-2-carboxylate (153 mg, 0.29 mmol) obtained in Step 4-3.

Step 4-5: Preparation of 4-(4-amino-1-(2-propioloyl-2-azabicyclo[2.2.1]heptan-6-yl)-1H-pyrazolo[3,4-d]pyrimidin-3-yl)-N-(pyridin-2-yl)benzamide

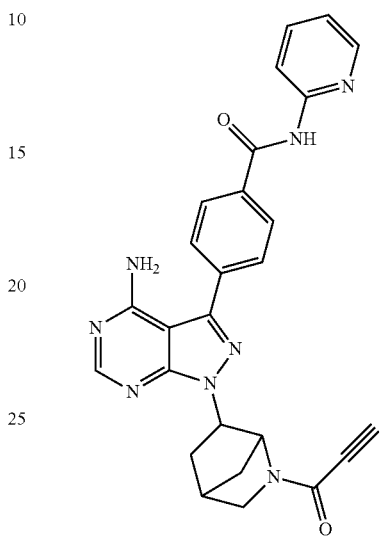

A title compound (26 mg, yield: 45%) was prepared in the same manner as in Step 1-4 of Example 1, except for using 4-(4-amino-1-(2-azabicyclo[2.2.1]heptan-6-yl)-1H-pyrazolo[3,4-d]pyrimidin-3-yl)-N-(pyridin-2-yl)benzamide (51 mg, 0.12 mmol) obtained in Step 4-4 and propioloyl chloride (12 uL, 0.13 mmol).

$^1$H NMR (500 MHz, CDCl$_3$): 8.42-8.65 (m, 4H), 8.16-8.18 (m, 2H), 7.84-7.91 (m, 3H), 5.28-5.47 (m, 1H), 4.81-4.92 (m, 1H), 3.53-3.72 (m, 1H), 3.33-3.52 (m, 1H), 3.09-3.11 (m, 1H), 2.89 (s, 1H), 3.45-3.72 (m, 2H), 3.31-3.41 (m, 1H), 1.79-1.82 (m, 1H)

Example 5: Preparation of 1-(6-(4-amino-3-(4-phenoxyphenyl)-1H-pyrazolo[3,4-d]pyrimidin-1-yl)-2-azabicyclo[2.2.1]heptan-2-yl)but-2-yn-1-one

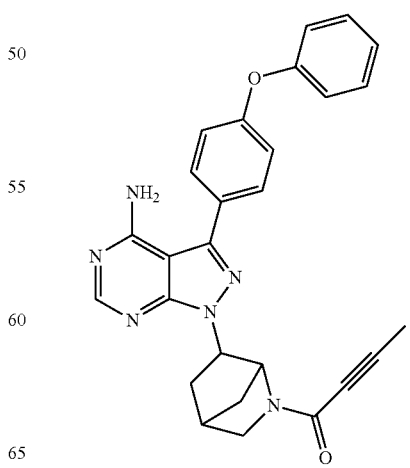

A title compound (45 mg, yield: 69%) was prepared in the same manner as in Step 1-4 of Example 1, except for using 1-(2-azabicyclo[2.2.1]heptan-6-yl)-3-(4-phenoxyphenyl)-1H-pyrazolo[3,4-d]pyrimidin-4-amine (60 mg, 0.15 mmol) obtained in Step 1-3 and but-2-ynoyl chloride (17 uL, 0.17 mmol).

$^1$H NMR (500 MHz, CDCl$_3$): 8.35-8.38 (m, 1H), 7.60-7.64 (m, 2H), 7.39-7.42 (m, 2H), 7.09-7.18 (m, 5H), 5.85 (s, 2H), 5.23-5.25 (m, 1H), 4.68-4.85 (m, 1H), 3.47-3.55 (m, 1H), 3.24-3.35 (m, 1H), 3.24-3.26 (m, 1H), 2.67-2.70 (m, 1H), 2.35-2.45 (m, 1H), 2.13-2.18 (m, 1H), 1.97 (s, 3H), 1.72-1.77 (m, 1H).

Example 6: Preparation of 4-(4-amino-1-(2-propioloyl-2-azabicyclo[2.2.1]heptan-6-yl)-1H-pyrazolo[3,4-d]pyrimidin-3-yl)-N-(4-(trifluoromethyl)pyridin-2-yl)benzamide Step 6-1: Preparation of 4-(4,4,5,5-tetramethyl-1,3,2-dioxaborolan-2-yl)-N-(4-trifluoromethyl)pyridin-2-yl)benzamide

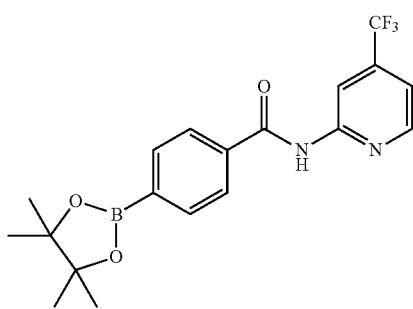 [SMILES: CC1(C)OB(c2ccc(C(=O)Nc3cc(C(F)(F)F)ccn3)cc2)OC1(C)C]

A title compound (102 mg, yield: 65%) was prepared in the same manner as in Step 4-2 of Example 4, except for using 4-(4,4,5,5-tetramethyl-1,3,2-dioxaborolan-2-yl)benzoyl chloride (107 mg, 0.40 mmol) obtained in Step 4-1 and 4-(trifluoro methyl)pyridin-2-amine (72 mg, 0.44 mmol).

Step 6-2: Preparation of tert-butyl 6-(4-amino-3-(4-((4-(trifluoromethyl)pyridin-2-yl)carbamoyl)phenyl)-1H-pyrazolo[3,4-d]pyrimidin-1-yl)-2-azabicyclo[2.2.1]heptane-2-carboxylate

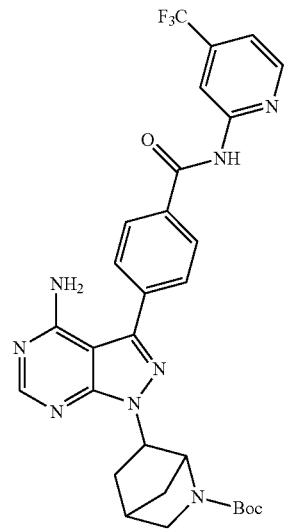 [SMILES: CC(C)(C)OC(=O)N1CC2CC1C(n1nc(-c3ccc(C(=O)Nc4cc(C(F)(F)F)ccn4)cc3)c3c(N)ncnc31)C2]

A title compound (85 mg, yield: 65%) was prepared in the same manner as in Step 1-2 of Example 1, except for using 4-(4,4,5,5-tetramethyl-1,3,2-dioxaborolan-2-yl)-N-(4-trifluoromethyl)pyridin-2-yl)benzamide (102 mg, 0.26 mmol) obtained in Step 6-1 and tert-butyl 6-(4-amino-3-iodo-1H-pyrazolo[3,4-d]pyrimidin-1-yl)-2-azabicyclo[2.2.1]heptane-2-carboxylate (100 mg, 0.22 mmol).

Step 6-3: Preparation of 4-(4-amino-1-(2-azabicyclo[2.2.1]heptan-6-yl)-1H-pyrazolo[3,4-d]pyrimidin-3-yl)-N-(4-(trifluoromethyl)pyridin-2-yl)benzamide

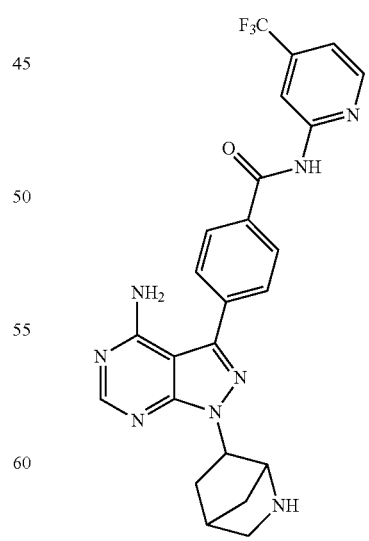

A title compound (95 mg, yield: 67%) was prepared in the same manner as in Step 1-3 of Example 1, except for using tert-butyl 6-(4-amino-3-(4-((4-(trifluoromethyl)pyridin-2- yl)carbamoyl)phenyl)-1H-pyrazolo[3,4-d]pyrimidin-1-yl)-2-azabicyclo[2.2.1]heptane-2-carboxylate (85 mg, 0.14 mmol) obtained in Step 6-2.

Step 6-4: Preparation of 4-(4-amino-1-(2-propioloyl-2-azabicyclo[2.2.1]heptan-6-yl)-1H-pyrazolo[3,4-d]pyrimidin-3-yl)-N-(4-(trifluoromethyl)pyridin-2-yl)benzamide

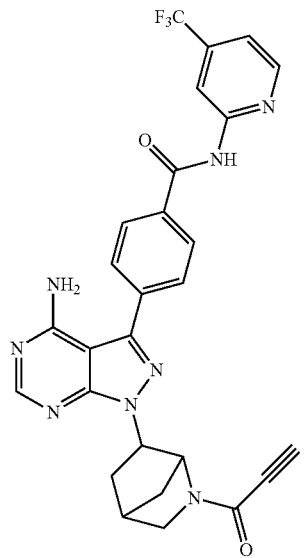 [SMILES: C#CC(=O)N1CC2CC1C(n1nc(-c3ccc(C(=O)Nc4cc(C(F)(F)F)ccn4)cc3)c3c(N)ncnc31)C2]

A title compound (43 mg, yield: 65%) was prepared in the same manner as in Step 1-4 of Example 1, except for using 4-(4-amino-1-(2-azabicyclo[2.2.1]heptan-6-yl)-1H-pyrazolo[3,4-d]pyrimidin-3-yl)-N-(4-(trifluoromethyl)pyridin-2-yl)benzamide (60 mg, 0.12 mmol) obtained in Step 6-3 and propioloyl chloride (12 uL, 0.13 mmol).

$^1$H NMR (500 MHz, CDCl$_3$): 8.72-8.75 (m, 2H), 8.51-8.52 (m, 1H), 8.39-8.41 (m, 1H), 8.12-8.14 (m, 2H), 7.85-7.88 (m, 2H), 5.28-5.30 (m, 1H), 4.74-4.88 (m, 1H), 3.27-3.50 (m, 2H), 3.03-3.06 (m, 1H), 2.92 (s, 1H), 2.54-2.62 (m, 2H), 2.22-2.35 (m, 1H), 1.79-1.82 (m, 1H).

Example 7: Preparation of 3-(4-amino-1-(2-propioloyl-2-azabicyclo[2.2.1]heptan-6-yl)-1H-pyrazolo[3,4-d]pyrimidin-3-yl)-N-(4-isopropylphenyl)benzamide Step 7-1: Preparation of 3-(4,4,5,5-tetramethyl-1,3,2-dioxaborolan-2-yl)benzoyl chloride

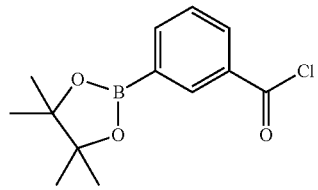 [SMILES: CC1(C)OB(c2cccc(C(=O)Cl)c2)OC1(C)C]

A title compound was prepared in the same manner as in Step 4-1 of Example 4, except for using 3-(4,4,5,5-tetramethyl-1,3,2-dioxaborolan-2-yl)benzoic acid (100 mg, 1.61 mmol).

Step 7-2: Preparation of N-(4-isopropylphenyl)-3-(4,4,5,5-tetramethyl-1,3,2-dioxaborolan-2-yl)benzamide

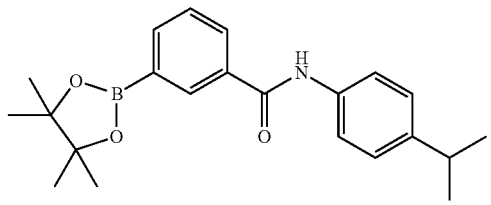 [SMILES: CC(C)c1ccc(NC(=O)c2cccc(B3OC(C)(C)C(C)(C)O3)c2)cc1]

A title compound (385 mg, yield: 65% over two steps) was prepared in the same manner as in Step 4-2 of Example 4, except for using 3-(4,4,5,5-tetramethyl-1,3,2-dioxaborolan-2-yl)benzoyl chloride (430 mg, 1.613 mmol) obtained in step 7-1 and 4-isopropylaniline (253 mg, 1.775 mmol)

Step 7-3: Preparation of tert-butyl 6-(4-amino-3-(3-((4-isopropylphenyl)carbamoyl)phenyl)-1H-pyrazolo[3,4-d]pyrimidin-1-yl)-2-azabicyclo[2.2.1]heptane-2-carboxylate

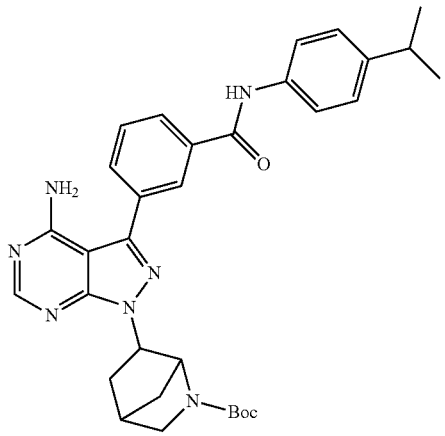 [SMILES: CC(C)c1ccc(NC(=O)c2cccc(-c3nn(C4CC5CC4N(C(=O)OC(C)(C)C)C5)c4ncnc(N)c34)c2)cc1]

A title compound (133 mg, yield: 89%) was prepared in the same manner as in Step 1-2 of Example 1, except for using N-(4-isopropylphenyl)-3-(4,4,5,5-tetramethyl-1,3,2-dioxaborolan-2-yl)benzamide (125 mg, 0.33 mmol) obtained in Step 7-2 and tert-butyl 6-(4-amino-3-iodo-1H-pyrazolo[3,4-d]pyrimidin-1-yl]-2-azabicyclo[2.2.1]heptan-2-carboxylate (120 mg, 0.22 mmol).

Step 7-4: Preparation of 3-(4-amino-1-(2-azabicyclo[2.2.1]heptan-6-yl)-1H-pyrazolo[3,4-d]pyrimidin-3-yl)-N-(4-isopropylphenyl)benzamide

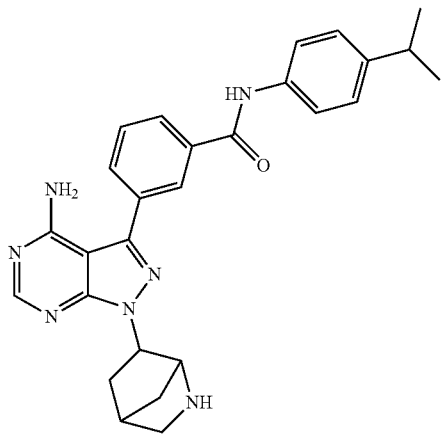 [SMILES: CC(C)c1ccc(NC(=O)c2cccc(-c3nn(C4CC5CNC4C5)c4ncnc(N)c34)c2)cc1]

A title compound (65 mg, yield: 59%) was prepared in the same manner as in Step 1-3 of Example 1, except for using tert-butyl 6-(4-amino-3-(3-((4-isopropylphenyl)carbamoyl)phenyl)-1H-pyrazolo[3,4-d]pyrimidin-1-yl)-2-azabicyclo[2.2.1]heptane-2-carboxylate (133 mg, 0.23 mmol) obtained in Step 7-3.

Step 7-5: Preparation of 3-(4-amino-1-(2-propioloyl-2-azabicyclo[2.2.1]heptan-6-yl)-1H-pyrazolo[3,4-d]pyrimidin-3-yl)-N-(4-isopropylphenyl)benzamide

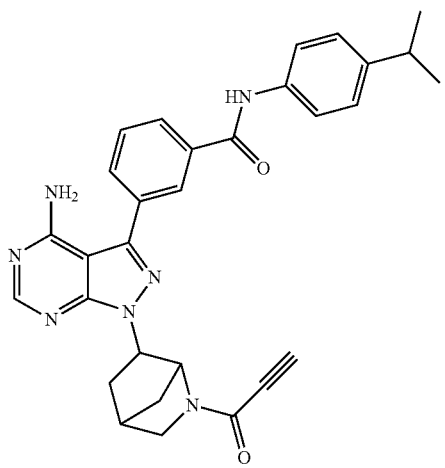 [SMILES: C#CC(=O)N1CC2CC1C(n1nc(-c3cccc(C(=O)Nc4ccc(C(C)C)cc4)c3)c3c(N)ncnc31)C2]

A title compound (17 mg, yield: 51%) was prepared in the same manner as in Step 1-4 of Example 1, except for using 3-(4-amino-1-(2-azabicyclo[2.2.1]heptan-6-yl)-1H-pyrazolo[3,4-d]pyrimidin-3-yl)-N-(4-isopropylphenyl)benzamide (30 mg, 0.06 mmol) obtained in Step 7-4 and propioloyl chloride (6 uL, 0.07 mmol).

$^1$H NMR (500 MHz, CDCl$_3$): 8.29-8.39 (m, 1H), 8.21-8.22 (m, 1H), 7.86-7.96 (m, 3H), 7.55-7.70 (m, 4H), 5.85 (s, 2H), 5.08-5.26 (m, 1H), 4.73-4.92 (m, 1H), 3.42-3.44 (m, 1H), 3.25-3.28 (m, 1H), 3.02-3.06 (m, 1H), 2.60-2.93 (m, 3H), 2.35-2.59 (m, 1H), 2.20-2.23 (m, 1H), 1.77-1.80 (m, 1H), 1.26 (s, 6H).

Example 8: Preparation of 3-(1-(2-acryloyl-2-azabicyclo[2.2.1]heptan-6-yl)-4-amino-1H-pyrazolo[3,4-d]pyrimidin-3-yl)-N-(4-isopropylphenyl)benzamide

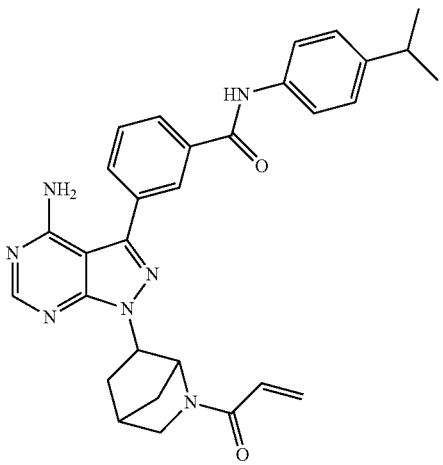 [SMILES: C=CC(=O)N1CC2CC1C(n1nc(-c3cccc(C(=O)Nc4ccc(C(C)C)cc4)c3)c3c(N)ncnc31)C2]

A title compound (20 mg, yield: 60%) was prepared in the same manner as in Step 1-4 of Example 1, except for using 3-(4-amino-1-(2-azabicyclo[2.2.1]heptan-6-yl)-1H-pyrazolo[3,4-d]pyrimidin-3-yl)-N-(4-isopropylphenyl)benzamide (30 mg, 0.06 mmol) obtained in Step 7-4 and acryloyl chloride (6 uL, 0.07 mmol).

$^1$H NMR (500 MHz, CDCl$_3$): 8.38-8.41 (m, 1H), 8.23-8.28 (m, 1H), 7.87-7.98 (m, 3H), 7.57-7.71 (m, 4H), 6.44-6.85 (m, 2H), 5.77-5.79 (m, 1H), 5.11-5.12 (m, 1H), 4.55-5.12 (m, 1H), 3.47-3.61 (m, 1H), 3.25-3.45 (m, 1H), 2.57-2.94 (m, 3H), 3.25-3.32 (m, 1H), 2.14-2.20 (m, 1H), 1.74-1.76 (m, 1H), 1.23 (s, 6H).

Example 9: Preparation of 3-(4-amino-1-(2-propioloyl-2-azabicyclo[2.2.1]heptan-6-yl)-1H-pyrazolo[3,4-d]pyrimidin-3-yl)-N-(4-isopropyl-3-methylphenyl)benzamide Step 9-1: Preparation of N-(4-isopropyl-3-methylphenyl)-3-(4,4,5,5-tetramethyl-1,3,2-dioxaborolan-2-yl)benzamide

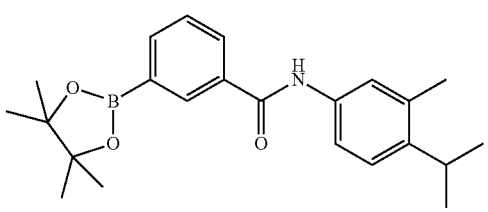 [SMILES: Cc1cc(NC(=O)c2cccc(B3OC(C)(C)C(C)(C)O3)c2)ccc1C(C)C]

A title compound (394 mg, yield: 64% over two steps) was prepared in the same manner as in Step 4-2 of Example 4, except for using 3-(4,4,5,5-tetramethyl-1,3,2-dioxaborolan-2-yl)benzoyl chloride (430 mg, 1.61 mmol) obtained in step 7-1 and 4-isopropyl-3-methylaniline (330 mg, 1.78 mmol).

Step 9-2: Preparation of tert-butyl 6-(4-amino-3-(3-((4-isopropyl-3-methylphenyl)carbamoyl)phenyl)-1H-pyrazolo[3,4-d]pyrimidin-1-yl)-2-azabicyclo[2.2.1]heptane-2-carboxylate

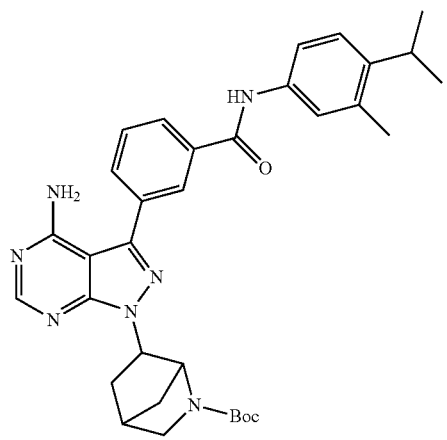 [SMILES: Cc1cc(NC(=O)c2cccc(-c3nn(C4CC5CC4N(C(=O)OC(C)(C)C)C5)c4ncnc(N)c34)c2)ccc1C(C)C]

A title compound (135 mg, yield: 88%) was prepared in the same manner as in Step 1-2 of Example 1, except for using N-(4-isopropyl-3-methylphenyl)-3-(4,4,5,5-tetramethyl-1,3,2-dioxaborolan-2-yl)benzamide (125 mg, 0.33 mmol) obtained in step 9-1 and tert-butyl 6-(4-amino-3-iodo-1H-pyrazolo[3,4-d]pyrimidin-1-yl)-2-azabicyclo[2.2.1]heptane-2-carboxylate (120 mg, 0.26 mmol).

Step 9-3: Preparation of 3-(4-amino-1-(2-azabicyclo[2.2.1]heptan-6-yl)-1H-pyrazolo[3,4-d]pyrimidin-3-yl)-N-(4-isopropyl-3-methylphenyl)benzamide

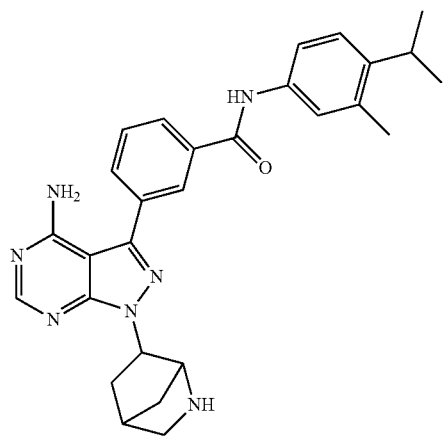 [SMILES: Cc1cc(NC(=O)c2cccc(-c3nn(C4CC5CNC4C5)c4ncnc(N)c34)c2)ccc1C(C)C]

A title compound (52 mg, yield: 46%) was prepared in the same manner as in Step 1-3 of Example 1, except for using tert-butyl 6-(4-amino-3-(3-((4-isopropyl-3-methylphenyl)carbamoyl)phenyl)-1H-pyrazolo[3,4-d]pyrimidin-1-yl)-2-azabicyclo[2.2.1]heptane-2-carboxylate (135 mg, 0.23 mmol) obtained in step 9-2.

Step 9-4: Preparation of 3-(4-amino-1-(2-propioloyl-2-azabicyclo[2.2.1]heptan-6-yl)-1H-pyrazolo[3,4-d]pyrimidin-3-yl)-N-(4-isopropyl-3-methylphenyl)benzamide

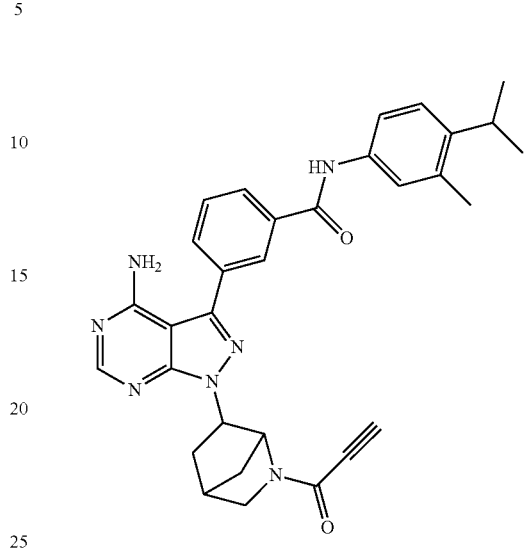

A title compound (16 mg, yield: 56%) was prepared in the same manner as in Step 1-4 of Example 1, except for using 3-(4-amino-1-(2-azabicyclo[2.2.1]heptan-6-yl)-1H-pyrazolo[3,4-d]pyrimidin-3-yl)-N-(4-isopropyl-3-methylphenyl)benzamide (26 mg, 0.05 mmol) obtained in step 9-3 and propioloyl chloride (7 uL, 0.08 mmol).

$^1$H NMR (500 MHz, CDCl$_3$): 8.30-8.36 (m, 1H), 8.20-8.21 (m, 1H), 7.79-7.96 (m, 3H), 7.67-7.69 (m, 1H), 7.41-7.45 (m, 2H), 5.11-5.25 (m, 1H), 4.71-4.88 (m, 1H), 3.38-3.61 (m, 2H), 3.25-3.28 (m, 1H), 3.10-3.16 (m, 1H), 2.97-3.05 (m, 1H), 2.90 (s, 1H), 2.50-2.58 (m, 2H), 2.37 (s, 3H), 2.21-2.23 (m, 1H), 1.77-1.80 (m, 1H), 1.26 (s, 6H).

Example 10: Preparation of 3-(1-(2-acryloyl-2-azabicyclo[2.2.1]heptan-6-yl)-4-amino-1H-pyrazolo[3,4-d]pyrimidin-3-yl)-N-(4-isopropyl-3-methylphenyl)benzamide

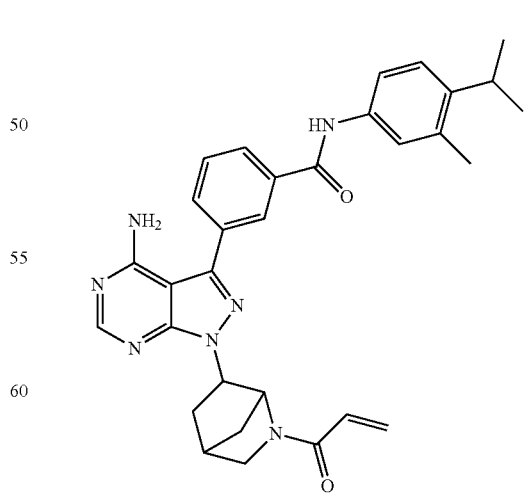

A title compound (20 mg, yield: 69%) was prepared in the same manner as in Step 1-4 of Example 1, except for using 3-(4-amino-1-(2-azabicyclo[2.2.1]heptan-6-yl)-1H-pyrazolo[3,4-d]pyrimidin-3-yl)-N-(4-isopropyl-3-methylphenyl)benzamide (26 mg, 0.05 mmol) obtained in Step 9-3 and acryloyl chloride (7 uL, 0.08 mmol).

¹H NMR (500 MHz, CDCl₃): 8.29-8.39 (m, 1H), 8.21-8.24 (m, 1H), 7.79-8.10 (m, 3H), 7.43-7.69 (m, 3H), 6.35-6.80 (m, 2H), 5.76-5.78 (m, 1H), 5.11-5.19 (m, 1H), 4.55-4.94 (m, 1H), 3.47-3.65 (m, 1H), 3.25-3.33 (m, 1H), 3.11-3.14 (m, 1H), 2.81-2.87 (m, 2H), 2.42-2.51 (m, 1H), 2.13-2.28 (m, 1H), 1.75-1.77 (m, 1H), 1.26 (s, 6H).

Example 11: Preparation of 1-(5-(4-amino-3-(4-phenoxyphenyl)-1H-pyrazolo[3,4-d]pyrimidin-1-yl)-2-azabicyclo[2.2.1]heptan-2-yl)prop-2-yn-1-one Step 11-1: Preparation of tert-butyl 5-(4-amino-3-iodo-1H-pyrazolo[3,4-d]pyrimidin-1-yl)-2-azabicyclo[2.2.1]heptane-2-carboxylate

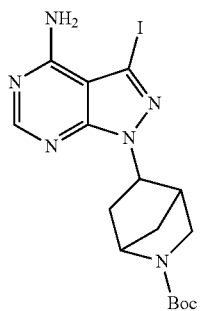

A title compound (200 mg, yield: 56%) was prepared in the same manner as in Step 1-1 of Example 1, except for using tert-butyl 5-hydroxy-2-azabicyclo[2.2.1]heptane-2-carboxylate (250 mg, 1.17 mmol) and 3-iodo-1H-pyrazolo[3,4-d]pyrimidin-1-amine (204 mg, 0.78 mmol).

Step 11-2: Preparation of tert-butyl 5-(4-amino-3-(4-phenoxyphenyl)-1H-pyrazolo[3,4-d]pyrimidin-1-yl)-2-azabicyclo[2.2.1]heptane-2-carboxylate

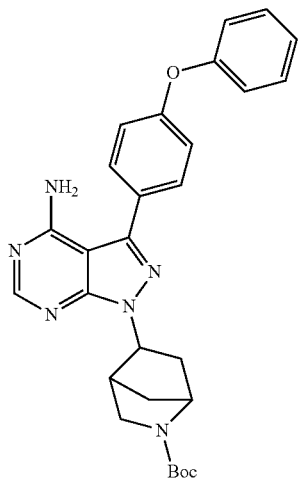 [SMILES: CC(C)(C)OC(=O)N1CC2CC1CC2n1nc(-c2ccc(Oc3ccccc3)cc2)c2c(N)ncnc21]

A title compound (180 mg, yield: 92%) was prepared in the same manner as in Step 1-2 of Example 1, except for using tert-butyl 5-(4-amino-3-iodo-1H-pyrazolo[3,4-d]pyrimidin-1-yl)-2-azabicyclo[2.2.1]heptane-2-carboxylate (200 mg, 0.44 mmol) obtained in Step 11-1 and (4-phenoxyphenyl)boronic acid (117 mg, 0.55 mmol).

Step 11-3: Preparation of 1-(2-azabicyclo[2.2.1]heptan-5-yl)-3-(4-phenoxyphenyl)-1H-pyrazolo[3,4-d]pyrimidin-4-amine

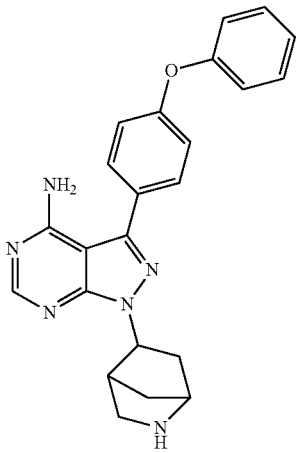 [SMILES: Nc1ncnc2c1c(-c1ccc(Oc3ccccc3)cc1)nn2C1CC2CC1CN2]

A title compound (83 mg, yield: 58%) was prepared in the same manner as in Step 1-3 of Example 1, except for using tert-butyl 5-(4-amino-3-(4-phenoxyphenyl)-1H-pyrazolo[3,4-d]pyrimidin-1-yl)-2-azabicyclo[2.2.1]heptane-2-carboxylate (180 mg, 0.36 mmol) obtained in Step 11-2.

Step 11-4: Preparation of 1-(6-(4-amino-3-(4-phenoxyphenyl)-1H-pyrazolo[3,4-d]pyrimidin-1-yl)-2-azabicyclo[2.2.1]heptan-2-yl)prop-2-yn-1-one

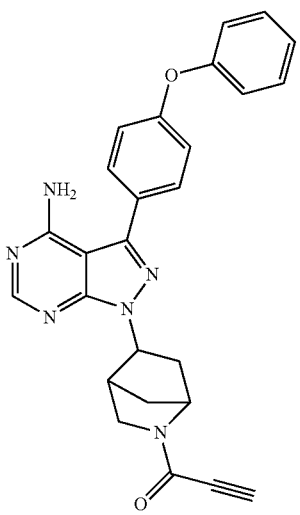 [SMILES: C#CC(=O)N1CC2CC1CC2n1nc(-c2ccc(Oc3ccccc3)cc2)c2c(N)ncnc21]

A title compound (24 mg, yield: 48%) was prepared in the same manner as in Step 1-4 of Example 1, except for using 1-(2-azabicyclo[2.2.1]heptan-5-yl)-3-(4-phenoxyphenyl)-1H-pyrazolo[3,4-d]pyrimidin-4-amine (45 mg, 0.10 mmol) obtained in Step 11-3 and propioloyl chloride (14 uL, 0.16 mmol).

¹H NMR (500 MHz, CDCl₃): 8.35-8.36 (m, 1H), 7.64-7.68 (m, 2H), 7.36-7.40 (m, 2H), 7.07-7.18 (m, 5H), 5.79 (s, 2H), 5.39-5.43 (m, 1H), 4.71-4.75 (m, 1H), 3.45-3.55 (m, 1H), 3.25-3.43 (m, 1H), 3.08-3.15 (m, 1H), 2.88-3.00 (m, 2H), 2.20-2.38 (m, 2H), 1.94-2.02 (m, 1H).

Example 12: Preparation of 1-(5-(4-amino-3-(4-phenoxyphenyl)-1H-pyrazolo[3,4-d]pyrimidin-1-yl)-2-azabicyclo[2.2.1]heptan-2-yl)prop-2-en-1-one

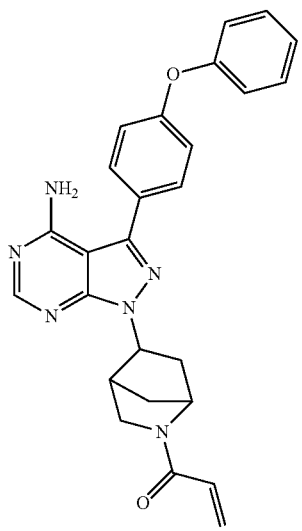 [SMILES: C=CC(=O)N1CC2CC1CC2n1nc(-c2ccc(Oc3ccccc3)cc2)c2c(N)ncnc21]

A title compound (24 mg, yield: 46%) was prepared in the same manner as in Step 1-4 of Example 1, except for using 1-(2-azabicyclo[2.2.1]heptan-5-yl)-3-(4-phenoxyphenyl)-1H-pyrazolo[3,4-d]pyrimidin-4-amine (45 mg, 0.10 mmol) obtained in Step 11-3 and acryloyl chloride (14 uL, 0.16 mmol).

¹H NMR (500 MHz, CDCl₃): 8.35-8.36 (m, 1H), 7.59-7.67 (m, 2H), 7.38-7.41 (m, 2H), 7.07-7.19 (m, 5H), 6.30-6.53 (m, 2H), 5.68 (s, 2H), 5.59-5.67 (m, 1H), 5.32-5.43 (m, 1H), 4.47-4.82 (m, 1H), 3.49-3.68 (m, 1H), 3.38-3.48 (m, 1H), 3.09-3.21 (m, 1H), 2.80-2.92 (m, 1H), 2.29-2.51 (m, 2H), 1.88-1.91 (m, 1H).

Example 13: Preparation of 1-((1S,4S,5R)-5-(4-amino-3-(4-phenoxyphenyl)-1H-pyrazolo[3,4-d]pyrimidin-1-yl)-2-azabicyclo[2.2.1]heptan-2-yl)prop-2-yn-1-one Step 13-1: Preparation of tert-butyl (1R,4R,5S)-5-(4-amino-3-iodo-1H-pyrazolo[3,4-d]pyrimidin-1-yl)-2-azabicyclo[2.2.1]heptane-2-carboxylate

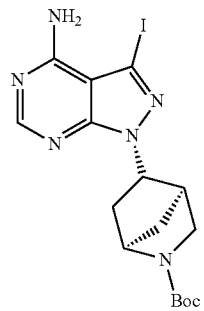

A title compound (172 mg, yield: 40%) was prepared in the same manner as in Step 1-1 of Example 1, except for using tert-butyl (1R,4R,5S)-5-hydroxy-2-azabicyclo[2.2.1]heptane-2-carboxylate (300 mg, 1.41 mmol) and 3-iodo-1H-pyrazolo[3,4-d]pyrimidin-4-amine (245 mg, 0.94 mmol).

Step 13-2: Preparation of tert-butyl (1S,4S,5R)-5-(4-amino-3-(4-phenoxyphenyl)-1H-pyrazolo[3,4-d]pyrimidin-1-yl)-2-azabicyclo[2.2.1]heptane-2-carboxylate

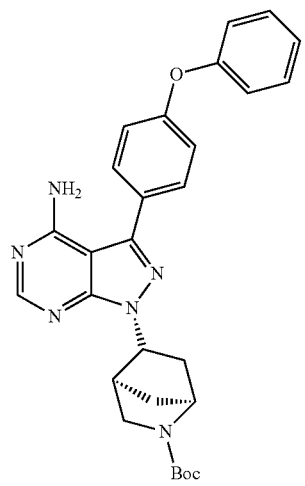

A title compound (164 mg, yield: 87%) was prepared in the same manner as in Step 1-2 of Example 1, except for using tert-butyl (1R,4R,5S)-5-(4-amino-3-iodo-1H-pyrazolo[3,4-d]pyrimidin-1-yl)-2-azabicyclo[2.2.1]heptane-2-carboxylate (172 mg, 0.38 mmol) obtained in Step 13-1 and (4-phenoxyphenyl)boronic acid (101 mg, 0.47 mmol).

Step 13-3: Preparation of 1-((1S,4S,5R)-(2-azabicyclo[2.2.1]heptan-5-yl)-3-(4-phenoxyphenyl)-1H-pyrazolo[3,4-d]pyrimidin-4-amine

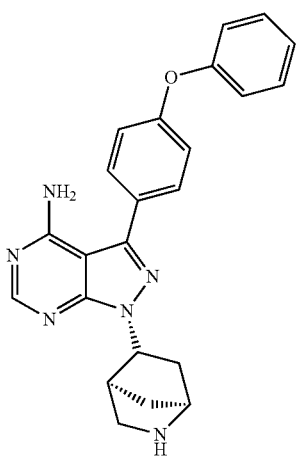

A title compound (105 mg, yield: 80%) was prepared in the same manner as in Step 1-3 of Example 1, except for using tert-butyl (1S,4S,5R)-5-(4-amino-3-(4-phenoxyphenyl)-1H-pyrazolo[3,4-d]pyrimidin-1-yl)-2-azabicyclo[2.2.1]heptane-2-carboxylate (164 mg, 0.33 mmol) obtained in Step 13-2.

Step 13-4: Preparation of 1-((1S,4S,5R)-5-(4-amino-3-(4-phenoxyphenyl)-1H-pyrazolo[3,4-d]pyrimidin-1-yl)-2-azabicyclo[2.2.1]heptan-2-yl)prop-2-yn-1-one

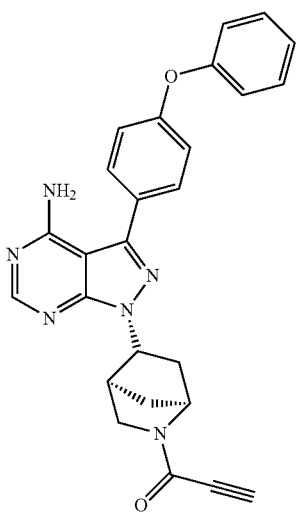

A title compound (28 mg, yield: 43%) was prepared in the same manner as in Step 1-4 of Example 1, except for using 1-((1S,4S,5R)-(2-azabicyclo[2.2.1]heptan-5-yl)-3-(4-phenoxyphenyl)-1H-pyrazolo[3,4-d]pyrimidin-4-amine (57 mg, 0.14 mmol) obtained in Step 13-3 and propionyl chloride (14 uL, 0.15 mmol).

$^1$H NMR (500 MHz, CDCl$_3$): 8.36-8.37 (m, 1H), 7.66-7.70 (m, 2H), 7.37-7.41 (m, 2H), 7.08-7.18 (m, 5H), 5.68 (s, 2H), 5.35-5.43 (m, 1H), 4.72-4.76 (m, 1H), 3.47-3.77 (m, 1H), 3.26-3.45 (m, 1H), 3.09-3.17 (m, 1H), 2.89-3.02 (m, 2H), 2.17-2.39 (m, 2H), 1.93-1.98 (m, 1H).

Example 14: Preparation of 1-((1S,4S,5R)-5-(4-amino-3-(4-phenoxyphenyl)-1H-pyrazolo[3,4-d]pyrimidin-1-yl)-2-azabicyclo[2.2.1]heptan-2-yl)prop-2-en-1-one

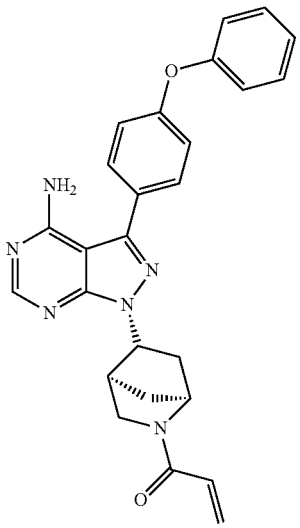

A title compound (32 mg, yield: 49%) was prepared in the same manner as in Step 1-4 of Example 1, except for using 1-((1S,4S,5R)-(2-azabicyclo[2.2.1]heptan-5-yl)-3-(4-phenoxyphenyl)-1H-pyrazolo[3,4-d]pyrimidin-4-amine (57 mg, 0.14 mmol) obtained in Step 13-3 and acryloyl chloride (12 uL, 0.15 mmol).

$^1$H NMR (500 MHz, CDCl$_3$): 8.35-8.36 (m, 1H), 7.59-7.67 (m, 2H), 7.37-7.40 (m, 2H), 7.07-7.17 (m, 5H), 6.30-6.39 (m, 2H), 5.66 (s, 2H), 5.59-5.65 (m, 1H), 5.32-5.43 (m, 1H), 4.47-4.82 (m, 1H), 3.38-3.68 (m, 2H), 3.09-3.20 (m, 1H), 2.80-2.92 (m, 1H), 2.25-2.41 (m, 2H), 1.88-1.94 (m, 1H).

Example 15: Preparation of 1-(6-(4-amino-3-(3-phenoxyphenyl)-1H-pyrazolo[3,4-d]pyrimidin-1-yl)-2-azabicyclo[2.2.1]heptan-2-yl)prop-2-yn-1-one

Step 15-1: Preparation of tert-butyl 6-(4-amino-3-(4-phenoxyphenyl)-1H-pyrazolo[3,4-d]pyrimidin-1-yl)-2-azabicyclo[2.2.1]heptane-2-carboxylate

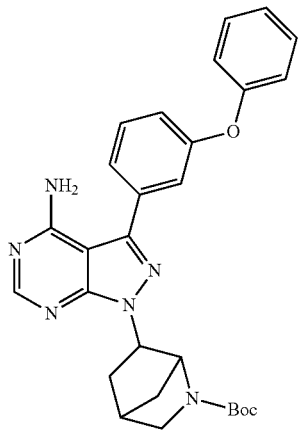 [SMILES: CC(C)(C)OC(=O)N1CC2CC1C(n1nc(-c3cccc(Oc4ccccc4)c3)c3c(N)ncnc31)C2]

A title compound (92 mg, yield: 84%) was prepared in the same manner as in Step 1-2 of Example 1, except for using 1-(6-(4-amino-3-(4-phenoxyphenyl)-1H-pyrazolo[3,4-d]pyrimidin-1-yl)-2-azabicyclo[2.2.1]heptan-2-yl)prop-2-en-1-one (100 mg, 0.22 mmol) obtained in Step 1-4 and (3-phenoxyphenyl)boronic acid (59 mg, 0.27 mmol)

Step 15-2: Preparation of 1-(2-azabicyclo[2.2.1]heptan-6-yl)-3-(3-phenoxyphenyl)-1H-pyrazolo[3,4-d]pyrimidin-4-amine

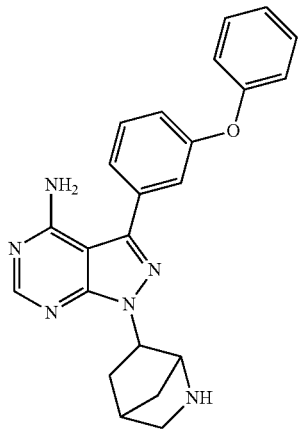 [SMILES: Nc1ncnc2c1c(-c1cccc(Oc3ccccc3)c1)nn2C1CC2CNC1C2]

A title compound (60 mg, yield: 81%) was prepared in the same manner as in Step 1-3 of Example 1, except for using tert-butyl 6-(4-amino-3-(4-phenoxyphenyl)-1H-pyrazolo[3,4-d]pyrimidin-1-yl)-2-azabicyclo[2.2.1]heptane-2-carboxylate (92 mg, 0.19 mmol) obtained in Step 15-1.

Step 15-3: Preparation of 1-(6-(4-amino-3-(3-phenoxyphenyl)-1H-pyrazolo[3,4-d]pyrimidin-1-yl)-2-azabicyclo[2.2.1]heptan-2-yl)prop-2-yn-1-one

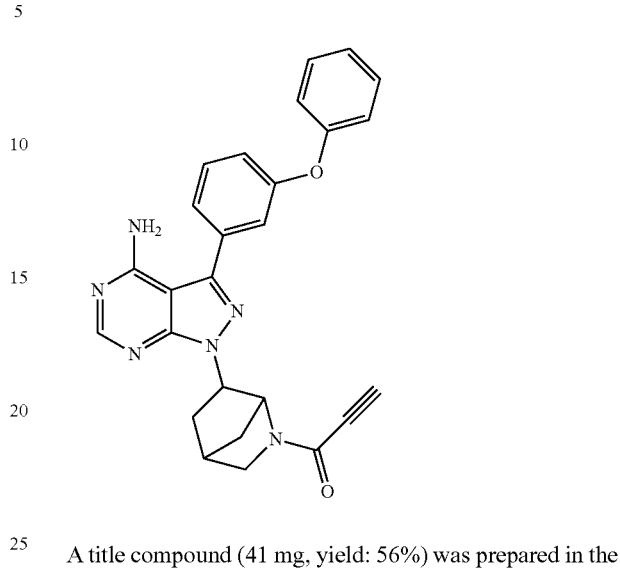

A title compound (41 mg, yield: 56%) was prepared in the same manner as in Step 1-4 of Example 1, except for using 1-(2-azabicyclo[2.2.1]heptan-6-yl)-3-(3-phenoxyphenyl)-1H-pyrazolo[3,4-d]pyrimidin-4-amine (65 mg, 0.16 mmol) obtained in Step 15-2 and propioloyl chloride (16 uL, 0.18 mmol).

$^1$H NMR (500 MHz, CDCl$_3$): 8.32-8.36 (m, 1H), 7.47-7.51 (m, 1H), 7.31-7.45 (m, 4H), 7.07-7.17 (m, 4H), 5.64 (s, 2H), 5.21-5.23 (m, 1H), 4.70-4.85 (m, 1H), 3.41-3.65 (m, 1H), 3.23-3.37 (m, 1H), 3.00-3.04 (m, 1H), 2.87 (s, 1H), 2.35-2.58 (m, 2H), 2.03-2.20 (m, 1H), 1.74-1.76 (m, 1H).

Example 16: Preparation of 1-(6-(4-amino-3-(4-phenoxyphenyl)-1H-pyrazolo[3,4-d]pyrimidin-1-yl)-2-azabicyclo[2.2.1]heptan-2-yl)pent-2-yn-1-one

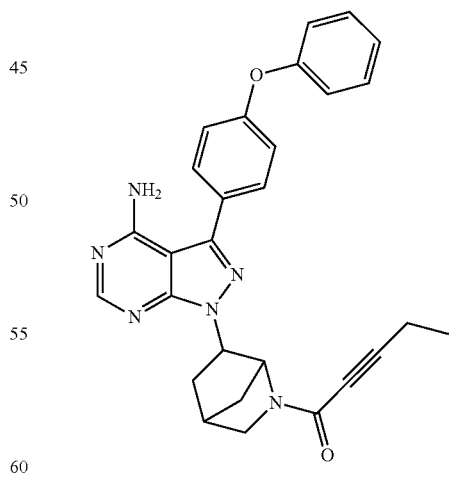

A title compound (34 mg, yield: 62%) was prepared in the same manner as in Step 1-4 of Example 1, except for using 1-(2-azabicyclo[2.2.1]heptan-6-yl)-3-(4-phenoxyphenyl)-1H-pyrazolo[3,4-d]pyrimidin-4-amine (50 mg, 0.11 mmol) obtained in Step 1-3 and pent-2-ynoyl chloride (14 uL, 0.12 mmol).

¹H NMR (500 MHz, CDCl₃): 8.34-8.35 (m, 1H), 7.60-7.64 (m, 2H), 7.38-7.41 (m, 2H), 7.17-7.20 (m, 3H), 7.13-7.16 (m, 2H), 5.80 (s, 2H), 5.17-5.31 (m, 1H), 4.66-4.85 (m, 1H), 3.41-3.60 (m, 1H), 3.23-3.39 (m, 1H), 2.86-2.90 (m, 1H), 2.65-2.72 (m, 1H), 2.46-2.63 (m, 1H), 2.37-2.44 (q, 2H), 2.13-2.15 (m, 1H), 1.72-1.74 (m, 1H), 1.12-1.14 (t, 3H),

Example 17: Preparation of 4-(4-amino-1-(2-propioloyl-2-azabicyclo[2.2.1]heptan-6-yl)-1H-pyrazolo[3,4-d]pyrimidin-3-yl)-N-phenylbenzamide Step 17-1: Preparation of N-phenyl-4-(4,4,5,5-tetramethyl-1,3,2-dioxaborolan-2-yl)benzamide

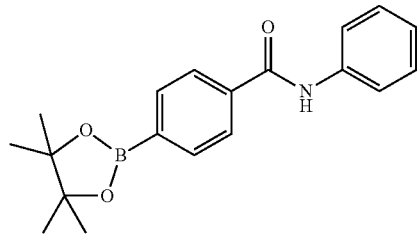 [SMILES: CC1(C)OB(c2ccc(C(=O)Nc3ccccc3)cc2)OC1(C)C]

A title compound (70 mg, yield: 65%) was prepared in the same manner as in Step 4-2 of Example 4, except for using 4-(4,4,5,5-tetramethyl-1,3,2-dioxaborolan-2-yl)benzoyl chloride (107 mg, 0.40 mmol) obtained in Step 4-1 and aniline (40 mg, 0.442 mmol).

Step 17-2: Preparation of tert-butyl 6-(4-amino-3-(4-(phenylcarbamoyl)phenyl)-1H-pyrazolo[3,4-d]pyrimidin-1-yl)-2-azabicyclo[2.2.1]heptane-2-carboxylate

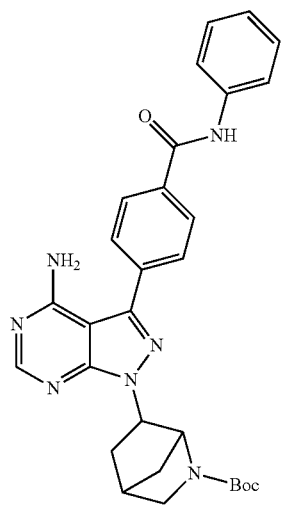 [SMILES: CC(C)(C)OC(=O)N1CC2CC1C(n1nc(-c3ccc(C(=O)Nc4ccccc4)cc3)c3c(N)ncnc31)C2]

A title compound (69 mg, yield: 95%) was prepared in the same manner as in Step 1-2 of Example 1, except for using N-phenyl-4-(4,4,5,5-tetramethyl-1,3,2-dioxaborolan-2-yl)benzamide (90 mg, 0.20 mmol) obtained in Step 17-1 and tert-butyl 6-(4-amino-3-iodo-1H-pyrazolo[3,4-d]pyrimidin-1-yl)-2-azabicyclo[2.2.1]heptane-2-carboxylate (72 mg, 0.16 mmol).

Step 17-3: Preparation of 4-(4-amino-1-(2-azabicyclo[2.2.1]heptan-6-yl)-1H-pyrazolo[3,4-d]pyrimidin-3-yl)-N-phenylbenzamide

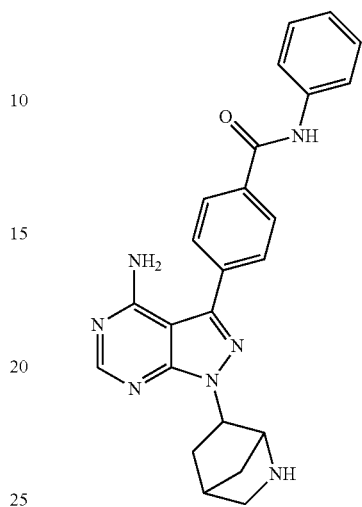

A title compound (46 mg, yield: 72%) was prepared in the same manner as in Step 1-3 of Example 1, except for using tert-butyl 6-(4-amino-3-(4-(phenylcarbamoyl)phenyl)-1H-pyrazolo[3,4-d]pyrimidin-1-yl)-2-azabicyclo[2.2.1]heptane-2-carboxylate (69 mg, 0.15 mmol) obtained in Step 17-2.

Step 17-4: Preparation of 4-(4-amino-1-(2-propioloyl-2-azabicyclo[2.2.1]heptan-6-yl)-1H-pyrazolo[3,4-d]pyrimidin-3-yl)-N-phenylbenzamide

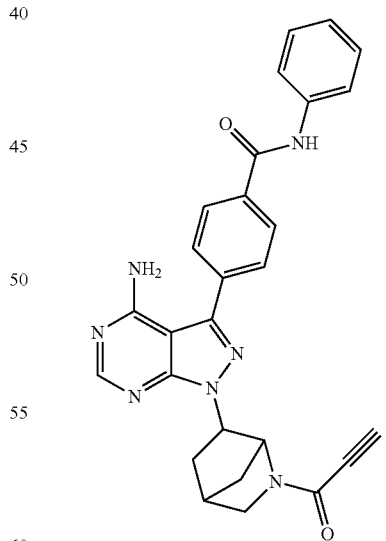

A title compound (33 mg, yield: 64%) was prepared in the same manner as in Step 1-4 of Example 1, except for using 4-(4-amino-1-(2-azabicyclo[2.2.1]heptan-6-yl)-1H-pyrazolo[3,4-d]pyrimidin-3-yl)-N-phenylbenzamide (46 mg, 0.11 mmol) obtained in Step 17-3 and propioloyl chloride (10 uL, 0.12 mmol).

¹H NMR (500 MHz, CDCl₃): 8.32-8.36 (m, 1H), 7.99-8.08 (m, 3H), 7.79-7.83 (m, 2H), 7.67-7.69 (m, 2H), 7.38-7.42 (m, 2H), 7.17-7.20 (m, 1H), 5.25-5.29 (m, 1H), 4.72-4.86 (m, 1H), 3.41-3.65 (m, 1H), 3.28-3.40 (m, 1H), 3.02-3.05 (m, 1H), 2.90 (s, 1H), 2.50-2.58 (m, 1H), 2.30-2.42 (m, 1H), 1.98-2.05 (m, 1H), 1.78-1.80 (m, 1H).

Example 18: Preparation of 3-(4-amino-1-(2-propioloyl-2-azabicyclo[2.2.1]heptan-6-yl)-1H-pyrazolo[3,4-d]pyrimidin-3-yl)-N-phenylbenzamide Step 18-1: Preparation of N-phenyl-3-(4,4,5,5-tetramethyl-1,3,2-dioxaborolan-2-yl)benzamide

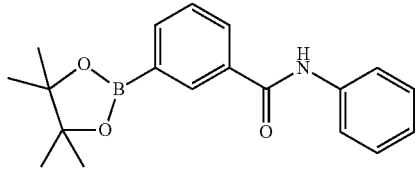 [SMILES: CC1(C)OB(c2cccc(C(=O)Nc3ccccc3)c2)OC1(C)C]

A title compound (60 mg, yield: 56%) was prepared in the same manner as in Step 4-2 of Example 4, except for using 3-(4,4,5,5-tetramethyl-1,3,2-dioxaborolan-2-yl)benzoyl chloride (107 mg, 0.40 mmol) obtained in Step 7-1 and aniline (40 mg, 0.442 mmol).

Step 18-2: Preparation of tert-butyl 6-(4-amino-3-(3-(phenylcarbamoyl)phenyl)-1H-pyrazolo[3,4-d]pyrimidin-1-yl)-2-azabicyclo[2.2.1]heptane-2-carboxylate

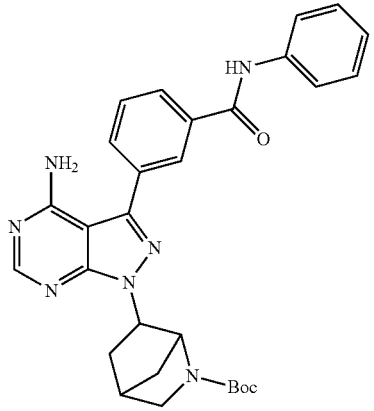 [SMILES: CC(C)(C)OC(=O)N1CC2CC1C(n1nc(-c3cccc(C(=O)Nc4ccccc4)c3)c3c(N)ncnc31)C2]

A title compound (64 mg, yield: 93%) was prepared in the same manner as in Step 1-2 of Example 1, except for using N-phenyl-3-(4,4,5,5-tetramethyl-1,3,2-dioxaborolan-2-yl)benzamide (60 mg, 0.19 mmol) obtained in Step 18-1 and tert-butyl 6-(4-amino-3-iodo-1H-pyrazolo[3,4-d]pyrimidin-1-yl)-2-azabicyclo[2.2.1]heptane-2-carboxylate (68 mg, 0.15 mmol).

Step 18-3: Preparation of 3-(4-amino-1-(2-azabicyclo[2.2.1]heptan-6-yl)-1H-pyrazolo[3,4-d]pyrimidin-3-yl)-N-phenylbenzamide

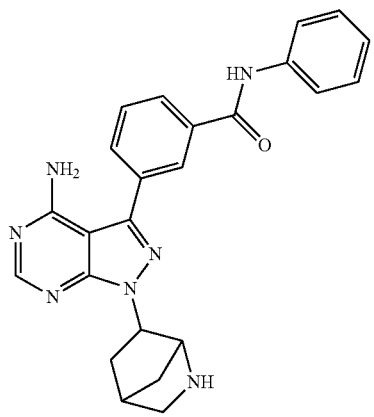 [SMILES: Nc1ncnc2c1c(-c1cccc(C(=O)Nc3ccccc3)c1)nn2C1CC2CNC1C2]

A title compound (30 mg, yield: 51%) was prepared in the same manner as in Step 1-3 of Example 1, except for using tert-butyl 6-(4-amino-3-(3-(phenylcarbamoyl)phenyl)-1H-pyrazolo[3,4-d]pyrimidin-1-yl)-2-azabicyclo[2.2.1]heptane-2-carboxylate (64 mg, 0.15 mmol) obtained in Step 18-2.

Step 18-4: Preparation of 3-(4-amino-1-(2-propioloyl-2-azabicyclo[2.2.1]heptan-6-yl)-1H-pyrazolo[3,4-d]pyrimidin-3-yl)-N-phenylbenzamide

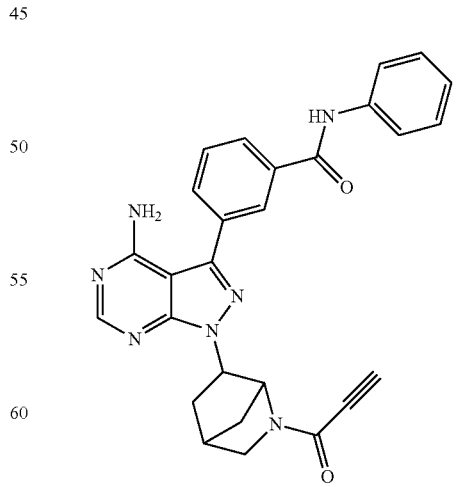

A title compound (23 mg, yield: 68%) was prepared in the same manner as in Step 1-4 of Example 1, except for using 3-(4-amino-1-(2-azabicyclo[2.2.1]heptan-6-yl)-1H-pyrazolo[3,4-d]pyrimidin-3-yl)-N-phenylbenzamide (30 mg, 0.07 mmol) obtained in Step 18-3 and propioloyl chloride (7 uL, 0.08 mmol).

$^1$H NMR (500 MHz, CDCl$_3$): 8.40-8.72 (m, 1H), 8.10-8.28 (m, 2H), 8.02-8.05 (m, 1H), 7.85-7.95 (m, 1H), 7.69-7.81 (m, 3H), 7.26-7.41 (m, 2H), 7.16-7.19 (m, 1H), 5.65-5.90 (m, 2H), 5.25-5.30 (m, 1H), 4.94-4.99 (m, 1H), 3.41-3.60 (m, 1H), 3.24-3.35 (m, 1H), 2.83-2.89 (m, 1H), 2.54-2.66 (m, 2H), 2.17-2.2.35 (m, 2H), 1.76-1.78 (m, 1H).

Example 19: Preparation of 4-(1-(2-acryloyl-2-azabicyclo[2.2.1]heptan-6-yl)-4-amino-1H-pyrazolo[3,4-d]pyrimidin-3-yl)-N-phenylbenzamide

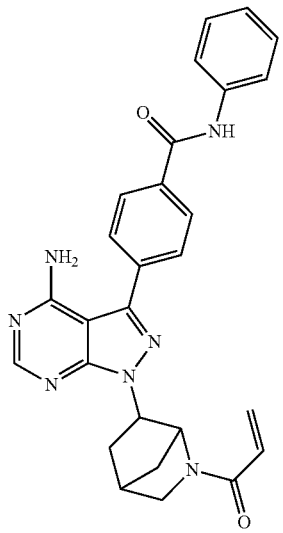 [SMILES: C=CC(=O)N1CC2CC1C(n1nc(-c3ccc(C(=O)Nc4ccccc4)cc3)c3c(N)ncnc31)C2]

A title compound (29 mg, yield: 60%) was prepared in the same manner as in Step 1-4 of Example 1, except for using 4-(4-amino-1-(2-azabicyclo[2.2.1]heptan-6-yl)-1H-pyrazolo[3,4-d]pyrimidin-3-yl)-N-phenylbenzamide (43 mg, 0.10 mmol) obtained in Step 17-3 and acryloyl chloride (10 uL, 0.11 mmol).

$^1$H NMR (500 MHz, CDCl$_3$): 8.37-8.43 (m, 1H), 8.03-8.13 (m, 3H), 7.80-7.83 (m, 2H), 7.69-7.70 (m, 2H), 7.39-7.42 (m, 2H), 7.19-7.20 (m, 1H), 6.48-6.80 (m, 1H), 6.45-6.48 (m, 1H), 5.76-5.78 (m, 1H), 5.54 (s, 2H), 5.02-5.21 (m, 1H), 4.53-4.92 (m, 1H), 3.45-3.48 (m, 1H), 3.28-3.30 (m, 1H), 2.55-2.86 (m, 2H), 2.04-2.42 (m, 2H), 1.72-1.74 (m, 1H).

Example 20: Preparation of 4-(4-amino-1-(2-(but-2-ynoyl)-2-azabicyclo[2.2.1]heptan-6-yl)-1H-pyrazolo[3,4-d]pyrimidin-3-yl)-N-phenylbenzamide

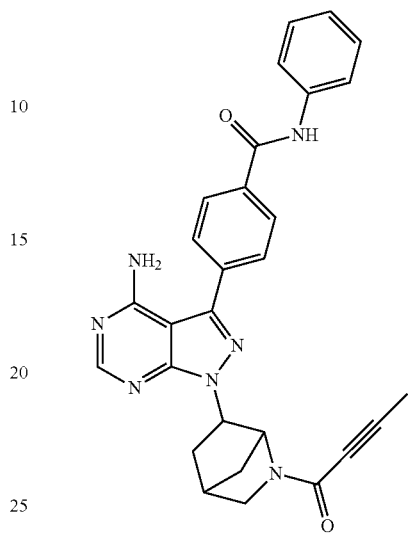

A title compound (33 mg, yield: 67%) was prepared in the same manner as in Step 1-4 of Example 1, except for using 4-(4-amino-1-(2-azabicyclo[2.2.1]heptan-6-yl)-1H-pyrazolo[3,4-d]pyrimidin-3-yl)-N-phenylbenzamide (43 mg, 0.10 mmol) obtained in Step 17-3 and but-2-ynoyl chloride (11 uL, 0.11 mmol).

$^1$H NMR (500 MHz, CDCl$_3$): 8.35-8.41 (m, 1H), 8.19-8.23 (m, 1H), 7.81-7.90 (m, 3H), 7.65-7.71 (m, 3H), 7.37-7.41 (m, 2H), 7.17-7.19 (m, 1H), 5.50-5.55 (m, 2H), 4.96-5.26 (m, 1H), 4.69-4.89 (m, 1H), 3.39-3.51 (m, 1H), 3.24-3.26 (m, 1H), 2.82-2.87 (m, 1H), 2.62-2.70 (m, 1H), 2.35-2.58 (m, 1H), 2.03-2.20 (m, 1H), 1.75-1.77 (m, 1H), 1.72-1.74 (m, 3H).

Example 21: Preparation of 3-(1-(2-acryloyl-2-azabicyclo[2.2.1]heptan-6-yl)-4-amino-1H-pyrazolo[3,4-d]pyrimidin-3-yl)-N-phenylbenzamide

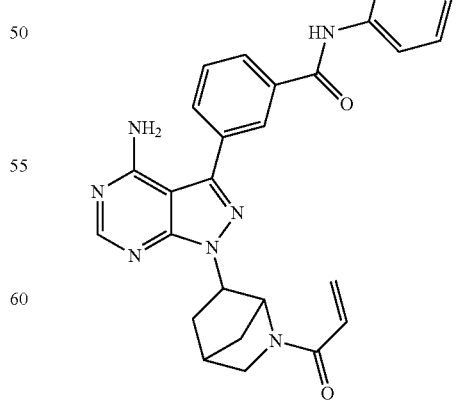

A title compound (32 mg, yield: 63%) was prepared in the same manner as in Step 1-4 of Example 1, except for using 3-(4-amino-1-(2-azabicyclo[2.2.1]heptan-6-yl)-1H-pyrazolo[3,4-d]pyrimidin-3-yl)-N-phenylbenzamide (45 mg, 0.11 mmol) obtained in Step 18-3 and acryloyl chloride (11 uL, 0.12 mmol).

$^1$H NMR (500 MHz, CDCl$_3$): 8.32-8.40 (m, 1H), 8.20-8.22 (m, 1H), 7.90-7.97 (m, 2H), 7.81-7.86 (m, 1H), 7.64-7.72 (m, 3H), 7.37-7.41 (m, 2H), 7.17-7.18 (m, 1H), 6.50-6.78 (m, 1H), 6.28-6.48 (m, 1H), 5.87-5.89 (m, 1H), 5.05-5.11 (m, 1H), 4.54-4.96 (m, 1H), 3.42-3.53 (m, 1H), 3.23-3.33 (m, 1H), 2.58-2.86 (m, 2H), 2.16-2.32 (m, 2H), 1.74-1.76 (m, 1H).

Example 22: Preparation of 3-(4-amino-1-(2-but-2-ynoyl-2-azabicyclo[2.2.1]heptan-6-yl)-1H-pyrazolo[3,4-d]pyrimidin-3-yl)-N-phenylbenzamide

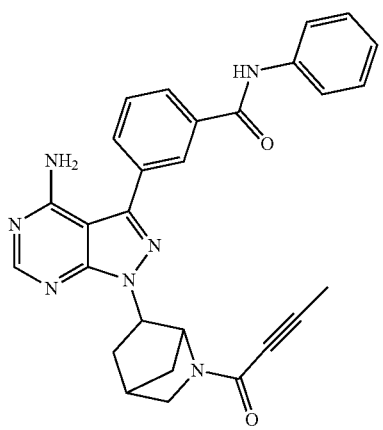 [SMILES: CC#CC(=O)N1CC2CC1C(n1nc(-c3cccc(C(=O)Nc4ccccc4)c3)c3c(N)ncnc31)C2]

A title compound (30 mg, yield: 57%) was prepared in the same manner as in Step 1-4 of Example 1, except for using 3-(4-amino-1-(2-azabicyclo[2.2.1]heptan-6-yl)-1H-pyrazolo[3,4-d]pyrimidin-3-yl)-N-phenylbenzamide (45 mg, 0.11 mmol) obtained in Step 18-3 and but-2-ynoyl chloride (12 uL, 0.12 mmol).

$^1$H NMR (500 MHz, CDCl$_3$): 8.40-8.42 (m, 1H), 8.04-8.07 (m, 2H), 7.82-7.91 (m, 3H), 7.67-7.68 (m, 2H), 7.39-7.42 (m, 2H), 7.18-7.20 (m, 1H), 5.48 (s, 2H), 5.26-5.34 (m, 1H), 4.69-4.88 (m, 1H), 3.47-3.60 (m, 1H), 3.32-3.45 (m, 1H), 2.87-2.90 (m, 1H), 2.57-2.78 (m, 1H), 2.42-2.45 (m, 1H), 2.08-2.18 (m, 1H), 1.74-1.76 (m, 1H), 1.70-1.74 (m, 3H).

Example 23: Preparation of 4-(1-(2-acryloyl-2-azabicyclo[2.2.1]heptan-5-yl)-4-amino-1H-pyrazolo[3,4-d]pyrimidin-3-yl)-N-phenylbenzamide Step 23-1: Preparation of tert-butyl 5-(4-amino-3-(4-(phenylcarbamoyl)phenyl)-1H-pyrazolo[3,4-d]pyrimidin-1-yl)azabicyclo[2.2.1]heptane-2-carboxylate

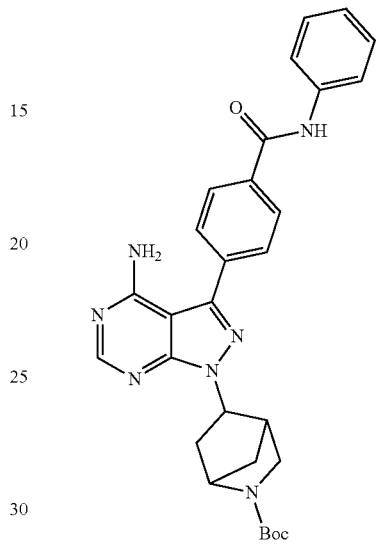

A title compound (130 mg, yield: 75%) was prepared in the same manner as in Step 1-2 of Example 1, except for using tert-butyl 5-(4-amino-3-iodo-1H-pyrazolo[3,4-d]pyrimidin-1-yl)-2-azabicyclo[2.2.1]heptane-2-carboxylate (150 mg, 0.33 mmol) obtained in Step 11-1 and N-phenyl-4-(4,4,5,5-tetramethyl-1,3,2-dioxaborolan-2-yl)benzamide (133 mg, 0.41 mmol) obtained in Step 17-1.

Step 23-2: Preparation of 4-(4-amino-1-(2-azabicyclo[2.2.1]heptan-5-yl)-1H-pyrazolo[3,4-d]pyrimidin-3-yl)-N-phenylbenzamide

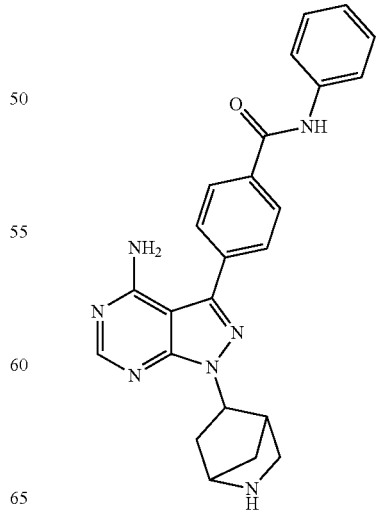

A title compound (109 mg, yield: 77%) was prepared in the same manner as in Step 1-3 of Example 1, except for using tert-butyl 5-(4-amino-3-(4-(phenylcarbamoyl)phenyl)-1H-pyrazolo[3,4-d]pyrimidin-1-yl)azabicyclo[2.2.1]heptane-2-carboxylate (130 mg, 0.31 mmol) obtained in Step 23-1.

Step 23-3: Preparation of 4-(1-(2-acryloyl-2-azabicyclo[2.2.1]heptan-5-yl)-4-amino-1H-pyrazolo[3,4-d]pyrimidin-3-yl)-N-phenylbenzamide

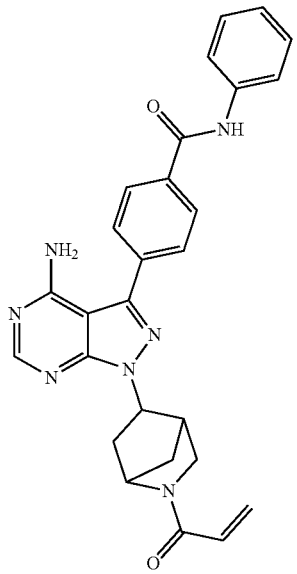 [SMILES: C=CC(=O)N1CC2CC1CC2n1nc(-c2ccc(C(=O)Nc3ccccc3)cc2)c2c(N)ncnc21]

A title compound (59 mg, yield: 48%) was prepared in the same manner as in Step 1-4 of Example 1, except for using 4-(4-amino-1-(2-azabicyclo[2.2.1]heptan-5-yl)-1H-pyrazolo[3,4-d]pyrimidin-3-yl)-N-phenylbenzamide (109 mg, 0.26 mmol) obtained in Step 23-2 and acryloyl chloride (81 uL, 0.28 mmol).

$^1$H NMR (500 MHz, DMSO): 10.30 (s, 1H), 8.26 (s, 1H), 8.06-8.10 (m, 2H), 7.73-7.81 (m, 4H), 7.33-7.37 (m, 2H), 7.08-7.11 (m, 1H), 6.72-6.78 (m, 1H), 6.42-6.44 (m, 1H), 6.12-6.19 (m, 1H), 5.66-5.69 (m, 1H), 5.32-5.40 (m, 1H), 4.51-4.63 (m, 1H), 3.41-3.43 (m, 1H), 3.09-3.11 (m, 1H), 2.95-2.98 (m, 1H), 2.22-2.30 (m, 1H), 1.81-1.98 (m, 2H).

Example 24: Preparation of 3-(1-(2-acryloyl-2-azabicyclo[2.2.1]heptan-5-yl)-4-amino-1H-pyrazolo[3,4-d]pyrimidin-3-yl)-N-phenylbenzamide Step 24-1: Preparation of tert-butyl 5-(4-amino-3-(3-(phenylcarbamoyl)phenyl)-1H-pyrazolo[3,4-d]pyrimidin-1-yl)-2-azabicyclo[2.2.1]heptane-2-carboxylate

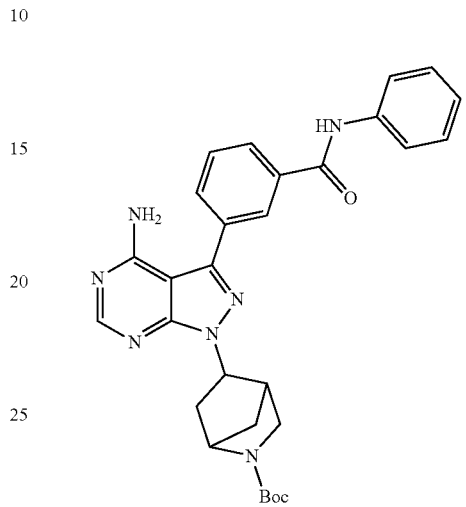

A title compound (123 mg, yield: 71%) was prepared in the same manner as in Step 1-2 of Example 1, except for using tert-butyl 5-(4-amino-3-iodo-1H-pyrazolo[3,4-d]pyrimidin-1-yl)-2-azabicyclo[2.2.1]heptane-2-carboxylate (150 mg, 0.33 mmol) obtained in Step 11-1 and N-phenyl-3-(4,4,5,5-tetramethyl-1,3,2-dioxaborolan-2-yl)benzamide (133 mg, 0.41 mmol) obtained in Step 18-1.

Step 24-2: Preparation of 3-(4-amino-1-(2-azabicyclo[2.2.1]heptan-5-yl)-1H-pyrazolo[3,4-d]pyrimidin-3-yl)-N-phenylbenzamide

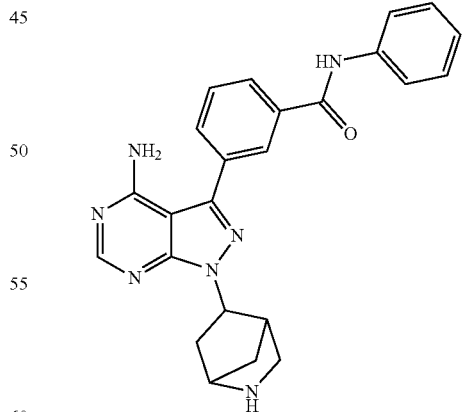

A title compound (82 mg, yield: 82%) was prepared in the same manner as in Step 1-3 of Example 1, except for using tert-butyl 5-(4-amino-3-(3-(phenylcarbamoyl)phenyl)-1H-pyrazolo[3,4-d]pyrimidin-1-yl)-2-azabicyclo[2.2.1]heptane-2-carboxylate (123 mg, 0.29 mmol) obtained in Step 24-1.

Step 24-3: Preparation of 3-(1-(2-acryloyl-2-azabicyclo[2.2.1]heptan-5-yl)-4-amino-1H-pyrazolo[3,4-d]pyrimidin-3-yl)-N-phenylbenzamide

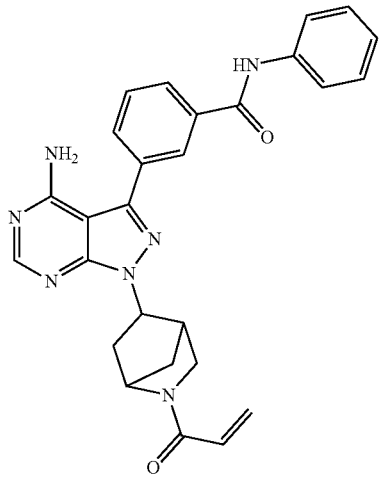 [SMILES: C=CC(=O)N1CC2CC1CC2n1nc(-c2cccc(C(=O)Nc3ccccc3)c2)c2c(N)ncnc21]

A title compound (51 mg, yield: 55%) was prepared in the same manner as in Step 1-4 of Example 1, except for using 3-(4-amino-1-(2-azabicyclo[2.2.1]heptan-5-yl)-1H-pyrazolo[3,4-d]pyrimidin-3-yl)-N-phenylbenzamide (82 mg, 0.19 mmol) obtained in Step 24-2 and acryloyl chloride (17 uL, 0.21 mmol).

$^1$H NMR (500 MHz, CDCl$_3$): 8.73 (s, 1H), 8.37-8.40 (m, 2H), 8.06-8.08 (m, 2H), 7.66-7.78 (m, 2H), 7.33-7.36 (m, 2H), 7.10-7.13 (m, 1H), 6.53-6.59 (m, 1H), 6.17-6.20 (m, 1H), 5.56-5.58 (m, 2H), 4.52-4.54 (m, 1H), 3.53-3.70 (m, 1H), 3.20-3.31 (m, 1H), 2.87-3.01 (m, 1H), 2.80-2.85 (m, 1H), 2.31-2.38 (m, 1H), 2.17-2.20 (m, 1H), 1.98-2.02 (m, 1H).

Example 25: Preparation of 1-(5-(4-amino-3-(3-phenoxyphenyl)-1H-pyrazolo[3,4-d]pyrimidin-1-yl)-2-azabicyclo[2.2.1]heptan-2-yl)prop-2-en-1-one

Step 25-1: Preparation of tert-butyl 5-(4-amino-3-(3-phenoxyphenyl)-1H-pyrazolo[3,4-d]pyrimidin-1-yl)-2-azabicyclo[2.2.1]heptane-2-carboxylate

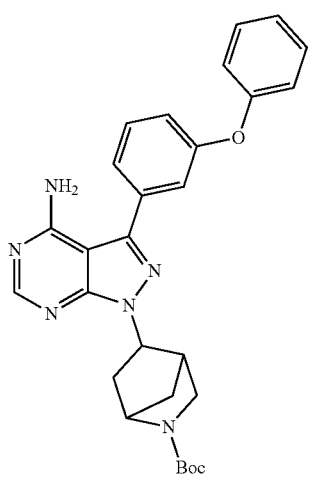 [SMILES: CC(C)(C)OC(=O)N1CC2CC1CC2n1nc(-c2cccc(Oc3ccccc3)c2)c2c(N)ncnc21]

A title compound (84 mg, yield: 77%) was prepared in the same manner as in Step 1-2 of Example 1, except for using tert-butyl 5-(4-amino-3-iodo-1H-pyrazolo[3,4-d]pyrimidin-1-yl)-2-azabicyclo[2.2.1]heptane-2-carboxylate (100 mg, 0.22 mmol) obtained in Step 11-1 and (3-phenoxyphenyl)boronic acid (59 mg, 0.27 mmol).

Step 25-2: Preparation of 1-(2-azabicyclo[2.2.1]heptan-5-yl)-3-(3-phenoxyphenyl)-1H-pyrazolo[3,4-d]pyrimidin-4-amine

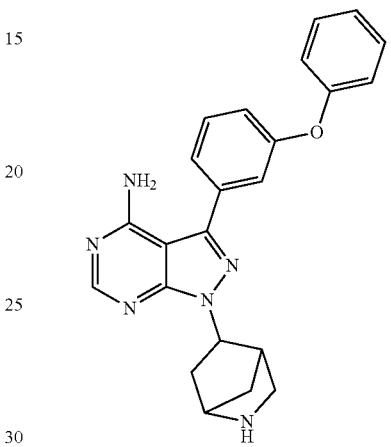

A title compound (45 mg, yield: 67%) was prepared in the same manner as in Step 1-3 of Example 1, except for using tert-butyl 5-(4-amino-3-(3-phenoxyphenyl)-1H-pyrazolo[3,4-d]pyrimidin-1-yl)-2-azabicyclo[2.2.1]heptane-2-carboxylate (84 mg, 0.17 mmol) obtained in Step 25-1.

Step 25-3: Preparation of 1-(5-(4-amino-3-(3-phenoxyphenyl)-1H-pyrazolo[3,4-d]pyrimidin-1-yl)-2-azabicyclo[2.2.1]heptan-2-yl)prop-2-en-1-one

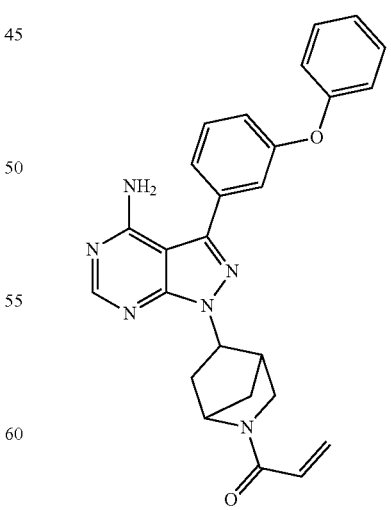

A title compound (26 mg, yield: 50%) was prepared in the same manner as in Step 1-4 of Example 1, except for using 1-(2-azabicyclo[2.2.1]heptan-5-yl)-3-(3-phenoxyphenyl)-

1H-pyrazolo[3,4-d]pyrimidin-4-amine (45 mg, 0.11 mmol) obtained in Step 25-2 and acryloyl chloride (10 uL, 0.12 mmol).

$^1$H NMR (500 MHz, CDCl$_3$): 8.30 (s, 1H), 7.43-7.46 (m, 2H), 7.31-7.39 (m, 3H), 7.03-7.16 (m, 4H), 6.26-6.49 (m, 2H), 5.55-5.59 (m, 1H), 5.32-5.37 (m, 1H), 4.42-4.78 (m, 1H), 3.58-3.62 (m, 1H), 3.29-3.34 (m, 1H), 3.08-3.17 (m, 1H), 2.78-2.88 (m, 1H), 2.15-2.29 (m, 2H), 1.88-1.90 (m, 1H).

Example 26: Preparation of 3-(1-(2-acryloyl-2-azabicyclo[2.2.1]heptan-6-yl)-4-amino-1H-pyrazolo[3,4-d]pyrimidin-3-yl)-N-(6-(trifluoromethyl)pyridin-3-yl)benzamide Step 26-1: Preparation of 3-(4,4,5,5-tetramethyl-1,3,2-dioxaborolan-2-yl)-N-(6-(trifluoromethyl)pyrimidin-3-yl)benzamide

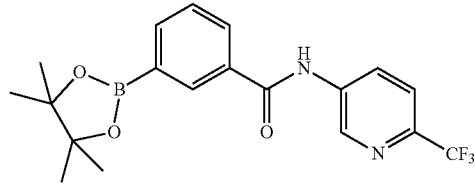 [SMILES: CC1(C)OB(c2cccc(C(=O)Nc3ccc(C(F)(F)F)nc3)c2)OC1(C)C]

A title compound (383 mg, yield: 61%) was prepared in the same manner as in Step 4-2 of Example 4, except for using 3-(4,4,5,5-tetramethyl-1,3,2-dioxaborolan-2-yl)benzoyl chloride (430 mg, 1.61 mmol) obtained in Step 7-1 and 6-(trifluoromethyl)pyridin-3-amine (288 mg, 1.78 mmol).

Step 26-2: Preparation of tert-butyl 6-(4-amino-3-(3-((6-(trifluoromethyl)pyridin-3-yl)carbamoyl)phenyl)-1H-pyrazolo[3,4-d]pyrimidin-1-yl)-2-azabicyclo[2.2.1]heptane-2-carboxylate

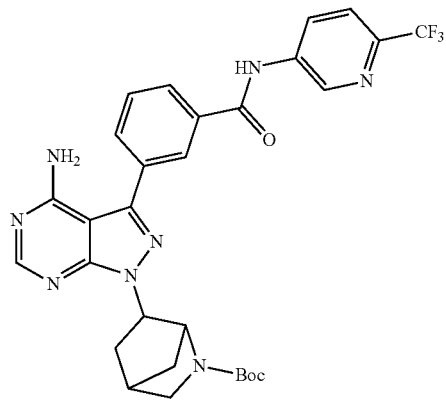 [SMILES: CC(C)(C)OC(=O)N1CC2CC1C(n1nc(-c3cccc(C(=O)Nc4ccc(C(F)(F)F)nc4)c3)c3c(N)ncnc31)C2]

A title compound (154 mg, yield: 59%) was prepared in the same manner as in Step 1-2 of Example 1, except for using 3-(4,4,5,5-tetramethyl-1,3,2-dioxaborolan-2-yl)-N-(6-(trifluoromethyl)pyrimidin-3-yl)benzamide (215 mg, 0.55 mmol) obtained in Step 26-1 and tert-butyl 6-(4-amino-3-iodo-1H-pyrazolo[3,4-d]pyrimidin-1-yl)-2-azabicyclo[2.2.1]heptane-2-carboxylate (200 mg, 0.44 mmol).

Step 26-3: Preparation of 3-(4-amino-1-(2-azabicyclo[2.2.1]heptan-6-yl)-1H-pyrazolo[3,4-d]pyrimidin-3-yl)-N-(6-(trifluoromethyl)pyridin-3-yl)benzamide

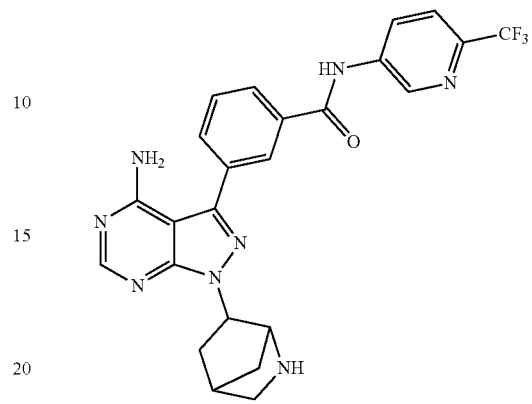

A title compound (101 mg, yield: 79%) was prepared in the same manner as in Step 1-3 of Example 1, except for using tert-butyl 6-(4-amino-3-(3-((6-(trifluoromethyl)pyridin-3-yl)carbamoyl)phenyl)-1H-pyrazolo[3,4-d]pyrimidin-1-yl)-2-azabicyclo[2.2.1]heptane-2-carboxylate (154 mg, 0.26 mmol) obtained in Step 26-2.

Step 26-4: Preparation of 3-(1-(2-acryloyl-2-azabicyclo[2.2.1]heptan-6-yl)-4-amino-1H-pyrazolo[3,4-d]pyrimidin-3-yl)-N-(6-(trifluoromethyl)pyridin-3-yl)benzamide

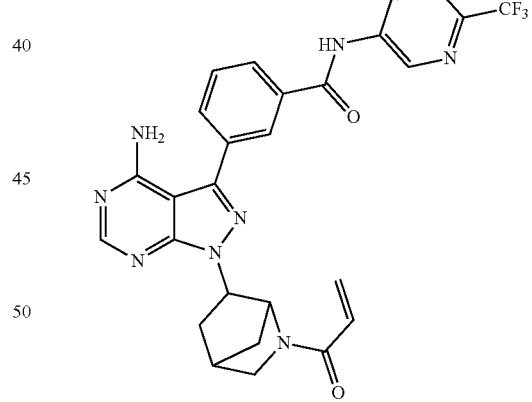

A title compound (39 mg, yield: 35%) was prepared in the same manner as in Step 1-4 of Example 1, except for using 3-(4-amino-1-(2-azabicyclo[2.2.1]heptan-6-yl)-1H-pyrazolo[3,4-d]pyrimidin-3-yl)-N-(6-(trifluoromethyl)pyridin-3-yl)benzamide (101 mg, 0.20 mmol) obtained in Step 26-3 and acryloyl chloride (18 uL, 0.22 mmol).

$^1$H NMR (500 MHz, CDCl$_3$): 8.99-9.02 (m, 1H), 8.78-8.82 (m, 1H), 8.58-8.60 (m, 1H), 7.98-8.30 (m, 3H), 7.77-7.88 (m, 1H), 7.63-7.70 (m, 2H), 6.32-6.77 (m, 2H), 5.72-5.75 (m, 1H), 4.51-4.99 (m, 2H), 3.21-3.49 (m, 2H), 2.82-2.85 (m, 2H), 2.38-2.40 (m, 1H), 2.11-2.20 (m, 1H), 1.71-1.73 (m, 1H).

Example 27: Preparation of 1-(6-(4-amino-3-(4-(methoxymethyl)phenyl)-1H-pyrazolo[3,4-d]pyrimidin-1-yl)-2-azabicyclo[2.2.1]heptan-2-yl)prop-2-en-1-one

Step 27-1: Preparation of tert-butyl 6-(4-amino-3-(4-(methoxymethyl)phenyl)-1H-pyrazolo[3,4-d]pyrimidin-1-yl)-2-azabicyclo[2.2.1]heptan-2-carboxylate

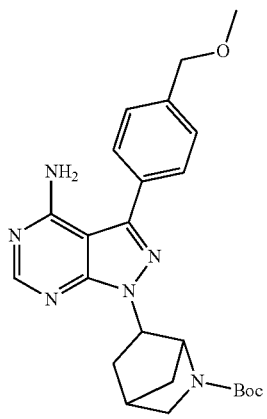 [SMILES: COCc1ccc(-c2nn(C3CC4CC3N(C(=O)OC(C)(C)C)C4)c3ncnc(N)c23)cc1]

A title compound (174 mg, yield: 88%) was prepared in the same manner as in Step 1-2 of Example 1, except for using 1-(2-azabicyclo[2.2.1]heptan-6-yl)-3-(4-phenoxyphenyl)-1H-pyrazolo[3,4-d]pyrimidin-4-amine (200 mg, 0.44 mmol) obtained in Step 1-3 and (4-(methoxymethyl)phenyl) boronic acid (136 mg, 0.55 mmol).

Step 27-2: Preparation of 1-(2-azabicyclo[2.2.1]heptan-6-yl)-3-(4-(methoxymethyl)phenyl)-1H-pyrazolo[3,4-d]pyrimidin-4-amine

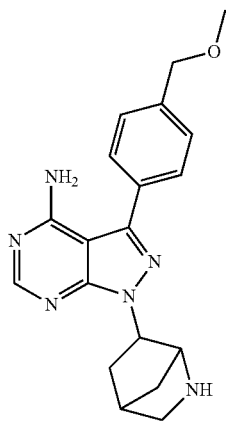 [SMILES: COCc1ccc(-c2nn(C3CC4CNC3C4)c3ncnc(N)c23)cc1]

A title compound (84 mg, yield: 62%) was prepared in the same manner as in Step 1-3 of Example 1, except for using tert-butyl 6-(4-amino-3-(4-(methoxymethyl)phenyl)-1H-pyrazolo[3,4-d]pyrimidin-1-yl)-2-azabicyclo[2.2.1]heptan-2-carboxylate (174 mg, 0.26 mmol) obtained in Step 27-1.

Step 27-3: Preparation of 1-(6-(4-amino-3-(4-(methoxymethyl)phenyl)-1H-pyrazolo[3,4-d]pyrimidin-1-yl)-2-azabicyclo[2.2.1]heptan-2-yl)prop-2-en-1-one

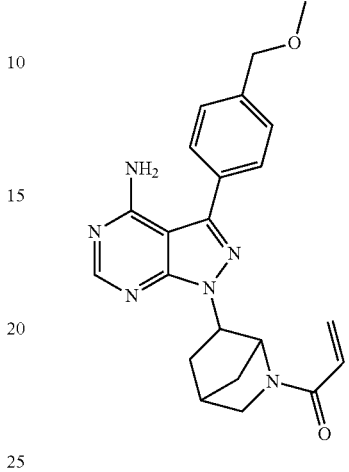

A title compound (49 mg, yield: 42%) was prepared in the same manner as in Step 1-4 of Example 1, except for using 1-(2-azabicyclo[2.2.1]heptan-6-yl)-3-(4-(methoxymethyl)phenyl)-1H-pyrazolo[3,4-d]pyrimidin-4-amine (101 mg, 0.20 mmol) obtained in Step 27-2 and acryloyl chloride (21 uL, 0.26 mmol).

$^1$H NMR (500 MHz, CDCl$_3$): 8.33-8.36 (m, 1H), 7.64-7.66 (m, 2H), 7.48-7.51 (m, 2H), 6.29-6.78 (m, 2H), 5.70-5.72 (m, 1H), 5.06-5.28 (m, 1H), 4.52-4.89 (m, 1H), 4.51 (s, 2H), 3.51-3.68 (m, 1H), 3.44 (s, 3H), 3.22-3.27 (m, 1H), 2.55-2.85 (m, 2H), 2.25-2.39 (m, 1H), 2.05-2.2.19 (m, 1H), 1.69-1.71 (m, 1H).

Example 28: Preparation of 1-(6-(4-amino-3-(4-phenoxyphenyl)-1H-pyrazolo[3,4-d]pyridin-1-yl)-2-azabicyclo[2.2.1]heptan-2-yl)-3-cyclopropylprop-2-yn-1-one

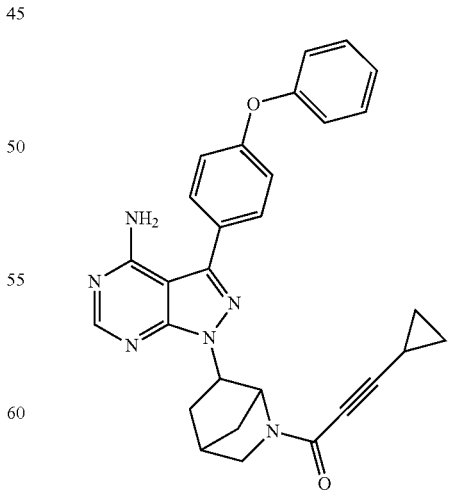

A title compound (31 mg, yield: 55%) was prepared in the same manner as in Step 1-4 of Example 1, except for using 1-(2-azabicyclo[2.2.1]heptan-6-yl)-3-(4-phenoxyphenyl)-

1H-pyrazolo[3,4-d]pyrimidin-4-amine (50 mg, 0.11 mmol) obtained in Step 1-3 and 3-cyclopropylpropioloyl chloride (15 uL, 0.12 mmol).

$^1$H NMR (500 MHz, CDCl$_3$): 8.27-8.32 (m, 1H), 7.59-7.62 (m, 2H), 7.36-7.40 (m, 2H), 7.06-7.18 (m, 5H), 5.10-5.19 (m, 1H), 4.55-4.81 (m, 1H), 3.32-3.49 (m, 1H), 3.19-3.30 (m, 1H), 2.81-2.90 (m, 1H), 2.53-2.87 (m, 1H), 2.25-2.38 (m, 1H), 2.11-2.20 (m, 1H), 1.65-1.80 (m, 1H), 1.34-1.36 (m, 1H), 0.82-0.90 (m, 4H).

Example 29: Preparation of 4-(1-(2-acryloyl-2-azabicyclo[2.2.1]heptan-6-yl)-4-amino-1H-pyrazolo[3,4-d]pyrimidin-3-yl)-N-(4-(trifluoromethyl)pyridin-2-yl)benzamide

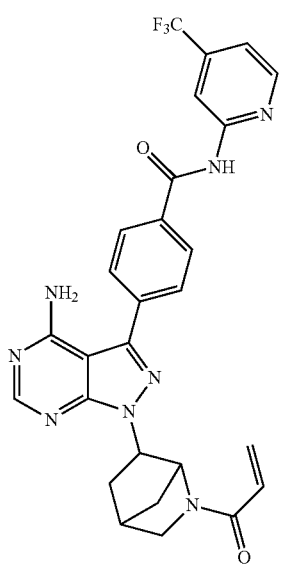 [SMILES: C=CC(=O)N1CC2CC1C(n1nc(-c3ccc(C(=O)Nc4cc(C(F)(F)F)ccn4)cc3)c3c(N)ncnc31)C2]

A title compound (39 mg, yield: 52%) was prepared in the same manner as in Step 1-4 of Example 1, except for using 4-(4-amino-1-(2-azabicyclo[2.2.1]heptan-6-yl)-1H-pyrazolo[3,4-d]pyrimidin-3-yl)-N-(4-(trifluoromethyl)pyridin-2-yl)benzamide (67 mg, 0.13 mmol) obtained in Step 6-3 and acryloyl chloride 12 uL, 0.14 mmol).

$^1$H NMR (500 MHz, CDCl$_3$): 8.96-8.98 (m, 1H), 8.72-8.74 (m, 1H), 8.38-8.51 (m, 2H), 8.14-8.15 (m, 2H), 7.86-7.88 (m, 2H), 7.35-7.36 (m, 1H), 6.33-6.75 (m, 2H), 5.77-5.82 (m, 1H), 5.12-5.21 (m, 1H), 4.55-4.89 (m, 1H), 3.70-3.77 (m, 1H), 3.51-3.58 (m, 1H), 3.27-3.37 (m, 1H), 2.81-90 (m, 2H), 2.42-2.50 (m, 1H), 2.03-2.20 (m, 1H).

Example 30: Preparation of 1-(6-(4-amino-3-(biphenyl-4-yl)-1H-pyrazolo[3,4-d]pyrimidin-1-yl)-2-azabicyclo[2.2.1]heptan-2-yl)prop-2-yn-1-one Step 30-1: Preparation of tert-butyl 6-(4-amino-3-(biphenyl-4-yl)-1H-pyrazolo[3,4-d]pyrimidin-1-yl)-2-azabicyclo[2.2.1]heptane-2-carboxylate

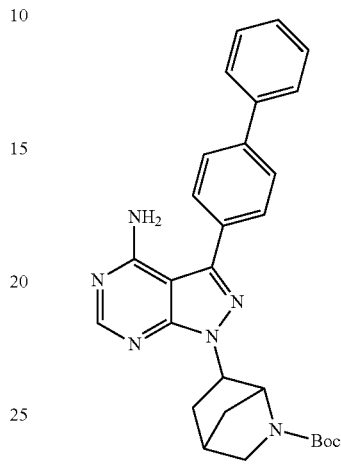

After tert-butyl 6-(4-amino-3-iodo-1H-pyrazolo[3,4-d]pyrimidin-1-yl)-2-azabicyclo[2.2.1]heptane-2-carboxylate (100 mg, 0.22 mmol) obtained in Step 1-1 of Example 1 was dissolved in 1,4-dioxane (2 mL) and water (300 uL), diphenylboronic acid (54.3 mg, 0.27 mmol), potassium carbonate (151.5 mg, 1.1 mmol) and [1,1'-bis(diphenylphosphino)ferrocene]dichloropalladium(II) (11.2 mg, 0.02 mmol) were sequentially added thereto, and the mixture was refluxed and stirred at 110° C. for 90 minutes. Upon completion of the reaction, the mixture was diluted with ethyl acetate and washed with saturated sodium chloride solution. The organic layer was collected, dried over magnesium sulfate, filtered and then concentrated under reduced pressure. The residue was purified by column chromatography (ethyl acetate 100%) to obtain a title compound (86 mg, yield: 81.3%).

Step 30-2: Preparation of 3-(biphenyl-4-yl)-1-(2-azabicyclo[2.2.1]heptan-6-yl)-1H-pyrazolo[3,4-d]pyrimidin-4-amine

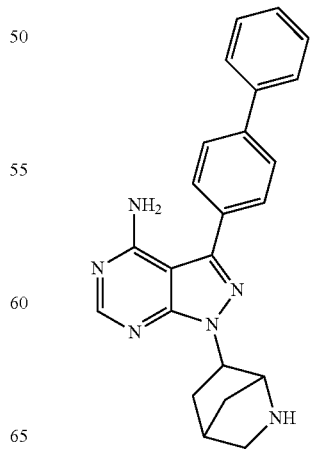

After tert-butyl 6-(4-amino-3-(biphenyl-4-yl)-1H-pyrazolo[3,4-d]pyrimidin-1-yl)-2-azabicyclo[2.2.1]heptane-2-carboxylate (80.0 mg, 0.17 mmol) obtained in Step 30-1 was dissolved in 1,4-dioxane (3 mL), 1 N hydrochloric acid aqueous solution (3 mL) dissolved in dioxane was added thereto, and then stirred at room temperature for 3 hours. Upon completion of the reaction, the mixture was concentrated under reduced pressure to obtain a title compound (60.0 mg, yield: 94.6%).

Step 30-3: Preparation of 1-(6-(4-amino-3-(biphenyl-4-yl)-1H-pyrazolo[3,4-d]pyrimidin-1-yl)-2-azabicyclo[2.2.1]heptan-2-yl)prop-2-yn-1-one

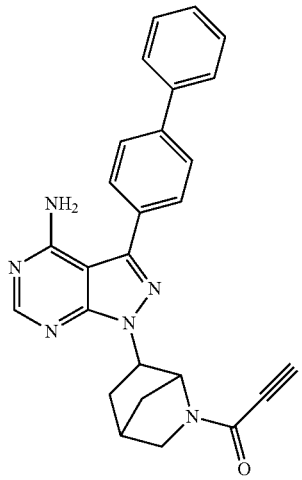 [SMILES: C#CC(=O)N1CC2CC1C(n1nc(-c3ccc(-c4ccccc4)cc3)c3c(N)ncnc31)C2]

3-(biphenyl-4-yl)-1-(2-azabicyclo[2.2.1]heptan-6-yl)-1H-pyrazolo[3,4-d]pyrimidin-4-amine (30 mg, 0.08 mmol) obtained in Step 30-2 was dissolved in tetrahydrofuran (1 mL) and water (0.2 mL), and cooled to 0° C. to which sodium bicarbonate (7.3 mg, 0.09 mmol) was added. Propionyl chloride (56 uL, 0.08 mmol, 1.4M dichloromethane solution) was slowly added to the reaction solution and then stirred at the same temperature for 30 minutes. Upon completion of the reaction, the reaction solution was diluted with ethyl acetate and washed with saturated sodium chloride solution. The organic layer was collected, dried over magnesium sulfate, filtered and then concentrated under reduced pressure. The residue was purified by column chromatography (chloromethane:methanol=9:1) to obtain a title compound (10.0 mg, yield: 29.0%).

$^1$H NMR (500 MHz, CDCl$_3$): 8.01-8.40 (m, 1H), 7.77-7.84 (m, 4H), 7.64-7.65 (m, 2H), 7.47-7.50 (m, 2H), 7.39-7.42 (m, 1H), 5.65 (s, 2H), 5.30-5.33 (m, 1H), 4.30-4.58 (m, 1H), 3.38-3.62 (m, 1H), 3.24-3.40 (m, 1H), 3.08-3.12 (m, 1H), 2.88 (s, 1H), 2.40-2.63 (m, 2H), 2.01-2.20 (m, 1H), 1.77-1.79 (m, 1H).

Example 31: Preparation of 1-(6-(4-amino-3-(4-(phenylamino)phenyl)-1H-pyrazolo[3,4-d]pyrimidin-1-yl)-2-azabicyclo[2.2.1]heptan-2-yl)prop-2-yn-1-one Step 31-1: Preparation of N-phenyl-4-(4,4,5,5-tetramethyl-1,3,2-dioxaborolan-2-yl)aniline

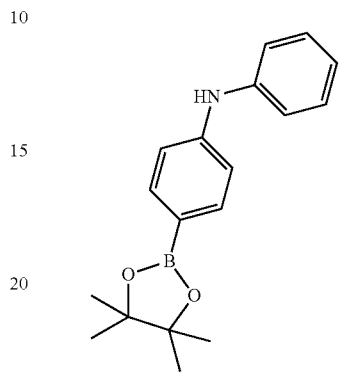

4-Bromo-N-phenylaniline (1 g, 4.03 mmol), bis(pinacolato)diboron (1.2 g, 4.84 mmol), potassium acetate (1.2 g, 12.09 mmol), and [1,1'-bis(diphenylphosphino)ferrocene]dichlopalladium(II) (295 mg, 0.40 mol) were dissolved in dimethylformamide (10 mL). The reaction solution was heated under reflux at 100° C. for 15 hours. The reaction solution was diluted with ethyl acetate and washed with water. The extracted organic layer was dried over magnesium sulfate, filtered and then concentrated to obtain a title compound (700 mg, yield: 58.8%).

Step 31-2: Preparation of tert-butyl 6-(4-amino-3-(4-(phenylamino)phenyl)-1H-pyrazolo[3,4-d]pyrimidin-1-yl)-2-azabicyclo[2.2.1]heptane-2-carboxylate

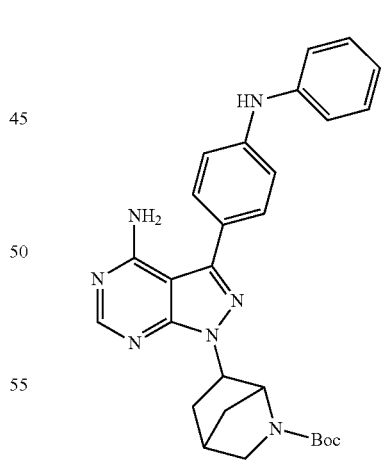

After tert-butyl 6-(4-amino-3-iodo-1H-pyrazolo[3,4-d]pyrimidin-1-yl)-2-azabicyclo[2.2.1]heptane-2-carboxylate (100 mg, 0.22 mmol) obtained in Step 1-1 of Example 1 was dissolved in 1,4-dioxane (2 mL) and water (300 uL), N-phenyl-4-(4,4,5,5-tetramethyl-1,3,2-dioxaborolan-2-yl)aniline (80.9 mg, 0.27 mmol) obtained in Step 31-1, potassium carbonate (151.5 mg, 1.1 mmol), and [1,1'-bis(diphenylphosphino)ferrocene]diclopalladium(II) (11.2 mg, 0.02 mmol) were sequentially added thereto, and the mixture was refluxed and stirred at 110° C. for 90 minutes. Upon completion of the reaction, the reaction solution was diluted with ethyl acetate and washed with saturated sodium chloride solution. The organic layer was collected, dried over magnesium sulfate, filtered and then concentrated under reduced pressure. The residue was purified by column chromatography (ethyl acetate 100%) to obtain a title compound (54.5 mg, yield: 50.0%).

Step 31-3: Preparation of 1-(2-azabicyclo[2.2.1]heptan-6-yl)-3-(4-(phenylamino)phenyl)-1H-pyrazolo[3,4-d]pyrimidin-4-amine

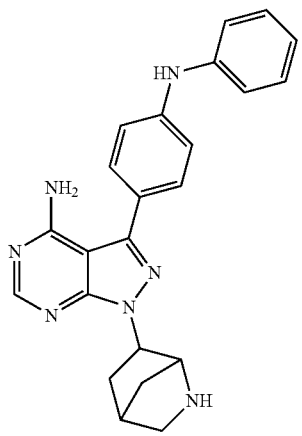 [SMILES: Nc1ncnc2c1c(-c1ccc(Nc3ccccc3)cc1)nn2C1CC2CNC1C2]

After tert-butyl 6-(4-amino-3-(4-(phenylamino)phenyl)-1H-pyrazolo[3,4-d]pyrimidin-1-yl)-2-azabicyclo[2.2.1]heptane-2-carboxylate (54.5 mg, 0.11 mmol) obtained in Step 31-2 was dissolved in 1,4-dioxane (1.5 mL), 1 N hydrochloric acid aqueous solution (2 mL) dissolved in dioxane was added thereto, and then stirred at room temperature for 3 hours. Upon completion of the reaction, the mixture was concentrated under reduced pressure to obtain a title compound (30.0 mg, yield: 68.8%).

Step 31-4: Preparation of 1-(6-(4-amino-3-(4-(phenylamino)phenyl)-1H-pyrazolo[3,4-d]pyrimidin-1-yl)-2-azabicyclo[2.2.1]heptan-2-yl)prop-2-yn-1-one

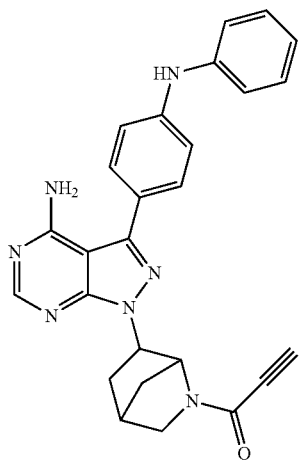 [SMILES: C#CC(=O)N1CC2CC1C(n1nc(-c3ccc(Nc4ccccc4)cc3)c3c(N)ncnc31)C2]

1-(2-azabicyclo[2.2.1]heptan-6-yl)-3-(4-(phenylamino)phenyl)-1H-pyrazolo[3,4-d]pyrimidin-4-amine (30 mg, 0.07 mmol) obtained in Step 31-3 was dissolved in tetrahydrofuran (1 mL) and water (60 uL) and then cooled to 0° C. to which sodium bicarbonate (8.9 mg, 0.11 mmol) was added. Propionyl chloride (50.0 uL, 0.07 mmol, 1.4 M dichloromethane solution) was slowly added to the reaction solution and then stirred at the same temperature for 30 minutes. Upon completion of the reaction, the reaction solution was diluted with ethyl acetate and washed with saturated sodium chloride solution. The organic layer was collected, dried over magnesium sulfate, filtered and then concentrated under reduced pressure. The residue was purified by column chromatography (chloromethane:methanol=9:1) to obtain a title compound (1.2 mg, yield: 38.7%).

$^1$H NMR (500 MHz, CDCl$_3$): 8.01-8.40 (m, 1H), 7.53-7.54 (m, 2H), 7.32-7.35 (m, 2H), 7.16-7.19 (m, 4H), 7.03-7.05 (m, 1H), 5.81 (s, 1H), 5.34 (s, 2H), 5.25-5.28 (m, 1H), 4.70-4.82 (m, 1H), 3.49-3.74 (m, 1H), 3.35-3.43 (m, 1H), 3.05-3.30 (m, 1H), 2.87 (s, 1H), 2.50-2.59 (m, 2H), 2.25-2.36 (m, 1H), 1.76-1.80 (m, 1H).

Example 32: Preparation of 1-(6-(4-amino-3-(4-(phenylsulfonyl)phenyl)-1H-pyrazolo[3,4-d]pyrimidin-1-yl)-2-azabicyclo[2.2.1]heptan-2-yl)prop-2-en-1-one Step 32-1: Preparation of 4,4,5,5-tetramethyl-2-(4-(phenylsulfonyl)phenyl)-1,3,2-dioxaborolane

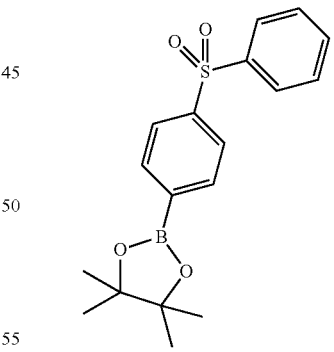

A title compound (711 mg, yield: 61.3%) was prepared in the same manner as in Step 31-1 of Example 31, except for using 1-bromo-4-(phenylsulfonyl)benzene (1 g, 3.36 mmol).

Step 32-2: Preparation of tert-butyl 6-(4-amino-3-(4-(phenylsulfonyl)phenyl)-1H-pyrazolo[3,4-d]pyrimidin-1-yl)-2-azabicyclo[2.2.1]heptane-2-carboxylate

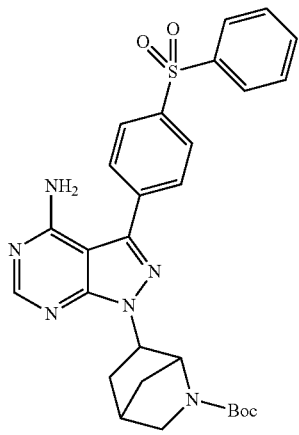 [SMILES: CC(C)(C)OC(=O)N1CC2CC1C(n1nc(-c3ccc(S(=O)(=O)c4ccccc4)cc3)c3c(N)ncnc31)C2]

A title compound (98.0 mg, yield: 82.4%) was prepared in the same manner as in Step 31-2 of Example 31, except for using tert-butyl 6-(4-amino-3-iodo-1H-pyrazolo[3,4-d]pyrimidin-1-yl)-2-azabicyclo[2.2.1]heptane-2-carboxylate (100 mg, 0.22 mmol) obtained in Step 1-1 of Example 1 and 4,4,5,5-tetramethyl-2-(4-(phenylsulfonyl)phenyl)-1,3,2-dioxaborolane (94.0 mg, 0.27 mmol) obtained in Step 32-1.

Step 32-3: Preparation of 1-(2-azabicyclo[2.2.1]heptan-6-yl)-3-(4-(phenylsulfonyl)phenyl)-1H-pyrazolo[3,4-d]pyrimidin-4-amine

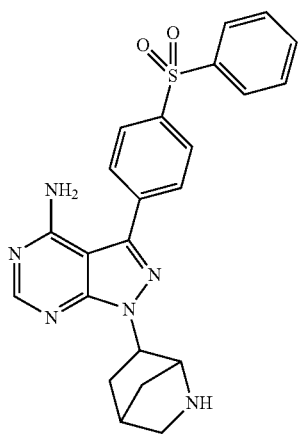 [SMILES: Nc1ncnc2c1c(-c1ccc(S(=O)(=O)c3ccccc3)cc1)nn2C1CC2CNC1C2]

A title compound (85.0 mg, yield: 98.2%) was prepared in the same manner as in Step 31-3 of Example 31, except for using tert-butyl 6-(4-amino-3-(4-(phenylsulfonyl)phenyl)-1H-pyrazolo[3,4-d]pyrimidin-1-yl)-2-azabicyclo[2.2.1]heptane-2-carboxylate (98.0 mg, 0.18 mol) obtained in Step 32-2.

Step 32-4: Preparation of 1-(6-(4-amino-3-(4-(phenylsulfonyl)phenyl)-1H-pyrazolo[3,4-d]pyrimidin-1-yl)-2-azabicyclo[2.2.1]heptan-2-yl)prop-2-en-1-one 1-(2-azabicyclo[2.2.1]heptan-6-yl)-3-(4-(phenylsulfonyl)phenyl)-1H-pyrazolo[3,4-d]pyrimidin-4-amine (85 mg, 0.17 mmol) obtained in Step 32-3 was dissolved in tetrahydrofuran (2 mL) and water (200 uL) and then cooled to 0° C. to which sodium bicarbonate (15.7 mg, 0.19 mmol) was added. Acryl chloride (14 uL, 0.17 mmol) was slowly added to the reaction solution and then stirred at the same temperature for 30 minutes. Upon completion of the reaction, the reaction solution was diluted with ethyl acetate and washed with saturated sodium chloride solution. The organic layer was collected, dried over magnesium sulfate, filtered and then concentrated under reduced pressure. The residue was purified by column chromatography (chloromethane:methanol=9:1) to obtain a title compound (30.0 mg, yield: 34.1%).

$^1$H NMR (500 MHz, CDCl$_3$): 8.01-8.40 (m, 1H), 7.53-7.54 (m, 2H), 7.32-7.35 (m, 2H), 7.16-7.19 (m, 4H), 7.03-7.05 (m, 1H), 5.81 (s, 1H), 5.34 (s, 2H), 5.25-5.28 (m, 1H), 4.70-4.82 (m, 1H), 3.49-3.74 (m, 1H), 3.35-3.43 (m, 1H), 3.05-3.30 (m, 1H), 2.87 (s, 1H), 2.50-2.59 (m, 2H), 2.25-2.36 (m, 1H), 1.76-1.80 (m, 1H).

Example 33: Preparation of 1-(6-(4-amino-3-(4-(phenylthio)phenyl)-1H-pyrazolo[3,4-d]pyrimidin-1-yl)-2-azabicyclo[2.2.1]heptan-2-yl)prop-2-en-1-one Step 33-1: Preparation of 4,4,5,5-tetramethyl-2-(4-(phenylthio)phenyl)-1,3,2-dioxaborolane

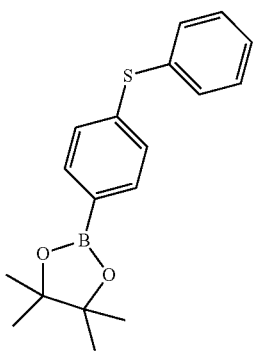 [SMILES: CC1(C)OB(c2ccc(Sc3ccccc3)cc2)OC1(C)C]

Tert-butyl lithium (1.7 M pentane solution, 5 mL, 8.48 mmol) was added to a reaction vessel and the inner part of the vessel was substituted by nitrogen and then cooled to −78° C. 1,4-Dibromobenzene (1 g, 4.24 mmol) and 2-isopropoxy-4,4,5,5-tetramethyl-1,3,2-dioxaborolane (0.9 mL, 4.32 mmol) were added to a separate reaction vessel, dissolved in tetrahydrofuran (24 mL), and then slowly added dropwise to the reaction vessel containing tert-butyllithium for 3 minutes. The reaction solution was stirred at the same temperature for 30 minutes to which tert-butyllithium (1.7 M pentane solution, 5 mL, 8.48 mmol) was added dropwise at −78° C. for 3 minutes. The mixture was then stirred at the same temperature for 20 minutes. 1,2-diphenyldisulfane (1.0 g, 4.66 mmol) was slowly added dropwise to the reaction solution, and the mixture was stirred for 1 hour while raising the temperature to room temperature. Upon completion of the reaction (TLC), a saturated aqueous ammonium chloride solution (24 mL) was slowly added dropwise and extracted with ethyl acetate. The extracted organic layer was dried over sodium sulfate and concentrated under reduced pressure. The residue was purified by column chromatography (ethyl acetate:n-hexane=1:100) to obtain a title compound (800 mg, yield: 75.8%).

Step 33-2: Preparation of tert-butyl 6-(4-amino-3-(4-(phenylthio)phenyl)-1H-pyrazolo[3,4-d]pyrimidin-1-yl)-2-azabicyclo[2.2.1]heptane-2-carboxylate

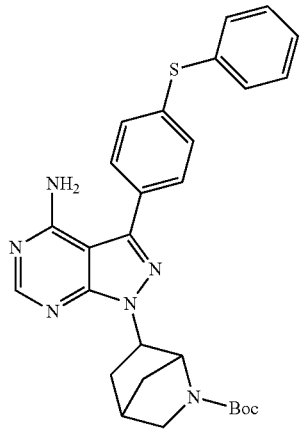 [SMILES: CC(C)(C)OC(=O)N1CC2CC1C(n1nc(-c3ccc(Sc4ccccc4)cc3)c3c(N)ncnc31)C2]

A title compound (70.0 mg, yield: 62.1%) was prepared in the same manner as in Step 31-2 of Example 31, except for using tert-butyl 6-(4-amino-3-iodo-1H-pyrazolo[3,4-d]pyrimidin-1-yl)-2-azabicyclo[2.2.1]heptane-2-carboxylate (100 mg, 0.22 mmol) obtained in Step 1-1 of Example 1 and 4,4,5,5-tetramethyl-2-(4-(phenylthio)phenyl)-1,3,2-dioxaborolane (86.0 mg, 0.27 mmol) obtained in Step 33-1.

Step 33-3: Preparation of 1-(2-azabicyclo[2.2.1]heptan-6-yl)-3-(4-(phenylthio)phenyl)-1H-pyrazolo[3,4-d]pyrimidin-4-amine

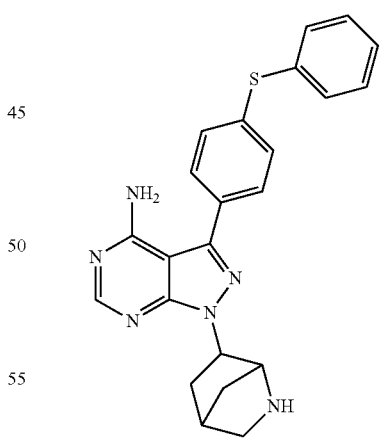

A title compound (52.0 mg, yield: 84.8%) was prepared in the same manner as in Step 31-3 of Example 31, except for using tert-butyl 6-(4-amino-3-(4-(phenylthio)phenyl)-1H-pyrazolo[3,4-d]pyrimidin-1-yl)-2-azabicyclo[2.2.1]heptane-2-carboxylate (70.0 mg, 0.14 mol) obtained in Step 33-2.

Step 33-4: Preparation of 1-(6-(4-amino-3-(4-(phenylthio)phenyl)-1H-pyrazolo[3,4-d]pyrimidin-1-yl)-2-azabicyclo[2.2.1]heptan-2-yl)prop-2-en-1-one

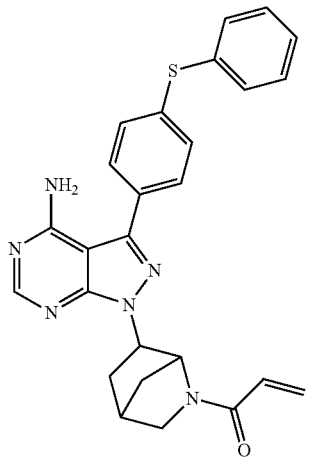 [SMILES: C=CC(=O)N1CC2CC1C(n1nc(-c3ccc(Sc4ccccc4)cc3)c3c(N)ncnc31)C2]

A title compound (16.6 mg, yield: 28.2%) was prepared in the same manner as in Step 32-4 of Example 32, except for using 1-(2-azabicyclo[2.2.1]heptan-6-yl)-3-(4-(phenylthio)phenyl)-1H-pyrazolo[3,4-d]pyrimidin-4-amine (52 mg, 0.13 mmol) obtained in Step 33-3.

$^1$H NMR (500 MHz, CDCl$_3$): 8.32-8.40 (m, 1H), 7.66-7.76 (m, 3H), 7.55-7.62 (m, 2H), 7.46-7.51 (m, 1H), 7.36-7.41 (m, 1H), 6.77-6.68 (dd, 1H), 6.42-6.46 (d, 1H), 6.35-6.38 (dd, 1H), 5.70-5.88 (m, 3H), 5.06-5.20 (m, 1H), 4.46-4.94 (m, 1H), 3.47-3.56 (m, 1H), 3.25-3.33 (m, 1H), 2.87 (s, 1H), 2.39-2.57 (m, 1H), 2.09-2.31 (m, 2H), 1.71-1.73 (m, 1H).

Example 34: Preparation of 1-(6-(4-amino-3-(4-(3-fluorophenoxy)phenyl)-1H-pyrazolo[3,4-d]pyrimidin-1-yl)-2-azabicyclo[2.2.1]heptan-2-yl)prop-2-en-1-one Step 34-1: Preparation of 1-(4-bromophenoxy)-3-fluorobenzene

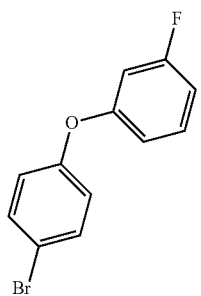 [SMILES: Fc1cccc(Oc2ccc(Br)cc2)c1]

4 Å molecular sieves (2 g) were added to a reaction vessel and activated for 10 minutes, to which 4-bromophenol (1 g, 5.78 mmol), copper (II) acetate (1.1 g, 5.78 mmol), and triethylamine (4 mL, 28.9 mmol) were sequentially added dropwise, dissolved in anhydrous dichloromethane (20 mL), and then stirred for 5 minutes. 3-Fluorophenylboronic acid was added dropwise to the reaction solution, and the mixture was stirred at room temperature for 24 hours. The reaction solution was filtered using diatomaceous earth and concentrated under reduced pressure. The residue was purified by column chromatography (ethyl acetate:n-hexane=1:50) to obtain a title compound (220 mg, yield: 14.3%).

Step 34-2: Preparation of 2-(4-(3-fluorophenoxy)phenyl)-4,4,5,5-tetramethyl-1,3,2-dioxaborolane

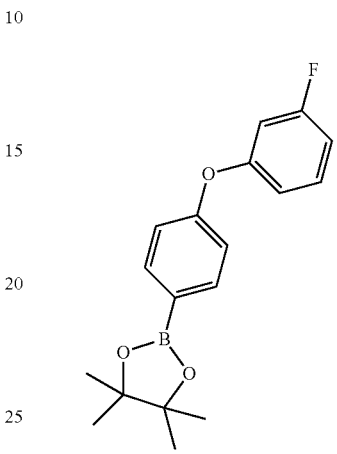

A title compound (50 mg, yield: 17.8%) was prepared in the same manner as in Step 31-1 of Example 31, except for using 1-(4-bromophenoxy)-3-fluorobenzene (220 mg, 0.82 mmol) obtained in Step 34-1.

Step 34-3: Preparation of tert-butyl 6-(4-amino-3-(4-(3-fluorophenoxy)phenyl)-1H-pyrazolo[3,4-d]pyrimidin-1-yl)-2-azabicyclo[2.2.1]heptane-2-carboxylate

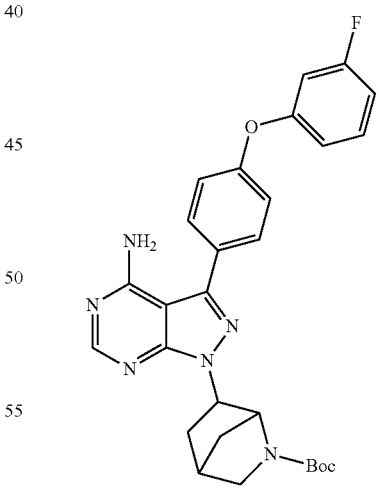

A title compound (25.0 mg, yield: 43.0%) was prepared in the same manner as in Step 31-2 of Example 31, except for using tert-butyl 6-(4-amino-3-iodo-1H-pyrazolo[3,4-d]pyrimidin-1-yl)-2-azabicyclo[2.2.1]heptane-2-carboxylate (51.7 mg, 0.11 mmol) (200 mg, 0.44 mmol) obtained in Step 1-1 of Example 1 and 2-(4-(3-fluorophenoxy)phenyl)-4,4,5,5-tetramethyl-1,3,2-dioxaborolane (48.0 mg, 0.14 mmol) obtained in Step 34-2.

Step 34-4: Preparation of 1-(2-azabicyclo[2.2.1]heptan-6-yl)-3-(4-(3-fluorophenoxy)phenyl)-1H-pyrazolo[3,4-d]pyrimidin-4-amine

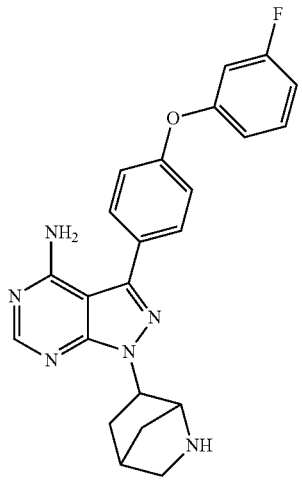 [SMILES: Nc1ncnc2c1c(-c1ccc(Oc3cccc(F)c3)cc1)nn2C1CC2CNC1C2]

A title compound (20.0 mg, yield: 91.3%) was prepared in the same manner as in Step 31-3 of Example 31, except for using tert-butyl 6-(4-amino-3-(4-(3-fluorophenoxy)phenyl)-1H-pyrazolo[3,4-d]pyrimidin-1-yl)-2-azabicyclo[2.2.1]heptane-2-carboxylate (25.0 mg, 0.04 mol) obtained in Step 34-3.

Step 34-5: Preparation of 1-(6-(4-amino-3-(4-(3-fluorophenoxy)phenyl)-1H-pyrazolo[3,4-d]pyrimidin-1-yl)-2-azabicyclo[2.2.1]heptan-2-yl)prop-2-en-1-one

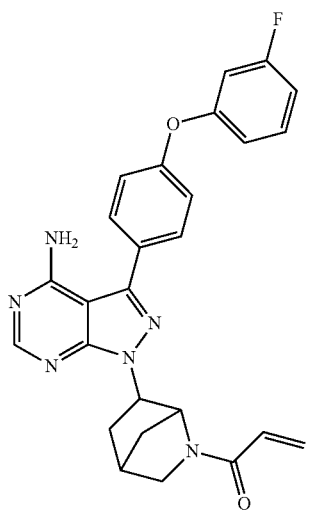 [SMILES: C=CC(=O)N1CC2CC1C(n1nc(-c3ccc(Oc4cccc(F)c4)cc3)c3c(N)ncnc31)C2]

A title compound (3.0 mg, yield: 14.4%) was prepared in the same manner as in Step 32-4 of Example 32, except for using 1-(2-azabicyclo[2.2.1]heptan-6-yl)-3-(4-(3-fluorophenoxy)phenyl)-1H-pyrazolo[3,4-d]pyrimidin-4-amine (20 mg, 0.02 mmol) obtained in Step 34-4.

$^1$H NMR (500 MHz, CDCl$_3$): 8.39-8.40 (m, 1H), 7.66-7.69 (m, 2H), 7.32-7.34 (m, 1H), 7.17-7.19 (m, 1H), 6.77-6.87 (m, 4H), 6.44-7.48 (m, 1H), 5.75-5.79 (m, 1H), 5.48 (s, 2H), 5.33 (s, 1H), 5.49-5.23 (m, 1H), 4.54 (s, 1H), 3.25-3.59 (m, 2H), 2.79-2.92 (m, 1H), 2.19-2.30 (m, 1H), 1.97-1.99 (m, 2H), 1.60-1.71 (m, 1H).

Example 35: Preparation of 1-(6-(4-amino-3-(2-fluoro-4-phenoxyphenyl)-1H-pyrazolo[3,4-d]pyrimidin-1-yl)-2-azabicyclo[2.2.1]heptan-2-yl)prop-2-en-1-one

Step 35-1: Preparation of 1-bromo-2-fluoro-4-phenoxybenzene

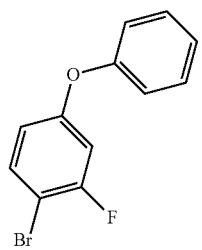 [SMILES: Fc1cc(Oc2ccccc2)ccc1Br]

A title compound (304.7 mg, yield: 7.3%) was prepared in the same manner as in Step 34-1 of Example 34, except for using 4-bromo-3-fluorophenol (3 g, 15.7 mmol) and phenylboronic acid (2.1 g, 17.3 mmol).

Step 35-2: Preparation of 2-(2-fluoro-4-phenoxyphenyl)-4,4,5,5-tetramethyl-1,3,2-dioxaborolane

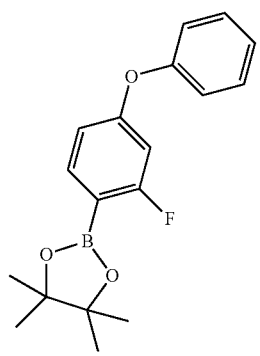 [SMILES: CC1(C)OB(c2ccc(Oc3ccccc3)cc2F)OC1(C)C]

A title compound (98 mg, yield: 83.3%) was prepared in the same manner as in Step 31-1 of Example 31, except for using 1-bromo-2-fluoro-4-phenoxybenzene (300 mg, 1.12 mmol) obtained in Step 35-1.

Step 35-3: Preparation of tert-butyl 6-(4-amino-3-(2-fluoro-4-phenoxyphenyl)-1H-pyrazolo[3,4-d]pyrimidin-1-yl)-2-azabicyclo[2.2.1]heptane-2-carboxylate

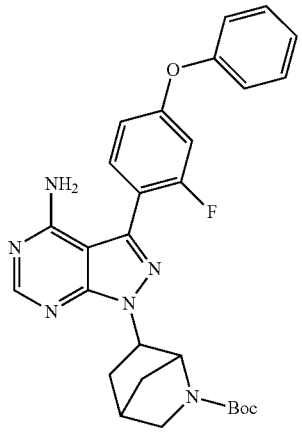 [SMILES: CC(C)(C)OC(=O)N1CC2CC1C(n1nc(-c3ccc(Oc4ccccc4)cc3F)c3c(N)ncnc31)C2]

A title compound (102 mg, yield: 79.1%) was prepared in the same manner as in Step 31-2 of Example 31, except for using tert-butyl 6-(4-amino-3-iodo-1H-pyrazolo[3,4-d]pyrimidin-1-yl)-2-azabicyclo[2.2.1]heptane-2-carboxylate (114.6 mg, 0.25 mmol) obtained in Step 1-1 of Example 1 and 2-(2-fluoro-4-phenoxyphenyl)-4,4,5,5-tetramethyl-1,3,2-dioxaborolane (98 mg, 0.31 mmol) obtained in Step 35-2.

Step 35-4: Preparation of 1-(2-azabicyclo[2.2.1]heptan-6-yl)-3-(2-fluoro-4-phenoxyphenyl)-1H-pyrazolo[3,4-d]pyrimidin-4-amine

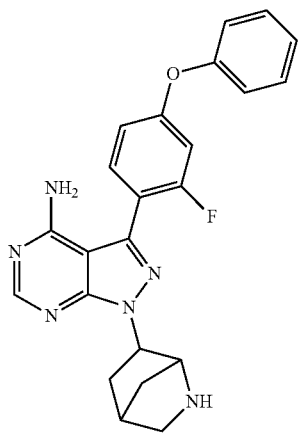 [SMILES: Nc1ncnc2c1c(-c1ccc(Oc3ccccc3)cc1F)nn2C1CC2CNC1C2]

A title compound (80.0 mg, yield: 91.3%) was prepared in the same manner as in Step 31-3 of Example 31, except for using tert-butyl 6-(4-amino-3-(2-fluoro-4-phenoxyphenyl)-1H-pyrazolo[3,4-d]pyrimidin-1-yl)-2-azabicyclo[2.2.1]heptane-2-carboxylate (100.0 mg, 0.19 mol) obtained in Step 35-3.

Step 35-5: Preparation of 1-(6-(4-amino-3-(2-fluoro-4-phenoxyphenyl)-1H-pyrazolo[3,4-d]pyrimidin-1-yl)-2-azabicyclo[2.2.1]heptan-2-yl)prop-2-en-1-one

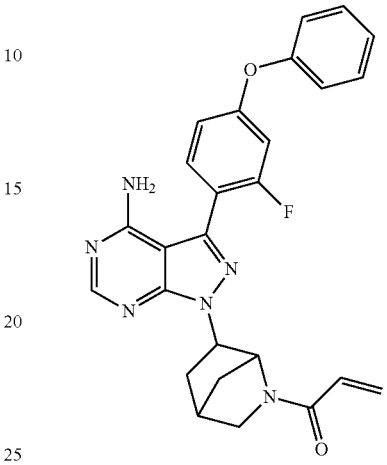

A title compound (53.0 mg, yield: 58.2%) was prepared in the same manner as in Step 32-4 of Example 32, except for using 1-(2-azabicyclo[2.2.1]heptan-6-yl)-3-(2-fluoro-4-phenoxyphenyl)-1H-pyrazolo[3,4-d]pyrimidin-4-amine (80 mg, 0.18 mmol) obtained in Step 35-4.

$^1$H NMR (500 MHz, CDCl$_3$): 8.22-8.27 (m, 1H), 7.51-7.54 (m, 1H), 7.43-7.47 (m, 2H), 7.15-7.23 (m, 3H), 6.99-7.01 (dd, 1H), 6.92-6.95 (dd, 1H), 6.82-6.88 (dd, 1H), 6.45-6.50 (dd, 1H), 6.17-6.22 (m, 1H), 5.69-5.74 (m, 1H), 5.4.53-4.58 (m, 1H), 3.99-4.08 (m, 1H), 3.65-3.70 (m, 2H), 2.75-2.82 (m, 2H), 2.06-2.08 (m, 1H), 1.58-1.71 (m, 2H).

Example 36: Preparation of 1-(6-(4-amino-3-(4-(pyridin-4-yloxy)phenyl)-1H-pyrazolo[3,4-d]pyrimidin-1-yl)-2-azabicyclo[2.2.1]heptan-2-yl)prop-2-en-1-one

Step 36-1: Preparation of 4-(4-bromophenoxy)pyridine

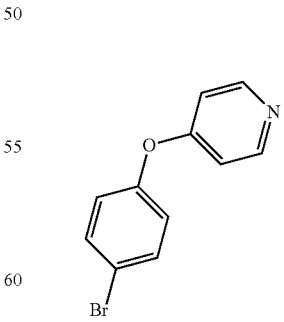

A title compound (427.5 mg, yield: 9.9%) was prepared in the same manner as in Step 34-1 of Example 34, except for using 4-bromophenol (3 g, 17.3 mmol) and pyridinylboronic acid (2.3 g, 19.1 mmol).

Step 36-2: Preparation of 4-(4-(4,4,5,5-tetramethyl-1,3,2-dioxaborolan-2-yl)phenoxy)pyridine

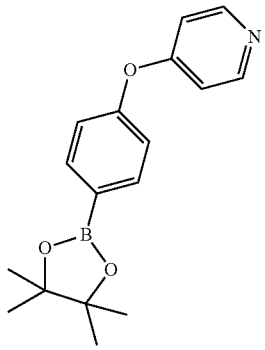 [SMILES: CC1(C)OB(c2ccc(Oc3ccncc3)cc2)OC1(C)C]

A title compound (328.2 mg, yield: 65.8%) was prepared in the same manner as in Step 31-1 of Example 31, except for using 4-(4-bromophenoxy)pyridine (420 mg, 1.67 mmol) obtained in Step 36-1.

Step 36-3: Preparation of tert-butyl 6-(4-amino-3-(4-(pyridin-4-yloxy)phenyl)-1H-pyrazolo[3,4-d]pyrimidin-1-yl)-2-azabicyclo[2.2.1]heptane-2-carboxylate

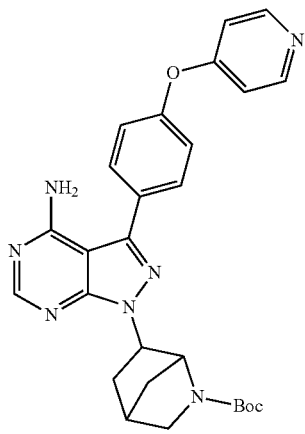 [SMILES: CC(C)(C)OC(=O)N1CC2CC1C(n1nc(-c3ccc(Oc4ccncc4)cc3)c3c(N)ncnc31)C2]

A title compound (10 mg, yield: 9.2%) was prepared in the same manner as in Step 31-2 of Example 31, except for using tert-butyl 6-(4-amino-3-iodo-1H-pyrazolo[3,4-d]pyrimidin-1-yl)-2-azabicyclo[2.2.1]heptane-2-carboxylate (100 mg, 0.22 mmol) obtained in Step 1-1 of Example 1 and 4-(4-(4,4,5,5-tetramethyl-1,3,2-dioxaborolan-2-yl)phenoxy)pyridine (80.9 mg, 0.27 mmol) obtained in Step 36-2.

Step 36-4: Preparation of 1-(2-azabicyclo[2.2.1]heptan-6-yl)-3-(4-(pyridin-4-yloxy)-1H-pyrazolo[3,4-d]pyrimidin-4-amine

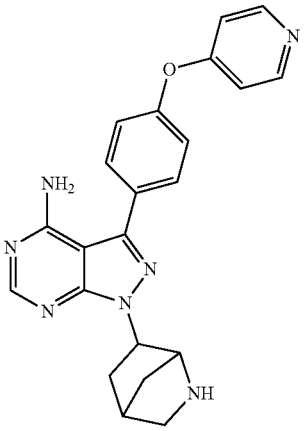 [SMILES: Nc1ncnc2c1c(-c1ccc(Oc3ccncc3)cc1)nn2C1CC2CNC1C2]

A title compound (6.0 mg, yield: 75.0%) was prepared in the same manner as in Step 31-3 of Example 31, except for using tert-butyl 6-(4-amino-3-(2-fluoro-4-phenoxyphenyl)-1H-pyrazolo[3,4-d]pyrimidin-1-yl)-2-azabicyclo[2.2.1]heptane-2-carboxylate (100.0 mg, 0.19 mol) obtained in Step 36-3.

Step 36-5: Preparation of 1-(6-(4-amino-3-(4-(pyridin-4-yloxy)phenyl)-1H-pyrazolo[3,4-d]pyrimidin-1-yl)-2-azabicyclo[2.2.1]heptan-2-yl)prop-2-en-1-one

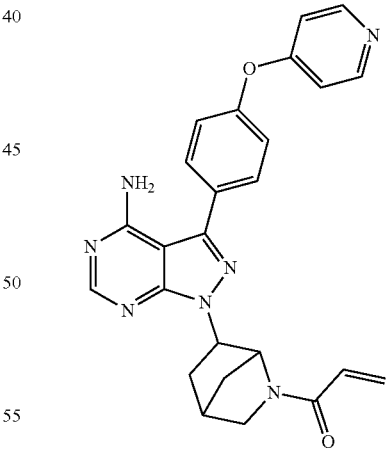

A title compound (1.0 mg, yield: 11.1%) was prepared in the same manner as in Step 32-4 of Example 32, except for using 1-(2-azabicyclo[2.2.1]heptan-6-yl)-3-(4-(pyridin-4-yloxy)-1H-pyrazolo[3,4-d]pyrimidin-4-amine (60 mg, 0.15 mmol) obtained in Step 36-4.

$^1$H NMR (500 MHz, CDCl$_3$): 7.65-7.68 (m, 2H), 7.47-7.56 (m, 4H), 7.24-7.26 (m, 2H), 6.96 (s, 1H), 6.31 (d, 1H), 6.12-6.18 (dd, 1H), 5.73 (d, 1H), 5.34-5.38 (m, 3H), 3.64-3.77 (m, 2H), 2.17-2.36 (m, 2H), 2.00-2.17 (m, 2H).

Example 37: Preparation of N-(4-(1-(2-acryloyl-2-azabicyclo[2.2.1]heptan-6-yl)-4-amino-1H-pyrazolo[3,4-d]pyrimidin-3-yl)phenyl)benzamide Step 37-1: Preparation of N-(4-(4,4,5,5-tetramethyl-1,3,2-dioxaborolan-2-yl)phenyl)benzamide

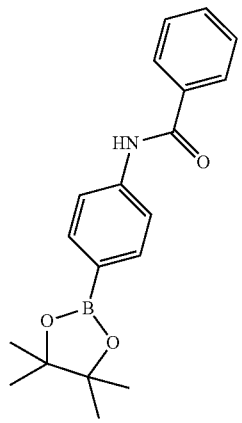 [SMILES: CC1(C)OB(c2ccc(NC(=O)c3ccccn3)cc2)OC1(C)C]

Benzyl chloride (248 uL, 2.28 mmol) and triethylamine (477 uL, 3.42 mmol) were dissolved in dichloromethane and then cooled to 0° C. 4-(4,4,5,5-tetramethyl-1,3,2-dioxaborolan-2-yl)aniline (0.5 g, 2.28 mmol) was slowly added dropwise to the reaction solution and stirred at room temperature for 15 hours. The reaction solution was diluted with ethyl acetate and washed with water. The extracted organic layer was dried over magnesium sulfate, filtered and concentrated under reduced pressure. The concentrated residue was washed with n-hexane to obtain a title compound (514.3 mg, yield 69.7%).

Step 37-2: Preparation of tert-butyl 6-(4-amino-3-(4-benzamidophenyl)-1H-pyrazolo[3,4-d]pyrimidin-1-yl)-2-azabicyclo[2.2.1]heptane-2-carboxylate

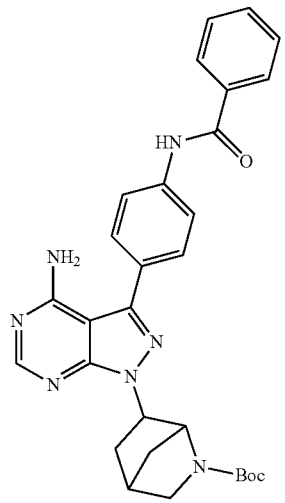 [SMILES: CC(C)(C)OC(=O)N1CC2CC1C(n1nc(-c3ccc(NC(=O)c4ccccn4)cc3)c3c(N)ncnc31)C2]

A title compound (85 mg, yield: 73.8%) was prepared in the same manner as in Step 31-2 of Example 31, except for using tert-butyl 6-(4-amino-3-iodo-1H-pyrazolo[3,4-d]pyrimidin-1-yl)-2-azabicyclo[2.2.1]heptane-2-carboxylate (100 mg, 0.22 mmol) obtained in Step 1-1 of Example 1 and N-(4-(4,4,5,5-tetramethyl-1,3,2-dioxaborolan-2-yl)phenyl)benzamide (88.5 mg, 0.27 mmol) obtained in Step 37-1.

Step 37-3: Preparation of N-(4-(4-amino-1-(2-azabicyclo[2.2.1]heptan-6-yl)-1H-pyrazolo[34-d]pyrimidin-3-yl)phenyl)benzamide

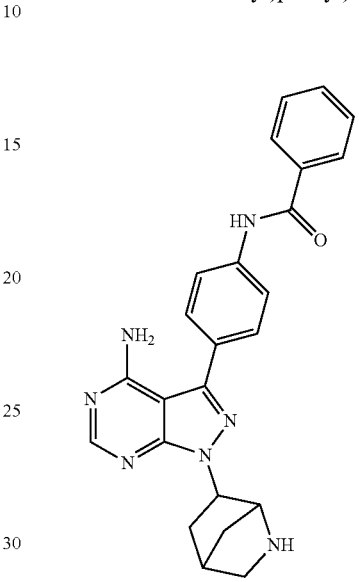

A title compound (70.7 mg, yield: 94.6%) was prepared in the same manner as in Step 31-3 of Example 31, except for using tert-butyl 6-(4-amino-3-(4-benzamidophenyl)-1H-pyrazolo[3,4-d]pyrimidin-1-yl)-2-azabicyclo[2.2.1]heptane-2-carboxylate (85.0 mg, 0.16 mol) obtained in Step 37-2.

Step 37-4: Preparation of N-(4-(1-(2-acryloyl-2-azabicyclo[2.2.1]heptan-6-yl)-4-amino-1H-pyrazolo[3,4-d]pyrimidin-3-yl)phenyl)benzamide

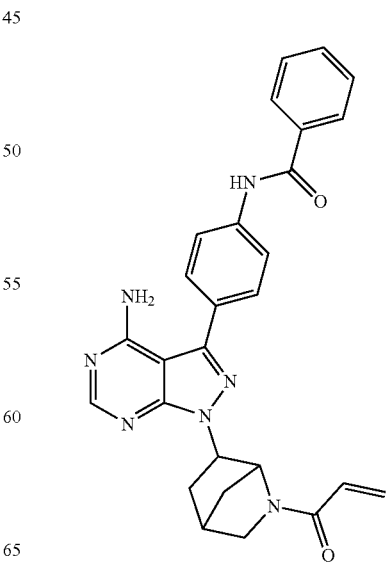

A title compound (22.8 mg, yield: 30.5%) was prepared in the same manner as in Step 32-4 of Example 32, except for using N-(4-(4-amino-1-(2-azabicyclo[2.2.1]heptan-6-yl)-1H-pyrazolo[3,4-d]pyrimidin-3-yl)phenyl)benzamide (70.7 mg, 0.15 mmol) obtained in Step 37-3.

$^1$H NMR (500 MHz, CDCl$_3$): 8.41 (s, 1H), 8.34 (s, 1H), 8.14 (s, 1H), 7.91-7.94 (m, 2H), 7.83-7.86 (m, 2H), 7.69 (d, 1H), 7.56-7.60 (m, 2H), 7.48-7.53 (m, 2H), 6.79-6.84 (dd, 1H), 6.32-6.47 (dd, 1H), 5.70-5.75 (dd, 1H), 5.59 (s, 2H), 5.07-5.20 (m, 1H), 4.53-4.89 (m, 1H), 3.46-3.55 (m, 1H), 3.25-3.19 (m, 1H), 2.84-2.86 (m, 2H), 2.28-2.60 (m, 1H), 2.16-2.21 (m, 1H), 1.68-1.75 (m, 1H).

Example 38: Preparation of N-(4-(1-(2-acryloyl-2-azabicyclo[2.2.1]heptan-6-yl)-4-amino-1H-pyrazolo[3,4-d]pyrimidin-3-yl)phenyl)picolinamide Step 38-1: Preparation of N-(4-(4,4,5,5-tetramethyl-1,3,2-dioxaborolan-2-yl)phenyl)picolinamide

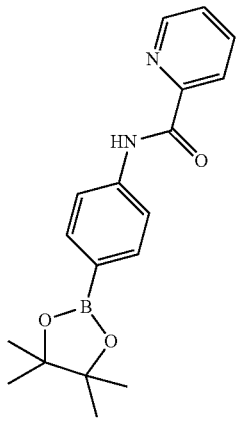

A title compound (610 mg, yield: 82.4%) was prepared in the same manner as in Step 37-1 of Example 37, except for using picolinoyl chloride (406.3 mg, 2.28 mmol).

Step 38-2: Preparation of tert-butyl 6-(4-amino-3-(4-(picolinamido)phenyl)-1H-pyrazolo[3,4-d]pyrimidin-1-yl)-2-azabicyclo[2.2.1]heptane-2-carboxylate

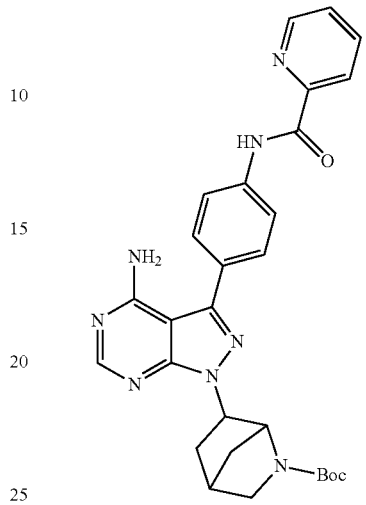

A title compound (26 mg, yield: 22.7%) was prepared in the same manner as in Step 31-2 of Example 31, except for using tert-butyl 6-(4-amino-3-iodo-1H-pyrazolo[3,4-d]pyrimidin-1-yl)-2-azabicyclo[2.2.1]heptane-2-carboxylate (100 mg, 0.22 mmol) obtained in Step 1-1 of Example 1 and N-(4-(4,4,5,5-tetramethyl-1,3,2-dioxaborolan-2-yl)phenyl)picolinamide (88.2 mg, 0.27 mmol) obtained in Step 38-1.

Step 38-3: Preparation of N-(4-(4-amino-1-(2-azabicyclo[2.2.1]heptan-6-yl)-1H-pyrazolo[3,4-d]pyrimidin-3-yl)phenyl)picolinamide

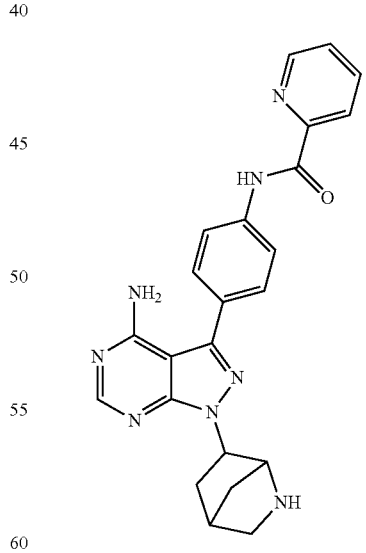

A title compound (22 mg, yield: 96.1%) was prepared in the same manner as in Step 31-3 of Example 31, except for using tert-butyl 6-(4-amino-3-(4-(picolinamido)phenyl)-1H-pyrazolo[3,4-d]pyrimidin-1-yl)-2-azabicyclo[2.2.1]heptane-2-carboxylate (26.0 mg, 0.05 mol) obtained in Step 38-2.

Step 38-4: Preparation of N-(4-(1-(2-acryloyl-2-azabicyclo[2.2.1]heptan-6-yl)-4-amino-1H-pyrazolo[3,4-d]pyrimidin-3-yl)phenyl)picolinamide

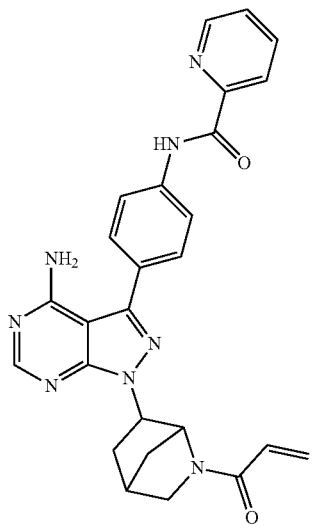 [SMILES: C=CC(=O)N1CC2CC1C(n1nc(-c3ccc(NC(=O)c4ccccn4)cc3)c3c(N)ncnc31)C2]

A title compound (22.8 mg, yield: 30.5%) was prepared in the same manner as in Step 32-4 of Example 32, except for using N-(4-(4-amino-1-(2-azabicyclo[2.2.1]heptan-6-yl)-1H-pyrazolo[3,4-d]pyrimidin-3-yl)phenyl)picolinamide (70.7 mg, 0.15 mmol) obtained in Step 38-3.

$^1$H NMR (500 MHz, CDCl$_3$): 10.21 (s, 1H), 8.64-8.65 (m, 1H), 8.29-8.32 (m, 1H), 7.88-7.99 (m, 3H), 7.67-7.68 (m, 2H), 7.51-7.53 (m, 1H), 6.66-6.79 (dd, 1H), 6.44-6.47 (dd, 1H), 5.75-5.77 (dd, 1H), 5.08-5.21 (m, 1H), 4.52-4.90 (m, 1H), 3.48-3.58 (m, 1H), 3.26-3.34 (m, 1H), 2.81-2.87 (m, 2H), 2.30-2.33 (m, 1H), 1.68-1.77 (m, 2H).

Example 39: Preparation of 1-(4-(1-(2-acryloyl-2-azabicyclo[2.2.1]heptan-6-yl)-4-amino-1H-pyrazolo[3,4-d]pyrimidin-3-yl)phenyl)-3-phenylurea

Step 39-1: Preparation of 1-phenyl-3-(4-(4,4,5,5-tetramethyl-1,3,2-dioxaborolan-2-yl)phenyl)urea

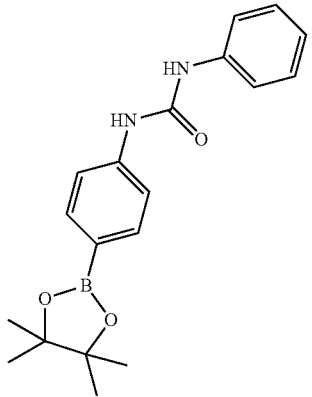 [SMILES: CC1(C)OB(c2ccc(NC(=O)Nc3ccccc3)cc2)OC1(C)C]

Phenylisocyanate (260.5 uL, 2.4 mmol) and 4-(4,4,5,5-tetramethyl-1,3,2-dioxaborolan-2-yl)aniline (0.5 g, 2.28 mmol) were dissolved in dichloromethane (5 mL) and then stirred at room temperature for 3 hours. The reaction solution was diluted with ethyl acetate and washed with aqueous sodium hydrogen carbonate solution. The extracted organic layer was dried with magnesium sulfate, filtered and then concentrated under reduced pressure. The concentrated residue was washed with n-hexane to obtain a title compound (613.1 mg, yield: 79.4%).

Step 39-2: Preparation of tert-butyl 6-(4-amino-3-(4-(3-phenylureido)phenyl)-1H-pyrazolo[3,4-d]pyrimidin-1-yl)-2-azabicyclo[2.2.1]heptane-2-carboxylate

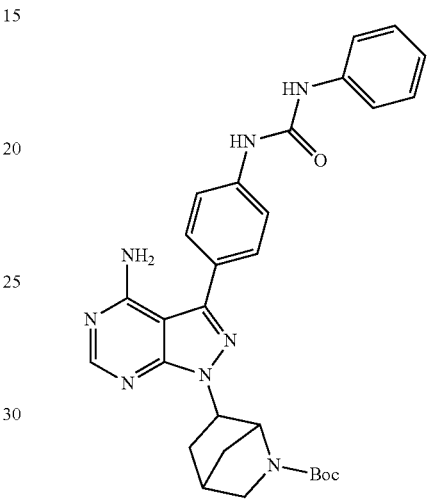

A title compound (56 mg, yield: 47.6%) was prepared in the same manner as in Step 31-2 of Example 31, except for using tert-butyl 6-(4-amino-3-iodo-1H-pyrazolo[3,4-d]pyrimidin-1-yl)-2-azabicyclo[2.2.1]heptane-2-carboxylate (100 mg, 0.22 mmol) obtained in Step 1-1 of Example 1 and 1-phenyl-3-(4-(4,4,5,5-tetramethyl-1,3,2-dioxaborolan-2-yl)phenyl)urea (92 mg, 0.27 mmol) obtained in Step 39-1.

Step 39-3: Preparation of 1-(4-(4-amino-1-(2-azabicyclo[2.2.1]heptan-6-yl)-1H-pyrazolo[3,4-d]pyrimidin-3-yl)phenyl)-3-phenylurea

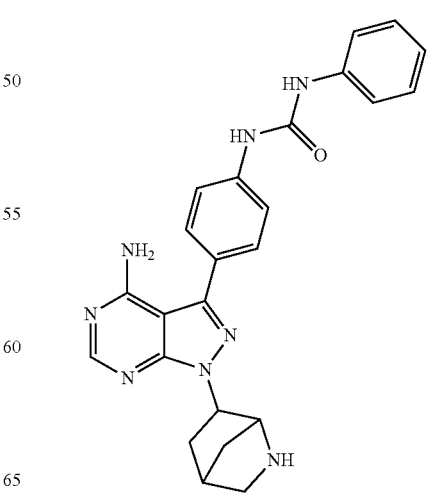

A title compound (50 mg, yield: 94.0%) was prepared in the same manner as in Step 31-3 of Example 31, except for using tert-butyl 6-(4-amino-3-(4-(3-phenylureido)phenyl)-1H-pyrazolo[3,4-d]pyrimidin-1-yl)-2-azabicyclo[2.2.1]heptane-2-carboxylate (56.0 mg, 0.1 mol) obtained in Step 39-2.

Step 39-4: Preparation of 1-(4-(1-(2-acryloyl-2-azabicyclo[2.2.1]heptan-6-yl)-4-amino-1H-pyrazolo[3,4-d]pyrimidin-3-yl)phenyl)-3-phenylurea

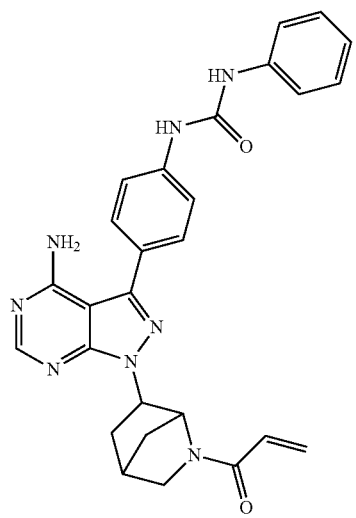 [SMILES: C=CC(=O)N1CC2CC1C(n1nc(-c3ccc(NC(=O)Nc4ccccc4)cc3)c3c(N)ncnc31)C2]

A title compound (42 mg, yield: 87.1%) was prepared in the same manner as in Step 32-4 of Example 32, except for using 1-(4-(4-amino-1-(2-azabicyclo[2.2.1]heptan-6-yl)-1H-pyrazolo[3,4-d]pyrimidin-3-yl)phenyl)-3-phenylurea (50 mg, 0.1 mmol) obtained in Step 39-3.

$^1$H NMR (500 MHz, CDCl$_3$): 8.19-8.33 (m, 1H), 8.05 (s, 1H), 7.66-7.70 (m, 1H), 7.56-7.60 (m, 2H), 7.32-7.51 (m, 3H), 7.00-7.13 (m, 2H), 6.44-6.55 (dd, 1H), 5.88-6.16 (dd, 1H), 5.04-5.29 (m, 1H), 4.52-4.83 (m, 1H), 3.63-3.77 (m, 1H), 3.30-3.46 (m, 1H), 2.72-2.90 (m, 2H), 2.22-2.28 (m, 1H), 1.64-1.74 (m, 2H).

Example 40: Preparation of 1-(6-(4-amino-3-(4-(m-tolyloxy)phenyl)-1H-pyrazolo[3,4-d]pyrimidin-1-yl)-2-azabicyclo[2.2.1]heptan-2-yl)prop-2-en-1-one Step 40-1: Preparation of 1-(4-bromophenoxy)-3-methylbenzene

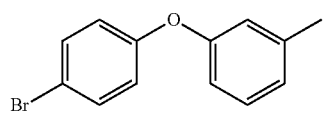

A title compound (262 mg, yield: 17.2%) was prepared in the same manner as in Step 34-1 of Example 34, except for using 4-bromophenol (1 g, 5.78 mmol) and 3-methylphenylboronic acid (0.86 g, 6.36 mmol).

Step 40-2: Preparation of 4,4,5,5-tetramethyl-2-(4-(m-tolyloxy)phenyl)-1,3,2-dioxaborolane

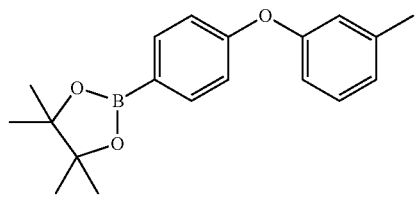

A title compound (270 mg, yield: 88.1%) was prepared in the same manner as in Step 31-1 of Example 31, except for using 1-(4-bromophenoxy)-3-methylbenzene (260 mg, 0.99 mmol) obtained in Step 40-1.

Step 40-3: Preparation of tert-butyl 6-(4-amino-3-(4-(m-tolyloxy)phenyl)-1H-pyrazolo[3,4-d]pyrimidin-1-yl)-2-azabicyclo[2.2.1]heptane-2-carboxylate

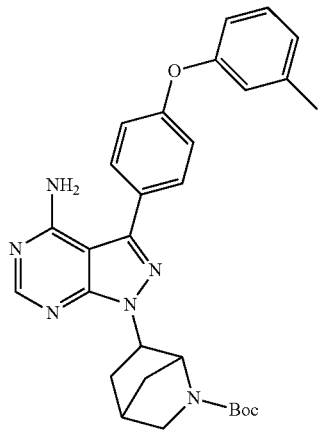 [SMILES: Cc1cccc(Oc2ccc(-c3nn(C4CC5CC4N(C(=O)OC(C)(C)C)C5)c4ncnc(N)c34)cc2)c1]

A title compound (207 mg, yield: 92.7%) was prepared in the same manner as in Step 31-2 of Example 31, except for using tert-butyl 6-(4-amino-3-iodo-1H-pyrazolo[3,4-d]pyrimidin-1-yl)-2-azabicyclo[2.2.1]heptane-2-carboxylate (200 mg, 4.35 mmol) obtained in Step 1-1 of Example 1 and 4,4,5,5-tetramethyl-2-(4-(m-tolyloxy)phenyl)-1,3,2-dioxaborolane (168.8 mg, 0.54 mmol) obtained in Step 40-2.

Step 40-4: Preparation of 1-(2-azabicyclo[2.2.1]heptan-6-yl)-3-(4-(m-tolyloxy)phenyl)-1H-pyrazolo[3,4-d]pyrimidin-4-amine

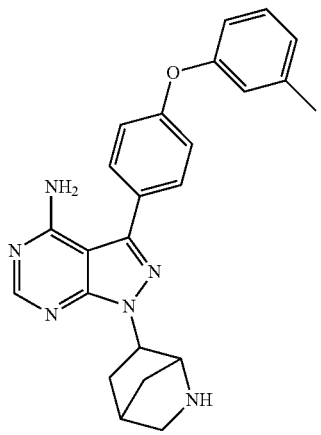 [SMILES: Cc1cccc(Oc2ccc(-c3nn(C4CC5CNC4C5)c4ncnc(N)c34)cc2)c1]

A title compound (150 mg, yield: 91.8%) was prepared in the same manner as in Step 31-3 of Example 31, except for using tert-butyl 6-(4-amino-3-(4-(m-tolyloxy)phenyl)-1H-pyrazolo[3,4-d]pyrimidin-1-yl)-2-azabicyclo[2.2.1]heptane-2-carboxylate (100.0 mg, 0.39 mol) obtained in Step 40-3.

Step 40-5: Preparation of 1-(6-(4-amino-3-(4-(m-tolyloxy)phenyl)-1H-pyrazolo[3,4-d]pyrimidin-1-yl)-2-azabicyclo[2.2.1]heptan-2-yl)prop-2-en-1-one

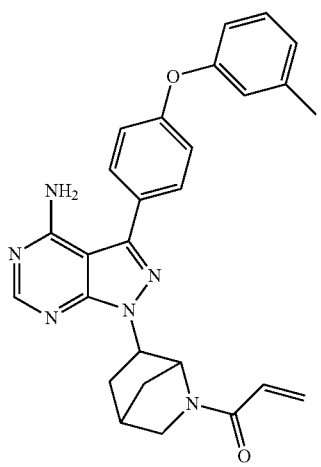 [SMILES: C=CC(=O)N1CC2CC1C(n1nc(-c3ccc(Oc4cccc(C)c4)cc3)c3c(N)ncnc31)C2]

A title compound (53.0 mg, yield: 58.2%) was prepared in the same manner as in Step 32-4 of Example 32, except for using 1-(2-azabicyclo[2.2.1]heptan-6-yl)-3-(4-(m-tolyloxy)phenyl)-1H-pyrazolo[3,4-d]pyrimidin-4-amine (80 mg, 0.18 mmol) obtained in Step 40-4.

$^1$H NMR (500 MHz, CDCl$_3$): 8.22-8.27 (m, 1H), 7.51-7.54 (m, 1H), 7.43-7.47 (m, 2H), 7.15-7.23 (m, 3H), 6.99-7.01 (dd, 1H), 6.92-6.95 (dd, 1H), 6.82-6.88 (dd, 1H), 6.45-6.50 (dd, 1H), 6.17-6.22 (m, 1H), 5.69-5.74 (m, 1H), 5.4.53-4.58 (m, 1H), 3.99-4.08 (m, 1H), 3.65-3.70 (m, 2H), 2.75-2.82 (m, 2H), 2.06-2.08 (m, 1H), 1.58-1.71 (m, 2H).

Example 41: Preparation of 1-(6-(4-amino-3-(4-(3-methoxyphenoxy)phenyl)-1H-pyrazolo[3,4-d]pyrimidin-1-yl)-2-azabicyclo[2.2.1]heptan-2-yl)prop-2-en-1-one

Step 41-1: Preparation of 4-(4,4,5,5-tetramethyl-1,3,2-dioxaborolan-2-yl)phenol

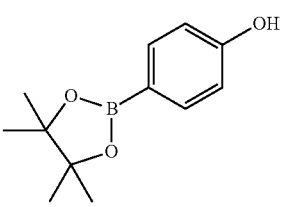 [SMILES: CC1(C)OB(c2ccc(O)cc2)OC1(C)C]

4-Bromophenol (5 g, 28.9 mmol), bis(pinacolato)diboron (8.8 g, 34.7 mmol), potassium acetate (8.5 g, 86.7 mmol), and [1,1'-bis(diphenylphosphino)ferrocene]diclopalladium (II) (2.1 g, 2.9 mol) were dissolved in 1,4-dioxane (50 mL). The reaction solution was heated under reflux at 110° C. for 15 hours. The reaction solution was diluted with ethyl acetate and washed with water. The extracted organic layer was dried over magnesium sulfate, filtered and concentrated to obtain a title compound (6 mg, yield: 94.3%).

Step 41-2: Preparation of 2-(4-(3-methoxyphenoxy)phenyl)-4,4,5,5-tetramethyl-1,3,2-dioxaborolane

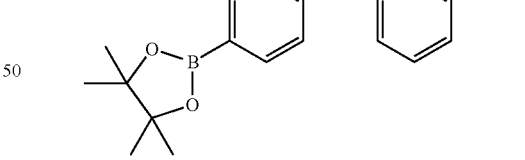

4-(4,4,5,5-tetramethyl-1,3,2-dioxaborolan-2-yl)phenol (1 g, 4.54 mmol) obtained in Step 41-1, copper(II) acetate (760 mg, 5.0 mmol) and triethylamine (1.3 mL, 9.1 mmol) were sequentially added dropwise thereto, dissolved in anhydrous dichloromethane (20 mL) and then stirred for 5 minutes. 3-Methoxyphenylboronic acid was added dropwise to the reaction solution, and the mixture was stirred at room temperature for 24 hours. The reaction solution was filtered using diatomaceous earth and concentrated under reduced pressure. The residue was purified by column chromatography (ethyl acetate:n-hexane=1:50) to obtain a title compound (120 mg, yield: 8%).

Step 41-3: Preparation of tert-butyl 3-(4-amino-3-(4-(3-methoxyphenoxy))phenyl)-1H-pyrazolo[3,4-d]pyrimidin-1-yl)-2-azabicyclo[2.2.1]heptane-2-carboxylate

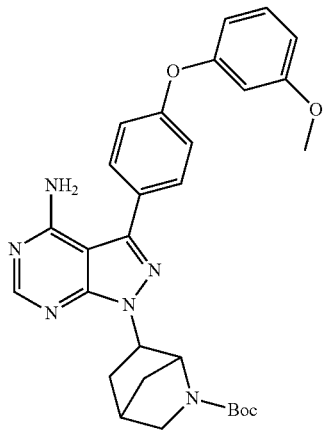 [SMILES: COc1cccc(Oc2ccc(-c3nn(C4CC5CC4N(C(=O)OC(C)(C)C)C5)c4ncnc(N)c34)cc2)c1]

A title compound (88 mg, yield: 80.5%) was prepared in the same manner as in Step 31-2 of Example 31, except for using tert-butyl 6-(4-amino-3-iodo-1H-pyrazolo[3,4-d]pyrimidin-1-yl)-2-azabicyclo[2.2.1]heptane-2-carboxylate (100 mg, 0.22 mmol) obtained in Step 1-1 of Example 1 and 2-(4-(3-methoxyphenoxy)phenyl)-4,4,5,5-tetramethyl-1,3,2-dioxaborolane (89 mg, 0.27 mmol) obtained in Step 41-2.

Step 41-4: Preparation of 1-(2-azabicyclo[2.2.1]heptan-6-yl)-3-(4-(3-methoxyphenoxy)phenyl)-1H-pyrazolo[3,4-d]pyrimidin-4-amine

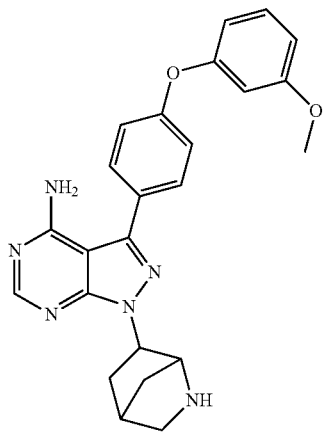 [SMILES: COc1cccc(Oc2ccc(-c3nn(C4CC5CNC4C5)c4ncnc(N)c34)cc2)c1]

A title compound (60.0 mg, yield: 78.1%) was prepared in the same manner as in Step 31-3 of Example 31, except for using tert-butyl 3-(4-amino-3-(4-(3-methoxyphenoxy))phenyl)-1H-pyrazolo[3,4-d]pyrimidin-1-yl)-2-azabicyclo[2.2.1]heptane-2-carboxylate (88.0 mg, 0.18 mol) obtained in Step 41-3.

Step 41-5: Preparation of 1-(6-(4-amino-3-(4-(3-methoxyphenoxy)phenyl)-1H-pyrazolo[3,4-d]pyrimidin-1-yl)-2-azabicyclo[2.2.1]heptan-2-yl)prop-2-en-1-one

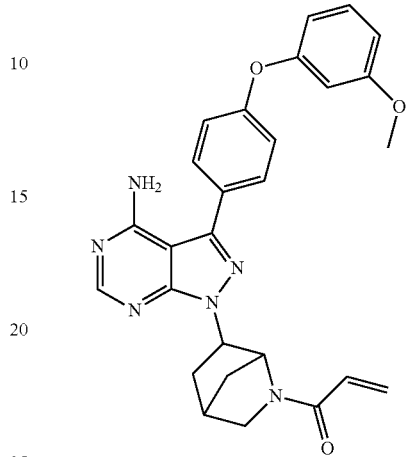

A title compound (50.0 mg, yield: 75.1%) was prepared in the same manner as in Step 32-4 of Example 32, except for using 1-(2-azabicyclo[2.2.1]heptan-6-yl)-3-(4-(3-methoxyphenoxy)phenyl)-1H-pyrazolo[3,4-d]pyrimidin-4-amine (60 mg, 0.14 mmol) obtained in Step 41-4.

$^1$H NMR (500 MHz, CDCl$_3$): 8.39-8.41 (m, 1H), 7.63-7.65 (m, 1H), 7.44-7.48 (m, 1H), 7.21-7.21 (m, 1H), 7.15-7.18 (m, 1H), 7.02-7.04 (m, 1H), 6.79-6.84 (dd, 1H), 6.64-6.67 (m, 2H), 6.64-6.67 (m, 1H), 6.37-6.39 (m, 1H), 5.73-5.77 (m, 1H), 5.48-5.54 (m, 1H), 5.08-5.23 (m, 1H), 4.54 (s, 1H), 3.88 (s, 3H), 3.64-3.81 (m, 1H), 3.47-3.50 (m, 1H), 3.25-3.34 (dd, 1H), 2.85-2.87 (m, 2H), 2.78-7.30 (d, 1H), 1.68-1.73 (m, 2H).

Example 42: Preparation of 1-(6-(4-amino-3-(4-(3-(dimethylamino)phenoxy)phenyl)-1H-pyrazolo[3,4-d]pyrimidin-1-yl)-2-azabicyclo[2.2.1]heptan-2-yl)prop-2-en-1-one

Step 42-1: Preparation of N,N-dimethyl-3-(4-(4,4,5,5-tetramethyl-1,3,2-dioxaborolan-2-yl)phenoxy)aniline

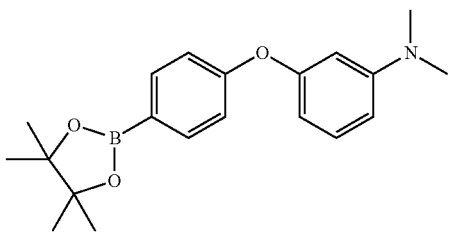

4-(4,4,5,5-tetramethyl-1,3,2-dioxaborolan-2-yl)phenol (1 g, 4.54 mmol) obtained in Step 41-1, copper (II) acetate (990 mg, 5.0 mmol) and triethylamine (1.9 mL, 9.1 mmol) were sequentially added dropwise thereto, and then dissolved in anhydrous dichloromethane (20 mL) and stirred for 5 minutes. 3-Methoxyphenylboronic acid was added dropwise to the reaction solution, and the mixture was stirred at room temperature for 24 hours. The reaction solution was filtered using diatomaceous earth, and concentrated under reduced pressure. The residue was purified by column chromatography (ethyl acetate:n-hexane=1:50) to obtain a title compound (486.8 mg, yield: 31.6%).

Step 42-2: Preparation of 1-(2-azabicyclo[2.2.1]heptan-6-yl)-3-iodo-1H-pyrazolo[3,4-d]pyrimidin-4-amine

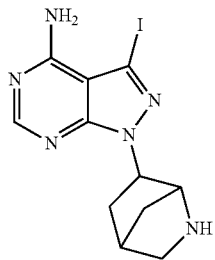 [SMILES: Nc1ncnc2c1c(I)nn2C1CC2CNC1C2]

After tert-butyl 6-(4-amino-3-iodo-1H-pyrazolo[3,4-d]pyrimidin-1-yl)-2-azabicyclo[2.2.1]heptane-2-carboxylate (200 mg, 0.44 mmol) obtained in Step 1-1 of Example 1 was dissolved in 1,4-dioxane (2 mL), 1 N hydrochloric acid aqueous solution (5 mL) dissolved in dioxane was added thereto, and then stirred at room temperature for 3 hours. Upon completion of the reaction, the mixture was concentrated under reduced pressure to obtain a title compound (150.0 mg, yield: 87.2%).

Step 42-3: Preparation of 1-(6-(4-amino-3-iodo-1H-pyrazolo[3,4-d]pyrimidin-1-yl)-2-azabicyclo[2.2.1]heptan-2-yl)prop-2-en-1-one

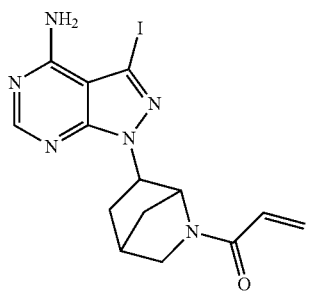 [SMILES: C=CC(=O)N1CC2CC1C(n1nc(I)c3c(N)ncnc31)C2]

1-(2-azabicyclo[2.2.1]heptan-6-yl)-3-iodo-1H-pyrazolo[3,4-d]pyrimidin-4-amine (150 mg, 0.38 mmol) obtained in Step 42-2 was dissolved in tetrahydrofuran (3 mL) and water (200 uL) and then cooled to 0° C. to which sodium bicarbonate (64.2 mg, 0.7 mmol) was added. Acryl chloride (31 uL, 0.38 mmol) was slowly added to the reaction solution and then stirred at the same temperature for 30 minutes. Upon completion of the reaction, the reaction solution was diluted with ethyl acetate and washed with saturated sodium chloride solution. The organic layer was collected, dried over magnesium sulfate, filtered and then concentrated under reduced pressure. The residue was purified by column chromatography (chloromethane:methanol=9:1) to obtain a title compound (150.0 mg, yield: 83.4%).

Step 42-4: Preparation of 1-(6-(4-amino-3-(4-(3-(dimethylamino)phenoxy)phenyl)-1H-pyrazolo[3,4-d]pyrimidin-1-yl)-2-azabicyclo[2.2.1]heptan-2-yl)prop-2-en-1-one

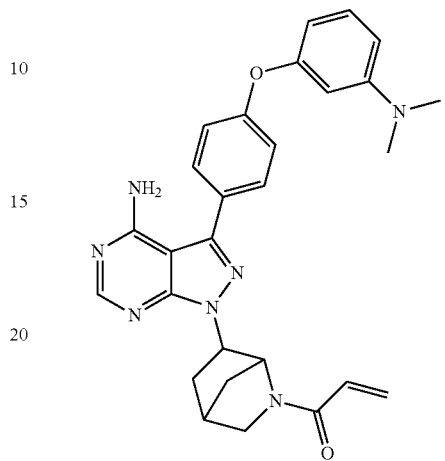

After 1-(6-(4-amino-3-iodo-1H-pyrazolo[3,4-d]pyrimidin-1-yl)-2-azabicyclo[2.2.1]heptan-2-yl)prop-2-en-1-one (130 mg, 0.32 mmol) obtained in Step 42-3 was dissolved in 1,4-dioxane (2 mL) and water (300 uL), N,N-dimethyl-3-(4-(4,4,5,5-tetramethyl-1,3,2-dioxaborolan-2-yl)phenoxy)aniline (118. mg, 0.35 mmol) obtained in Step 42-1, potassium carbonate (219 mg, 1.58 mmol) and [1,1'-bis(diphenylphosphino)ferrocene]diclopalladium(II) (16.2 mg, 0.02 mmol) were sequentially added thereto, and the mixture was refluxed and stirred at 110° C. for 90 minutes. Upon completion of the reaction, the mixture was diluted with ethyl acetate and washed with saturated sodium chloride solution. The organic layer was collected, dried over magnesium sulfate, filtered and then concentrated under reduced pressure. The residue was purified by column chromatography (chloromethane:methanol=9:1) to obtain a title compound (65 mg, yield: 41.4%).

$^1$H NMR (500 MHz, CDCl$_3$): 8.38-8.41 (m, 1H), 7.57-7.63 (m, 2H), 7.47-7.50 (m, 1H), 7.38-7.42 (m, 1H), 7.20-7.24 (t, 1H), 7.14-7.16 (m, 2H), 6.79-6.84 (m, 1H), 6.54-6.56 (dd, 1H), 6.39-6.48 (m, 2H), 5.71-5.77 (m, 1H), 5.46 (s, 2H), 5.07-5.08 (m, 1H), 4.54-4.91 (d, 1H), 4.26-4.72 (dd, 1H), 3.47-3.56 (m, 1H), 3.25-3.33 (m, 1H), 2.96 (s, 6H), 2.28-2.60 (dd, 1H), 2.10-2.14 (m, 1H).

Example 43: Preparation of 1-(6-(4-amino-3-(4-(3-(trifluoromethyl)phenoxy)phenyl)-1H-pyrazolo[3,4-d]pyrimidin-1-yl)-2-azabicyclo[2.2.1]heptan-2-yl)prop-2-en-1-one Step 43-1: Preparation of 1-(4-bromophenoxy)-3-(trifluoromethyl)benzene

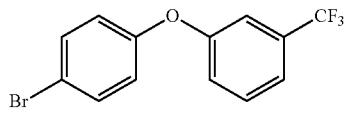 [SMILES: FC(F)(F)c1cccc(Oc2ccc(Br)cc2)c1]

A title compound (302 mg, yield: 16.5%) was prepared in the same manner as in Step 34-1 of Example 34, except for using 4-bromophenol (1 g, 5.78 mmol) and 3-(trifluoromethyl)boronic acid (1.21 g, 6.36 mmol).

Step 43-2: Preparation of 4,4,5,5-tetramethyl-2-(4-(3-(trifluoromethyl)phenoxy)phenyl)-1,3,2-dioxaborolane

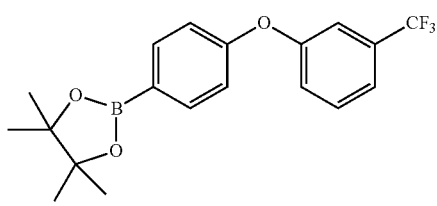 [SMILES: CC1(C)OB(c2ccc(Oc3cccc(C(F)(F)F)c3)cc2)OC1(C)C]

A title compound (172 mg, yield: 50.0%) was prepared in the same manner as in Step 31-1 of Example 31, except for using 1-(4-bromophenoxy)-3-(trifluoromethyl)benzene (300 mg, 0.95 mmol) obtained in Step 43-1.

Step 43-3: Preparation of tert-butyl 6-(4-amino-3-(4-(3-(trifluoromethyl)phenoxy)phenyl)-1H-pyrazolo[3,4-d]pyrimidin-1-yl)-2-azabicyclo[2.2.1]heptane-2-carboxylate

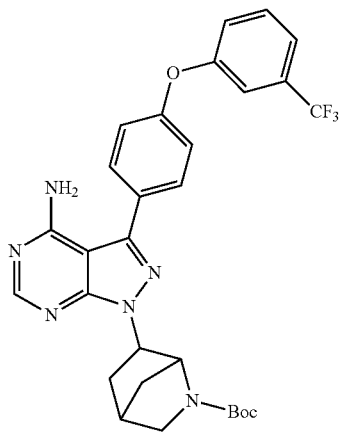 [SMILES: CC(C)(C)OC(=O)N1CC2CC1C(n1nc(-c3ccc(Oc4cccc(C(F)(F)F)c4)cc3)c3c(N)ncnc31)C2]

A title compound (196 mg, yield: 79.4%) was prepared in the same manner as in Step 31-2 of Example 31, except for using tert-butyl 6-(4-amino-3-iodo-1H-pyrazolo[3,4-d]pyrimidin-1-yl)-2-azabicyclo[2.2.1]heptane-2-carboxylate (200 mg, 4.35 mmol) obtained in Step 1-1 of Example 1 and 4,4,5,5-tetramethyl-2-(4-(3-(trifluoromethyl)phenoxy)phenyl)-1,3,2-dioxaborolane (198.2 mg, 0.54 mmol) obtained in Step 43-2.

Step 43-4: Preparation of 1-(2-azabicyclo[2.2.1]heptan-6-yl)-3-(4-(3-(trifluoromethyl)phenoxy)phenyl)-1H-pyrazolo[3,4-d]pyrimidin-4-amine

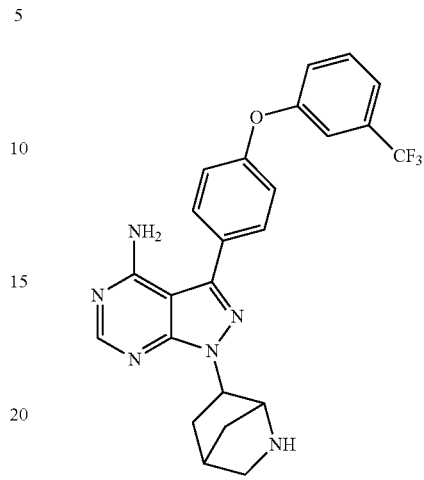

A title compound (150 mg, yield: 88.9%) was prepared in the same manner as in Step 31-3 of Example 31, except for using tert-butyl-6-(4-amino-3-(4-(3-(trifluoromethyl)phenoxy)phenyl)-1H-pyrazolo[3,4-d]pyrimidin-1-yl)-2-azabicyclo[2.2.1]heptan-2-carboxylate (200.0 mg, 0.39 mol) obtained in Step 43-3.

Step 43-5: Preparation of 1-(6-(4-amino-3-(4-(3-(trifluoromethyl)phenoxy)phenyl)-1H-pyrazolo[3,4-d]pyrimidin-1-yl)-2-azabicyclo[2.2.1]heptan-2-yl)prop-2-en-1-one

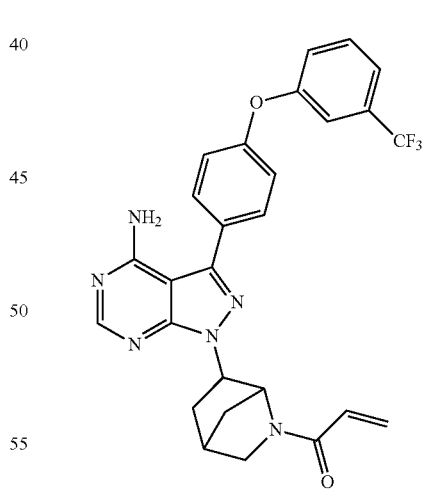

A title compound (118.0 mg, yield: 78.5%) was prepared in the same manner as in Step 32-4 of Example 32, except for using 1-(2-azabicyclo[2.2.1]heptan-6-yl)-3-(4-(3-(trifluoromethyl)phenoxy)phenyl)-1H-pyrazolo[3,4-d]pyrimidin-4-amine (150 mg, 0.36 mmol) obtained in Step 43-4.

$^1$H NMR (500 MHz, CDCl$_3$): 8.35-8.42 (m, 1H), 7.68-7.71 (m, 1H), 7.46-7.52 (m, 1H), 7.41-7.43 (m, 1H), 7.33 (s,

1H), 7.17-7.19 (m, 2H), 6.78-6.84 (dd, 1H), 6.33-6.47 (m, 1H), 5.71-5.77 (dd, 1H), 5.57 (s, 2H), 5.08-5.21 (m, 1H), 4.85-4.93 (m, 1H), 4.47-4.54 (m, 1H), 3.63-3.78 (m, 1H), 3.45-3.56 (m, 1H), 3.25-3.34 (m, 1H), 2.85-2.87 (m, 2H), 2.04-2.29 (m, 2H), 1.17-1.78 (m, 2H).

Example 44: Preparation of (E)-1-(6-(4-amino-3-(4-phenoxyphenyl)-1H-pyrazolo[3,4-d]pyrimidin-1-yl)-2-azabicyclo[2.2.1]heptan-2-yl)-4-bromobut-2-en-1-one

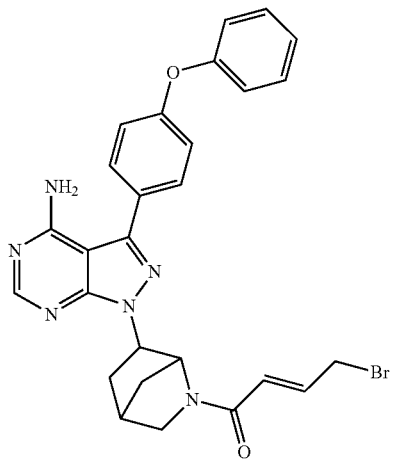 [SMILES: Nc1ncnc2c1c(-c1ccc(Oc3ccccc3)cc1)nn2C1CC2CC1N(C(=O)/C=C/CBr)C2]

1-(2-azabicyclo[2.2.1]heptan-6-yl)-3-(4-phenoxyphenyl)-1H-pyrazolo[3,4-d]pyrimidin-4-amine (60 mg, 1.2 mmol) obtained in Step 1-3 of Example 1 was dissolved in dichloromethane (12 mL), and then cooled to 0° C., to which triethylamine (801 uL, 5.8 mmol) was added. After stirring for 5 minutes, (E)-4-bromobut-2-enoyl chloride (230 mg, 1.3 mmol) was added and the mixture was stirred at room temperature for 1 hour. Upon completion of the reaction, the reaction solution was diluted with ethyl acetate and washed with saturated sodium chloride solution. The organic layer was collected, dried over magnesium sulfate, and then concentrated under reduced pressure. The residue was purified by column chromatography (chloromethane:methanol=9:1) to obtain a title compound (450 mg, yield: 66%).

$^1$H NMR (500 MHz, CDCl$_3$): 8.22-8.24 (m, 1H), 7.65-7.70 (m, 2H), 7.32-7.39 (m, 2H), 7.02-7.22 (m, 5H), 6.78-6.88 (m, 1H), 6.55-6.65 (m, 1H), 4.88-4.95 (m, 1H), 4.50-4.55 (m, 1H), 4.17-4.22 (m, 1H), 3.05-3.10 (m, 1H), 2.75-2.80 (m, 1H), 2.35-2.43 (m, 1H), 2.02-2.25 (m, 2H), 1.85-1.95 (m, 1H), 1.45-1.55 (m, 1H), 1.35-1.40 (m, 1H).

Example 45: Preparation of (E)-1-(6-(4-amino-3-(4-phenoxyphenyl)-1H-pyrazolo[3,4-d]pyrimidin-1-yl)-2-azabicyclo[2.2.1]heptan-2-yl)-4-(dimethylamino)but-2-en-1-one

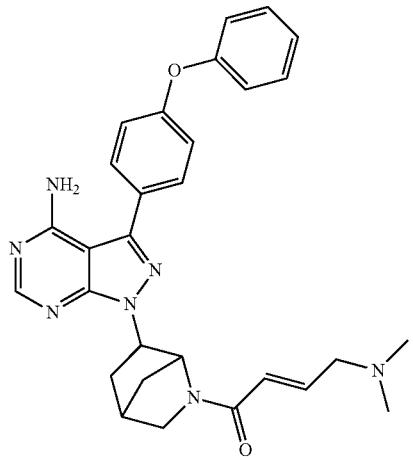 [SMILES: CN(C)C/C=C/C(=O)N1CC2CC1C(n1nc(-c3ccc(Oc4ccccc4)cc3)c3c(N)ncnc31)C2]

After (E)-1-(6-(4-amino-3-(4-phenoxyphenyl)-1H-pyrazolo[3,4-d]pyrimidin-1-yl)-2-azabicyclo[2.2.1]heptan-2-yl)-4-bromobut-2-en-1-one (30 mg, 0.055 mmol) obtained in Example 44 was dissolved in N,N-dimethylformamide (2 mL), N,N-dimethylamine (41 mg, 0.083 mmol) and sodium bicarbonate (38 mg, 0.28 mmol) were added thereto, and then stirred at 60° C. for 12 hours. Upon completion of the reaction, the reaction solution was diluted with ethyl acetate and washed with saturated sodium chloride solution. The organic layer was collected, dried over magnesium sulfate, and then concentrated under reduced pressure. The residue was purified by column chromatography (chloromethane:methanol=9:1) to obtain a title compound (17 mg, yield: 59%).

$^1$H NMR (500 MHz, CDCl$_3$): 8.38-8.41 (m, 1H), 7.63-7.64 (m, 2H), 7.38-7.41 (m, 2H), 7.14-7.20 (m, 3H), 7.08-7.10 (m, 2H), 6.78-6.83 (m, 1H), 6.36-6.48 (m, 1H), 5.71-5.77 (m, 1H), 5.56 (s, 2H), 5.08-5.23 (m, 1H), 4.53-4.91 (m, 1H), 3.54-3.56 (m, 1H), 3.26-3.34 (m, 1H), 2.57-2.86 (m, 2H), 2.30-2.51 (m, 1H), 2.12-2.27 (m, 1H), 1.70-1.74 (m, 1H).

Example 46: Preparation of 4-(1-(2-acryloyl-2-azabicyclo[2.2.1]heptan-6-yl)-4-amino-1H-pyrazolo[3,4-d]pyrimidin-3-yl)-N-(3-ethylphenyl)benzamide Step 46-1: Preparation of N-(3-ethylphenyl)-4-(4,4,5,5-tetramethyl-1,3,2-dioxaborolan-2-yl)benzamide

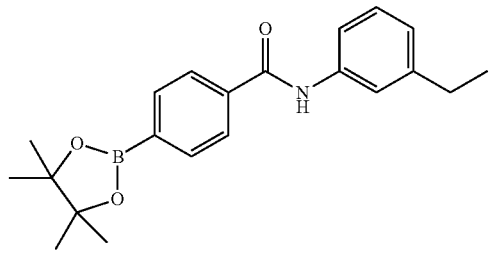 [SMILES: CCc1cccc(NC(=O)c2ccc(B3OC(C)(C)C(C)(C)O3)cc2)c1]

A title compound (102 mg, yield: 72%) was prepared in the same manner as in Step 4-2 of Example 4, except for using 4-(4,4,5,5-tetramethyl-1,3,2-dioxaborolan-2-yl)benzoyl chloride (72 mg, 0.54 mmol) obtained in Step 4-1 of Example 4.

Step 46-2: Preparation of tert-butyl 6-(4-amino-3-(4-((3-ethylphenyl)carbamoyl)phenyl)-1H-pyrazolo[3,4-d]pyrimidin-1-yl)-2-azabicyclo[2.2.1]heptane-2-carboxylate

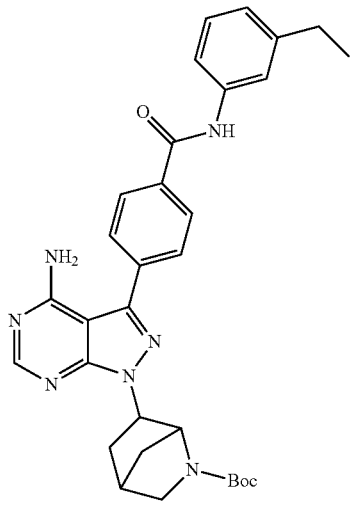 [SMILES: CCc1cccc(NC(=O)c2ccc(-c3nn(C4CC5CC4N(C(=O)OC(C)(C)C)C5)c4ncnc(N)c34)cc2)c1]

A title compound (111 mg, yield: 92%) was prepared in the same manner as in Step 1-2 of Example 1, except for using N-(3-ethylphenyl)-4-(4,4,5,5-tetramethyl-1,3,2-dioxaborolan-2-yl)benzamide (96 mg, 0.27 mmol) obtained in Step 46-1 and tert-butyl 6-(4-amino-3-iodo-1H-pyrazolo[3,4-d]pyrimidin-1-yl)-2-azabicyclo[2.2.1]heptane-2-carboxylate (100 mg, 0.22 mmol).

Step 46-3: Preparation of 4-(4-amino-1-(2-azabicyclo[2.2.1]heptan-6-yl)-1H-pyrazolo[3,4-d]pyrimidin-3-yl)-N-(3-ethylphenyl)benzamide

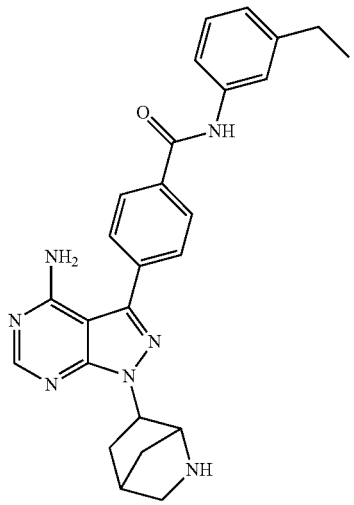 [SMILES: CCc1cccc(NC(=O)c2ccc(-c3nn(C4CC5CNC4C5)c4ncnc(N)c34)cc2)c1]

A title compound (70 mg, yield: 77%) was prepared in the same manner as in Step 1-3 of Example 1, except for using tert-butyl 6-(4-amino-3-(4-((3-ethylphenyl)carbamoyl)phenyl)-1H-pyrazolo[3,4-d]pyrimidin-1-yl)-2-azabicyclo[2.2.1]heptane-2-carboxylate (111 mg, 0.20 mmol) obtained in Step 46-2.

Step 46-4: Preparation of 4-(1-(2-acryloyl-2-azabicyclo[2.2.1]heptan-6-yl)-4-amino-1H-pyrazolo[3,4-d]pyrimidin-3-yl)-N-(3-ethylphenyl)benzamide

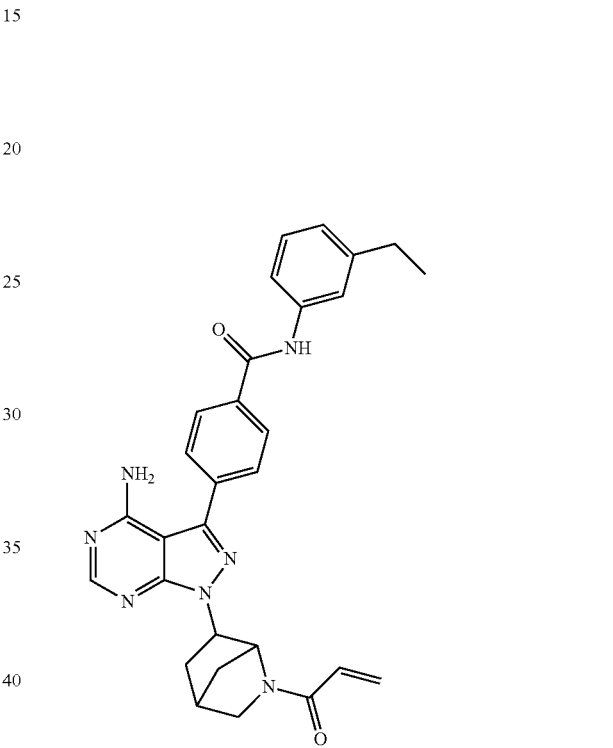

A title compound (47 mg, yield: 70%) was prepared in the same manner as in Step 1-4 of Example 1, except for using 4-(4-amino-1-(2-azabicyclo[2.2.1]heptan-6-yl)-1H-pyrazolo[3,4-d]pyrimidin-3-yl)-N-(3-ethylphenyl)benzamide (60 mg, 0.13 mmol) obtained in Step 46-3 and acryloyl chloride (12 uL, 0.15 mmol).

$^1$H NMR (500 MHz, CDCl$_3$): 8.38-8.41 (m, 1H), 7.99-8.10 (m, 3H), 7.78-7.82 (m, 2H), 7.50-7.57 (m, 1H), 7.41-7.47 (m, 1H), 7.28-7.31 (m, 1H), 7.03-7.11 (m, 1H), 6.37-6.81 (m, 1H), 6.44-6.48 (m, 1H), 5.82 (s, 2H), 5.75-5.78 (m, 1H), 5.05-5.19 (m, 1H), 4.50-4.78 (m, 1H), 3.45-3.50 (m, 1H), 3.28-3.30 (m, 1H), 2.52-2.81 (m, 2H), 2.67 (m, 2H), 2.25-2.40 (m, 1H), 2.12-2.21 (m, 1H), 1.72-1.73 (m, 1H), 1.24-1.27 (m, 3H).

Example 47: Preparation of 4-(1-(2-acryloyl-2-azabicyclo[2.2.1]heptan-6-yl)-4-amino-1H-pyrazolo[3,4-d]pyrimidin-3-yl)-N-(3-isopropylphenyl)benzamide Step 47-1: Preparation of N-(3-isopropylphenyl)-4-(4,4,5,5-tetramethyl-1,3,2-dioxaborolan-2-yl)benzamide

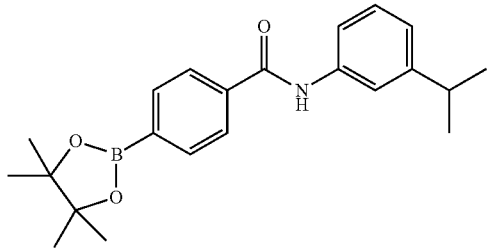 [SMILES: CC(C)c1cccc(NC(=O)c2ccc(B3OC(C)(C)C(C)(C)O3)cc2)c1]

A title compound (110 mg, yield: 75%) was prepared in the same manner as in Step 4-2 of Example 4, except for using 4-(4,4,5,5-tetramethyl-1,3,2-dioxaborolan-2-yl)benzoyl chloride 107 mg, 0.40 mmol) obtained in Step 4-1 of Example 4 and 3-isopropylaniline (59 mg, 0.44 mmol).

Step 47-2: Preparation of tert-butyl 6-(4-amino-3-(4-((3-isopropylphenyl)carbamoyl)phenyl)-1H-pyrazolo[3,4-d]pyrimidin-1-yl)-2-azabicyclo[2.2.1]heptane-2-carboxylate

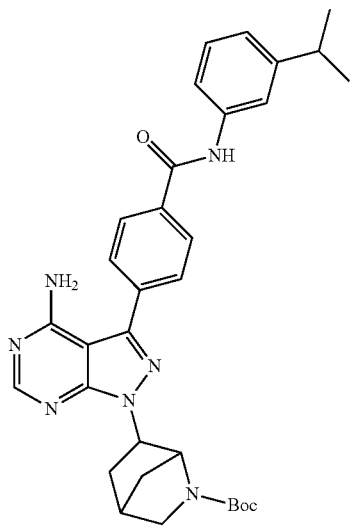 [SMILES: CC(C)c1cccc(NC(=O)c2ccc(-c3nn(C4CC5CC4N(C(=O)OC(C)(C)C)C5)c4ncnc(N)c34)cc2)c1]

A title compound (108 mg, yield: 87%) was prepared in the same manner as in Step 1-2 of Example 1, except for using N-(3-isopropylphenyl)-4-(4,4,5,5-tetramethyl-1,3,2-dioxaborolan-2-yl)benzamide (80 mg, 0.22 mmol) obtained in Step 47-1 and tert-butyl 6-(4-amino-3-iodo-1H-pyrazolo[3,4-d]pyrimidin-1-yl)-2-azabicyclo[2.2.1]heptane-2-carboxylate (100 mg, 0.18 mmol).

Step 47-3: Preparation of 4-(4-amino-1-(2-azabicyclo[2.2.1]heptan-6-yl)-1H-pyrazolo[3,4-d]pyrimidin-3-yl)-N-(3-isopropylphenyl)benzamide

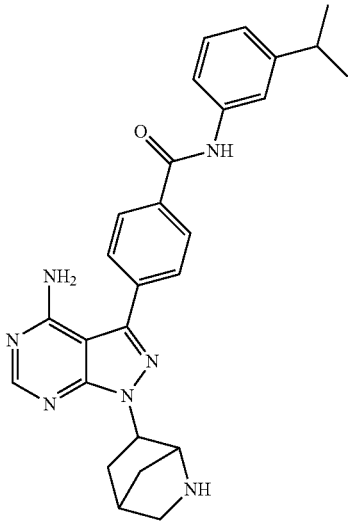 [SMILES: CC(C)c1cccc(NC(=O)c2ccc(-c3nn(C4CC5CNC4C5)c4ncnc(N)c34)cc2)c1]

A title compound (86 mg, yield: 72%) was prepared in the same manner as in Step 1-3 of Example 1, except for using tert-butyl 6-(4-amino-3-(4-((3-isopropylphenyl)carbamoyl)phenyl)-1H-pyrazolo[3,4-d]pyrimidin-1-yl)-2-azabicyclo[2.2.1]heptane-2-carboxylate (108 mg, 0.23 mmol) obtained in Step 47-2.

Step 47-4: Preparation of 4-(1-(2-acryloyl-2-azabicyclo[2.2.1]heptan-6-yl)-4-amino-1H-pyrazolo[3,4-d]pyrimidin-3-yl)-N-(3-isopropylphenyl)benzamide

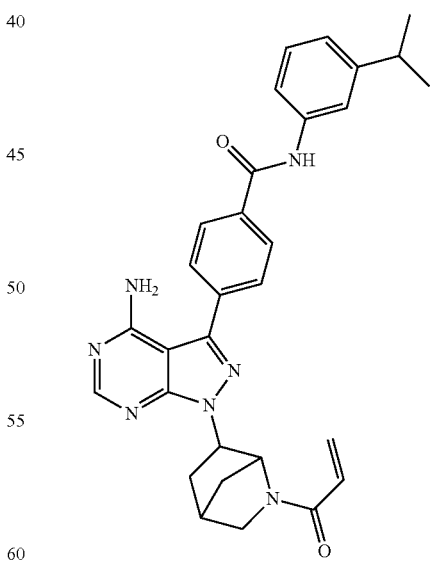

A title compound (40 mg, yield: 60%) was prepared in the same manner as in Step 1-4 of Example 1, except for using 4-(4-amino-1-(2-azabicyclo[2.2.1]heptan-6-yl)-1H-pyrazolo[3,4-d]pyrimidin-3-yl)-N-(3-isopropylphenyl)benzamide (60 mg, 0.13 mmol) obtained in Step 47-3 and acryloyl chloride (11 uL, 0.14 mmol).

¹H NMR (500 MHz, CDCl₃): 8.33-8.41 (m, 1H), 7.93-8.10 (m, 3H), 7.79-7.82 (m, 2H), 7.40-7.52 (m, 2H), 7.21-7.25 (m, 1H), 7.04-7.06 (m, 1H), 6.32-6.81 (m, 1H), 6.44-6.48 (m, 1H), 5.78-5.5.88 (m, 1H), 5.77 (s, 2H), 4.92-5.20 (m, 1H), 4.52-4.87 (m, 1H), 3.42-3.52 (m, 1H), 3.27-3.30 (m, 1H), 2.92-2.95 (m, 1H), 2.51-2.87 (m, 2H), 2.35-2.41 (m, 1H), 2.10-2.21 (m, 1H), 1.72-1.74 (m, 1H), 1.25 (s, 6H).

Example 48: Preparation of 4-(1-(2-acryloyl-2-azabicyclo[2.2.1]heptan-6-yl)-4-amino-1H-pyrazolo[3,4-d]pyrimidin-3-yl)-N-(3-chlorophenyl)benzamide Step 48-1: Preparation of N-(3-chlorophenyl)-4-(4,4,5,5-tetramethyl-1,3,2-dioxaborolan-2-yl)benzamide

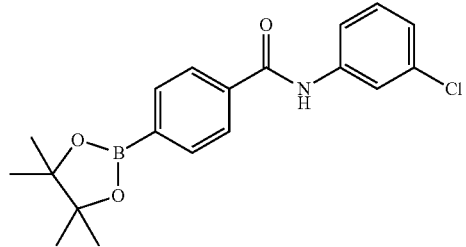 [SMILES: CC1(C)OB(c2ccc(C(=O)Nc3cccc(Cl)c3)cc2)OC1(C)C]

A title compound (106 mg, yield: 74%) was prepared in the same manner as in Step 4-2 of Example 4, except for using 4-(4,4,5,5-tetramethyl-1,3,2-dioxaborolan-2-yl)benzoyl chloride (107 mg, 0.40 mmol) obtained in Step 4-1 of Example 4 and 3-chloroaniline (56 mg, 0.44 mmol).

Step 48-2: Preparation of tert-butyl 6-(4-amino-3-(4-((3-chlorophenyl)carbamoyl)phenyl)-1H-pyrazolo[3,4-d]pyrimidin-1-yl)-2-azabicyclo[2.2.1]heptane-2-carboxylate

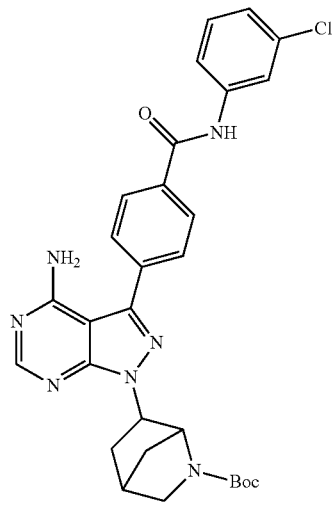 [SMILES: CC(C)(C)OC(=O)N1CC2CC1C(n1nc(-c3ccc(C(=O)Nc4cccc(Cl)c4)cc3)c3c(N)ncnc31)C2]

A title compound (109 mg, yield: 88%) was prepared in the same manner as in Step 1-2 of Example 1, except for using N-(3-chlorophenyl)-4-(4,4,5,5-tetramethyl-1,3,2-dioxaborolan-2-yl)benzamide (93 mg, 0.26 mmol) obtained in Step 48-1 and tert-butyl 6-(4-amino-3-iodo-1H-pyrazolo[3,4-d]pyrimidin-1-yl)-2-azabicyclo[2.2.1]heptane-2-carboxylate (100 mg, 0.22 mmol).

Step 48-3: Preparation of 4-(4-amino-1-(2-azabicyclo[2.2.1]heptan-6-yl)-1H-pyrazolo[3,4-d]pyrimidin-3-yl)-N-(3-chlorophenyl)benzamide

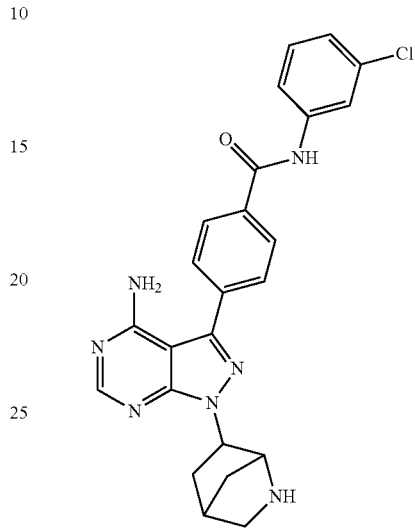

A title compound (67 mg, yield: 75%) was prepared in the same manner as in Step 1-3 of Example 1, except for using tert-butyl 6-(4-amino-3-(4-((3-chlorophenyl)carbamoyl)phenyl)-1H-pyrazolo[3,4-d]pyrimidin-1-yl)-2-azabicyclo[2.2.1]heptane-2-carboxylate (109 mg, 0.19 mmol) obtained in Step 48-2.

Step 48-4: Preparation of 4-(1-(2-acryloyl-2-azabicyclo[2.2.1]heptan-6-yl)-4-amino-1H-pyrazolo[3,4-d]pyrimidin-3-yl)-N-(3-chlorophenyl)benzamide

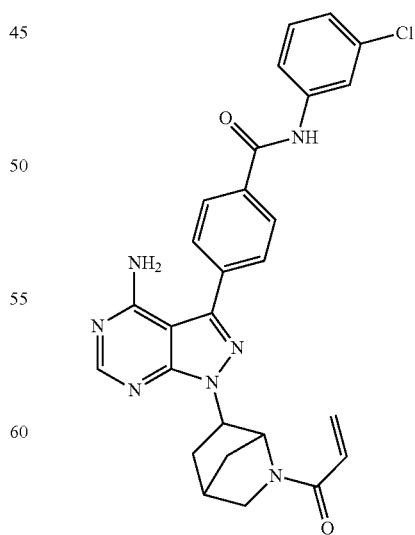

A title compound (34 mg, yield: 51%) was prepared in the same manner as in Step 1-4 of Example 1, except for using 4-(4-amino-1-(2-azabicyclo[2.2.1]heptan-6-yl)-1H-pyrazolo[3,4-d]pyrimidin-3-yl)-N-(3-chlorophenyl)benzamide (60 mg, 0.13 mmol) obtained in Step 48-3 and acryloyl chloride (12 uL, 0.14 mmol).

¹H NMR (500 MHz, CDCl₃): 8.41-8.50 (m, 1H), 8.25-8.35 (m, 1H), 7.97-8.03 (m, 2H), 7.82-7.85 (m, 2H), 7.76-7.78 (m, 1H). 7.56-7.58 (m, 1H), 6.78-6.83 (m, 1H), 6.36-6.48 (m, 1H), 5.76-5.78 (m, 1H), 5.52 (s, 2H), 4.90-5.10 (m, 1H), 4.50-4.87 (m, 1H), 3.42-3.57 (m, 1H), 3.23-3.26 (m, 1H), 2.42-2.83 (m, 2H), 2.20-2.31 (m, 1H), 2.04-2.12 (m, 1H), 1.72-1.74 (m, 1H).

Example 49: Preparation of 4-(1-(2-acryloyl-2-azabicyclo[2.2.1]heptan-6-yl)-4-amino-1H-pyrazolo[3,4-d]pyrimidin-3-yl)-N-(pyridin-2-yl)benzamide

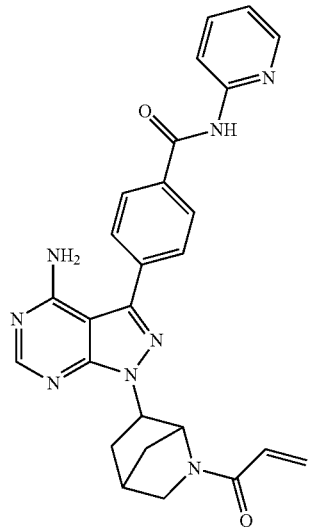 [SMILES: C=CC(=O)N1CC2CC1C(n1nc(-c3ccc(C(=O)Nc4ccccn4)cc3)c3c(N)ncnc31)C2]

A title compound (59 mg, yield: 43%) was prepared in the same manner as in Step 1-4 of Example 1, except for using tert-butyl 6-(4-amino-3-(4-(pyridin-2-yl)carbamoyl)phenyl)-1H-pyrazolo[3,4-d]pyrimidin-1-yl)-2-azabicyclo[2.2.1]heptane-2-carboxylate (153 mg, 0.29 mmol) obtained in Step 4-3 of Example 4.

¹H NMR (500 MHz, CDCl₃): 8.73-8.80 (m, 1H), 8.37-8.44 (m, 2H), 8.07-8.11 (m, 2H), 7.79-7.87 (m, 3H), 7.05-7.10 (m, 1H), 6.35-6.82 (m, 1H), 6.45-6.49 (m, 1H), 5.75-5.80 (m, 1H), 5.51 (s, 2H), 5.10-5.25 (m, 1H), 4.55-4.89 (m, 1H), 3.49-3.55 (m, 1H), 3.24-3.34 (m, 1H), 2.56-2.89 (m, 2H), 2.27-2.46 (m, 1H), 2.11-2.25 (m, 1H), 1.74-1.76 (m, 1H).

Example 50: Preparation of N-(4-(1-(2-acryloyl-2-azabicyclo[2.2.1]heptan-6-yl)-4-amino-1H-pyrazolo[3,4-d]pyrimidin-3-yl)phenyl)-3-(dimethylamino)benzamide

Step 50-1: Preparation of 3-(dimethylamino)-N-(4-(4,4,5,5-tetramethyl-1,3,2-dioxaborolan)phenyl)benzamide

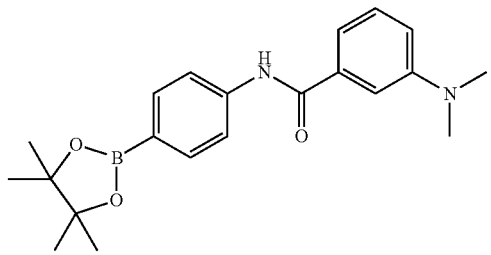

A title compound (650 mg, yield: 50.2%) was prepared in the same manner as in Step 37-1 of Example 37, except for using 3-(dimethylamino)benzoyl chloride (1.11 g, 6.04 mmol).

Step 50-2: Preparation of tert-butyl 6-(4-amino-3-(4-(3-(dimethylamino)benzamido)phenyl)-1H-pyrazolo[3,4-d]pyrimidin-1-yl)-2-azabicyclo[2.2.1]heptane-2-carboxylate

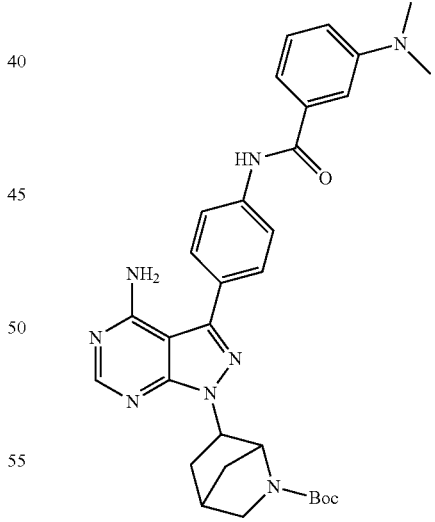

A title compound (188 mg, yield: 75.9%) was prepared in the same manner as in Step 31-2 of Example 31, except for using tert-butyl 6-(4-amino-3-iodo-1H-pyrazolo[3,4-d]pyrimidin-1-yl)-2-azabicyclo[2.2.1]heptane-2-carboxylate (200 mg, 0.44 mmol) obtained in Step 1-1 of Example 1 and 3-(dimethylamino)-N-(4-(4,4,5,5-tetramethyl-1,3,2-dioxaborolan)phenyl)benzamide (199.4 mg, 0.54 mmol) obtained in Step 50-1.

Step 50-3: Preparation of N-(4-(4-amino-1-(2-azabicyclo[2.2.1]heptan-6-yl)-1H-pyrazolo[3,4-d]pyrimidin-3-yl)phenyl)-3-(dimethylamino)benzamide

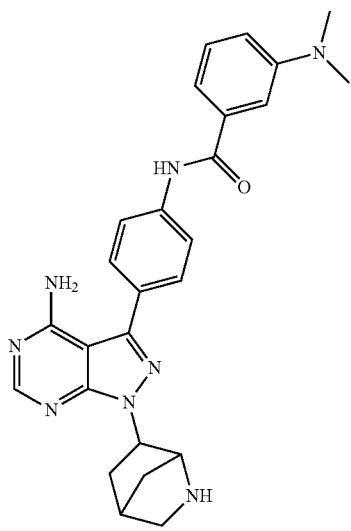 [SMILES: CN(C)c1cccc(C(=O)Nc2ccc(-c3nn(C4CC5CNC4C5)c4ncnc(N)c34)cc2)c1]

A title compound (185 mg, yield: 96.8%) was prepared in the same manner as in Step 31-3 of Example 31, except for using tert-butyl 6-(4-amino-3-(4-(3-(dimethylamino)benzamido)phenyl)-1H-pyrazolo[3,4-d]pyrimidin-1-yl)-2-azabicyclo[2.2.1]heptane-2-carboxylate (188 mg, 0.33 mol) obtained in Step 50-2.

Step 50-4: Preparation of N-(4-(1-(2-acryloyl-2-azabicyclo[2.2.1]heptan-6-yl)-4-amino-1H-pyrazolo[3,4-d]pyrimidin-3-yl)phenyl)-3-(dimethylamino)benzamide

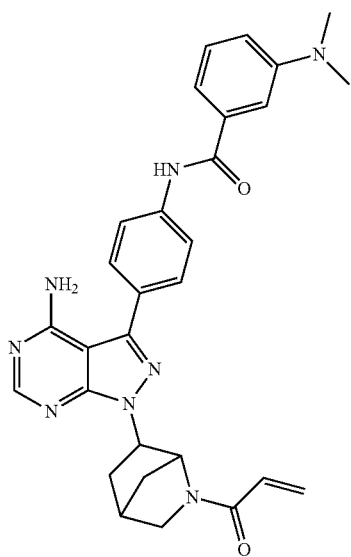 [SMILES: C=CC(=O)N1CC2CC1C(n1nc(-c3ccc(NC(=O)c4cccc(N(C)C)c4)cc3)c3c(N)ncnc31)C2]

A title compound (30 mg, yield: 17.5%) was prepared in the same manner as in Step 32-4 of Example 32, except for using N-(4-(4-amino-1-(2-azabicyclo[2.2.1]heptan-6-yl)-1H-pyrazolo[3,4-d]pyrimidin-3-yl)phenyl)-3-(dimethylamino)benzamide (185 mg, 0.33 mmol) obtained in Step 38-3 of Example 38.

$^1$H NMR (500 MHz, DMSO-$d_6$): 10.31 (s, 1H), 8.24-8.33 (m, 1H), 7.96-7.97 (m, 2H), 7.63-7.65 (d, 2H), 7.31-7.34 (t, 1H), 7.22-7.24 (m, 2H), 6.92-6.94 (d, 1H), 6.83-6.88 (dd, 1H), 6.46-6.51 (dd, 1H), 6.17-6.23 (dd, 1H), 5.70-5.72 (d, 1H), 4.92-4.96 (m, 1H), 4.54-5.48 (d, 1H), 4.36-4.37 (m, 1H), 3.50-3.51 (m, 1H), 3.16-3.18 (m, 1H), 2.78-2.83 (m, 1H), 2.07-2.26 (m, 2H), 1.62-1.67 (m, 2H).

Example 51: Preparation of 1-(6-(4-amino-3-(4-(3-aminophenoxy)phenyl)-1H-pyrazolo[3,4-d]pyrimidin-1-yl)-2-azabicyclo[2.2.1]heptan-2-yl)prop-2-en-1-one hydrochloride

Step 51-1: Preparation of tert-butyl (3-(4-bromophenoxy)phenylcarbamate

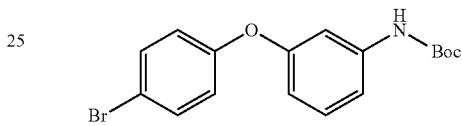

A title compound (140 mg, yield: 6.7%) was prepared in the same manner as in Step 34-1 of Example 34, except for using bromophenol (1 g, 5.78 mmol) and (3-((tert-butoxycarbonyl)amino)phenyl)boronic acid (1.5 g, 6.36 mmol).

Step 51-2: Preparation of tert-butyl (3-(4-(4,4,5,5-tetramethyl-1,3,2-dioxaborolan-2-yl)phenoxy)phenyl)carbamate

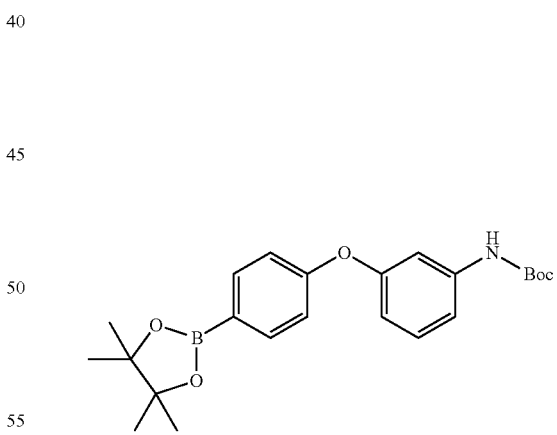

A title compound (22 mg, yield: 13.9%) was prepared in the same manner as in Step 31-1 of Example 31, except for using tert-butyl (3-(4-bromophenoxy)phenylcarbamate (140 mg, 0.38 mmol) obtained in Step 51-1.

Step 51-3: Preparation of tert-butyl (3-(4-(1-(2-acryloyl-2-azabicyclo[2.2.1]heptan-6-yl)-amino-1H-pyrazolo[3,4-d]pyrimidin-3-yl)phenoxy)phenyl)carbamate

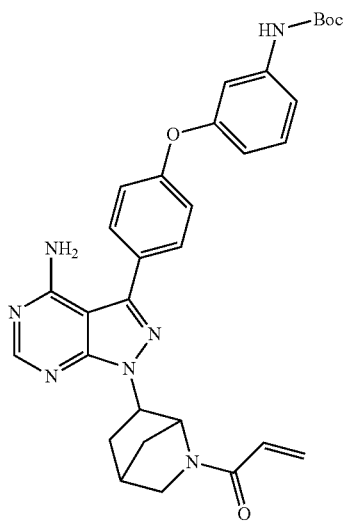 [SMILES: C=CC(=O)N1CC2CC1C(n1nc(-c3ccc(Oc4cccc(NC(=O)OC(C)(C)C)c4)cc3)c3c(N)ncnc31)C2]

A title compound (10 mg, yield: 40.2%) was prepared in the same manner as in Step 42-4 of Example 42, except for using 1-(6-(4-amino-3-iodo-1H-pyrazolo[3,4-d]pyrimidin-1-yl)-2-azabicyclo[2.2.1]heptan-2-yl)prop-2-en-1-one (18 mg, 0.04 mmol) obtained in Step 42-3 of Example 42 and tert-butyl (3-(4-(4,4,5,5-tetramethyl-1,3,2-dioxaborolan-2-yl)phenoxy)phenyl)carbamate (22 mg, 0.05 mmol) obtained in Step 51-2.

Step 51-4: Preparation of 1-(6-(4-amino-3-(4-(3-aminophenoxy)phenyl)-1H-pyrazolo[3,4-d]pyrimidin-1-yl)-2-azabicyclo[2.2.1]heptan-2-yl)prop-2-en-1-one hydrochloride

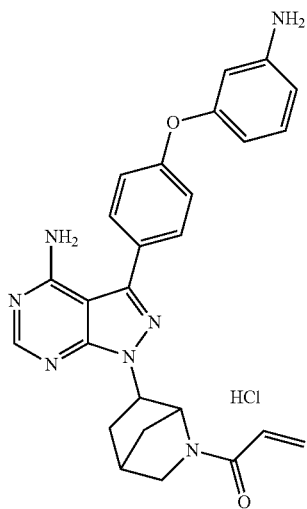 [SMILES: C=CC(=O)N1CC2CC1C(n1nc(-c3ccc(Oc4cccc(N)c4)cc3)c3c(N)ncnc31)C2 ; Cl]

After tert-butyl (3-(4-(1-(2-acryloyl-2-azabicyclo[2.2.1]heptan-6-yl)-amino-1H-pyrazolo[3,4-d]pyrimidin-3-yl)phenoxy)phenyl)carbamate (10.0 mg, 0.02 mmol) obtained in Step 51-3 was dissolved in 1,4-dioxane (1 mL), 1N aqueous hydrochloric acid solution (2 mL) dissolved in dioxane was added thereto, followed by stirring at room temperature for 3 hours.

Upon completion of the reaction, the mixture was concentrated under reduced pressure to obtain a title compound (3.5 mg, yield: 39.4%).

$^1$H NMR (500 MHz, DMSO-d$_6$): 8.39 (s, 1H), 8.26-8.27 (m, 1H), 7.64-7.66 (m, 2H), 7.47-7.55 (m, 2H), 7.23-7.32 (m, 1H), 7.12-7.16 (m, 2H), 6.69-6.68 (dd, 1H), 6.60-6.62 (d, 1H), 6.52 (s, 1H), 4.94-5.02 (m, 1H), 4.81-4.90 (m, 1H), 3.37-3.41 (m, 1H), 3.18-3.16 (m, 1H), 2.93-2.97 (m, 1H), 2.74-7.29 (m, 2H), 2.10-2.18 (m, 2H), 1.58-1.1.52 (m, 1H).

Example 52: Preparation of 4-(1-(2-acryloyl-2-azabicyclo[2.2.1]heptan-6-yl)-4-amino-1H-pyrazolo[3,4-d]pyrimidin-3-yl)-3-fluoro-N-phenylbenzamide

Step 52-1: Preparation of 3-fluoro-4-(4,4,5,5-tetramethyl-1,3,2-dioxaborolan-2-yl)benzoyl chloride

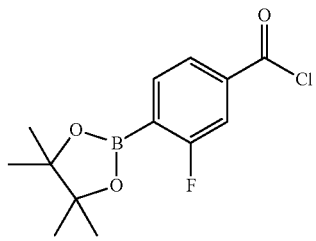 [SMILES: CC1(C)OB(c2ccc(C(=O)Cl)cc2F)OC1(C)C]

3-Fluoro-4-(4,4,5,5-tetramethyl-1,3,2-dioxaborolan-2-yl)benzoic acid (100 mg, 0.38 mmol) was dissolved in dichloromethane (2 mL) and then cooled to 0° C. One drop of N,N-dimethylformamide was added and oxalyl chloride (81 uL, 0.94 mmol) was slowly added. After stirring at 0° C. for 30 minutes, the temperature was raised to room temperature and then the mixture was stirred for 3 hours. Upon completion of the reaction, the reaction solution was concentrated under reduced pressure and the subsequent reaction was carried out without purification.

Step 52-2: Preparation of 3-fluoro-N-phenyl-4-(4,4,5,5-tetramethyl-1,3,2-dioxaborolan-2-yl)-benzamide

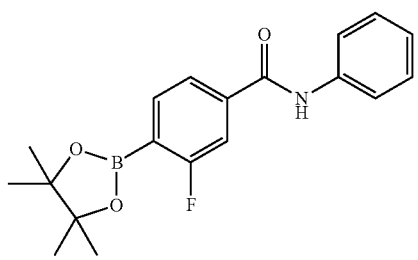 [SMILES: CC1(C)OB(c2ccc(C(=O)Nc3ccccc3)cc2F)OC1(C)C]

Aniline (38 mg, 0.41 mmol) and N,N-dimethylaminopyridine (46 mg, 0.38 mmol) was dissolved in acetonitrile (1 mL), and then 3-fluoro-4-(4,4,5,5-tetramethyl-1,3,2-dioxaborolan-2-yl)benzoyl chloride obtained in Step 52-1 of Example 52 was dissolved in acetonitrile (1 mL) and then slowly added to the reaction solution, followed by stirring at room temperature for 12 hours. Upon completion of the reaction, the reaction was diluted with chloromethane and washed with 0.2N aqueous hydrochloric acid solution. The organic layer was collected, dried over magnesium sulfate, and then concentrated under reduced pressure. The residue was purified by column chromatography (hexane:ethyl acetate=1:1) to obtain a title compound (43 mg, yield: 34% over two steps).

Step 52-3: Preparation of tert-butyl 6-(4-amino-3-(2-fluoro-4-(phenylcarbamoyl)phenyl)-1H-pyrazolo[3,4-d]pyrimidin-1-yl)-2-azabicyclo[2.2.1]heptane-2-carboxylate

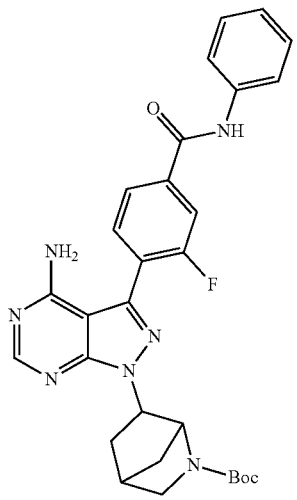 [SMILES: CC(C)(C)OC(=O)N1CC2CC1C(n1nc(-c3ccc(C(=O)Nc4ccccc4)cc3F)c3c(N)ncnc31)C2]

A title compound (39 mg, yield: 82%) was prepared in the same manner as in Step 1-2 of Example 1, except for using 3-fluoro-N-phenyl-4-(4,4,5,5-tetramethyl-1,3,2-dioxaborolan-2-yl)-benzamide (38 mg, 0.11 mmol) obtained in Step 52-2 and tert-butyl 6-(4-amino-3-iodo-1H-pyrazolo[3,4-d]pyrimidin-1-yl)-2-azabicyclo[2.2.1]heptana-2-carboxylate (40 mg, 0.088 mmol)

Step 52-4: Preparation of 4-(4-amino-1-(2-azabicyclo[2.2.1]heptan-6-yl)-1H-pyrazolo[3,4-d]pyrimidin-3-yl)-3-fluoro-N-phenylbenzamide

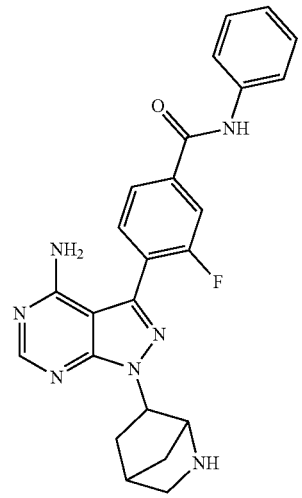 [SMILES: Nc1ncnc2c1c(-c1ccc(C(=O)Nc3ccccc3)cc1F)nn2C1CC2CNC1C2]

A title compound (260 mg, yield: 82%) was prepared in the same manner as in Step 1-3 of Example 1, except for using tert-butyl 6-(4-amino-3-(2-fluoro-4-(phenylcarbamoyl)phenyl)-1H-pyrazolo[3,4-d]pyrimidin-1-yl)-2-azabicyclo[2.2.1]heptane-2-carboxylate (390 mg, 0.72 mmol) obtained in Step 52-3.

Step 52-5: Preparation of 4-(1-(2-acryloyl-2-azabicyclo[2.2.1]heptan-6-yl)-4-amino-1H-pyrazolo[3,4-d]pyrimidin-3-yl)-3-fluoro-N-phenylbenzamide

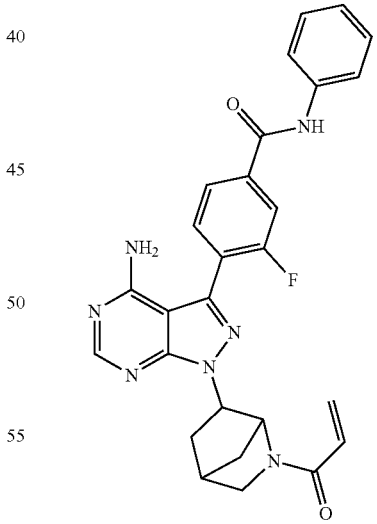

A title compound (98 mg, yield: 65%) was prepared in the same manner as in Step 1-4 of Example 1, except for using 4-(4-amino-1-(2-azabicyclo[2.2.1]heptan-6-yl)-1H-pyrazolo[3,4-d]pyrimidin-3-yl)-3-fluoro-N-phenylbenzamide (120 mg, 0.25 mmol) obtained in Step 52-4 and acryloyl chloride (102 uL, 1.3 mmol).

$^1$H NMR (500 MHz, CDCl$_3$): 8.35-8.40 (m, 1H), 7.70-7.82 (m, 2H), 7.67-7.69 (m, 3H), 7.38-7.40 (m, 2H), 7.18-

7.21 (m, 1H), 6.36-6.78 (m, 1H), 6.48-6.52 (m, 1H), 5.75-5.78 (m, 1H), 5.01-5.19 (m, 1H), 4.52-4.89 (m, 1H), 3.37-3.50 (m, 1H), 3.28-3.34 (m, 1H), 2.51-2.82 (m, 2H), 2.21-2.40 (m, 1H), 1.95-2.17 (m, 1H), 1.70-1.72 (m, 1H).

Example 53: Preparation of 4-(1-(2-acryloyl-2-azabicyclo[2.2.1]heptan-6-yl)-4-amino-1H-pyrazolo[3,4-d]pyrimidin-3-yl)-N-(pyrazin-2-yl)benzamide Step 53-1: Preparation of N-(pyrazin-2-yl)-4-(4,4,5,5-tetramethyl-1,3,2-dioxaborolan-2-yl)benzamide

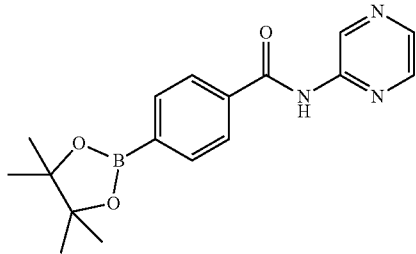 [SMILES: CC1(C)OB(c2ccc(C(=O)Nc3cnccn3)cc2)OC1(C)C]

A title compound (50 mg, yield: 38% over two steps) was prepared in the same manner as in Step 4-2 of Example 4, except for using 4-(4,4,5,5-tetramethyl-1,3,2-dioxaborolan-2-yl)benzoyl chloride (107 mg, 0.40 mmol) obtained in Step 4-1 and pyrazin-2-amine (72 mg, 0.44 mmol).

Step 53-2: Preparation of tert-butyl 6-(4-amino-3-(4-(pyrazin-2-ylcarbamoyl)phenyl)-1H-pyrazolo[3,4-d]pyrimidin-1-yl)-2-azabicyclo[2.2.1]heptane-2-carboxylate

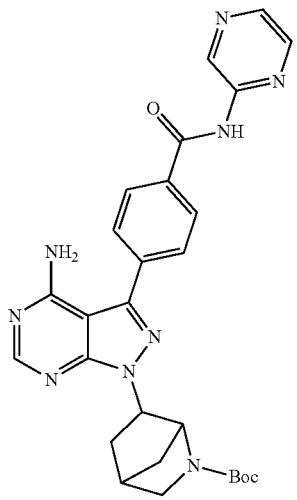 [SMILES: CC(C)(C)OC(=O)N1CC2CC1C(n1nc(-c3ccc(C(=O)Nc4cnccn4)cc3)c3c(N)ncnc31)C2]

A title compound (28 mg, yield: 60%) was prepared in the same manner as in Step 1-2 of Example 1, except for using N-(pyrazin-2-yl)-4-(4,4,5,5-tetramethyl-1,3,2-dioxaborolan-2-yl)benzamide (36 mg, 0.11 mmol) obtained in Step 53-1 and tert-butyl 6-(4-amino-3-iodo-1H-pyrazolo[3,4-d]pyrimidin-1-yl)-2-azabicyclo[2.2.1]heptane-2-carboxylate (40 mg, 0.088 mmol).

Step 53-3: Preparation of 4-(4-amino-1-(2-azabicyclo[2.2.1]heptan-6-yl)-1H-pyrazolo[3,4-d]pyrimidin-3-yl)-N-(pyrazin-2-yl)benzamide

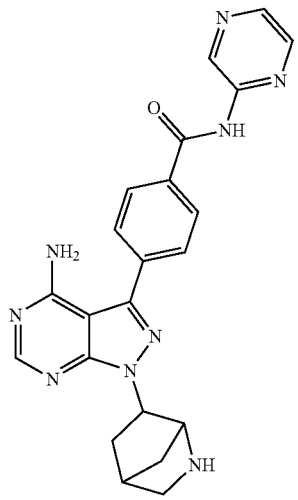 [SMILES: Nc1ncnc2c1c(-c1ccc(C(=O)Nc3cnccn3)cc1)nn2C1CC2CNC1C2]

A title compound (20 mg, yield: 88%) was prepared in the same manner as in Step 1-3 of Example 1, except for using tert-butyl 6-(4-amino-3-(4-(pyrazin-2-ylcarbamoyl)phenyl)-1H-pyrazolo[3,4-d]pyrimidin-1-yl)-2-azabicyclo[2.2.1]heptane-2-carboxylate (28 mg, 0.066 mmol) obtained in Step 53-2.

Step 53-4: Preparation of 4-(1-(2-acryloyl-2-azabicyclo[2.2.1]heptan-6-yl)-4-amino-1H-pyrazolo[3,4-d]pyrimidin-3-yl)-N-(pyrazin-2-yl)benzamide

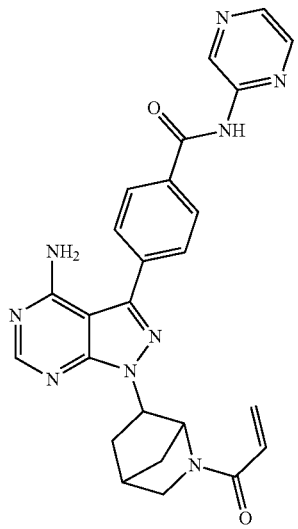 [SMILES: C=CC(=O)N1CC2CC1C(n1nc(-c3ccc(C(=O)Nc4cnccn4)cc3)c3c(N)ncnc31)C2]

A title compound (16 mg, yield: 70%) was prepared in the same manner as in Step 1-4 of Example 1, except for using 4-(4-amino-1-(2-azabicyclo[2.2.1]heptan-6-yl)-1H-pyrazolo[3,4-d]pyrimidin-3-yl)-N-(pyrazin-2-yl)benzamide (20 mg, 0.047 mmol) obtained in Step 53-3 and acryloyl chloride (19 uL, 0.23 mmol), $^1$H NMR (500 MHz, CDCl$_3$): 9.72-9.74 (m, 1H), 8.64-8.66 (m, 1H), 8.42-8.43 (m, 1H), 8.31-8.33 (m, 1H), 8.11-

8.13 (m, 2H), 7.86-7.88 (m, 2H), 6.37-6.81 (m, 1H), 6.44-6.48 (m, 1H), 5.77-5.78 (m, 1H), 5.75 (s, 2H), 4.92-5.29 (m, 1H), 4.54-4.85 (m, 1H), 3.42-3.48 (m, 1H), 3.31-3.33 (m, 1H), 2.56-2.89 (m, 2H), 2.31-2.45 (m, 1H), 2.15-2.17 (m, 1H), 1.73-1.75 (m, 1H).

Example 54: Preparation of 4-(1-(2-acryloyl-2-azabicyclo[2.2.1]heptan-6-yl)-4-amino-1H-pyrazolo[3,4-d]pyrimidin-3-yl)-N-phenylbenzenesulfonamide Step 54-1: Preparation of 4-bromo-N-phenylbenzenesulfonamide

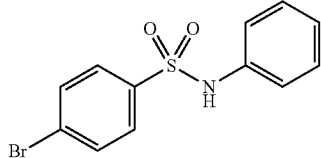 [SMILES: O=S(=O)(Nc1ccccc1)c1ccc(Br)cc1]

4-Bromobenzenesulfonyl chloride (1 g, 3.9 mmol), aniline (0.4 mL, 4.3 mmol) and pyridine (0.85 mL, 10.6 mmol) were dissolved in dichloromethane (10 mL) and then stirred at room temperature for 1 hour. The reaction mixture was diluted with ethyl acetate, and the organic layer was washed sequentially with 1 N hydrochloric acid, distilled water and aqueous sodium hydrogencarbonate solution. The organic layer was collected, dried over magnesium sulfate, and concentrated under reduced pressure to give a title compound (1.2 g, yield: 98.4%).

Step 54-2: Preparation of N-phenyl-4-(4,4,5,5-tetramethyl-1,3,2-dioxaborolan-2-yl)benzenesulfonamide

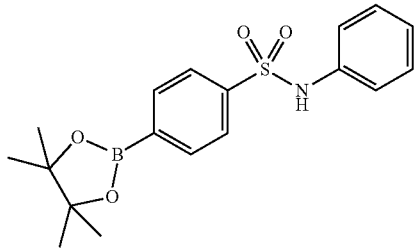 [SMILES: CC1(C)OB(c2ccc(S(=O)(=O)Nc3ccccc3)cc2)OC1(C)C]

A title compound (1 g, yield: 72.5%) was prepared in the same manner as in Step 31-1 of Example 31, except for using 4-bromo-N-phenylbenzenesulfonamide (1.2 g, 3.84 mmol) obtained in Step 54-1.

Step 54-3: Preparation of 4-(1-(2-acryloyl-2-azabicyclo[2.2.1]heptan-6-yl)-4-amino-1H-pyrazolo[3,4-d]pyrimidin-3-yl)-N-phenylbenzenesulfonamide

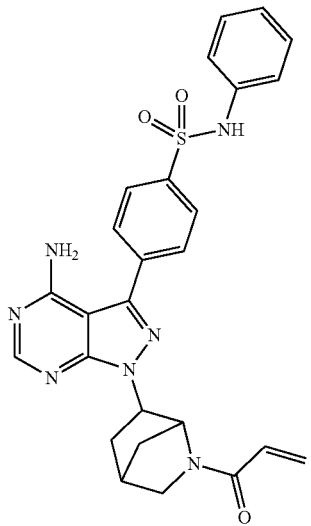 [SMILES: C=CC(=O)N1CC2CC1C(n1nc(-c3ccc(S(=O)(=O)Nc4ccccc4)cc3)c3c(N)ncnc31)C2]

A title compound (50 mg, yield: 39.8%) was prepared in the same manner as in Step 42-4 of Example 42, except for using 1-(6-(4-amino-3-iodo-1H-pyrazolo[3,4-d]pyrimidin-1-yl)-2-azabicyclo[2.2.1]heptan-2-yl)prop-2-en-1-one (100 mg, 0.24 mmol) obtained in Step 42-3 of Example 42 and N-phenyl-4-(4,4,5,5-tetramethyl-1,3,2-dioxaborolan-2-yl)benzenesulfonamide (109.5 mg, 0.3 mmol) obtained in Step 52-2.

$^1$H NMR (500 MHz, CDCl$_3$): 8.36-8.43 (m, 1H), 7.93-7.96 (t, 1H), 7.75-7.79 (t, 2H), 7.55-7.62 (m, 2H), 7.46-7.50 (m, 1H), 7.39-7.43 (m, 1H), 7.12-7.16 (m, 2H), 7.04-7.08 (m, 1H), 6.77-6.83 (dd, 1H), 6.45-6.48 (d, 1H), 5.72-7.77 (m, 1H), 5.09-5.22 (m, 1H), 4.71-4.91 (d, 1H), 4.26-4.53 (d, 1H), 3.49-3.57 (m, 1H), 3.26-3.42 (m, 1H), 2.39-2.49 (m, 1H), 2.11-2.12 (m, 2H), 1.72-1.74 (m, 1H).

Example 55: Preparation of 4-(1-(2-acryloyl-2-azabicyclo[2.2.1]heptan-6-yl)-4-amino-1H-pyrazolo[3,4-d]pyrimidin-3-yl)-N-(2-(dimethylamino)phenyl)benzamide Step 55-1: Preparation of N-(2-(dimethylamino)phenyl)-4-(4,4,5,5-tetramethyl-1,3,2-dioxaborolan-2-yl)benzamide

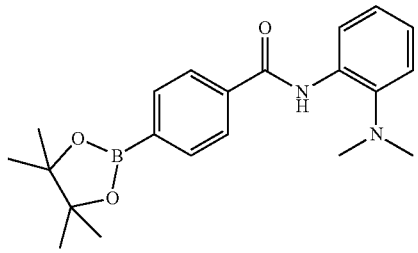

A title compound (110 mg, yield: 75%) was prepared in the same manner as in Step 4-2 of Example 4, except for using 4-(4,4,5,5-tetramethyl-1,3,2-dioxaborolan-2-yl)benzoyl chloride (107 mg, 0.40 mmol) obtained in Step 4-1 of Example 4 and N,N-dimethylbenzene-1,2-diamine (60 mg, 0.44 mmol).

Step 55-2: Preparation of tert-butyl 6-(4-amino-3-(4-((2-(dimethylamino)phenylcarbamoyl)phenyl)-1H-pyrazolo[3,4-d]pyrimidin-1-yl)-2-azabicyclo[2.2.1]heptane-2-carboxylate

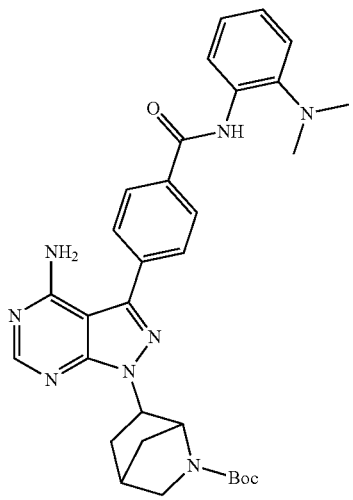 [SMILES: CN(C)c1ccccc1NC(=O)c1ccc(-c2nn(C3CC4CC3N(C(=O)OC(C)(C)C)C4)c3ncnc(N)c23)cc1]

A title compound (115 mg, yield: 92%) was prepared in the same manner as in Step 1-2 of Example 1, except for using N-(2-(dimethylamino)phenyl)-4-(4,4,5,5-tetramethyl-1,3,2-dioxaborolan-2-yl)benzamide (95 mg, 0.26 mmol) obtained in Step 55-1 and tert-butyl 6-(4-amino-3-iodo-1H-pyrazolo[3,4-d] pyrimidin-1-yl)-2-azabicyclo[2.2.1]heptane-2-carboxylate (100 mg, 0.22 mmol).

Step 55-3: Preparation of 4-(4-amino-1-(2-azabicyclo[2.2.1]heptan-6-yl)-1H-pyrazolo[3,4-d]pyrimidin-3-yl)-N-(2-(dimethylamino)phenyl)benzamide

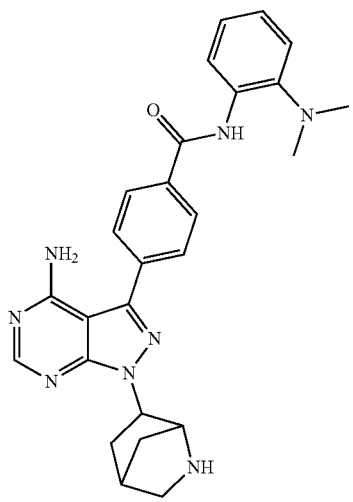 [SMILES: CN(C)c1ccccc1NC(=O)c1ccc(-c2nn(C3CC4CNC3C4)c3ncnc(N)c23)cc1]

A title compound (71 mg, yield: 75%) was prepared in the same manner as in Step 1-3 of Example 1, except for using tert-butyl 6-(4-amino-3-(4-((2-(dimethylamino)phenylcarbamoyl)phenyl)-1H-pyrazolo[3,4-d]pyrimidin-1-yl)-2-azabicyclo[2.2.1]heptane-2-carboxylate (115 mg, 0.20 mmol) obtained in Step 55-2.

Step 55-4: Preparation of 4-(1-(2-acryloyl-2-azabicyclo[2.2.1]heptan-6-yl)-4-amino-1H-pyrazolo[3,4-d]pyrimidin-3-yl)-N-(2-(dimethylamino)phenyl)benzamide

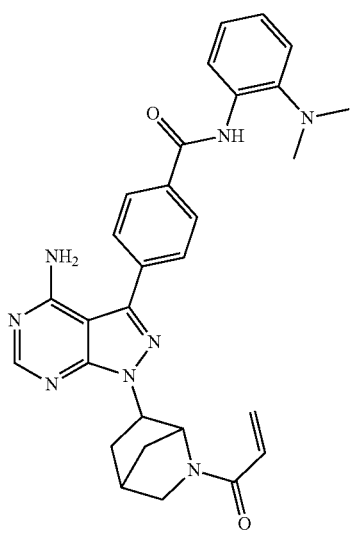 [SMILES: C=CC(=O)N1CC2CC1C(n1nc(-c3ccc(C(=O)Nc4ccccc4N(C)C)cc3)c3c(N)ncnc31)C2]

A title compound (45 mg, yield: 67%) was prepared in the same manner as in Step 1-4 of Example 1, except for using 4-(4-amino-1-(2-azabicyclo[2.2.1]heptan-6-yl)-1H-pyrazolo[3,4-d]pyrimidin-3-yl)-N-(2-(dimethylamino)phenyl)benzamide (60 mg, 0.13 mmol) obtained in Step 55-3 and acryloyl chloride (12 uL, 0.14 mmol).

$^1$H NMR (500 MHz, CDCl$_3$): 8.41-8.50 (m, 1H), 8.25-8.35 (m, 1H), 7.97-8.03 (m, 2H), 7.82-7.85 (m, 2H), 7.76-7.78 (m, 1H). 7.56-7.58 (m, 1H), 6.78-6.83 (m, 1H), 6.36-6.48 (m, 1H), 5.76-5.78 (m, 1H), 5.52 (s, 2H), 4.90-5.10 (m, 1H), 4.50-4.87 (m, 1H), 3.42-3.57 (m, 1H), 3.23-3.26 (m, 1H), 2.42-2.83 (m, 2H), 2.20-2.31 (m, 1H), 2.04-2.12 (m, 1H), 1.72-1.74 (m, 1H).

Example 56: Preparation of 4-(1-(2-acryloyl-2-azabicyclo[2.2.1]heptan-6-yl)-4-amino-1H-pyrazolo[3,4-d]pyrimidin-3-yl)-N-(1-methyl-1H-pyrazol-4-yl)benzamide

Step 56-1: Preparation of N-(1-methyl-1H-pyrazol-4-yl)-4-(4,4,5,5-tetramethyl-1,3,2-dioxaborolan-2-yl)benzamide

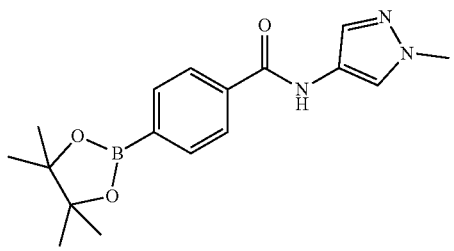

A title compound (85 mg, yield: 65%) was prepared in the same manner as in Step 4-2 of Example 4, except for using 4-(4,4,5,5-tetramethyl-1,3,2-dioxaborolan-2-yl)benzoyl chloride (107 mg, 0.40 mmol) obtained in Step 4-1 of Example 4 and 1-methyl-1H-pyrazol-4-amine (43 mg, 0.44 mmol).

Step 56-2: Preparation of tert-butyl 6-(4-amino-3-(4-((1-methyl-1H-pyrazol-4-yl)carbamoyl)phenyl)-1H-pyrazolo[3,4-d]pyrimidin-1-yl)-2-azabicyclo[2.2.1]heptane-2-carboxylate

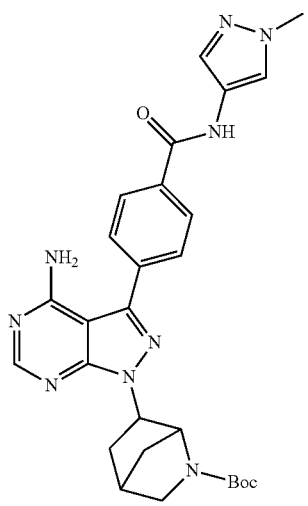 [SMILES: Cn1cc(NC(=O)c2ccc(-c3nn(C4CC5CC4N(C(=O)OC(C)(C)C)C5)c4ncnc(N)c34)cc2)cn1]

A title compound (104 mg, yield: 90%) was prepared in the same manner as in Step 1-2 of Example 1, except for using N-(1-methyl-1H-pyrazol-4-yl)-4-(4,4,5,5-tetramethyl-1,3,2-dioxaborolan-2-yl)benzamide (85 mg, 0.26 mmol) obtained in Step 56-1 and tert-butyl 6-(4-amino-3-iodo-1H-pyrazolo[3,4-d]pyrimidin-1-yl)-2-azabicyclo[2.2.1]heptane-2-carboxylate (100 mg, 0.22 mmol).

Step 56-3: Preparation of 4-(4-amino-1-(2-azabicyclo[2.2.1]heptan-6-yl)-1H-pyrazolo[3,4-d]pyrimidin-3-yl)-N-(1-methyl-1H-pyrazol-4-yl)benzamide

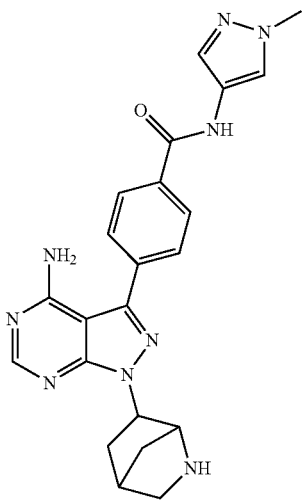 [SMILES: Cn1cc(NC(=O)c2ccc(-c3nn(C4CC5CNC4C5)c4ncnc(N)c34)cc2)cn1]

A title compound (51 mg, yield: 60%) was prepared in the same manner as in Step 1-3 of Example 1, except for using tert-butyl 6-(4-amino-3-(4-((1-methyl-1H-pyrazol-4-yl)carbamoyl)phenyl)-1H-pyrazolo[3,4-d]pyrimidin-1-yl)-2-azabicyclo[2.2.1]heptane-2-carboxylate (104 mg, 0.24 mmol) obtained in Step 56-2.

Step 56-4: Preparation of 4-(1-(2-acryloyl-2-azabicyclo[2.2.1]heptan-6-yl)-4-amino-1H-pyrazolo[3,4-d]pyrimidin-3-yl)-N-(1-methyl-1H-pyrazol-4-yl)benzamide

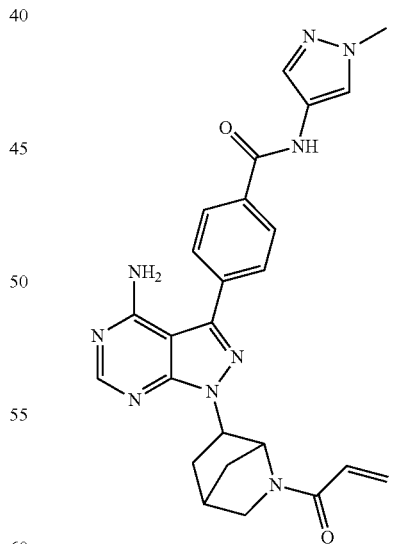

A title compound (33 mg, yield: 49%) was prepared in the same manner as in Step 1-4 of Example 1, except for using 4-(4-amino-1-(2-azabicyclo[2.2.1]heptan-6-yl)-1H-pyrazolo[3,4-d]pyrimidin-3-yl)-N-(1-methyl-1H-pyrazol-4-yl)benzamide (60 mg, 0.14 mmol) obtained in Step 56-3 and acryloyl chloride (12 uL, 0.15 mmol).

¹H NMR (500 MHz, CDCl₃): 8.48-8.65 (m, 1H), 8.25-8.36 (m, 1H), 7.92-8.08 (m, 3H), 7.70-7.78 (m, 2H), 7.55-7.60 (m, 1H), 6.88-6.42 (m, 1H), 6.43-6.47 (m, 1H), 5.75-5.77 (m, 1H), 4.89-5.10 (m, 1H), 4.50-4.89 (m, 1H), 3.90 (s, 3H), 3.51-3.60 (m, 1H), 3.23-3.25 (m, 1H), 2.75-2.89 (m, 2H), 2.37-2.49 (m, 1H), 2.20-2.27 (m, 1H), 1.71-1.74 (m, 1H).

Example 57: Preparation of N-(4-(1-(2-acryloyl-2-azabicyclo[2.2.1]heptan-6-yl)-4-amino-1H-pyrazolo[3,4-d]pyrimidin-3-yl)phenyl)-2-(dimethylamino)benzamide Step 57-1: Preparation of tert-butyl 6-(4-amino-3-(4-nitrophenyl)-1H-pyrazolo[3,4-d]pyrimidin-1-yl)-azabicyclo[2.2.1]heptane-2-carboxylate

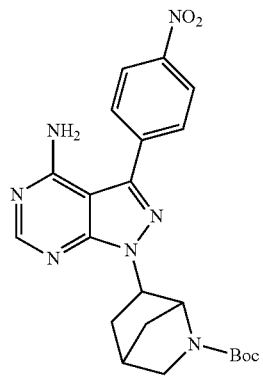 [SMILES: CC(C)(C)OC(=O)N1CC2CC1C(n1nc(-c3ccc([N+](=O)[O-])cc3)c3c(N)ncnc31)C2]

A title compound (697.0 mg, yield: 70.9%) was prepared in the same manner as in Step 31-2 of Example 31, except for using tert-butyl 6-(4-amino-3-iodo-1H-pyrazolo[3,4-d]pyrimidin-1-yl)-2-azabicyclo[2.2.1]heptane-2-carboxylate (1 g, 2.18 mmol) obtained in Step 1-1 of Example 1 and 4-nitrophenylboronic acid (166.9 mg, 2.7 mmol).

Step 57-2: Preparation of 1-(2-azabicyclo[2.2.1]heptan-6-yl)-3-(4-nitrophenyl)-1H-pyrazolo[3,4-d]pyrimidin-4-amine

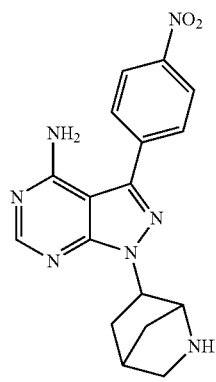 [SMILES: Nc1ncnc2c1c(-c1ccc([N+](=O)[O-])cc1)nn2C1CC2CNC1C2]

A title compound (500 mg, yield: 97.1%) was prepared in the same manner as in Step 31-3 of Example 31, except for using tert-butyl 6-(4-amino-3-(4-nitrophenyl)-1H-pyrazolo[3,4-d]pyrimidin-1-yl)-azabicyclo[2.2.1]heptane-2-carboxylate (600 mg, 1.33 mol) obtained in Step 57-1.

Step 57-3: Preparation of 1-(6-(4-amino-3-(4-nitrophenyl)-1H-pyrazolo[3,4-d]pyrimidin-1-yl)-2-azabicyclo[2.2.1]heptan-2-yl)prop-2-en-1-one

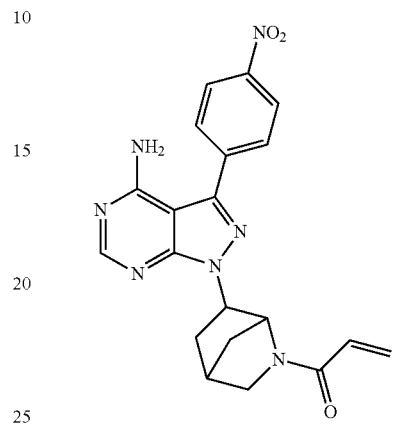

A title compound (576.9 mg, yield: 99.3%) was prepared in the same manner as in Step 32-4 of Example 32, except for using 1-(2-azabicyclo[2.2.1]heptan-6-yl)-3-(4-nitrophenyl)-1H-pyrazolo[3,4-d]pyrimidin-4-amine (500 mg, 1.29 mmol) obtained in Step 57-2.

Step 57-4: Preparation of 1-(6-(4-amino-3-(4-aminophenyl)-1H-pyrazolo[3,4-d]pyrimidin-1-yl)-2-azabicyclo[2.2.1]heptan-2-yl)prop-2-en-1-one

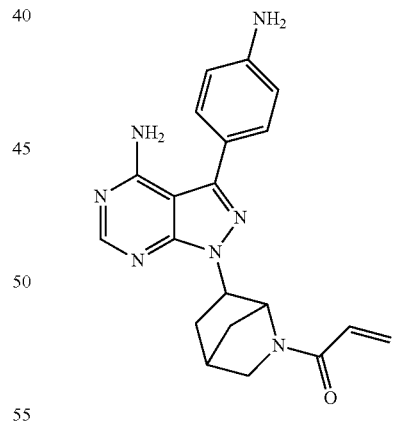

1-(6-(4-amino-3-(4-nitrophenyl)-1H-pyrazolo[3,4-d]pyrimidin-1-yl)-2-azabicyclo[2.2.1]heptan-2-yl)prop-2-en-1-one (400 mg, 0.88 mmol) obtained in Step 57-3 was dissolved in ethanol (3 mL). Iron (496 mg, 8.9 mmol) and concentrated hydrochloric acid (124 uL) were added dropwise to the reaction product, and then heated under reflux for 2 hours. The reaction was cooled to room temperature, neutralized with sodium bicarbonate and extracted with ethyl acetate. The organic layer was collected, dried over magnesium sulfate, filtered and concentrated under reduced pressure to obtain a title compound (200 mg, yield: 60%).

Step 57-5: Preparation of N-(4-(1-(2-acryloyl-2-azabicyclo[2.2.1]heptan-6-yl)-4-amino-1H-pyrazolo[3,4-d]pyrimidin-3-yl)phenyl)-2-(dimethylamino)benzamide

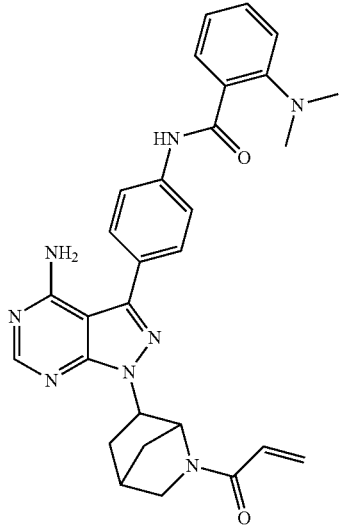 [SMILES: C=CC(=O)N1CC2CC1C(n1nc(-c3ccc(NC(=O)c4ccccc4N(C)C)cc3)c3c(N)ncnc31)C2]

After 2-(dimethylamino)benzoic acid (200 mg, 1.21 mmol) was dissolved in dichloromethane (2 mL), thionyl chloride (265 uL, 3.63 mmol) was slowly added dropwise and then stirred for 1 hour. The reaction mixture was concentrated and dissolved in dichloromethane (1 mL), and then 264 uL was added to another reaction vessel. Dichloromethane (2 mL) was added dropwise thereto and then 1-(6-(4-amino-3-(4-aminophenyl)-1H-pyrazolo[3,4-d]pyrimidin-1-yl)-2-azabicyclo[2.2.1]heptan-2-yl)prop-2-en-1-one (100 mg, 0.27 mmol) obtained in Step 57-4 and triethylamine (56 uL, 0.4 mmol) were sequentially added dropwise. The reaction product was stirred at room temperature for 15 hours, diluted with dichloromethane and then washed with water. The organic layer was collected, dried over magnesium sulfate, and concentrated under reduced pressure to obtain a title compound (30.3 mg, yield 21.8%).

$^1$H NMR (500 MHz, DMSO-$d_6$): 11.43 (s, 1H), 8.36-8.38 (m, 1H), 8.24-8.32 (dd, 1H), 7.90-7.96 (m, 2H), 7.62-7.69 (m, 2H), 7.35-7.47 (m, 1H), 7.22-7.24 (d, 1H), 7.08-7.11 (t, 1H), 6.82-6.88 (dd, 1H), 6.46-6.51 (dd, 1H), 6.17-6.23 (m, 1H), 5.69-5.74 (m, 2H), 4.89-5.01 (m, 1H), 4.56-4.61 (m, 1H), 3.49-3.55 (m, 1H), 2.79-2.83 (m, 7H), 2.60-2.61 (m, 1H), 2.07-2.41 (m, 2H), 1.63-1.65 (m, 1H).

Example 58: Preparation of (E)-1-(6-(4-amino-3-(4-phenoxyphenyl)-1H-pyrazolo[3,4-d]pyrimidin-1-yl)-2-azabicyclo[2.2.1]heptan-2-yl)-4-morpholinobut-2-en-1-one

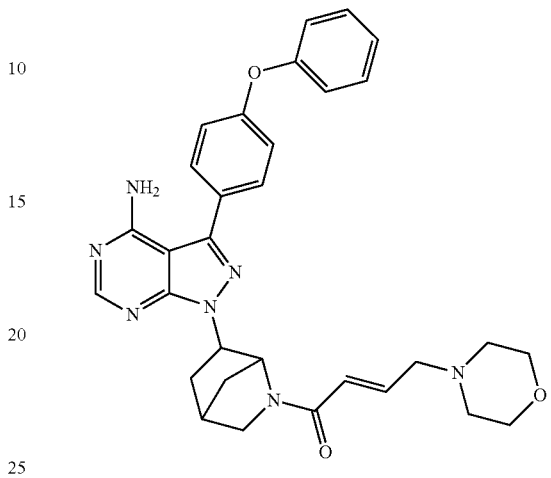

A title compound (26 mg, yield: 51%) was prepared in the same manner as in Example 45, except for using (E)-1-(6-(4-amino-3-(4-phenoxyphenyl)-1H-pyrazolo[3,4-d]pyrimidin-1-yl)-2-azabicyclo[2.2.1]heptan-2-yl)-4-bromobut-2-en-1-one (50 mg, 0.092 mmol) obtained in Example 44 and morpholine (12 mg, 0.14 mmol).

$^1$H NMR (500 MHz, CDCl$_3$): 8.34-8.37 (m, 1H), 7.62-7.64 (m, 2H), 7.36-7.40 (m, 2H), 7.12-7.25 (m, 5H), 6.96-7.08 (m, 1H), 6.20-6.71 (m, 1H), 5.50-5.70 (s, 2H), 5.06-5.19 (m, 1H), 4.50-4.89 (m, 1H), 3.68-3.73 (m, 4H), 3.44-3.47 (m, 1H), 3.30-3.32 (m, 1H), 3.14-3.19 (m, 2H), 2.83-2.86 (m, 2H), 2.42-2.50 (m, 4H), 2.02-2.27 (m, 2H), 1.70-1.72 (m, 1H).

Example 59: Preparation of 1-(6-(4-amino-3-(4-phenoxyphenyl)-1H-pyrazolo[3,4-d]pyrimidin-1-yl)-2-azabicyclo[2.2.1]octan-2-yl)prop-2-en-1-ene

Step 59-1: Preparation of tert-butyl 6-(4-amino-3-iodo-1H-pyrazolo[3,4-d]pyrimidin-1-yl)-2-azabicyclo[2.2.1]octan-2-carboxylate

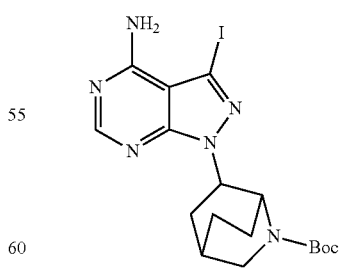

A title compound (200 mg, yield: 56%) was prepared in the same manner as in Step 1-1 of Example 1, except for using tert-butyl 6-hydroxy-1-azabicyclo[2.2.2]octane-2-carboxylate (880 mg, 3.89 mmol) and 3-iodo-1H-pyrazolo[3,4-d]pyrimidin-4-amine (680 mg, 2.59 mmol).

Step 59-2: Preparation of tert-butyl 6-(4-amino-3-(4-phenoxyphenyl)-1H-pyrazolo[3,4-d]pyrimidin-1-yl)-2-azabicyclo[2.2.2]octane-2-carboxylate

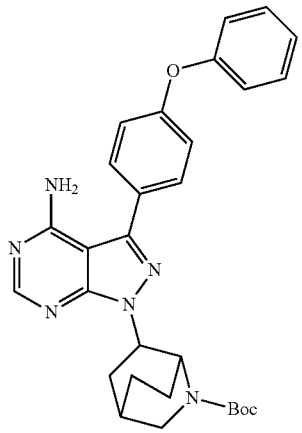 [SMILES: CC(C)(C)OC(=O)N1CC2CCC1C(n1nc(-c3ccc(Oc4ccccc4)cc3)c3c(N)ncnc31)C2]

A title compound (660 mg, yield: 54%) was prepared in the same manner as in Step 1-2 of Example 1, except for using tert-butyl 6-(4-amino-3-iodo-1H-pyrazolo[3,4-d]pyrimidin-1-yl)-2-azabicyclo[2.2.1]octan-2-carboxylate (1.13 g, 2.41 mmol) obtained in Step 59-1 and (4-phenoxyphenyl)boronic acid (640 mg, 3.00 mmol).

Step 59-3: Preparation of 1-(2-azabicyclo[2.2.2]octan-6-yl)-3-(4-phenoxyphenyl)-1H-pyrazolo[3,4-d]pyrimidin-4-amine hydrochloride

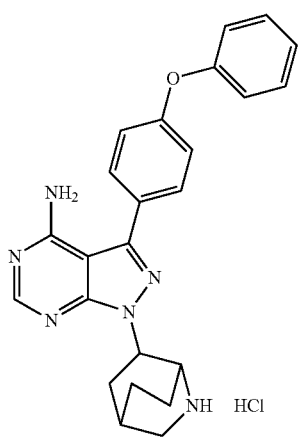 [SMILES: Nc1ncnc2c1c(-c1ccc(Oc3ccccc3)cc1)nn2C1CC2CCC1NC2 ; Cl]

A title compound (410 mg, yield: 71%) was prepared in the same manner as in Step 1-3 of Example 1, except for using tert-butyl 6-(4-amino-3-(4-phenoxyphenyl)-1H-pyrazolo[3,4-d]pyrimidin-1-yl)-2-azabicyclo[2.2.2]octane-2-carboxylate (660 mg, 1.29 mmol) obtained in Step 59-2.

Step 59-4: Preparation of 1-(6-(4-amino-3-(4-phenoxyphenyl)-1H-pyrazolo[3,4-d]pyrimidin-1-yl)-2-azabicyclo[2.2.1]octan-2-yl)prop-2-en-1-one

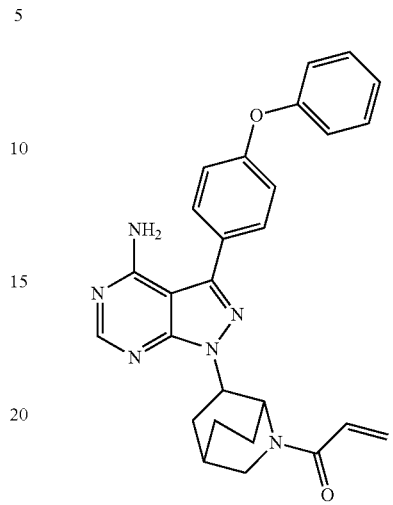

A title compound (57 mg, yield: 55%) was prepared in the same manner as in Step 1-4 of Example 1, except for using 1-(2-azabicyclo[2.2.2]octan-6-yl)-3-(4-phenoxyphenyl)-1H-pyrazolo[3,4-d]pyrimidin-4-amine hydrochloride (100 mg, 0.22 mmol) obtained in Step 59-3 and acryloyl chloride (90 uL, 1.11 mmol).

$^1$H NMR (500 MHz, CDCl$_3$): 8.22-8.25 (m, 1H), 7.65-7.67 (m, 2H), 7.39-7.43 (m, 2H), 7.09-7.185 (m, 5H), 6.61-6.68 (m, 1H), 6.14-6.22 (m, 1H), 5.65-5.75 (m, 1H), 5.12 (m, 1H), 4.52 (m, 1H), 4.20 (m, 1H), 3.45-3.65 (m, 1H), 3.35-3.38 (m, 1H), 2.41-2.51 (m, 2H), 1.87-1.90 (m, 2H), 1.55-1.60 (m, 2H).

Example 60: Preparation of (E)-4-(4-amino-1-(2-(4-(dimethylamino)but-2-enoyl)-2-azabicyclo[2.2.1]heptan-6-yl)-1H-pyrazolo[3,4-d]pyrimidin-3-yl)-N-(pyridin-2-yl)benzamide

Step 60-1: Preparation of (E)-4-(4-amino-1-(2-(4-bromobut-2-enoyl)-2-azabicyclo[2.2.1]heptan-6-yl)-1H-pyrazolo[3,4-d]pyrimidin-3-yl)-N-(pyridin-2-yl)benzamide

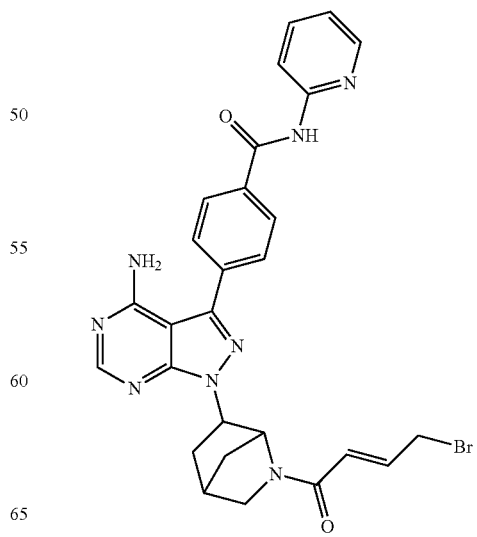

A title compound (110 mg, yield: 54%) was prepared in the same manner as in Example 44, except for using 4-(4-amino-1-(2-azabicyclo[2.2.1]heptan-6-yl)-1H-pyrazolo[3,4-d]pyrimidin-3-yl)-N-(pyridin-2-yl)benzamide hydrochloride (160 mg, 0.35 mmol) obtained in Step 4-4 of Example 49 and (E)-4-bromobut-2-enoyl chloride (70 mg, 0.39 mmol).

Step 60-2: Preparation of (E)-4-(4-amino-1-(2-(4-(dimethylamino)but-2-enoyl)-2-azabicyclo[2.2.1]heptan-6-yl)-1H-pyrazolo[3,4-d]pyrimidin-3-yl)-N-(pyridin-2-yl)benzamide

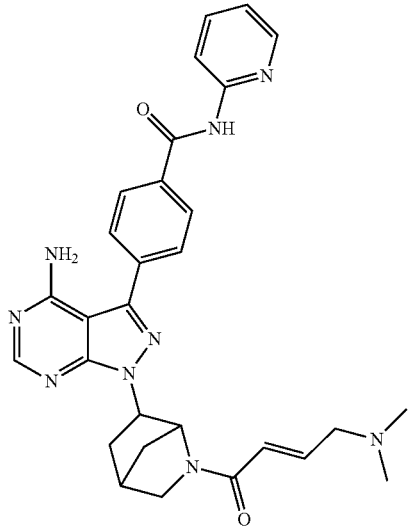 [SMILES: CN(C)C/C=C/C(=O)N1CC2CC1C(n1nc(-c3ccc(C(=O)Nc4ccccn4)cc3)c3c(N)ncnc31)C2]

A title compound (32 mg, yield: 68%) was prepared in the same manner as in Example 45, except for using (E)-4-(4-amino-1-(2-(4-bromobut-2-enoyl)-2-azabicyclo[2.2.1]heptan-6-yl)-1H-pyrazolo[3,4-d]pyrimidin-3-yl)-N-(pyridin-2-yl)benzamide (50 mg, 0.055 mmol) obtained in Step 60-1 and N,N-dimethylamine (6 mg, 0.13 mmol).

$^1$H NMR (500 MHz, CDCl$_3$): 8.41-8.50 (m, 1H), 8.25-8.35 (m, 1H), 7.97-8.03 (m, 2H), 7.82-7.85 (m, 2H), 7.76-7.78 (m, 1H). 7.56-7.58 (m, 1H), 6.78-6.83 (m, 1H), 6.36-6.48 (m, 1H), 5.76-5.78 (m, 1H), 5.52 (s, 2H), 4.90-5.10 (m, 1H), 4.50-4.87 (m, 1H), 3.42-3.57 (m, 1H), 3.23-3.26 (m, 1H), 2.42-2.83 (m, 2H), 2.20-2.31 (m, 1H), 2.04-2.12 (m, 1H), 1.72-1.74 (m, 1H).

Example 61: Preparation of (E)-4-(4-amino-1-(2-(4-(4-methylpiperazin-1-yl)but-2-enoyl)-2-azabicyclo[2.2.1]heptan-6-yl)-1H-pyrazolo[3,4-d]pyrimidin-3-yl)-N-(pyridin-2-yl)benzamide

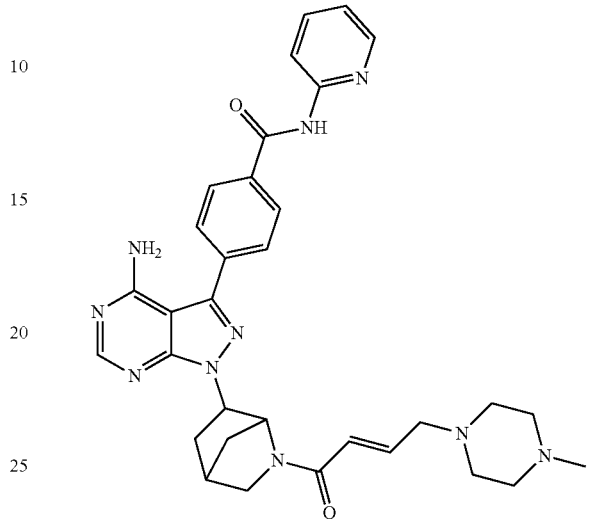

A title compound (17 mg, yield: 33%) was prepared in the same manner as in Example 45, except for using (E)-4-(4-amino-1-(2-(4-bromobut-2-enoyl)-2-azabicyclo[2.2.1]heptan-6-yl)-1H-pyrazolo[3,4-d]pyrimidin-3-yl)-N-(pyridin-2-yl)benzamide (50 mg, 0.087 mmol) obtained in Step 60-1 of Example 60 and 1-methylpyperazine (15 mg, 0.13 mmol).

$^1$H NMR (500 MHz, CDCl$_3$): 8.41-8.44 (m, 2H), 8.32-8.33 (m, 2H), 8.10-8.13 (m, 3H), 7.80-7.86 (m, 4H), 7.12-7.15 (m, 1H), 5.80-5.95 (s, 2H), 5.01-5.21 (m, 1H), 4.80-4.85 (m, 1H), 4.20-4.35 (m, 2H), 3.34-3.40 (m, 8H), 3.00-3.05 (m, 1H), 2.80-2.82 (m, 2H), 2.71-2.75 (m, 1H), 2.15-2.25 (m, 2H), 1.95-2.05 (m, 3H), 1.72-1.74 (m, 1H).

Example 62: Preparation of (E)-1-(6-(4-amino-3-(4-phenoxyphenyl)-1H-pyrazolo[3,4-d]pyrimidin-1-yl)-2-azabicyclo[2.2.1]heptan-2-yl)-4-(4-methylpiperazin-1-yl)but-2-en-1-one

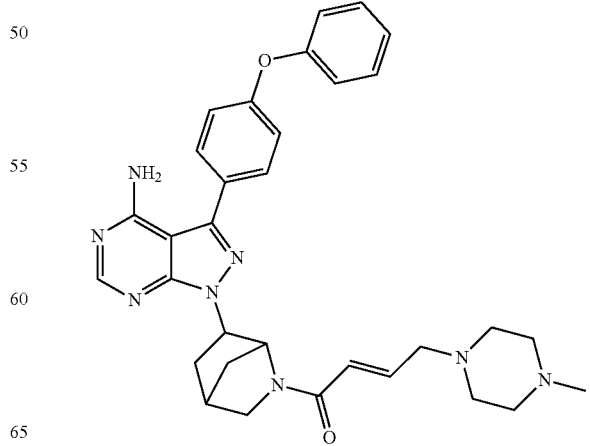

A title compound (41 mg, yield: 52%) was prepared in the same manner as in Example 45, except for using (E)-1-(6-(4-amino-3-(4-phenoxyphenyl)-1H-pyrazolo[3,4-d]pyrimidin-1-yl)-2-azabicyclo[2.2.1]heptan-2-yl)-4-bromobut-2-en-1-one (50 mg, 0.092 mmol) obtained in Example 44 and 1-methylpyperazine (15 mg, 0.14 mmol).

¹H NMR (500 MHz, CDCl₃): 8.33-8.37 (m, 1H), 7.61-7.65 (m, 2H), 7.36-7.40 (m, 2H), 7.07-7.20 (m, 4H), 6.88-6.90 (m, 2H), 6.25-6.70 (m, 1H), 5.60-5.80 (s, 2H), 5.01-5.17 (m, 1H), 4.82-4.92 (m, 1H), 4.48-4.50 (m, 1H), 4.45-4.50 (m, 4H), 4.25-4.35 (m, 4H), 3.01-3.10 (m, 1H), 2.78-2.80 (m, 2H), 2.70-2.72 (m, 1H), 2.50-2.55 (m, 2H), 2.27-2.30 (m, 1H), 1.95-2.05 (m, 3H), 1.70-1.72 (m, 1H).

Example 63: Preparation of (E)-1-(6-(4-amino-3-(4-phenoxyphenyl)-1H-pyrazolo[3,4-d]pyrimidin-1-yl)-2-azabicyclo[2.2.1]heptan-2-yl)-4-(piperidin-1-yl)but-2-en-1-one

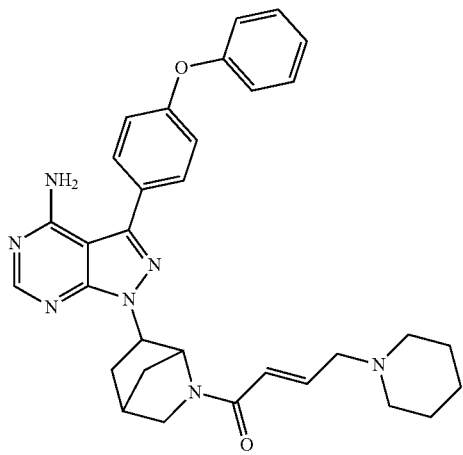 [SMILES: Nc1ncnc2c1c(-c1ccc(Oc3ccccc3)cc1)nn2C1CC2CC1N(C(=O)/C=C/CN1CCCCC1)C2]

A title compound (40 mg, yield: 70%) was prepared in the same manner as in Example 45, except for using (E)-1-(6-(4-amino-3-(4-phenoxyphenyl)-1H-pyrazolo[3,4-d]pyrimidin-1-yl)-2-azabicyclo[2.2.1]heptan-2-yl)-4-bromobut-2-en-1-one (50 mg, 0.092 mmol) obtained in Example 44 and piperidine (14 mg, 0.14 mmol).

¹H NMR (500 MHz, CDCl₃): 8.34-8.37 (m, 1H), 7.63-7.65 (m, 2H), 7.38-7.41 (m, 2H), 7.17-7.27 (m, 3H), 6.95-7.15 (m, 3H). 6.20-6.82 (m, 1H), 5.60-5.70 (s, 2H), 5.11-5.19 (m, 1H), 4.51-4.87 (m, 1H), 3.45-3.51 (m, 1H), 3.22-3.30 (m, 3H), 2.83-2.86 (m, 2H), 2.40-2.50 (m, 4H), 2.25-2.30 (m, 2H), 2.05-2.20 (m, 2H), 1.72-1.74 (m, 1H), 1.50-1.59 (m, 4H).

Example 64: Preparation of 4-(1-(2-acryloyl-2-azabicyclo[2.2.1]heptan-6-yl)-4-amino-1H-pyrazolo[3,4-d]pyrimidin-3-yl)-3-fluoro-N-(pyridin-2-yl)benzamide Step 64-1: Preparation of tert-butyl 6-(4-amino-3-(2-fluoro-4-(pyridin-2-ylcarbamoyl)phenyl)-1H-pyrazolo[3,4-d]pyrimidin-1-yl)-2-azabicyclo[2.2.1]heptane-2-carboxylate

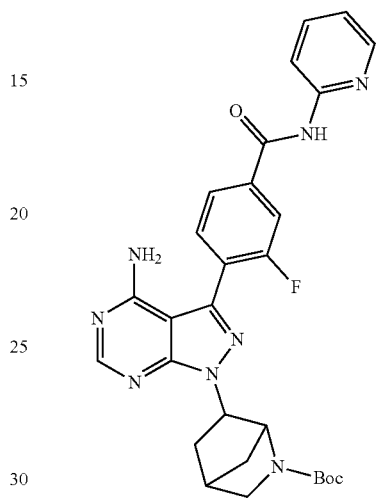

A title compound (590 mg, yield: 99%) was prepared in the same manner as in Step 1-2 of Example 1, except for using tert-butyl 6-(4-amino-3-iodo-1H-pyrazolo[3,4-d]pyrimidin-1-yl)-2-azabicyclo[2.2.1]heptane-2-carboxylate (500 mg, 1.10 mmol) obtained in Step 1-1 of Example 1 and (2-fluoro-4-(pyridin-2-ylcarbamoyl)phenyl)boronic acid (470 mg, 1.37 mmol).

Step 64-2: Preparation of 4-(4-amino-1-(2-azabicyclo[2.2.1]heptan-6-yl)-1H-pyrazolo[3,4-d]pyrimidin-3-yl)-3-fluoro-N-(pyridin-2-yl)benzamide hydrochloride

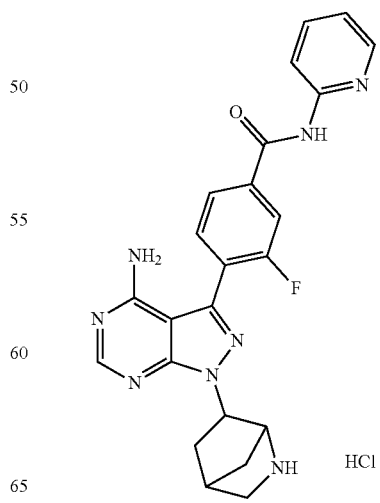

A title compound (302 mg, yield: 56%) was prepared in the same manner as in Step 1-3 of Example 1, except for using tert-butyl 6-(4-amino-3-(2-fluoro-4-(pyridin-2-ylcarbamoyl)phenyl)-1H-pyrazolo[3,4-d]pyrimidin-1-yl)-2-azabicyclo[2.2.1]heptane-2-carboxylate hydrochloride (615 mg, 1.13 mmol) obtained in Step 64-1.

Step 64-3: Preparation of 4-(1-(2-acryloyl-2-azabicyclo[2.2.1]heptan-6-yl)-4-amino-1H-pyrazolo[3,4-d]pyrimidin-3-yl)-3-fluoro-N-(pyridin-2-yl)benzamide

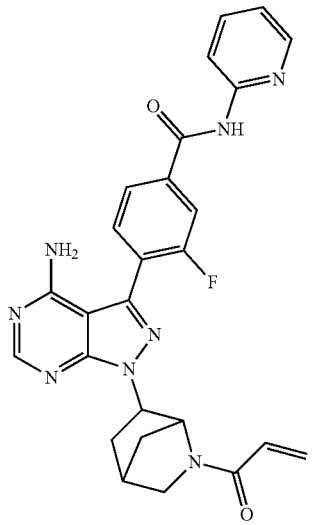 [SMILES: C=CC(=O)N1CC2CC1C(n1nc(-c3ccc(C(=O)Nc4ccccn4)cc3F)c3c(N)ncnc31)C2]

A title compound (160 mg, yield: 51%) was prepared in the same manner as in Step 1-4 of Example 1, except for using 4-(4-amino-1-(2-azabicyclo[2.2.1]heptan-6-yl)-1H-pyrazolo[3,4-d]pyrimidin-3-yl)-3-fluoro-N-(pyridin-2-yl) benzamide hydrochloride (302 mg, 0.63 mmol) obtained in Step 64-2 and acryloyl chloride (260 uL, 3.14 mmol).

$^1$H NMR (500 MHz, CDCl$_3$): 8.41-8.50 (m, 1H), 8.25-8.35 (m, 1H), 7.97-8.03 (m, 2H), 7.82-7.85 (m, 2H), 7.76-7.78 (m, 1H), 7.56-7.58 (m, 1H), 6.78-6.83 (m, 1H), 6.36-6.48 (m, 1H), 5.76-5.78 (m, 1H), 5.52 (s, 2H), 4.90-5.10 (m, 1H), 4.50-4.87 (m, 1H), 3.42-3.57 (m, 1H), 3.23-3.26 (m, 1H), 2.42-2.83 (m, 2H), 2.20-2.31 (m, 1H), 2.04-2.12 (m, 1H), 1.72-1.74 (m, 1H).

Example 65: Preparation of (E)-1-(5-(4-amino-3-(4-phenoxyphenyl)-1H-pyrazolo[3,4-d]pyrimidin-1-yl)-2-azabicyclo[2.2.1]heptan-2-yl)-4-bromobut-2-en-1-one

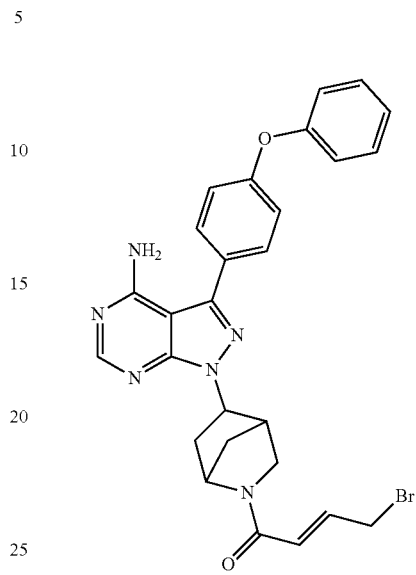

A title compound (57 mg, yield: 41%) was prepared in the same manner as in Example 44, except for using 1-(2-azabicyclo[2.2.1]heptan-5-yl)-3-(4-phenoxyphenyl)-1H-pyrazolo[3,4-d]pyrimidin-4-amine hydrochloride (110 mg, 0.25 mmol) obtained in Step 11-3 of Example 11 and (E)-4-bromobut-2-enoyl chloride (140 mg, 0.76 mmol).

$^1$H NMR (500 MHz, CDCl$_3$): 8.24-8.26 (m, 1H), 7.70-7.77 (m, 2H), 7.40-7.42 (m, 2H), 7.11-7.20 (m, 5H), 6.97-7.02 (m, 1H), 6.88-6.90 (m, 1H), 5.21-5.24 (m, 2H), 3.76 (s, 2H), 2.97-3.05 (m, 1H), 2.88-2.90 (m, 1H), 2.75-2.78 (m, 1H), 2.68-2.70 (m, 1H), 2.20-2.25 (m, 1H), 1.85-1.88 (m, 1H), 1.70-1.72 (m, 1H).

Example 66: Preparation of (E)-1-(5-(4-amino-3-(4-phenoxyphenyl)-1H-pyrazolo[3,4-d]pyrimidin-1-yl)-2-azabicyclo[2.2.1]heptan-2-yl)-4-(piperidin-1-yl)but-2-en-1-one

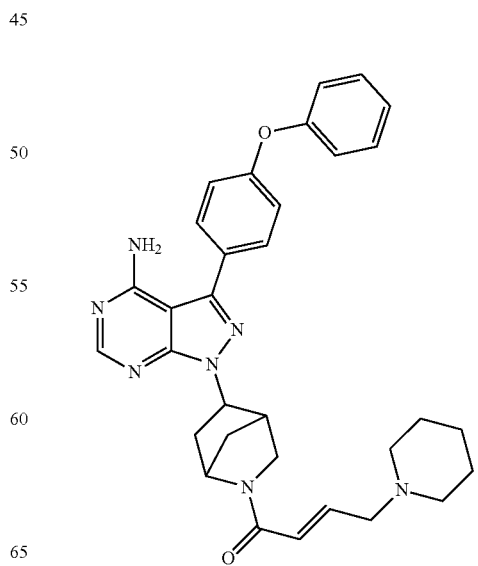

A title compound (21 mg, yield: 37%) was prepared in the same manner as in Example 45, except for using (E)-1-(5-(4-amino-3-(4-phenoxyphenyl)-1H-pyrazolo[3,4-d]pyrimidin-1-yl)-2-azabicyclo[2.2.1]heptan-2-yl)-4-bromobut-2-en-1-one (57 mg, 0.11 mmol) obtained in Example 65 and piperidine (17 mg, 0.16 mmol).

$^1$H NMR (500 MHz, CDCl$_3$): 8.29-8.30 (m, 1H), 7.55-7.62 (m, 2H), 7.30-7.35 (m, 3H), 7.05-7.40 (m, 5H), 6.88-6.90 (m, 1H), 6.25-6.62 (m, 1H), 5.70-5.95 (s, 2H), 5.35-5.40 (m, 1H), 4.72-4.75 (m, 1H), 4.50-4.60 (m, 1H), 3.55-3.60 (m, 1H), 3.10-3.30 (m, 2H), 2.95-3.05 (m, 2H), 2.75-2.80 (m, 2H), 2.65-2.70 (m, 2H), 2.20-2.35 (m, 2H), 1.95-2.05 (m, 2H), 1.70-1.72 (m, 1H).

Example 67: Preparation of 4-(1-(2-acryloyl-2-azabicyclo[2.2.1]heptan-6-yl)-4-amino-1H-pyrazolo[3,4-d]pyrimidin-3-yl)-N-(4-fluoropyridin-2-yl)benzamide

Step 67-1: Preparation of tert-butyl 6-(4-amino-3-(4-((4-fluoropyridin-2-yl)carbamoyl)phenyl)-1H-pyrazolo[3,4-d]pyrimidin-1-yl)-2-azabicyclo[2.2.1]heptane-2-carboxylate

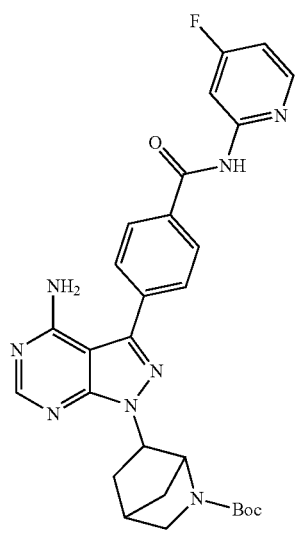 [SMILES: CC(C)(C)OC(=O)N1CC2CC1C(n1nc(-c3ccc(C(=O)Nc4cc(F)ccn4)cc3)c3c(N)ncnc31)C2]

A title compound (73 mg, yield: 61%) was prepared in the same manner as in Step 1-2 of Example 1, except for using tert-butyl 6-(4-amino-3-iodo-1H-pyrazolo[3,4-d]pyrimidin-1-yl)-2-azabicyclo[2.2.1]heptane-2-carboxylate (100 mg, 0.22 mmol) obtained in Step 1-1 of Example 1 and N-(4-fluoropyridin-2-yl)-4-(4,4,5,5-tetramethyl-1,3,2-dioxaborolan-2-yl)-benzamide (94 mg, 0.27 mmol).

Step 67-2: Preparation of 4-(4-amino-1-(2-azabicyclo[2.2.1]heptan-6-yl)-1H-pyrazolo[3,4-d]pyrimidin-3-yl)-(4-fluoropyridin-2-yl)benzamide hydrochloride

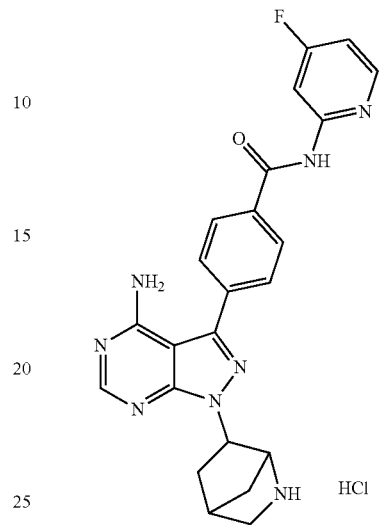

A title compound (49 mg, yield: 82%) was prepared in the same manner as in Step 1-3 of Example 1, except for using tert-butyl 6-(4-amino-3-(4-((4-fluoropyridin-2-yl)carbamoyl)phenyl)-1H-pyrazolo[3,4-d]pyrimidin-1-yl)-2-azabicyclo[2.2.1]heptane-2-carboxylate (73 mg, 0.13 mmol) obtained in Step 67-1.

Step 67-3: Preparation of 4-(1-(2-acryloyl-2-azabicyclo[2.2.1]heptan-6-yl)-4-amino-1H-pyrazolo[3,4-d]pyrimidin-3-yl)-N-(4-fluoropyridin-2-yl)benzamide

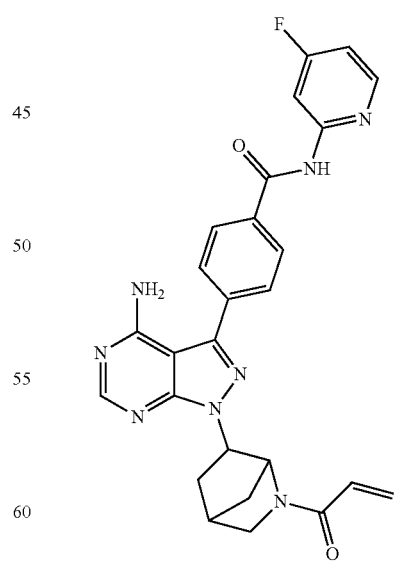

A title compound (28 mg, yield: 55%) was prepared in the same manner as in Step 1-4 of Example 1, except for using 4-(4-amino-1-(2-azabicyclo[2.2.1]heptan-6-yl)-1H-pyrazolo[3,4-d]pyrimidin-3-yl)-(4-fluoropyridin-2-yl)benzamide hydrochloride (49 mg, 0.10 mmol) obtained in Step 67-2 and acryloyl chloride (41 uL, 0.51 mmol).

¹H NMR (500 MHz, CDCl₃): 8.73-8.80 (m, 1H), 8.41-8.46 (m, 1H), 8.22-8.30 (m, 2H), 8.09-8.12 (m, 2H), 7.87-7.89 (m, 2H). 6.85-6.90 (m, 1H), 6.81-6.84 (m, 0.6H), 6.46-6.50 (m, 1H), 6.30-6.35 (m, 0.4H), 5.78-5.80 (m, 1H), 5.47-5.52 (s, 2H), 5.15-5.27 (m, 1H), 4.50-4.89 (m, 1H), 3.52-3.60 (m, 1H), 3.28-3.35 (m, 1H), 2.87-2.89 (m, 1H), 2.41-2.46 (m, 1H), 2.10-2.27 (m, 2H), 1.75-1.77 (m, 1H).

Example 68: Preparation of 4-(1-(2-acryloyl-2-azabicyclo[2.2.1]heptan-6-yl)-4-amino-1H-pyrazolo[3,4-d]pyrimidin-3-yl)-N-(4-methylpyridin-2-yl)benzamide Step 68-1: Preparation of tert-butyl 6-(4-amino-3-(4-((4-methylpyridin-2-yl)carbamoyl)phenyl)-1H-pyrazolo[3,4-d]pyrimidin-2-yl)-2-azabicyclo[2.2.1]heptane-2-carboxylate

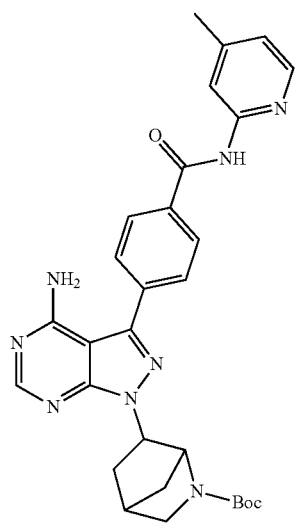 [SMILES: Cc1ccnc(NC(=O)c2ccc(-c3nn(C4CC5CC4N(C(=O)OC(C)(C)C)C5)c4ncnc(N)c34)cc2)c1]

A title compound (74 mg, yield: 63%) was prepared in the same manner as in Step 1-2 of Example 1, except for using tert-butyl 6-(4-amino-3-iodo-1H-pyrazolo[3,4-d]pyrimidin-1-yl)-2-azabicyclo[2.2.1]heptane-2-carboxylate (100 mg, 0.21 mmol) obtained in Step 1-1 of Example 1 and N-(4-methylpyridin-2-yl)-4-(4,4,5,5-tetramethyl-1,3,2-dioxaborolan-2-yl)-benzamide (93 mg, 0.27 mmol).

Step 68-2: Preparation of 4-(4-amino-1-(2-azabicyclo[2.2.1]heptan-6-yl)-1H-pyrazolo[3,4-d]pyrimidin-3-yl)-N-(4-methylpyridin-2-yl)benzamide hydrochloride

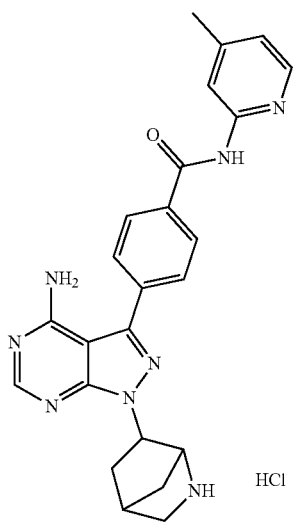 [SMILES: Cc1ccnc(NC(=O)c2ccc(-c3nn(C4CC5CNC4C5)c4ncnc(N)c34)cc2)c1 ; Cl]

A title compound (59 mg, yield: 91%) was prepared in the same manner as in Step 1-3 of Example 1, except for using tert-butyl 6-(4-amino-3-(4-((4-methylpyridin-2-yl)carbamoyl)phenyl)-1H-pyrazolo[3,4-d]pyrimidin-2-yl)-2-azabicyclo[2.2.1]heptane-2-carboxylate (74 mg, 0.14 mmol) obtained in Step 68-1.

Step 68-3: Preparation of 4-(1-(2-acryloyl-2-azabicyclo[2.2.1]heptan-6-yl)-4-amino-1H-pyrazolo[3,4-d]pyrimidin-3-yl)-N-(4-methylpyridin-2-yl)benzamide

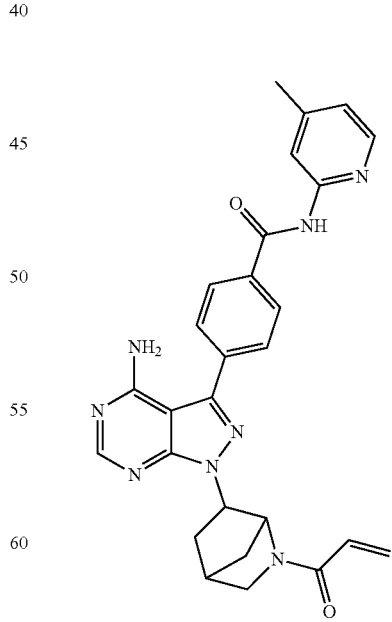

A title compound (35 mg, yield: 57%) was prepared in the same manner as in Step 1-4 of Example 1, except for using 4-(4-amino-1-(2-azabicyclo[2.2.1]heptan-6-yl)-1H-pyrazolo[3,4-d]pyrimidin-3-yl)-N-(4-methylpyridin-2-yl)benzamide hydrochloride (59 mg, 0.12 mmol) obtained in Step 68-2 and acryloyl chloride (50 uL, 0.62 mmol).

$^{1}$H NMR (500 MHz, CDCl$_{3}$): 8.85-8.90 (s, 1H), 8.25-8.41 (m, 2H), 8.08-8.15 (m, 3H), 7.82-7.89 (m, 2H), 6.92-6.97 (m, 1H), 6.37-6.78 (m, 1H), 6.42-6.46 (m, 1H), 5.75-6.80 (m, 1H), 5.60-5.70 (s, 2H), 5.11-5.24 (m, 1H), 4.55-4.87 (m, 1H), 3.72-3.74 (m, 1H), 3.47-3.52 (m, 1H), 3.27-3.35 (m, 1H), 2.85-2.87 (m, 1H), 2.57-2.60 (m, 1H), 2.43 (s, 3H), 2.25-2.30 (m, 1H), 1.72-1.74 (m, 1H).

Example 69: Preparation of 4-(1-((1R,4R,6S)-2-acryloyl-2-azabicyclo[2.2.1]heptan-6-yl)-4-amino-1H-pyrazolo[3,4-d]pyrimidin-3-yl)-N-(pyridin-2-yl)benzamide Step 69-1: Preparation of tert-butyl (1R,4S,6R)-6-hydroxy-2-azabicyclo[2.2.1]heptane-2-carboxylate

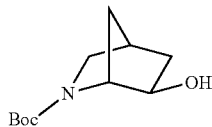 [SMILES: CC(C)(C)OC(=O)N1CC2CC(O)C1C2]

Tert-butyl(1R,4S)-2-azabicyclo[2.2.1]hept-5-en-2-carboxylate (7.8 g, 40.0 mmol) was dissolved in tetrahydrofuran (20 mL) and then cooled to 0° C. 1M borane-tetrahydrofuran solution (40 mL, 40.0 mmol) was slowly added thereto and then stirred at 0° C. for 3 hours. Upon completion of the reaction, water (1 mL) was added to remove the remaining borane, and sodium perborate (15.4 g, 100.0 mmol) was dissolved in water (60 mL) and added at once, followed by stirring at 20° C. for 12 hours. The reaction mixture was diluted with ethyl acetate and washed with saturated aqueous sodium chloride solution. The organic layer was collected, dried over magnesium sulfate, filtered and then concentrated under reduced pressure. The residue was purified by column chromatography (ethyl acetate: 100%) to obtain a title compound (3.0 g, yield: 35%).

Step 69-2: Preparation of tert-butyl (1S,4R,6S)-6-(4-amino-3-iodo-1H-pyrazolo[3,4-d]pyrimidin-1-yl)-2-azabicyclo[2.2.1]heptane-2-carboxylate

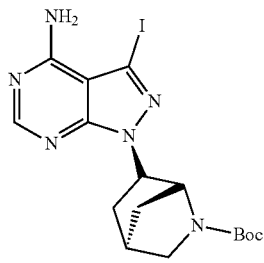

After tert-butyl (1R,4S,6R)-6-hydroxy-2-azabicyclo[2.2.1]heptane-2-carboxylate (613 mg, 2.9 mmol) obtained in Step 69-1 was dissolved in tetrahydrofuran (22 mL), diisopropyl azodicarboxylate (0.6 mL, 2.9 mmol) was slowly added thereto. After stirring the reaction solution for 1 minute, 3-iodo-1H-pyrazolo[3,4-d]pyrimidin-4-amine (500 mg, 1.9 mmol) was added thereto, and heated for 3 to 5 minutes until the solid remaining in the reaction solution was completely dissolved, followed by stirring at 20° C. for 1 hour. Upon completion of the reaction, the reaction mixture was concentrated under reduced pressure, and the residue was purified by column chromatography (ethyl acetate: 100%) to give a title compound (47 mg, yield: 54%).

Step 69-3: Preparation of tert-butyl (1S,4R,6S)-6-(4-amino-3-(4-(pyridin-2-ylcarbamoyl)phenyl)-1H-pyrazolo[3,4-d]pyrimidin-1-yl)-2-azabicyclo[2.2.1]heptane-2-carboxylate

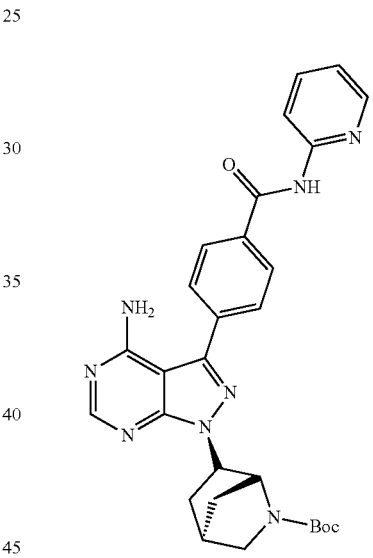

After tert-butyl (1S,4R,6S)-6-(4-amino-3-iodo-1H-pyrazolo[3,4-d]pyrimidin-1-yl)-2-azabicyclo[2.2.1]heptane-2-carboxylate (300 mg, 0.6 mmol) obtained in Step 69-2 was dissolved in 1,4-dioxane (7 mL) and water (1 mL), (4-(pyridin-2-ylcarbamoyl) phenyl)boronic acid (199 mg, 0.8 mmol), potassium carbonate (454 mg, 3.3 mmol) and [1,1'-bis(diphenylphosphino)ferrocene]dichloro palladium(II) (34 mg, 0.1 mmol) were sequentially added thereto, and the mixture was refluxed and stirred at 110° C. for 90 minutes. Upon completion of the reaction, the mixture was diluted with ethyl acetate and washed with saturated sodium chloride solution. The organic layer was collected, dried over magnesium sulfate, filtered and then concentrated under reduced pressure. The residue was purified by column chromatography (ethyl acetate 100%) to obtain a title compound (330 mg, yield: 96%).

Step 69-4: Preparation of 4-(4-amino-1-((1S,4R, 6S)-2-azabicyclo[2.2.1]heptan-6-yl)-1H-pyrazolo[3, 4-d]pyrimidin-3-yl)-N-(pyridin-2-yl)benzamide hydrochloride

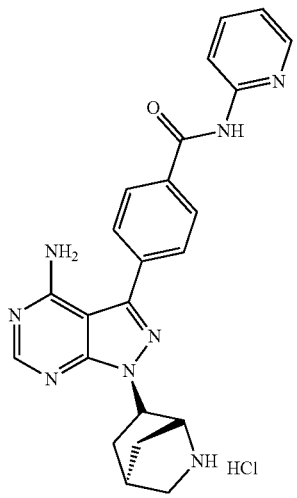

After tert-butyl (1S,4R,6S)-6-(4-amino-3-(4-(pyridin-2-ylcarbamoyl)phenyl)-1H-pyrazolo[3,4-d]pyrimidin-1-yl)-2-azabicyclo[2.2.1]heptane-2-carboxylate (300 mg, 0.6 mmol) obtained in Step 69-3 was dissolved in ethyl acetate (2 mL), 1 N hydrochloric acid (5 mL) dissolved in ethyl acetate was added thereto, followed by stirring at 20° C. for 4 hours. Upon completion of the reaction, the solution was filtered to obtain a title compound (240 mg, yield: 98%).

Step 69-5: Preparation of 4-(1-((1R,4R,6S)-2-acryloyl-2-azabicyclo[2.2.1]heptan-6-yl)-4-amino-1H-pyrazolo[3,4-d]pyrimidin-3-yl)-N-(pyridin-2-yl)benzamide

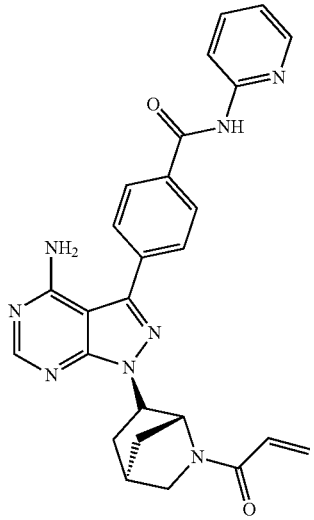

4-(4-Amino-1-((1S,4R,6S)-2-azabicyclo[2.2.1]heptan-6-yl)-1H-pyrazolo[3,4-d]pyrimidin-3-yl)-N-(pyridin-2-yl)benzamide hydrochloride (240 mg, 0.51 mmol) obtained in Step 69-4 was dissolved in tetrahydrofuran (24 mL) and water (8 mL), and then cooled to 0° C., to which sodium bicarbonate (220 mg, 2.6 mmol) was added. Acryloyl chloride (0.2 mL, 2.6 mmol) was dissolved in tetrahydrofuran (1 mL) and slowly added to the reaction solution, followed by stirring at 20° C. for 10 minutes. Upon completion of the reaction, the mixture was diluted with ethyl acetate, washed with saturated ammonium chloride aqueous solution and saturated sodium chloride aqueous solution, dried over anhydrous magnesium sulfate, filtered and concentrated under reduced pressure to obtain a title compound (90 mg, yield: 37%).

$^1$H NMR (500 MHz, CDCl$_3$): 8.72-8.74 (m, 1H), 8.42-8.45 (m, 2H), 8.32-8.33 (m, 1H), 8.10-8.15 (m, 2H), 7.86-7.90 (m, 2H). 7.81-7.83 (m, 1H), 7.10-7.12 (m, 1H), 6.47-6.82 (m, 1H), 6.40-6.47 (m, 1H), 5.74-5.77 (m, 1H), 5.50-5.73 (s, 2H), 5.15-5.20 (m, 1H), 4.55-4.95 (m, 1H), 3.51-3.60 (m, 1H), 3.25-3.29 (m, 1H), 2.87-2.88 (m, 1H), 2.41-2.50 (m, 1H), 2.22-2.30 (m, 2H), 1.73-1.75 (m, 1H).

Example 70: Preparation of 4-(1-(2-acryloyl-2-azabicyclo [2.2.1]heptan-6-yl)-4-amino-1H-pyrazolo [3,4-d]pyrimidin-3-yl)-N-(6-(trifluoromethyl)pyridin-2-yl)benzamide

Step 70-1: Preparation of tert-butyl 6-(4-amino-3-(4-((6-(trifluoromethyl)pyridin-2-yl)carbamoyl)phenyl)-1H-pyrazolo[3,4-d]pyrimidin-1-yl)-2-azabicyclo[2.2.1]heptane-2-carboxylate A title compound (110 mg, yield: 83%) was prepared in the same manner as in Step 1-2 of Example 1, except for using tert-butyl 6-(4-amino-3-iodo-1H-pyrazolo[3,4-d]pyrimidin-1-yl)-2-azabicyclo[2.2.1]heptane-2-carboxylate (100 mg, 0.22 mmol) obtained in Step 1-1 of Example 1 and 4-(4,4,5,5-tetramethyl-1,3,2-dioxaborolan-2-yl)-N-(6-(trifluoromethyl)pyridin-2-yl)benzamide (110 mg, 0.27 mmol).

Step 70-2: Preparation of 4-(4-amino-1-(2-azabicyclo[2.2.1]heptan-6-yl)-1H-pyrazolo[3,4-d]pyrimidin-3-yl)-N-(6-(trifluoromethyl)pyridin-2-yl)benzamide hydrochloride

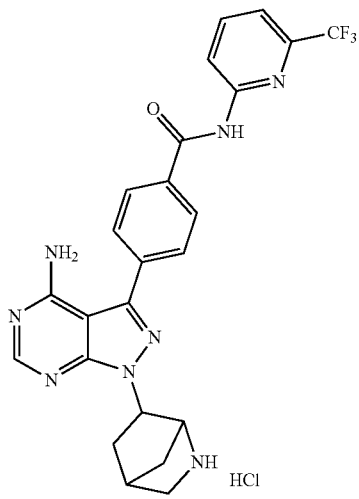 [SMILES: Nc1ncnc2c1c(-c1ccc(C(=O)Nc3cccc(C(F)(F)F)n3)cc1)nn2C1CC2CNC1C2 ; Cl]

A title compound (83 mg, yield: 86%) was prepared in the same manner as in Step 1-3 of Example 1, except for using tert-butyl 6-(4-amino-3-(4-((6-(trifluoromethyl)pyridin-2-yl)carbamoyl)phenyl)-1H-pyrazolo[3,4-d]pyrimidin-1-yl)-2-azabicyclo[2.2.1]heptane-2-carboxylate (110 mg, 0.18 mmol) obtained in Step 70-1

Step 70-3: Preparation of 4-(1-(2-acryloyl-2-azabicyclo [2.2.1]heptan-6-yl)-4-amino-1H-pyrazolo[3,4-d]pyrimidin-3-yl)-N-(6-(trifluoromethyl)pyridin-2-yl)benzamide

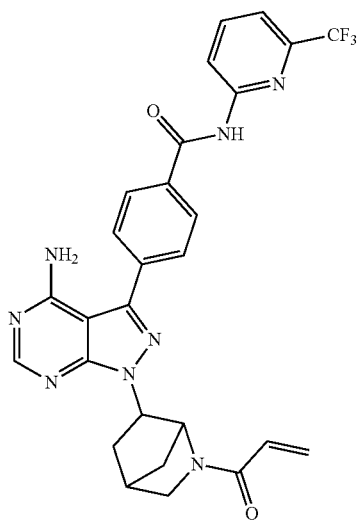 [SMILES: C=CC(=O)N1CC2CC1C(n1nc(-c3ccc(C(=O)Nc4cccc(C(F)(F)F)n4)cc3)c3c(N)ncnc31)C2]

A title compound (35 mg, yield: 41%) was prepared in the same manner as in Step 1-4 of Example 1, except for using 4-(4-amino-1-(2-azabicyclo[2.2.1]heptan-6-yl)-1H-pyrazolo[3,4-d]pyrimidin-3-yl)-N-(6-(trifluoromethyl)pyridin-2-yl)benzamide hydrochloride (83 mg, 0.16 mmol) obtained in Step 70-2 and acryloyl chloride (71 uL, 0.78 mmol).

$^1$H NMR (500 MHz, CDCl$_3$): 8.82-8.83 (m, 1H), 8.60-8.62 (m, 1H), 8.39-8.42 (m, 1H), 8.10-8.12 (m, 2H), 7.93-7.95 (m, 1H), 7.84-7.86 (m, 2H), 7.47-7.48 (m, 1H), 6.76-6.80 (m, 0.6H), 6.42-6.45 (m, 1H), 6.31-6.35 (m, 0.4H), 5.45-5.55 (s, 2H), 5.10-5.22 (m, 1H), 4.53-4.89 (m, 1H), 3.42-3.50 (m, 1H), 3.27-3.32 (m, 1H), 2.86-2.90 (m, 1H), 2.52-2.57 (m, 1H), 2.10-2.35 (m, 2H), 1.71-1.74 (m, 1H).

Example 71: Preparation of 4-(1-(2-acryloyl-2-azabicyclo[2.2.1]heptan-6-yl)-4-amino-1H-pyrazolo[3,4-d]pyrimidin-3-yl)-N-(4-cyanopyridin-2-yl)benzamide Step 71-1: Preparation of tert-butyl 6-(4-amino-3-(4-((4-cyanopyridin-2-yl)carbamoyl)phenyl)-1H-pyrazolo[3,4-d]pyrimidin-1-yl)-2-azabicyclo[2.2.1]heptane-2-carboxylate

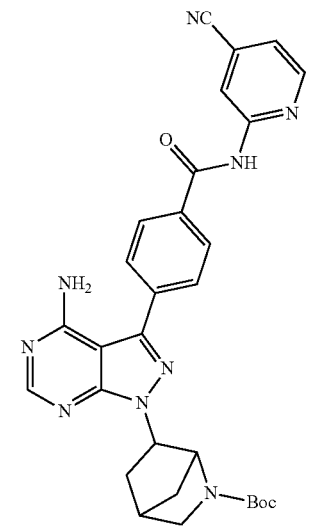 [SMILES: CC(C)(C)OC(=O)N1CC2CC1C(n1nc(-c3ccc(C(=O)Nc4cc(C#N)ccn4)cc3)c3c(N)ncnc31)C2]

A title compound (57 mg, yield: 47%) was prepared in the same manner as in Step 1-2 of Example 1, except for using tert-butyl 6-(4-amino-3-iodo-1H-pyrazolo[3,4-d]pyrimidin-1-yl)-2-azabicyclo[2.2.1]heptane-2-carboxylate (100 mg, 0.22 mmol) obtained in Step 1-1 of Example 1 and N-(4-cyanopyridin-2-yl)-4-(4,4,5,5-tetramethyl-1,3,2-dioxaborolan-2-yl)-benzamide (96 mg, 0.27 mmol).

Step 71-2: Preparation of 4-(4-amino-1-(2-azabicyclo[2.2.1]heptan-6-yl)-1H-pyrazolo[3,4-d]pyrimidin-3-yl)-N-(4-cyanopyridin-2-yl)benzamide hydrochloride

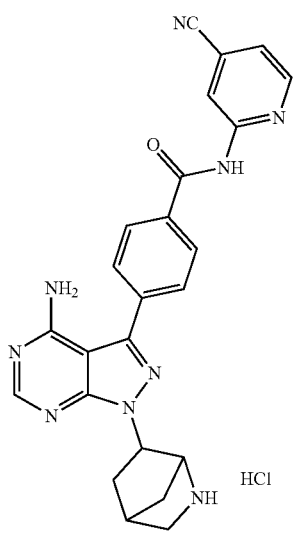 [SMILES: N#Cc1ccnc(NC(=O)c2ccc(-c3nn(C4CC5CNC4C5)c4ncnc(N)c34)cc2)c1 ; Cl]

A title compound (42 mg, yield: 84%) was prepared in the same manner as in Step 1-3 of Example 1, except for using tert-butyl 6-(4-amino-3-(4-((4-cyanopyridin-2-yl)carbamoyl)phenyl)-1H-pyrazolo[3,4-d]pyrimidin-1-yl)-2-azabicyclo[2.2.1]heptane-2-carboxylate (57 mg, 0.10 mmol) obtained in Step 71-1.

Step 71-3: Preparation of 4-(I-(2-acryloyl-2-azabicyclo[2.2.1]heptan-6-yl)-4-amino-1H-pyrazolo[3,4-d]pyrimidin-3-yl)-N-(4-cyanopyridin-2-yl)benzamide

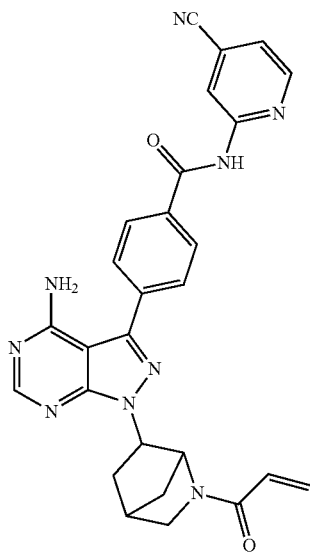 [SMILES: C=CC(=O)N1CC2CC1C(n1nc(-c3ccc(C(=O)Nc4cc(C#N)ccn4)cc3)c3c(N)ncnc31)C2]

A title compound (15 mg, yield: 35%) was prepared in the same manner as in Step 1-4 of Example 1, except for using 4-(4-amino-1-(2-azabicyclo[2.2.1]heptan-6-yl)-1H-pyrazolo[3,4-d]pyrimidin-3-yl)-N-(4-cyanopyridin-2-yl)benzamide hydrochloride (42 mg, 0.086 mmol) obtained in Step 71-2 and acryloyl chloride (39 uL, 0.43 mmol).

$^1$H NMR (500 MHz, CDCl$_3$): 8.85-8.91 (m, 1H), 8.74-8.79 (m, 1H), 8.37-8.50 (m, 2H), 8.12-8.20 (m, 2H), 7.87-7.89 (m, 2H). 7.33-7.34 (m, 1H), 6.85-6.90 (m, 0.6H), 6.47-6.49 (m, 1H), 6.30-6.35 (m, 0.4H), 5.75-5.78 (m, 1H), 5.55-5.57 (s, 2H), 5.15-5.30 (m, 1H), 4.50-4.89 (m, 1H), 3.42-3.57 (m, 1H), 3.22-3.27 (m, 1H), 2.87-2.90 (m, 1H), 2.45-2.52 (m, 1H), 2.14-2.27 (m, 2H), 1.73-1.75 (m, 1H).

Example 72: Preparation of 4-(1-((1S,4R,6S)-2-acryloyl-2-azabicyclo[2.2.1]heptan-6-yl)-4-amino-1H-pyrazolo[3,4-d]pyrimidin-3-yl)-N-(4-fluoropyridin-2-yl)benzamide Step 72-1: Preparation of tert-butyl (1S,4R,6S)-6-(4-amino-3-(4-((4-fluoropyridin-2-yl)carbamoyl)phenyl-1H-pyrazolo[3,4-d]pyrimidin-1-yl)-2-azabicyclo[2.2.1]heptane-2-carboxylate A title compound (260 mg, yield: 74%) was prepared in the same manner as in Step 69-3 of Example 69, except for using tert-butyl (1S,4R,6S)-6-(4-amino-3-iodo-1H-pyrazolo[3,4-d]pyrimidin-1-yl)-2-azabicyclo[2.2.1]heptane-2-carboxylate (100 mg, 0.22 mmol) obtained in Step 69-2 of Example 69 and N-(4-fluoropyridin-2-yl)-4-(4,4,5,5-tetramethyl-1,3,2-dioxaborolan-2-yl)benzamide (94 mg, 0.27 mmol).

Step 72-2: Preparation of 4-(4-amino-1-(1S,4R,6S)-2-azabicyclo[2.2.1]heptan-6-yl)-1H-pyrazolo[3,4-d]pyrimidin-3-yl)-N-(4-fluoropyridin-2-yl)benzamide hydrochloride

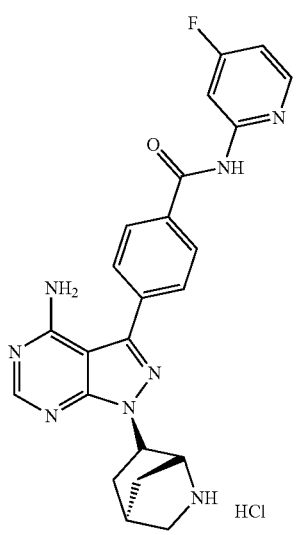

A title compound (220 mg, yield: 99%) was prepared in the same manner as in Step 69-4 of Example 69, except for using tert-butyl (1S,4R,6S)-6-(4-amino-3-(4-(4-fluoropyridin-2-yl)carbamoyl)phenyl-1H-pyrazolo[3,4-d]pyrimidin-1-yl)-2-azabicyclo[2.2.1]heptane-2-carboxylate (260 mg, 0.48 mmol) obtained in Step 72-1.

Step 72-3: Preparation of 4-(I-((1S,4R,6S)-2-acryloyl-2-azabicyclo[2.2.1]heptan-6-yl)-4-amino-1H-pyrazolo[3,4-d]pyrimidin-3-yl)-N-(4-fluoropyridin-2-yl)benzamide

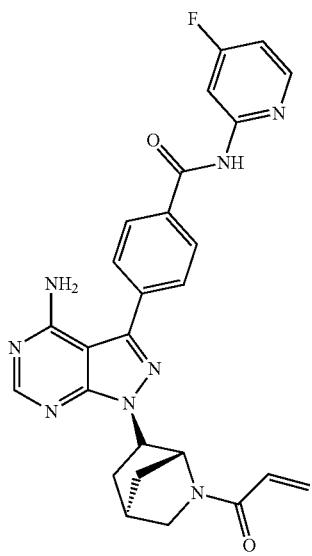

A title compound (81 mg, yield: 32%) was prepared in the same manner as in Step 69-5 of Example 69, except for using 4-(4-amino-1-(1S,4R,6S)-2-azabicyclo[2.2.1]heptan-6-yl)-1H-pyrazolo[3,4-d]pyrimidin-3-yl)-N-(4-fluoropyridin-2-yl)benzamide hydrochloride (240 mg, 0.50 mmol) obtained in Step 72-2 and acryloyl chloride (120 uL, 1.5 mmol).

$^1$H NMR (500 MHz, CDCl$_3$): 8.81 (s, 1H), 8.43-8.50 (m, 1H), 8.31-8.35 (m, 1H), 8.25-8.32 (m, 2H), 8.10-8.20 (m, 2H). 7.88-7.92 (m, 2H), 6.91-6.93 (m, 1H), 6.41-6.87 (m, 1H), 6.51-6.55 (m, 1H), 5.77-5.82 (m, 1H), 5.50-5.70 (s, 2H), 5.15-5.30 (m, 1H), 4.60-4.95 (m, 1H), 3.50-3.59 (m, 1H), 3.31-3.41 (m, 1H), 2.92-2.97 (m, 1H), 2.42-2.59 (m, 1H), 2.15-2.29 (m, 2H), 1.77-1.80 (m, 1H).

Example 73: Preparation of 4-(1-((1S,4R,6S)-2-acryloyl-2-azabicyclo[2.2.1]heptan-6-yl)-4-amino-1H-pyrazolo[3,4-d]pyrimidin-3-yl)-3-fluoro-N-(4-fluoropyridin-2-yl)benzamide Step 73-1: Preparation of tert-butyl (1S,4R,6S)-6-(4-amino-3-(2-fluoro-4-((4-fluoropyridin-2-yl)carbamoyl)phenyl-1H-pyrazolo[3,4-d]pyrimidin-1-yl)-2-azabicyclo[2.2.1]heptane-2-carboxylate

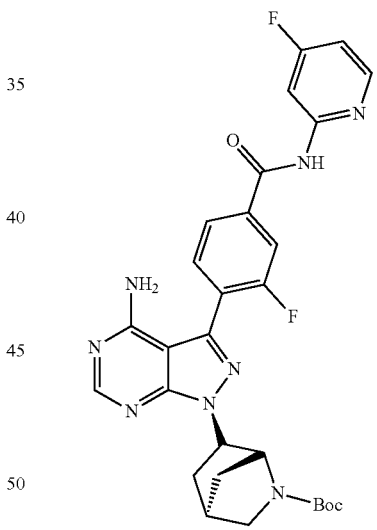

A title compound (82 mg, yield: 33%) was prepared in the same manner as in Step 69-3 of Example 69, except for using tert-butyl (1S,4R,6S)-6-(4-amino-3-iodo-1H-pyrazolo[3,4-d]pyrimidin-1-yl)-2-azabicyclo[2.2.1]heptane-2-carboxylate (100 mg, 0.22 mmol) obtained in Step 69-2 of Example 69 and 3-fluoro-N-(4-fluoropyridin-2-yl)-4-(4,4,5,5-tetramethyl-1,3,2-dioxaborolan-2-yl)benzamide (99 mg, 0.27 mmol).

Step 73-2: Preparation of 4-(4-amino-1-((1S,4R,6S)-2-azabicyclo[2.2.1]heptan-6-yl)-1H-pyrazolo[3,4-d]pyrimidin-3-yl)-3-fluoro-N-(4-fluoropyridin-2-yl)benzamide hydrochloride

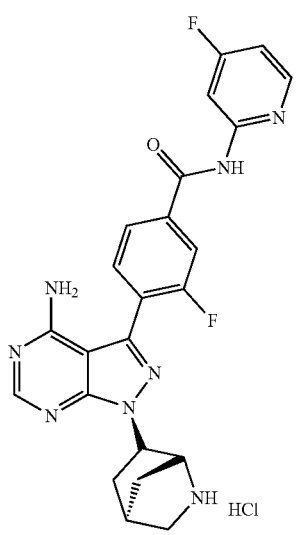

A title compound (67 mg, yield: 99%) was prepared in the same manner as in Step 69-4 of Example 69, except for using tert-butyl (1S,4R,6S)-6-(4-amino-3-(2-fluoro-4-((4-fluoropyridin-2-yl)carbamoyl)phenyl-1H-pyrazolo[3,4-d]pyrimidin-1-yl)-2-azabicyclo[2.2.1]heptane-2-carboxylate (82 mg, 0.15 mmol) obtained in Step 73-1.

Step 73-3: Preparation of 4-(I-((1S,4R,6S)-2-acryloyl-2-azabicyclo[2.2.1]heptan-6-yl)-4-amino-1H-pyrazolo[3,4-d]pyrimidin-3-yl)-3-fluoro-N-(4-fluoropyridin-2-yl)benzamide

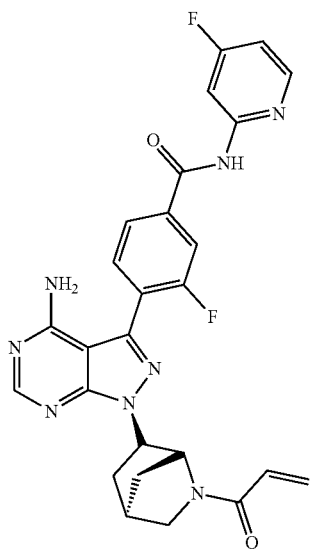

A title compound (15 mg, yield: 20%) was prepared in the same manner as in Step 69-5 of Example 69, except for using 4-(4-amino-1-((1S,4R,6S)-2-azabicyclo[2.2.1]heptan-6-yl)-1H-pyrazolo[3,4-d]pyrimidin-3-yl)-3-fluoro-N-(4-fluoropyridin-2-yl)benzamide hydrochloride (71 mg, 0.14 mmol) obtained in Step 73-2 and acryloyl chloride (35 uL, 0.43 mmol).

$^1$H NMR (500 MHz, CDCl$_3$): 8.71 (s, 1H), 8.42-8.50 (m, 1H), 8.31-8.35 (m, 1H), 8.21-8.27 (m, 1H), 7.90-7.95 (m, 2H). 7.85-7.88 (m, 1H), 6.91-6.95 (m, 1H), 6.43-6.90 (m, 1H), 6.51-6.54 (m, 1H), 5.81-5.85 (m, 1H), 5.42-5.50 (s, 2H), 5.17-5.30 (m, 1H), 4.55-4.97 (m, 1H), 3.41-3.51 (m, 1H), 3.20-3.31 (m, 1H), 2.82-2.85 (m, 1H), 2.40-2.47 (m, 1H), 2.19-2.31 (m, 2H), 1.77-1.80 (m, 1H).

Example 74: Preparation of 4-(4-amino-1-((1R,4R,6S)-2-(2-cyanoacetyl)-2-azabicyclo[2.2.1]heptan-6-yl)-1H-pyrazolo[3,4-d]pyrimidin-3-yl)-N-(pyridin-2-yl)benzamide

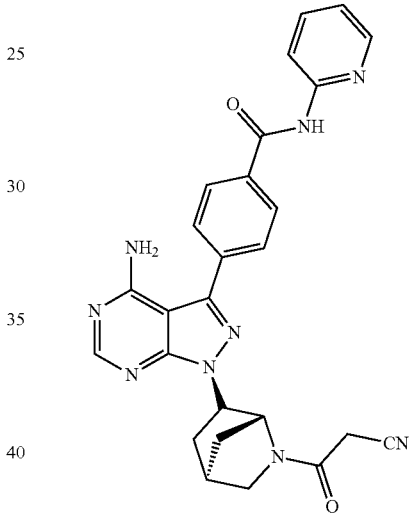

After 4-(4-amino-1-((1S,4R,6S)-2-azabicyclo[2.2.1]heptan-6-yl)-1H-pyrazolo[3,4-d]pyrimidin-3-yl)-N-(pyridin-2-yl)benzamide hydrochloride (500 mg, 1.1 mmol) obtained in Step 69-4 of Example 69 was dissolved in tetrahydrofuran (11 mL) and N,N-dimethylformamide (3 mL), 2-cyanoacetic acid (92 mg, 1.1 mmol), (1-[bis(dimethylamino)methylene]-1H-1,2,3-triazolo[4,5-b]pyridinium 3-oxid hexafluorophosphate) (493 mg, 1.3 mmol) and N,N-diisopropylethylamine (560 uL, 3.2 mmol) were sequentially added thereto, followed by stirring at 20° C. for 12 hours. Upon completion of the reaction, the mixture was diluted with ethyl acetate and washed with saturated sodium chloride. The organic layer was collected, dried over magnesium sulfate, filtered and concentrated under reduced pressure. The residue was purified by column chromatography (ethyl acetate: 100%) to obtain a title compound (460 mg, yield: 86%).

$^1$H NMR (500 MHz, CDCl$_3$): 8.52-8.62 (m, 1H), 8.34-8.50 (m, 3H), 8.21-8.23 (m, 1H), 7.97-8.02 (m, 2H), 7.84-7.86 (m, 1H), 7.35-7.38 (m, 1H), 5.01-5.18 (m, 1H), 4.25-4.80 (m, 1H), 3.82-3.87 (m, 2H), 3.47-3.57 (m, 1H), 3.20-3.40 (m, 1H), 3.16-3.18 (m, 1H), 2.82-2.90 (m, 1H), 2.27-2.50 (m, 1H), 2.11-2.21 (m, 1H), 1.72-1.74 (m, 1H).

Example 75: Preparation of 4-(4-amino-1-((1R,4R)-2-(2-cyano-3-cyclopropylacryloyl)-2-azabicyclo[2.2.1]heptan-6-yl)-1H-pyrazolo[3,4-d]pyrimidin-3-yl)-N-(pyridin-2-yl)benzamide

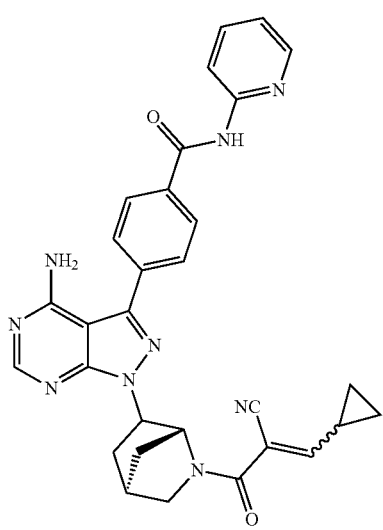 [SMILES: N#CC(=CC1CC1)C(=O)N1C[C@H]2CC(n3nc(-c4ccc(C(=O)Nc5ccccn5)cc4)c4c(N)ncnc43)[C@H]1C2]

After 4-(4-amino-1-((1R,4R,6S)-2-(2-cyanoacetyl)-2-azabicyclo[2.2.1]heptan-6-yl)-1H-pyrazolo[3,4-d]pyrimidin-3-yl)-N-(pyridin-2-yl)benzamide (50 mg, 0.10 mmol) obtained in Example 74 was dissolved in methanol (2 mL), cyclopropanecarbaldehyde (12 uL, 0.15 mmol) and piperidine (20 uL, 0.20 mmol) were added thereto, followed by stirring at 20° C. for 2 hours.

Upon completion of the reaction, the mixture was concentrated under reduced pressure and the solvent was removed. The residue was purified by column chromatography (methylene chloride/methanol=9/1) to obtain a title compound (23 mg, yield: 42%).

$^1$H NMR (500 MHz, CDCl$_3$): 9.37 (s, 1H), 8.42-8.44 (m, 1H), 8.24-8.33 (m, 2H), 8.10-8.12 (m, 2H), 7.79-7.89 (m, 3H), 6.85-7.15 (m, 2H). 5.22-5.25 (m, 1H), 4.76-4.80 (m, 1H), 3.55-3.90 (m, 1H), 3.15-3.40 (m, 1H), 2.55-2.61 (m, 1H), 2.41-2.49 (m, 1H), 2.12-2.20 (m, 1H), 2.05-2.10 (m, 1H), 1.82-1.89 (m, 1H), 0.94-1.02 (m, 1H), 0.87-0.93 (m, 4H).

Example 76: Preparation of 4-(4-amino-1-((1R,4R)-2-(2-cyano-4-methylpent-2-enoyl)-2-azabicyclo[2.2.1]heptan-6-yl)-1H-pyrazolo[3,4-d]pyrimidin-3-yl)-N-(pyridin-2-yl)benzamide

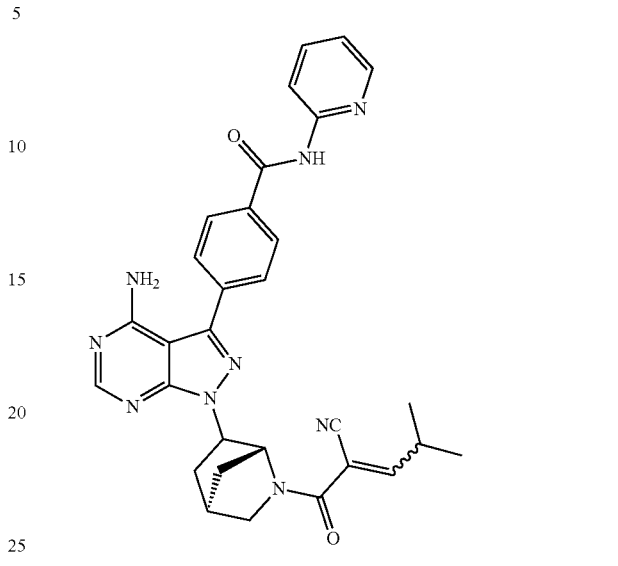

A title compound (15 mg, yield: 27%) was prepared in the same manner as in Example 75, except for using 4-(4-amino-1-((1R,4R,6S)-2-(2-cyanoacetyl)-2-azabicyclo[2.2.1]heptan-6-yl)-1H-pyrazolo[3,4-d]pyrimidin-3-yl)-N-(pyridin-2-yl)benzamide (60 mg, 0.15 mmol) obtained in Step 74 and isobutyraldehyde (13 uL, 0.17 mmol).

$^1$H NMR (500 MHz, CDCl$_3$): 8.78-8.80 (m, 1H), 8.31-8.42 (m, 3H), 8.10-8.15 (m, 2H), 7.75-7.85 (m, 3H), 7.20-7.25 (m, 1H), 5.61-5.95 (m, 1H), 5.25-5.30 (m, 1H), 4.78-4.85 (m, 1H), 3.25-3.40 (m, 2H), 2.85-3.02 (m, 2H), 2.52-2.58 (m, 1H), 2.10-2.20 (m, 1H), 1.75-1.80 (m, 1H), 1.25-1.27 (m, 3H), 1.22-1.25 (m, 3H).

Example 77: Preparation of 4-(1-((1S,4R,6S)-2-acryloyl-2-azabicyclo[2.2.1]heptan-6-yl)-4-amino-1H-pyrazolo[3,4-d]pyrimidin-3-yl)-N-(3-methylpyridin-2-yl)benzamide Step 77-1: Preparation of tert-butyl (1S,4R,6S)-6-(4-amino-3-(4-((3-methylpyridin-2-yl)carbamoyl)phenyl)-1H-pyrazolo[3,4-d]pyrimidin-1-yl)-2-azabicyclo[2.2.1]heptane-2-carboxylate

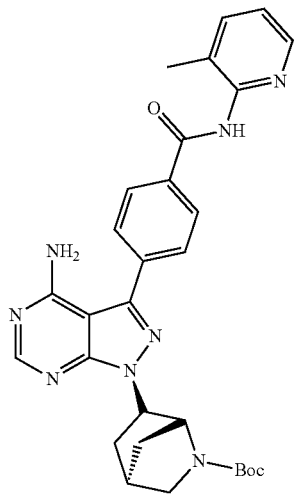

A title compound (84 mg, yield: 82%) was prepared in the same manner as in Step 69-3 of Example 69, except for using tert-butyl (1S,4R,6S)-6-(4-amino-3-iodo-1H-pyrazolo[3,4-d]pyrimidin-1-yl)-2-azabicyclo[2.2.1]heptane-2-carboxylate (86 mg, 0.19 mmol) obtained in Step 69-2 of Example 69 and N-(3-methylpyridin-2-yl)-4-(4,4,5,5-tetramethyl-1,3,2-dioxaborolan-2-yl)benzamide (80 mg, 0.24 mmol).

Step 77-2: Preparation of 4-(4-amino-1-((1S,4R,6S)-2-azabicyclo[2.2.1]heptan-6-yl)-1H-pyrazolo[3,4-d]pyrimidin-3-yl)-N-(3-methylpyridin-2-yl)benzamide hydrochloride

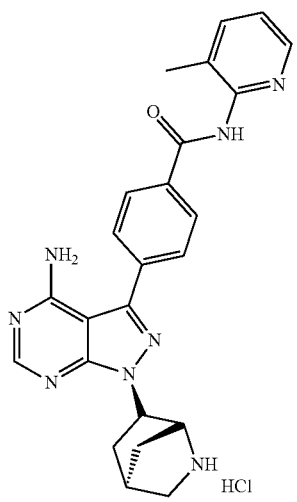

A title compound (73 mg, yield: 99%) was prepared in the same manner as in Step 69-4 of Example 69, except for using tert-butyl (1S,4R,6S)-6-(4-amino-3-(4-((3-methylpyridin-2-yl)carbamoyl)phenyl)-1H-pyrazolo[3,4-d]pyrimidin-1-yl)-2-azabicyclo[2.2.1]heptane-2-carboxylate (84 mg, 0.06 mmol) obtained in Step 77-1.

Step 77-3: Preparation of 4-(1-((1S,4R,6S)-2-acryloyl-2-azabicyclo[2.2.1]heptan-6-yl)-4-amino-1H-pyrazolo[3,4-d]pyrimidin-3-yl)-N-(3-methylpyridin-2-yl)benzamide

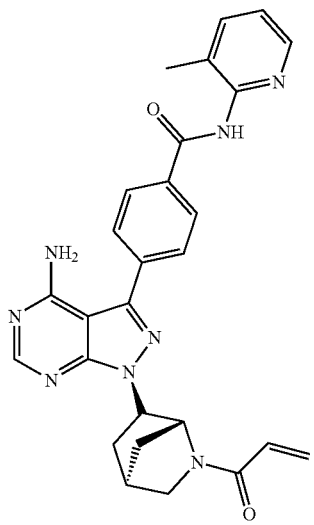

A title compound (30 mg, yield: 34%) was prepared in the same manner as in Step 69-5 of Example 69, except for using 4-(4-amino-1-((1S,4R,6S)-2-azabicyclo[2.2.1]heptan-6-yl)-1H-pyrazolo[3,4-d]pyrimidin-3-yl)-N-(3-methylpyridin-2-yl)benzamide hydrochloride (84 mg, 0.18 mmol) obtained in Step 77-2 and acryloyl chloride (22 uL, 0.26 mmol).

$^1$H NMR (500 MHz, CDCl$_3$): 8.61-8.71 (s, 1H), 8.42-8.50 (m, 1H), 8.10-8.36 (m, 2H), 7.79-7.83 (m, 2H), 7.62-7.72 (m, 1H), 7.45-7.50 (m, 1H), 7.14-7.20 (m, 1H), 6.33-6.80 (m, 1H), 6.44-6.47 (m, 1H), 5.74-5.76 (m, 1H), 5.02-5.19 (m, 1H), 4.53-4.87 (m, 1H), 3.42-3.48 (m, 1H), 3.20-3.30 (m, 1H), 2.85-2.87 (m, 1H), 2.51-2.58 (m, 1H), 2.36 (s, 3H), 2.31-2.34 (m, 1H), 2.11-2.15 (m, 1H), 1.72-1.74 (m, 1H).

Example 78: Preparation of 4-(1-((1S,4R,6S)-2-acryloyl-2-azabicyclo[2.2.1]heptan-6-yl)-4-amino-1H-pyrazolo[3,4-d]pyrimidin-3-yl)-N-(3-(trifluoromethyl)pyridin-2-yl)benzamide Step 78-1: Preparation of tert-butyl (1S,4R,6S)-6-(4-amino-3-(4-(3-(trifluoromethyl)pyridin-2-yl)carbamoyl)phenyl)-1H-pyrazolo[3,4-d]pyrimidin-1-yl)-2-azabicyclo[2.2.1]heptane-2-carboxylate

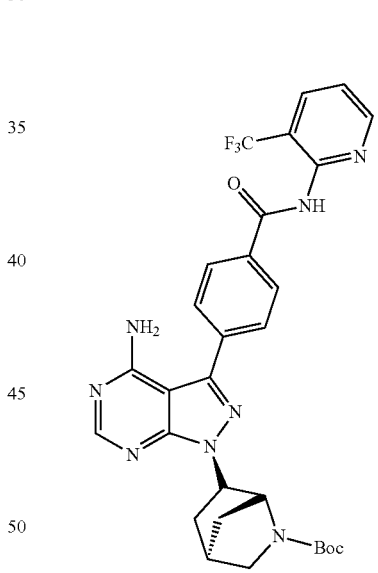

A title compound (48 mg, yield: 43%) was prepared in the same manner as in Step 69-3 of Example 69, except for using tert-butyl (1S,4R,6S)-6-(4-amino-3-iodo-1H-pyrazolo[3,4-d]pyrimidin-1-yl)-2-azabicyclo[2.2.1]heptane-2-carboxylate (86 mg, 0.19 mmol) obtained in Step 69-2 of Example 69 and N-(3-(trifluoromethyl)pyridin-2-yl)-4-(4,4,5,5-tetramethyl-1,3,2-dioxaborolan-2-yl)benzamide (92 mg, 0.24 mmol).

Step 78-2: Preparation of 4-(4-amino-1-((1S,4R, 6S)-2-azabicyclo[2.2.1]heptan-6-yl)-1H-pyrazolo[3,4-d]pyrimidin-3-yl)-N-(3-(trifluoromethyl)pyridin-2-yl)benzamide hydrochloride

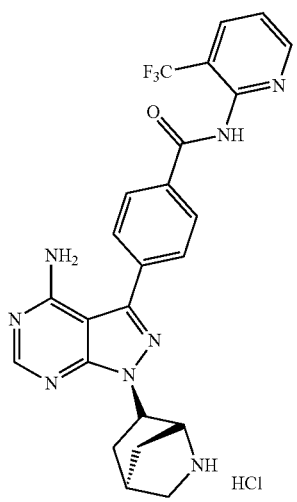

A title compound (36 mg, yield: 88%) was prepared in the same manner as in Step 69-4 of Example 69, except for using tert-butyl (1S,4R,6S)-6-(4-amino-3-(4-(3-(trifluoromethyl)pyridin-2-yl)carbamoyl)phenyl)-1H-pyrazolo[3,4-d]pyrimidin-1-yl)-2-azabicyclo[2.2.1]heptane-2-carboxylate (48 mg, 0.081 mmol) obtained in Step 78-1.

Step 78-3: Preparation of 4-(1-((1S,4R,6S)-2-acryloyl-2-azabicyclo[2.2.1]heptan-6-yl)-4-amino-1H-pyrazolo[3,4-d]pyrimidin-3-yl)-N-(3-(trifluoromethyl)pyridin-2-yl)benzamide

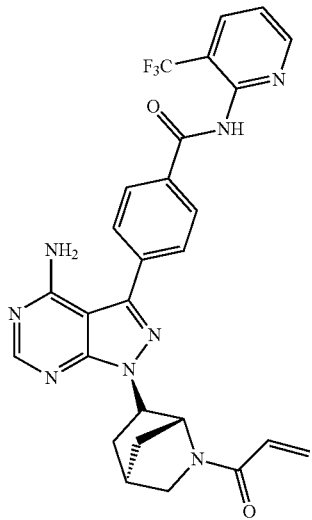

A title compound (23 mg, yield: 46%) was prepared in the same manner as in Step 69-5 of Example 69, except for using 4-(4-amino-1-((1S,4R,6S)-2-azabicyclo[2.2.1]heptan-6-yl)-1H-pyrazolo[3,4-d]pyrimidin-3-yl)-N-(3-(trifluoromethyl)pyridin-2-yl)benzamide hydrochloride (48 mg, 0.09 mmol) obtained in Step 78-2 and acryloyl chloride (11 uL, 0.14 mmol).

$^1$H NMR (500 MHz, CDCl$_3$): 8.76-8.78 (m, 1H), 8.31-8.40 (m, 2H), 7.97-8.07 (m, 3H), 7.80-7.85 (m, 2H), 7.27-7.34 (m, 1H), 6.34-6.82 (m, 1H), 6.44-6.48 (m, 1H), 5.71-5.77 (m, 1H), 5.56 (s, 2H), 5.11-5.21 (m, 1H), 4.54-4.88 (m, 1H), 3.42-3.48 (m, 1H), 3.29-3.34 (m, 1H), 2.86-2.90 (m, 2H), 2.31-2.49 (m, 1H), 2.20-2.27 (m, 1H), 1.72-1.74 (m, 1H).

Example 79: Preparation of 4-(I-((1S,4R,6S)-2-acryloyl-2-azabicyclo[2.2.1]heptan-6-yl)-4-amino-1H-pyrazolo[3,4-d]pyrimidin-3-yl)-3-fluoro-N-methylbenzamide Step 79-1: Preparation of tert-butyl (1S,4R,6S)-6-(4-amino-3-(2-fluoro-4-(methylcarbamoyl)phenyl)-1H-pyrazolo[3,4-d]pyrimidin-1-yl)-2-azabicyclo[2.2.1]heptane-2-carboxylate

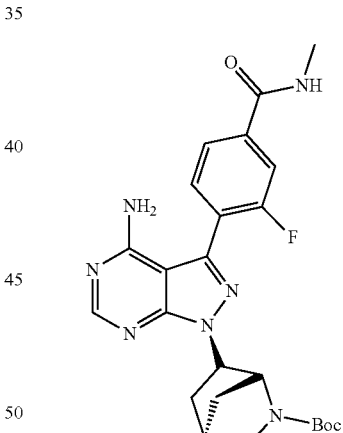

A title compound (100 mg, yield: 95%) was prepared in the same manner as in Step 69-3 of Example 69, except for using tert-butyl (1S,4R,6S)-6-(4-amino-3-iodo-1H-pyrazolo[3,4-d]pyrimidin-1-yl)-2-azabicyclo[2.2.1]heptane-2-carboxylate (100 mg, 0.22 mmol) obtained in Step 69-2 and (2-fluoro-4-(methylcarbamoyl)phenyl)boronic acid (54 mg, 0.27 mmol).

Step 79-2: Preparation of 4-(4-amino-1-((1S,4R,6S)-2-azabicyclo[2.2.1]heptan-6-yl)-1H-pyrazolo[3,4-d]pyrimidin-3-yl)-3-fluoro-N-methylbenzamide hydrochloride

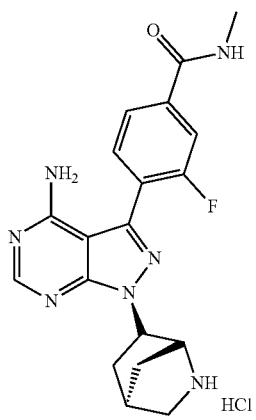

A title compound (63 mg, yield: 73%) was prepared in the same manner as in Step 69-4 of Example 69, except for using tert-butyl (1S,4R,6S)-6-(4-amino-3-(2-fluoro-4-(methylcarbamoyl)phenyl)-1H-pyrazolo[3,4-d]pyrimidin-3-yl)-2-azabicyclo[2.2.1]heptane-2-carboxylate (100 mg, 0.21 mmol) obtained in Step 79-1.

Step 79-3: Preparation of 4-(I-((1S,4R,6S)-2-acryloyl-2-azabicyclo[2.2.1]heptan-6-yl)-4-amino-1H-pyrazolo[3,4-d]pyrimidin-3-yl)-3-fluoro-N-methylbenzamide

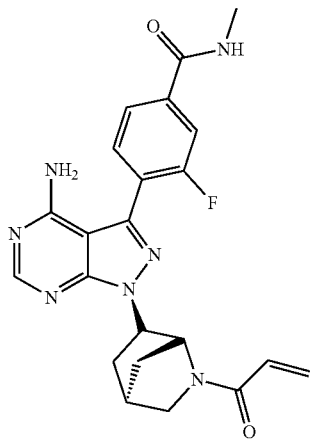

A title compound (38 mg, yield: 58%) was prepared in the same manner as in Step 69-5 of Example 69, except for using 4-(4-amino-1-((1S,4R,6S)-2-azabicyclo[2.2.1]heptan-6-yl)-1H-pyrazolo[3,4-d]pyrimidin-3-yl)-3-fluoro-N-methylbenzamide hydrochloride (63 mg, 0.15 mmol) obtained in Step 79-2 and acryloyl chloride (18 uL, 0.23 mmol).

$^1$H NMR (500 MHz, CDCl$_3$): 8.38-8.42 (m, 1H), 7.64-7.72 (m, 3H), 6.76-6.80 (m, 0.6H), 6.42-6.45 (m, 1H), 6.30-6.35 (m, 0.4H), 5.74-5.77 (m, 1H), 5.29-5.32 (s, 2H), 5.09-5.19 (m, 1H), 4.53-4.88 (m, 1H), 3.41-3.48 (m, 1H), 3.21-3.30 (m, 1H), 3.07 (s, 3H), 2.83-2.85 (m, 1H), 2.41-2.48 (m, 1H), 2.12-2.25 (m, 2H), 1.75-1.78 (m, 1H).

Example 80: Preparation of 4-(1-((1S,4R,6S)-2-acryloyl-2-azabicyclo[2.2.1]heptan-6-yl)-4-amino-1H-pyrazolo[3,4-d]pyrimidin-3-yl)-3-chloro-N-(pyridin-2-yl)benzamide Step 80-1: Preparation of tert-butyl (1S,4R,6S)-6-(4-amino-3-(2-chloro-4-(pyridin-2-ylcarbamoyl)phenyl)-1H-pyrazolo[3,4-d]pyrimidin-1-yl)-2-azabicyclo[2.2.1]heptane-2-carboxylate

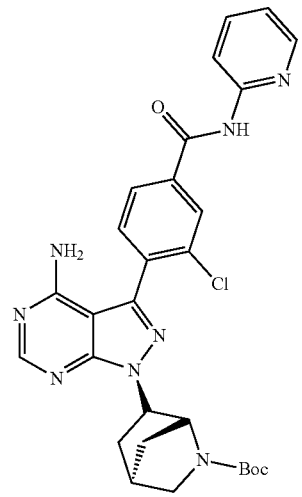

A title compound (120 mg, yield: 99%) was prepared in the same manner as in Step 69-3 of Example 69, except for using tert-butyl (1S,4R,6S)-6-(4-amino-3-iodo-1H-pyrazolo[3,4-d]pyrimidin-1-yl)-2-azabicyclo[2.2.1]heptane-2-carboxylate (100 mg, 0.22 mmol) obtained in Step 69-2 of Example 69 and 3-chloro-N-(pyridin-2-yl)-4-(4,4,5,5-tetramethyl-1,3,2-dioxaborolan-2-yl)benzamide (98 mg, 0.27 mmol).

Step 80-2: Preparation of 4-(4-amino-1-((1S,4R,6S)-2-azabicyclo[2.2.1]heptan-6-yl)-1H-pyrazolo[3,4-d]pyrimidin-3-yl)-2-chloro-N-(pyridin-2-yl)benzamide hydrochloride

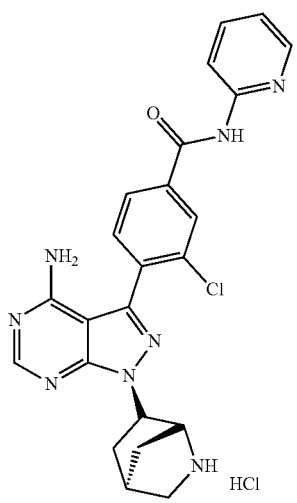

A title compound (98 mg, yield: 78%) was prepared in the same manner as in Step 69-4 of Example 69, except for using tert-butyl (1S,4R,6S)-6-(4-amino-3-(2-chloro-4-(pyridin-2-ylcarbamoyl)phenyl)-1H-pyrazolo[3,4-d]pyrimidin-1-yl)-2-azabicyclo[2.2.1]heptane-2-carboxylate (140 mg, 0.25 mmol) obtained in Step 80-1.

Step 80-3: Preparation of 4-(I-((1S,4R,6S)-2-acryloyl-2-azabicyclo[2.2.1]heptan-6-yl)-4-amino-1H-pyrazolo[3,4-d]pyrimidin-3-yl)-3-chloro-N-(pyridin-2-yl)benzamide

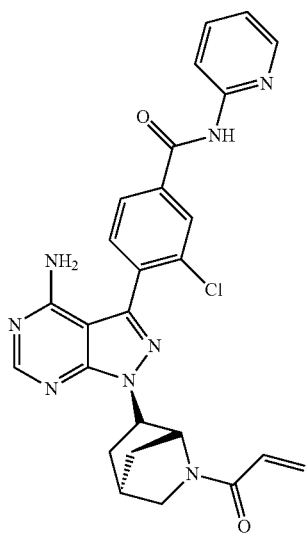

A title compound (56 mg, yield: 55%) was prepared in the same manner as in Step 69-5 of Example 69, except for using 4-(4-amino-1-((1S,4R,6S)-2-azabicyclo[2.2.1]heptan-6-yl)-1H-pyrazolo[3,4-d]pyrimidin-3-yl)-2-chloro-N-(pyridin-2-yl)benzamide hydrochloride (98 mg, 0.20 mmol) obtained in Step 80-2 and acryloyl chloride (24 uL, 0.30 mmol).

$^1$H NMR (500 MHz, CDCl$_3$): 9.12-9.20 (m, 1H), 8.31-8.40 (m, 1H), 8.25-8.27 (m, 1H), 8.16-8.18 (m, 1H), 7.95-7.98 (m, 1H). 7.80-7.83 (m, 1H), 7.64-7.66 (m, 1H), 7.12-7.15 (m, 1H), 6.77-6.81 (m, 0.6H), 6.45-6.48 (m, 1H), 6.28-6.31 (m, 0.4H), 5.72-5.77 (m, 1H), 5.11-5.29 (m, 1H), 4.54-4.90 (m, 1H), 3.41-3.51 (m, 1H), 3.25-3.33 (m, 1H), 2.80-2.90 (m, 1H), 2.42-2.50 (m, 1H), 2.17-2.30 (m, 2H), 1.70-1.73 (m, 1H).

Example 81: Preparation of 4-(1-((1S,4R,6S)-2-acryloyl-2-azabicyclo[2.2.1]heptan-6-yl)-4-amino-1H-pyrazolo[3,4-d]pyrimidin-3-yl)-3-methoxy-N-(pyridin-2-yl)benzamide Step 81-1: Preparation of tert-butyl (1S,4R,6S)-6-(4-amino-3-(2-methoxy-4-(pyridin-2-ylcarbamoyl)phenyl-1H-pyrazolo[3,4-d]pyrimidin-1-yl)-2-azabicyclo[2.2.1]heptane-2-carboxylate

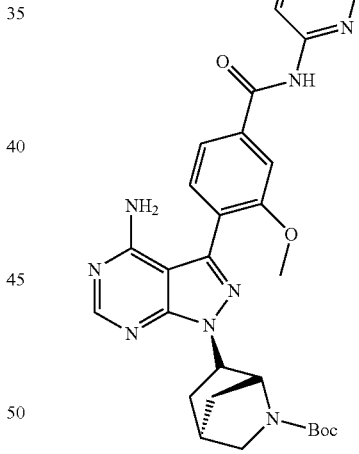

A title compound (120 mg, yield: 99%) was prepared in the same manner as in Step 69-3 of Example 69, except for using tert-butyl (1S,4R,6S)-6-(4-amino-3-iodo-1H-pyrazolo[3,4-d]pyrimidin-1-yl)-2-azabicyclo[2.2.1]heptane-2-carboxylate (100 mg, 0.22 mmol) obtained in Step 69-2 of Example 69 and (2-methoxy-(phenylcarbamoyl)phenyl)boronic acid (97 mg, 0.27 mmol).

Step 81-2: Preparation of 4-(4-amino-1-((1S,4R, 6S)-2-azabicyclo[2.2.1]heptan-6-yl)-1H-pyrazolo[3, 4-d]pyrimidin-3-yl)-3-methoxy-N-(pyridin-2-yl) benzamide hydrochloride

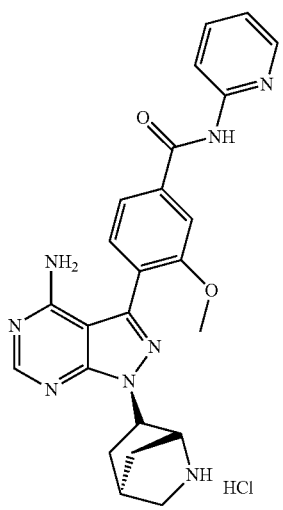

A title compound (85 mg, yield: 77%) was prepared in the same manner as in Step 69-4 of Example 69, except for using tert-butyl (1S,4R,6S)-6-(4-amino-3-(2-methoxy-4-(pyridin-2-ylcarbamoyl)phenyl-1H-pyrazolo[3,4-d]pyrimidin-1-yl)-2-azabicyclo[2.2.1]heptane-2-carboxylate (120 mg, 0.22 mmol) obtained in Step 81-1.

Step 81-3: Preparation of 4-(I-((1S,4R,6S)-2-acryloyl-2-azabicyclo[2.2.1]heptan-6-yl)-4-amino-1H-pyrazolo[3,4-d]pyrimidin-3-yl)-3-methoxy-N-(pyridin-2-yl)benzamide

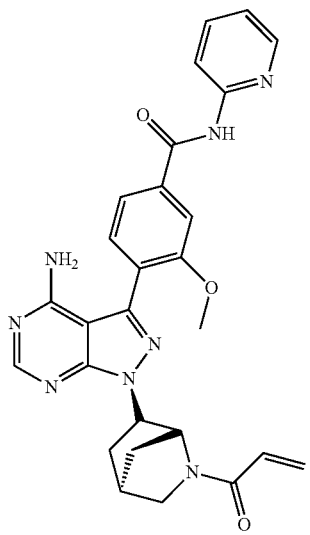

A title compound (41 mg, yield: 47%) was prepared in the same manner as in Step 69-5 of Example 69, except for using 4-(4-amino-1-((1S,4R,6S)-2-azabicyclo[2.2.1]heptan-6-yl)-1H-pyrazolo[3,4-d]pyrimidin-3-yl)-3-methoxy-N-(pyridin-2-yl)benzamide hydrochloride (85 mg, 0.17 mmol) obtained in Step 81-2 and acryloyl chloride (21 uL, 0.26 mmol).

$^1$H NMR (500 MHz, CDCl$_3$): 9.05-9.07 (m, 1H), 8.24-8.42 (m, 3H), 7.78-7.82 (m, 1H), 7.70-7.71 (m, 1H), 7.60-7.62 (m, 2H), 7.10-7.13 (m, 1H), 6.80-6.84 (m, 0.6H), 6.43-6.46 (m, 1H), 6.27-6.30 (m, 0.4H), 5.78-5.80 (m, 1H), 5.07-5.17 (m, 1H), 4.41-4.82 (m, 1H), 3.94 (s, 3H), 3.43-3.55 (m, 1H), 3.26-3.32 (m, 1H), 2.84-2.86 (m, 1H), 2.37-2.50 (m, 1H), 2.11-2.25 (m, 2H), 1.70-1.73 (m, 1H).

Example 82: Preparation of 4-(4-amino-1-((1R,4R, 6S)-2-(2-cyano-3-cyclopropylacryloyl)-2-azabicyclo [2.2.1]heptan-6-yl)-1H-pyrazolo[3,4-d]pyrimidin-3-yl)-3-fluoro-N-(pyridin-2-yl) benzamide

Step 82-1: Preparation of tert-butyl (1S,4R,6S)-6-(4-amino-3-(2-fluoro-4-(pyridin-2-yl)carbamoyl) phenyl)-1H-pyrazolo[3,4-d]pyrimidin-1-yl)-2-azabicyclo[2.2.1]heptane-2-carboxylate

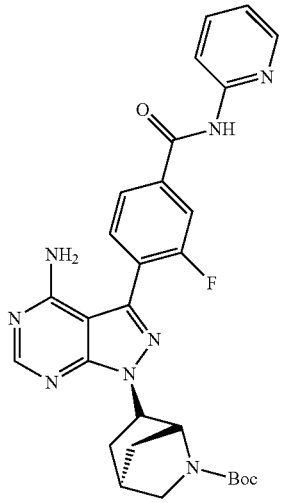

A title compound (77 mg, yield: 65%) was prepared in the same manner as in Step 69-3 of Example 69, except for using tert-butyl (1S,4R,6S)-6-(4-amino-3-iodo-1H-pyrazolo[3,4-d]pyrimidin-1-yl)-2-azabicyclo[2.2.1]heptane-2-carboxylate (100 mg, 0.22 mmol) obtained in Step 69-2 of Example 69 and (2-fluoro-4-(pyridin-2-ylcarbamoyl)phenyl)boronic acid (71 mg, 0.27 mmol).

Step 82-2: Preparation of 4-(4-amino-1-((1S,4R, 6S)-2-azabicyclo[2.2.1]heptan-6-yl]-1H-pyrazolo[3, 4-d]pyrimidin-3-yl)-3-fluoro-N-(pyridin-2-yl)benz-amide hydrochloride

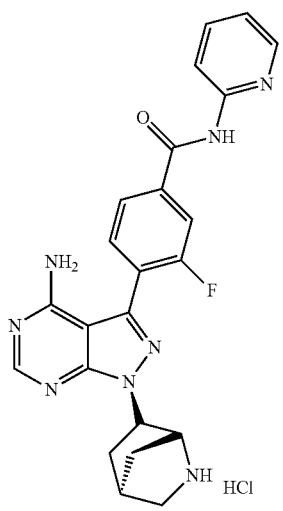

A title compound (68 mg, yield: 99%) was prepared in the same manner as in Step 69-4 of Example 69, except for using tert-butyl (1S,4R,6S)-6-(4-amino-3-(2-fluoro-4-(pyridin-2-yl)carbamoyl)phenyl)-1H-pyrazolo[3,4-d]pyrimidin-1-yl)-2-azabicyclo[2.2.1]heptane-2-carboxylate (77 mg, 0.14 mmol) obtained in Step 82-1.

Step 82-3: Preparation of 4-(4-amino-1-((1R,4R, 6S)-2-(2-cyanoacetyl)-2-azabicyclo[2.2.1]heptan-6-yl)-1H-pyrazolo[3,4-d]pyrimidin-3-yl)-3-fluoro-N-(pyridin-2-yl)benzamide

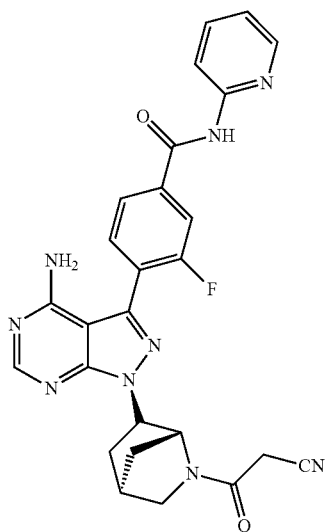

A title compound (71 mg, yield: 97%) was prepared in the same manner as in Example 74, except for using 4-(4-amino-1-((1S,4R,6S)-2-azabicyclo[2.2.1]heptan-6-yl]-1H-pyrazolo[3,4-d]pyrimidin-3-yl)-3-fluoro-N-(pyridin-2-yl) benzamide hydrochloride (68 mg, 0.14 mmol) obtained in Step 82-2 and 2-cyanoacetic acid (12 mg, 0.14 mmol).

Step 82-4: Preparation of 4-(4-amino-1-((1R,4R, 6S)-2-(2-cyano-3-cyclopropylmethacryloyl)-2-azabicyclo[2.2.1]heptan-6-yl)-1H-pyrazolo[3,4-d]pyrimidin-3-yl)-3-fluoro-N-(pyridin-2-yl) benzamide

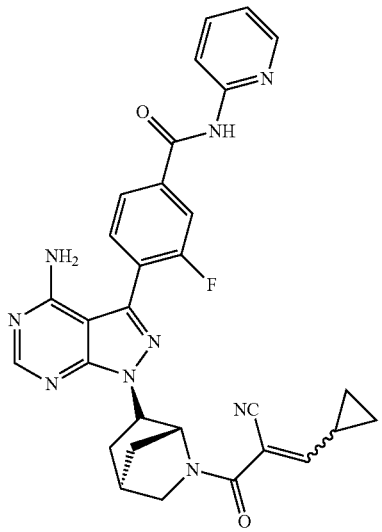

A title compound (52 mg, yield: 67%) was prepared in the same manner as in Example 75, except for using 4-(4-amino-1-((1R,4R,6S)-2-(2-cyanoacetyl)-2-azabicyclo[2.2.1]heptan-6-yl)-1H-pyrazolo[3,4-d]pyrimidin-3-yl)-3-fluoro-N-(pyridin-2-yl)benzamide (71 mg, 0.14 mmol) obtained in Step 82-3 and cyclopropanecarbaldehyde (16 mg, 0.21 mmol).

$^1$H NMR (500 MHz, CDCl$_3$): 9.75 (s, 1H), 8.49-8.51 (m, 1H), 8.27-8.32 (m, 2H), 7.89-7.95 (m, 3H), 7.77-7.78 (m, 1H), 7.19-7.22 (m, 1H), 6.82-7.15 (m, 1H), 5.25-5.31 (m, 1H), 4.79-4.99 (m, 1H), 3.93-4.25 (m, 1H), 3.41-3.49 (m, 1H), 2.89-2.97 (m, 1H), 2.48-2.54 (m, 1H), 2.25-2.33 (m, 1H), 2.15-2.17 (m, 1H), 1.80-1.82 (m, 1H), 0.90-0.96 (m, 4H).

Example 83: Preparation of 4-(4-amino-1-((1R,4R,6S)-2-(2-cyano-3-cyclopropylmethacryloyl)-2-azabicyclo[2.2.1]heptan-6-yl)-1H-pyrazolo[3,4-d]pyrimidin-3-yl)-3-fluoro-N-(4-fluoropyridin-2-yl)benzamide Step 83-1: Preparation of 4-(4-amino-1-((1R,4R,6S)-2-(2-cyanoacetyl)-2-azabicyclo[2.2.1]heptan-6-yl)-1H-pyrazolo[3,4-d]pyrimidin-3-yl)-3-fluoro-N-(4-fluoropyridin-2-yl)benzamide

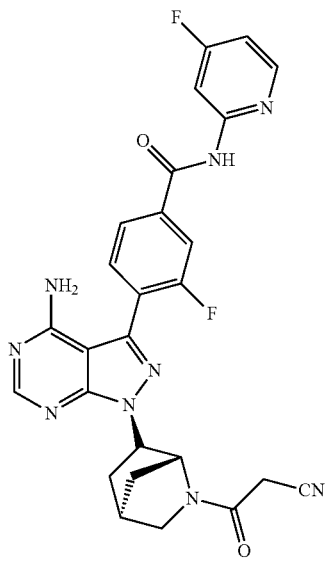

A title compound (68 mg, yield: 85%) was prepared in the same manner as in Example 74, except for using 4-(4-amino-1-((1S,4R,6S)-2-azabicyclo[2.2.1]heptan-6-yl)-1H-pyrazolo[3,4-d]pyrimidin-3-yl)-3-fluoro-N-(4-fluoropyridin-2-yl)benzamide hydrochloride (75 mg, 0.15 mmol) obtained in Step 73-2 of Example 73 and 2-cyanoacetic acid (13 mg, 0.15 mmol).

Step 83-2: Preparation of 4-(4-amino-1-((1R,4R,6S)-2-(2-cyano-3-cyclopropylacryloyl)-2-azabicyclo[2.2.1]heptan-6-yl)-1H-pyrazolo[3,4-d]pyrimidin-3-yl)-3-fluoro-N-(4-fluoropyridin-2-yl)benzamide

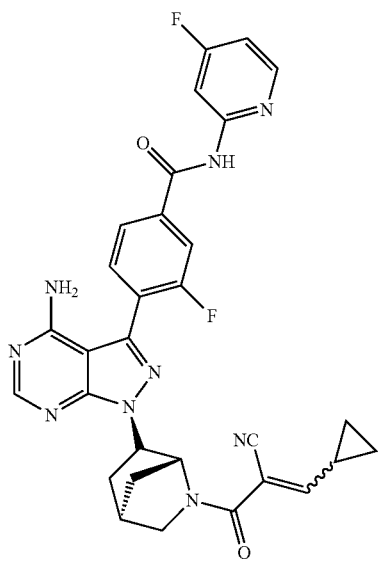

A title compound (46 mg, yield: 62%) was prepared in the same manner as in Example 75, except for using 4-(4-amino-1-((1R,4R,6S)-2-(2-cyanoacetyl)-2-azabicyclo[2.2.1]heptan-6-yl)-1H-pyrazolo[3,4-d]pyrimidin-3-yl)-3-fluoro-N-(4-fluoropyridin-2-yl)benzamide (68 mg, 0.13 mmol) obtained in Step 83-1 and cyclopropanecarbobaldehyde (14 uL, 0.19 mmol).

$^1$H NMR (500 MHz, CDCl$_3$): 9.27 (s, 1H), 8.22-8.32 (m, 3H), 7.87-7.89 (m, 2H), 7.72-7.75 (m, 1H), 6.88-7.15 (m, 1H), 6.89-6.90 (m, 1H), 5.55-5.85 (m, 2H), 5.24-5.26 (m, 1H), 4.75-4.85 (m, 1H), 3.87-3.91 (m, 1H), 3.22-3.45 (m, 1H), 2.88-2.91 (m, 1H), 2.54-2.56 (m, 1H), 2.22-2.23 (m, 1H), 1.76-1.78 (m, 1H), 1.05-1.07 (m, 1H), 0.89-0.96 (m, 4H).

Example 84: Preparation of 4-(4-amino-1-((1R,4R,6S)-2-methacryloyl-2-azabicyclo[2.2.1]heptan-6-yl)-1H-pyrazolo[3,4-d]pyrimidin-3-yl)-N-(pyridin-2-yl)benzamide

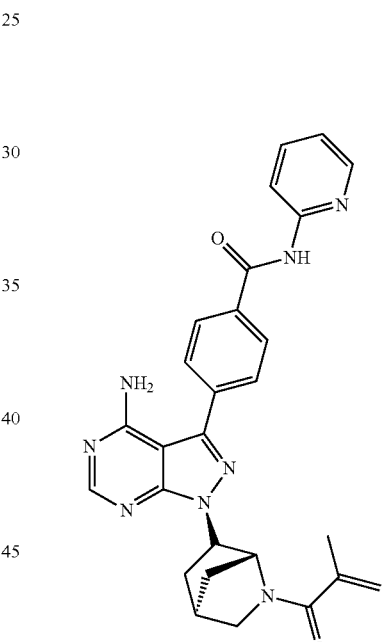

A title compound (22 mg, yield: 41%) was prepared in the same manner as in Step 69-5 of Example 69, except for using 4-(4-amino-1-((1S,4R,6S)-2-azabicyclo[2.2.1]heptan-6-yl)-1H-pyrazolo[3,4-d]pyrimidin-3-yl)-N-(pyridin-2-yl)benzamide hydrochloride (50 mg, 0.10 mmol) and methacryloyl chloride (15 uL, 0.15 mmol).

$^1$H NMR (500 MHz, CDCl$_3$): 8.91 (s, 1H), 8.31-8.43 (m, 3H), 8.09-8.11 (m, 2H), 7.78-7.85 (m, 3H), 7.10-7.13 (m, 1H), 5.88 (s, 2H), 5.46 (d, 1H), 5.23-5.29 (m, 2H), 4.40-4.85 (m, 1H), 3.49-3.51 (m, 1H), 3.17-3.19 (m, 1H), 2.87-2.89 (m, 1H), 2.61-2.62 (m, 1H), 2.44-2.45 (m, 1H), 2.21-2.22 (m, 1H), 2.05 (s, 3H), 1.67-1.69 (m, 1H).

Example 85: Preparation of 4-(1-((1R,4R,6S)-2-acryloyl-2-azabicyclo[2.2.1]heptan-6-yl)-4-amino-1H-pyrazolo[3,4-d]pyrimidin-3-yl)-3-fluoro-N-(pyridin-2-yl)benzamide

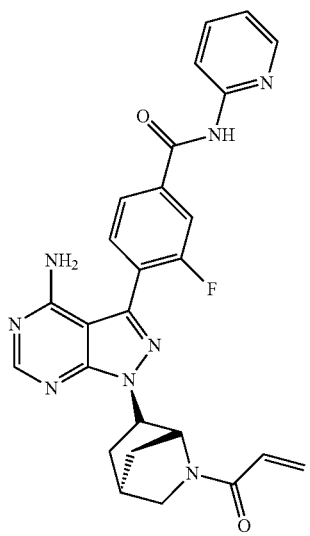

A title compound (207 mg, yield: 33%) was prepared in the same manner as in Step 69-5 of Example 69, except for using 4-(4-amino-1-((1S,4R,6S)-2-azabicyclo[2.2.1]heptan-6-yl)-1H-pyrazolo[3,4-d]pyrimidin-3-yl)-3-fluoro-N-(pyridin-2-yl)benzamide hydrochloride (608 mg, 1.3 mmol) obtained in Step 82-2 of Example 82 and acryloyl chloride (308 uL, 3.8 mmol).

$^1$H NMR (500 MHz, CDCl$_3$): 8.74 (s, 1H), 8.33-8.42 (m, 3H), 7.78-7.88 (m, 4H), 7.12-7.14 (m, 1H), 6.25-6.84 (m, 1H), 6.44-6.47 (m, 1H), 5.74-5.77 (m, 1H), 5.43-5.60 (s, 2H), 5.10-5.25 (m, 1H), 4.54-4.91 (m, 1H), 3.47-3.49 (m, 1H), 3.25-3.34 (m, 1H), 2.86 (m, 1H), 2.42-2.50 (m, 1H), 2.17-2.25 (m, 2H), 1.72-1.74 (m, 1H).

Experimental Example 1: Inhibitory Activity Against BTK

Inhibitory activities against BTK were measured for the compounds prepared in the above examples.

The inhibitory activities against BTK were evaluated using 'ADP-Glo™+BTK Kinase enzyme system' kit (Promega Corporation). In a white 96-well plate, 10 ul of BTK enzyme prepared so as to have a final concentration of 1 ng/uL was mixed with 5 ul of compounds having a final concentration of 1 uM in the case of evaluating a single concentration of compound and a concentration of 1000, 300, 100, 30, 10, 3, 1, 0.3, 0.1 and 0.03 nM in the case of IC$_{50}$ evaluation, and then reacted at room temperature for 15 minutes. 5 uL of substrate and 5 uL of ATP prepared so as to have a final concentration of 10 uM were added to the plate on which reactions were completed, and then allowed to react at 30° C. for 1 hour. All wells of the plate were treated with 25 uL of ADP-Glo™ reagent and allowed to react at 30° C. for 40 minutes. After that, all wells were treated with 50 uL of kinase detection buffer, and then reacted at 30° C. for 30 minutes under light shielding conditions. For the plate on which all reactions were completed, luminescence was measured and the results were calculated. Evaluation was carried out in duplicate, and negative control and positive control were calculated depending on whether or not the enzyme was added without treatment of the compound. The IC$_{50}$ were calculated based on the calculated values. The results were shown in Tables 1 and 2 below.

TABLE 1

| | IC$_{50}$(nM) |
|---|---|
| Ex. 1 | 2.1 |
| Ex. 2 | 0.8 |
| Ex. 3 | 201.8 |
| Ex. 4 | 2.8 |
| Ex. 5 | 27.6 |
| Ex. 6 | 22.7 |
| Ex. 7 | 31.6 |
| Ex. 8 | 138.6 |
| Ex. 9 | 53.8 |
| Ex. 10 | 88.0 |
| Ex. 11 | 2.8 |
| Ex. 12 | 3.3 |
| Ex. 13 | 2.0 |
| Ex. 14 | 2.6 |
| Ex. 15 | 2.1 |
| Ex. 16 | >1000 |
| Ex. 17 | 4.7 |
| Ex. 18 | 6.9 |
| Ex. 19 | 10.8 |
| Ex. 20 | >1000 |
| Ex. 21 | 63.0 |
| Ex. 22 | >1000 |
| Ex. 23 | 78.8 |
| Ex. 24 | 560.4 |
| Ex. 25 | 72.3 |
| Ex. 26 | 295.1 |
| Ex. 27 | 29.6 |
| Ex. 28 | 25.2 |
| Ex. 29 | 16.9 |
| Ex. 30 | >1000 |
| Ex. 31 | 12.5 |
| Ex. 32 | 4.0 |
| Ex. 33 | 3.3 |
| Ex. 34 | 4.4 |
| Ex. 35 | 2.2 |
| Ex. 36 | >1000 |
| Ex. 37 | 5.1 |
| Ex. 38 | 8.2 |
| Ex. 39 | 15.2 |
| Ex. 40 | 5.5 |
| Ex. 41 | 4.5 |
| Ex. 42 | 3.4 |
| Ex. 43 | 3.1 |
| Ex. 44 | 5.9 |
| Ex. 45 | 11.4 |
| Ex. 46 | 72.0 |
| Ex. 47 | 10.9 |
| Ex. 48 | 4.7 |
| Ex. 49 | 3.5 |
| Ex. 50 | 28.6 |
| Ex. 51 | 106.7 |
| Ex. 52 | 5.1 |
| Ex. 53 | 2.7 |
| Ex. 54 | 2.2 |
| Ex. 55 | 8.5 |
| Ex. 56 | 142.8 |
| Ex. 57 | 8.8 |
| Ex. 58 | 5.3 |
| Ex. 59 | 2.8 |
| Ex. 60 | 36.4 |

TABLE 2

| | IC$_{50}$(nM) |
|---|---|
| Ex. 61 | 135.6 |
| Ex. 62 | 5.8 |

TABLE 2-continued

| | IC$_{50}$(nM) |
|---|---|
| Ex. 63 | 1.5 |
| Ex. 64 | 1.6 |
| Ex. 65 | 6.7 |
| Ex. 66 | 49.6 |
| Ex. 67 | 0.5 |
| Ex. 68 | 2.4 |
| Ex. 69 | 1.3 |
| Ex. 70 | 6.3 |
| Ex. 71 | 0.9 |
| Ex. 72 | 1.5 |
| Ex. 73 | 1.1 |
| Ex. 74 | 122.6 |
| Ex. 75 | 4 |
| Ex. 76 | 10 |
| Ex. 77 | 6.4 |
| Ex. 78 | 5.2 |
| Ex. 79 | 77.1 |
| Ex. 80 | 1.2 |
| Ex. 81 | 1 |
| Ex. 82 | 3.6 |
| Ex. 83 | 2.8 |
| Ex. 84 | >100 |
| Ex. 85 | 1.6 |

Experimental Example 2: Selectivity for Inhibitory Activity of BTK Vs. ITK (Based on IC$_{50}$)

In order to confirm the selectivity for BTK vs. ITK inhibitory activity of the compounds prepared in the above Examples, the concentration (IC$_{50}$) at which 50% of ITK activities of some of the above compounds was inhibited was measured as follows.

The inhibitory activity against ITK was evaluated using 'ADP-Glo™+ITK Kinase enzyme system' kit (Promega Corporation). In a white 96-well plate, 10 ul of ITK enzyme prepared so as to have a final concentration of 0.4 ng/uL was mixed with 5 ul of compounds having a final concentration of 3000, 1000, 300, 100, 30, 10 and 3 nM and then allowed to react at room temperature for 15 minutes. To the plate on which reactions were completed, 5 uL of substrate and 5 uL of ATP prepared so as to have a final concentration of 25 uM were added and then allowed to react at 30° C. for 1 hour. All wells of the plate were treated with 25 uL of ADP-Glo™ reagent and then allowed to react at 30° C. for 40 minutes. After that, all wells were treated with 50 uL of kinase detection buffer, and then reacted at 30° C. for 30 minutes under light shielding conditions. For the plate on which all reactions were completed, luminescence was measured and the results were calculated. Evaluation was carried out in duplicate, and negative control and positive control were calculated depending on whether or not the enzyme was added without treatment of the compound. The IC$_{50}$ was calculated based on the calculated values.

In addition, the concentration inhibiting 50% of the BTK inhibitory activity (IC$_{50}$) of the comparative example compound (1-[(3R)-3-[4-amino-3-(4-phenoxyphenyl)-1H-pyrazolo[3,4-d]pyrimidin-1-yl]piperidin-1-yl]prop-2-en-1-one, trade name: Imbruvica, Pharmacyclics LLC) was measured by the same method as in Experimental Example 1, and the concentration inhibiting 50% of BTK inhibitory activity (IC$_{50}$) was measured by the above-described method.

The selectivity for the inhibitory activity of BTK vs. ITK based on the IC$_{50}$ of the test compounds was calculated according to the following Equation 1, and the results were shown in Table 3 below.

Selectivity for the inhibitory activity of BTK vs. ITK (based on % IC$_{50}$)=(IC$_{50}$ against BTK)/(IC$_{50}$ against ITK)  [Equation 1]

TABLE 3

| | IC$_{50}$ against BTK (nM) | IC$_{50}$ against ITK (nM) | Selectivity (based on IC$_{50}$) |
|---|---|---|---|
| Ex. 1 | 2.1 | 188.8 | 89.9 |
| Ex. 2 | 0.8 | 26.3 | 32.9 |
| Ex. 4 | 2.8 | 103.9 | 37.1 |
| Ex. 12 | 3.3 | >1000 | >303.3 |
| Ex. 14 | 2.6 | >1000 | >384.6 |
| Ex. 15 | 2.1 | 122.5 | 58.3 |
| Ex. 17 | 4.7 | >1000 | >212.8 |
| Ex. 32 | 4 | >1000 | >250 |
| Ex. 33 | 3.3 | >1000 | >303.0 |
| Ex. 34 | 4.4 | 307.5 | 69.9 |
| Ex. 35 | 2.2 | 132 | 60.0 |
| Ex. 41 | 4.5 | >1000 | >222.2 |
| Ex. 42 | 3.4 | >500 | >147 |
| Ex. 43 | 3.1 | 267.9 | 86.4 |
| Ex. 48 | 4.7 | 400.8 | 85.3 |
| Ex. 49 | 3.5 | >500 | >142.9 |
| Ex. 53 | 2.7 | >1000 | >370.3 |
| Ex. 54 | 2.2 | >1000 | >454.5 |
| Ex. 59 | 2.8 | 109.5 | 39.1 |
| Ex. 63 | 1.5 | >500 | >333.3 |
| Ex. 64 | 1.6 | 71.5 | 44.7 |
| Ex. 67 | 0.5 | 54.1 | 108.2 |
| Ex. 68 | 2.4 | 175.5 | 73.1 |
| Ex. 69 | 1.3 | 235.5 | 181.2 |
| Ex. 71 | 0.9 | 132.9 | 147.7 |
| Ex. 72 | 1.5 | 47.9 | 31.9 |
| Ex. 75 | 4.0 | 304.6 | 76.2 |
| Ex. 80 | 1.2 | 32.1 | 26.8 |
| Ex. 81 | 1.0 | >200 | >200 |
| Ex. 82 | 3.6 | >200 | 55.6 |
| Ex. 83 | 2.8 | 228.7 | 81.7 |
| Ex. 85 | 1.6 | 60.6 | 37.9 |
| Comparative Example | 2 | 30 | 15 |

From the results of Experimental Examples 1 and 2, it could be seen that the compound according to one embodiment of the present invention not only has excellent BTK inhibitory activity but also exhibits high selectivity for the inhibitory activity of BTK vs. ITK. In particular, it was confirmed that the compound according to one embodiment of the present invention had remarkably high selectivity for the inhibitory activity of BTK vs. ITK, as compared with a compound that is structurally similar to the compound represented by Chemical Formula 1, for example, the compound of Comparative Example in which the piperidine derivative was introduced instead of the azabicyclo compound at hydrogen position of 4-aminopyrazolo[3,4-d]pyrimidine derivative.

What is claimed is:

1. A compound represented by the following Chemical Formula 1, or a pharmaceutically acceptable salt thereof:

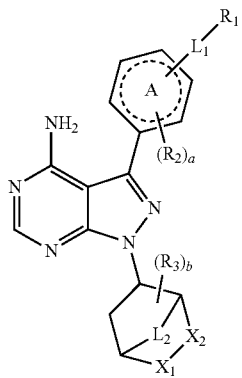

[Chemical Formula 1]

in Chemical Formula 1,

A is a benzene ring, or a 6-membered heteroaromatic ring containing one to three nitrogen atoms, $R_1$ is $C_{1-10}$ alkyl; $C_{6-10}$ aryl; $C_{1-10}$ heteroaryl containing one to four heteroatoms each independently selected from the group consisting of nitrogen, oxygen, and sulfur; or $C_{3-10}$ heterocycloalkyl containing one to four heteroatoms each independently selected from the group consisting of nitrogen, oxygen, and sulfur, wherein $R_1$ is unsubstituted or substituted with one to three substituents each independently selected from the group consisting of halogen, cyano, hydroxy, amino, $NH(C_{1-4}$ alkyl), $N(C_{1-4}$ alkyl)$_2$, $C_{1-4}$ alkyl, $C_{1-4}$ haloalkyl, and $C_{1-4}$ alkoxy, $R_2$ and $R_3$ are each independently hydrogen, halogen, $C_{1-4}$ alkyl, $C_{1-4}$ alkoxy, or $C_{1-4}$ haloalkyl, $L_1$ is a bond, O, S, $SO_2$, NH, $N(C_{1-4}$ alkyl), NHCO, $N(C_{1-4}$ alkyl)CO, NHCONH, $N(C_{1-4}$ alkyl)CONH, NHCON($C_{1-4}$ alkyl), $N(C_{1-4}$ alkyl)CON($C_{1-4}$ alkyl), CONH, CON($C_{1-4}$ alkyl), $SO_2NH$, or $SO_2N(C_{1-4}$ akyl), $L_2$ is methylene, or ethylene, one of $X_1$ and $X_2$ is $CH_2$, and the other is N—CO—R', wherein R' is $C_{1-4}$ alkyl; $C_{2-4}$ alkenyl; or $C_{2-4}$ alkynyl, each of which is unsubstituted or substituted by one to three substituents each independently selected from the group consisting of halogen, cyano, hydroxy, amino, $NH(C_{1-4}$ alkyl), $N(C_{1-4}$ alkyl)$_2$, $C_{3-10}$ cycloalkyl, and $C_{3-10}$ heterocycloalkyl containing one or two heteroatoms each independently selected from the group consisting of nitrogen, and oxygen, and each of a and b independently represents an integer of 0 to 4.

2. The compound or a pharmaceutically acceptable salt thereof according to claim 1, wherein A is a benzene ring or a pyridine ring.

3. The compound or a pharmaceutically acceptable salt thereof according to claim 1, wherein $R_1$ is methyl, phenyl, pyridinyl, pyrazinyl, pyrimidinyl, pyridazinyl, pyrrolyl, imidazolyl, pyrazolyl, triazolyl, tetrazolyl, oxazolyl, thiazolyl, oxadiazolyl, piperidinyl, piperazinyl, or pyrrolidinyl, and wherein $R_1$ is unsubstituted or substituted by one or two substituents each independently selected from the group consisting of fluoro, chloro, bromo, cyano, hydroxy, $NHCH_3$, $N(CH_3)_2$, methyl, ethyl, propyl, isopropyl, fluoromethyl, difluoromethyl, trifluoromethyl, and methoxy.

4. The compound or a pharmaceutically acceptable salt thereof according to claim 1, wherein each of $R_2$ and $R_3$ is independently hydrogen, fluoro, chloro, bromo, methyl, ethyl, propyl, isopropyl, butyl, isobutyl, sec-butyl, tert-butyl, methoxy, fluoromethyl, difluoromethyl, or trifluoromethyl, and each of a and b is independently 0 or 1.

5. The compound or a pharmaceutically acceptable salt thereof according to claim 1, wherein $L_1$ is a bond, O, S, $SO_2$, NH, NHCO, NHCONH, CONH, or $SO_2NH$.

6. The compound or a pharmaceutically acceptable salt thereof according to claim 1, wherein $X_1$ is $CH_2$, and $X_2$ is N—CO—R', and wherein R' is methyl, vinyl, propenyl, ethynyl, propynyl, or butynyl, each of which is unsubstituted or substituted by halogen, cyano, hydroxy, amino, $NH(CH_3)$, $N(CH_3)_2$, cyclopropyl, piperidinyl, piperazinyl, morpholino, or pyrrolidinyl.

7. The compound or a pharmaceutically acceptable salt thereof according to claim 1, wherein $X_1$ is N—CO—R' and $X_2$ is $CH_2$, and wherein R' is methyl, vinyl, propenyl, ethynyl, propynyl, or butynyl, each of which is unsubstituted or substituted by halogen, cyano, hydroxy, amino, $NH(CH_3)$, $N(CH_3)_2$, cyclopropyl, piperidinyl, piperazinyl, morpholino, or pyrrolidinyl.

8. The compound or a pharmaceutically acceptable salt thereof according to claim 1, wherein the compound is represented by the following Chemical Formula 1-1:

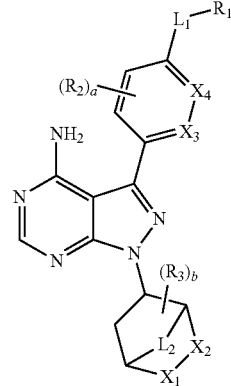

[Chemical Formula 1-1]

in Chemical Formula 1-1, each of $X_3$ and $X_4$ is independently N, or CH, and each of $R_1$ to $R_3$, $L_1$, $L_2$, $X_1$, $X_2$, a, and b is defined in claim 1.

9. The compound or a pharmaceutically acceptable salt thereof according to claim 8, wherein $R_1$ is methyl, phenyl, pyridinyl, pyrazinyl, pyrazolyl, or piperidinyl, wherein $R_1$ is unsubstituted or substituted by one or two substituents each independently selected from the group consisting of fluoro, chloro, bromo, cyano, hydroxy, methyl, ethyl, propyl, isopropyl, fluoromethyl, difluoromethyl, trifluoromethyl, $NH_3$, and $N(CH_3)_2$, $R_2$ and $R_3$ are each independently hydrogen, fluoro, chloro, bromo, methyl, ethyl, propyl, isopropyl, butyl, isobutyl, sec-butyl, tert-butyl, fluoromethyl, difluoromethyl, or trifluoromethyl, each of a and b is independently 0 or 1, $L_1$ is a bond, O, S, $SO_2$, NH, NHCO, NHCONH, CONH, or $SO_2NH$, $L_2$ is methylene, or ethylene, $X_1$ is $CH_2$, and $X_2$ is N—CO—R', wherein R' is methyl, vinyl, propenyl, ethynyl, propynyl, or butynyl, each of which is unsubstituted or substituted by halogen, cyano, hydroxy, amino, NH(CH₃), N(CH₃)₂, cyclopropyl, piperidinyl, or pyrrolidinyl, and
each of X₃ and X₄ is CH.

10. The compound or a pharmaceutically acceptable salt thereof according to claim 8, wherein R₁ is phenyl, pyridinyl, or piperidinyl,
wherein R₁ is unsubstituted or substituted by one or two substituents each of which I independently selected from the group consisting of fluoro, chloro, bromo, cyano, hydroxy, methyl, ethyl, propyl, isopropyl, fluoromethyl, difluoromethyl, and trifluoromethyl,
each of R₂ and R₃ is independently hydrogen, fluoro, chloro, bromo, methyl, ethyl, propyl, isopropyl, butyl, isobutyl, sec-butyl, tert-butyl, fluoromethyl, difluoromethyl, or trifluoromethyl,
each of a and b is independently 0 or 1,
L₁ is O,
L₂ is methylene,
X₁ is CH₂, and X₂ is N—CO—R',
wherein R' is methyl, vinyl, propenyl, ethynyl, propynyl or butynyl, each of which is unsubstituted or substituted by halogen, cyano, amino, NH(CH₃) or N(CH₃)₂,
X₃ is N, and
X₄ is CH.

11. The compound or a pharmaceutically acceptable salt thereof according to claim 8, wherein R₁ is phenyl, pyridinyl, or piperidinyl,
wherein R₁ is unsubstituted or substituted by one or two substituents each of which is independently selected from the group consisting of fluoro, chloro, bromo, cyano, hydroxy, methyl, ethyl, propyl, isopropyl, fluoromethyl, difluoromethyl and trifluoromethyl,
each of R₂ and R₃ is independently hydrogen, fluoro, chloro, bromo, methyl, ethyl, propyl, isopropyl, butyl, isobutyl, sec-butyl, tert-butyl, fluoromethyl, difluoromethyl, or trifluoromethyl,
each of a and b is independently 0 or 1,
L₁ is O, NHCO, or CONH,
L₂ is methylene or ethylene,
X₁ is N—CO—R' and X₂ is CH₂,
wherein R' is methyl, vinyl, propenyl, ethynyl, propynyl or butynyl, each of which is unsubstituted or substituted by halogen, cyano, amino, NH(CH₃) or N(CH₃)₂, and
each of X₃ and X₄ is CH.

12. The compound or a pharmaceutically acceptable salt thereof according to claim 1, wherein the compound is represented by the following Chemical Formula 1-2:

[Chemical Formula 1-2]

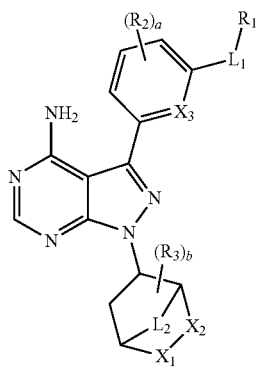

in Chemical Formula 1-2,
X₃ is N or CH, and
each of R₁ to R₃, L₁, L₂, X₁, X₂, a, and b is defined in claim 1.

13. The compound or a pharmaceutically acceptable salt thereof according to claim 12, wherein R₁ is phenyl, pyridinyl, or piperidinyl,
wherein R₁ is is unsubstituted or substituted by one or two substituents each of which is independently selected from the group consisting of fluoro, chloro, bromo, cyano, hydroxy, methyl, ethyl, propyl, isopropyl, fluoromethyl, difluoromethyl, and trifluoromethyl,
each of R₂ and R₃ is independently hydrogen, fluoro, chloro, bromo, methyl, ethyl, propyl, isopropyl, butyl, isobutyl, sec-butyl, tert-butyl, fluoromethyl, difluoromethyl, or trifluoromethyl,
each of a and b is independently 0 or 1,
L₁ is O or CONH,
L₂ is methylene,
X₁ is CH₂ and X₂ is N—CO—R',
wherein R' is methyl, vinyl, propenyl, ethynyl, propynyl or butynyl, each of which is unsubstituted or substituted by halogen, cyano, amino, NH(CH₃), or N(CH₃)₂, and
X₃ is CH.

14. The compound or a pharmaceutically acceptable salt thereof according to claim 12, wherein R₁ is phenyl, pyridinyl, or piperidinyl,
wherein R₁ is is unsubstituted or substituted by one or two substituents each of which is independently selected from the group consisting of fluoro, chloro, bromo, cyano, hydroxy, methyl, ethyl, propyl, isopropyl, fluoromethyl, difluoromethyl, and trifluoromethyl,
each of R₂ and R₃ is independently hydrogen, fluoro, chloro, bromo, methyl, ethyl, propyl, isopropyl, butyl, isobutyl, sec-butyl, tert-butyl, fluoromethyl, difluoromethyl, or trifluoromethyl,
each of a and b is independently 0 or 1,
L₁ is O or CONH,
L₂ is methylene,
X₁ is N—CO—R' and X₂ is CH₂,
wherein R' is methyl, vinyl, propenyl, ethynyl, propynyl or butynyl, each of which is unsubstituted or substituted by halogen, cyano, amino, NH(CH₃), or N(CH₃)₂, and
X₃ is CH.

15. The compound or a pharmaceutically acceptable salt thereof according to claim 1, wherein the compound or the pharmaceutically acceptable salt thereof is selected from the group consisting of:

1) 1-(6-(4-amino-3-(4-phenoxyphenyl)-1H-pyrazolo[3,4-d]pyrimidin-1-yl)-2-azabicyclo[2.2.1]heptan-2-yl)prop-2-en-1-one,
2) 1-(6-(4-amino-3-(4-phenoxyphenyl)-1H-pyrazolo[3,4-d]pyrimidin-1-yl)-2-azabicyclo[2.2.1]heptan-2-yl)prop-2-yn-1-one,
3) (E)-1-(6-(4-amino-3-(4-phenoxyphenyl)-1H-pyrazolo[3,4-d]pyrimidin-1-yl)-2-azabicyclo[2.2.1]heptan-2-yl)but-2-en-1-one,
4) 4-(4-amino-1-(2-propioloyl-2-azabicyclo[2.2.1]heptan-6-yl)-1H-pyrazolo[3,4-d]pyrimidin-3-yl)-N-(pyridin-2-yl)benzamide,
5) 1-(6-(4-amino-3-(4-phenoxyphenyl)-1H-pyrazolo[3,4-d]pyrimidin-1-yl)-2-azabicyclo[2.2.1]heptan-2-yl)but-2-yn-1-one, 6) 4-(4-amino-1-(2-propioloyl-2-azabicyclo[2.2.1]heptan-6-yl)-1H-pyrazolo[3,4-d]pyrimidin-3-yl)-N-(4-(trifluoromethyl)pyridin-2-yl)benzamide,
7) 3-(4-amino-1-(2-propioloyl-2-azabicyclo[2.2.1]heptan-6-yl)-1H-pyrazolo[3,4-d]pyrimidin-3-yl)-N-(4-isopropylphenyl)benzamide,
8) 3-(1-(2-acryloyl-2-azabicyclo[2.2.1]heptan-6-yl)-4-amino-1H-pyrazolo[3,4-d]pyrimidin-3-yl)-N-(4-isopropylphenyl)benzamide,
9) 3-(4-amino-1-(2-propioloyl-2-azabicyclo[2.2.1]heptan-6-yl)-1H-pyrazolo[3,4-d]pyrimidin-3-yl)-N-(4-isopropyl-3-methylphenyl)benzamide,
10) 3-(1-(2-acryloyl-2-azabicyclo[2.2.1]heptan-6-yl)-4-amino-1H-pyrazolo[3,4-d]pyrimidin-3-yl)-N-(4-isopropyl-3-methylphenyl)benzamide,
11) 1-(5-(4-amino-3-(4-phenoxyphenyl)-1H-pyrazolo[3,4-d]pyrimidin-1-yl)-2-azabicyclo[2.2.1]heptan-2-yl)prop-2-yn-1-one,
12) 1-(5-(4-amino-3-(4-phenoxyphenyl)-1H-pyrazolo[3,4-d]pyrimidin-1-yl)-2-azabicyclo[2.2.1]heptan-2-yl)prop-2-en-1-one,
13) 1-((1S,4S,5R)-5-(4-amino-3-(4-phenoxyphenyl)-1H-pyrazolo[3,4-d]pyrimidin-1-yl)-2-azabicyclo[2.2.1]heptan-2-yl)prop-2-yn-1-one,
14) 1-((1S,4S,5R)-5-(4-amino-3-(4-phenoxyphenyl)-1H-pyrazolo[3,4-d]pyrimidin-1-yl)-2-azabicyclo[2.2.1]heptan-2-yl)prop-2-en-1-one,
15) 1-(6-(4-amino-3-(3-phenoxyphenyl)-1H-pyrazolo[3,4-d]pyrimidin-1-yl)-2-azabicyclo[2.2.1]heptan-2-yl)prop-2-yn-1-one,
16) 1-(6-(4-amino-3-(4-phenoxyphenyl)-1H-pyrazolo[3,4-d]pyrimidin-1-yl)-2-azabicyclo[2.2.1]heptan-2-yl)pent-2-yn-1-one,
17) 4-(4-amino-1-(2-propioloyl-2-azabicyclo[2.2.1]heptan-6-yl)-1H-pyrazolo[3,4-d]pyrimidin-3-yl)-N-phenylbenzamide,
18) 3-(4-amino-1-(2-propioloyl-2-azabicyclo[2.2.1]heptan-6-yl)-1H-pyrazolo[3,4-d]pyrimidin-3-yl)-N-phenylbenzamide,
19) 4-(1-(2-acryloyl-2-azabicyclo[2.2.1]heptan-6-yl)-4-amino-1H-pyrazolo[3,4-d]pyrimidin-3-yl)-N-phenylbenzamide,
20) 4-(4-amino-1-(2-but-2-ynoyl-2-azabicyclo[2.2.1]heptan-6-yl)-1H-pyrazolo[3,4-d]pyrimidin-3-yl)-N-phenylbenzamide,
21) 3-(1-(2-acryloyl-2-azabicyclo[2.2.1]heptan-6-yl)-4-amino-1H-pyrazolo[3,4-d]pyrimidin-3-yl)-N-phenylbenzamide,
22) 3-(4-amino-1-(2-but-2-ynoyl-2-azabicyclo[2.2.1]heptan-6-yl)-1H-pyrazolo[3,4-d]pyrimidin-3-yl)-N-phenylbenzamide,
23) 4-(1-(2-acryloyl-2-azabicyclo[2.2.1]heptan-5-yl)-4-amino-1H-pyrazolo[3,4-d]pyrimidin-3-yl)-N-phenylbenzamide,
24) 3-(1-(2-acryloyl-2-azabicyclo[2.2.1]heptan-5-yl)-4-amino-1H-pyrazolo[3,4-d]pyrimidin-3-yl)-N-phenylbenzamide,
25) 1-(5-(4-amino-3-(3-phenoxyphenyl)-1H-pyrazolo[3,4-d]pyrimidin-1-yl)-2-azabicyclo[2.2.1]heptan-2-yl)prop-2-en-1-one,
26) 3-(1-(2-acryloyl-2-azabicyclo[2.2.1]heptan-6-yl)-4-amino-1H-pyrazolo[3,4-d]pyrimidin-3-yl)-N-(6-(trifluoromethyl)pyridin-3-yl)benzamide,
27) 1-(6-(4-amino-3-(4-(methoxymethyl)phenyl)-1H-pyrazolo[3,4-d]pyrimidin-1-yl)-2-azabicyclo[2.2.1]heptan-2-yl)prop-2-en-1-one,
28) 1-(6-(4-amino-3-(4-phenoxyphenyl)-1H-pyrazolo[3,4-d]pyrimidin-1-yl)-2-azabicyclo[2.2.1]heptan-2-yl)-3-cyclopropylprop-2-yn-1-one,
29) 4-(1-(2-acryloyl-2-azabicyclo[2.2.1]heptan-6-yl)-4-amino-1H-pyrazolo[3,4-d]pyrimidin-3-yl)-N-(4-(trifluoromethyl)pyridin-2-yl)benzamide,
30) 1-(6-(4-amino-3-(biphenyl-4-yl)-1H-pyrazolo[3,4-d]pyrimidin-1-yl)-2-azabicyclo[2.2.1]heptan-2-yl)prop-2-yn-1-one,
31) 1-(6-(4-amino-3-(4-(phenylamino)phenyl)-1H-pyrazolo[3,4-d]pyrimidin-1-yl)-2-azabicyclo[2.2.1]heptan-2-yl)prop-2-yn-1-one,
32) 1-(6-(4-amino-3-(4-(phenylsulfonyl)phenyl)-1H-pyrazolo[3,4-d]pyrimidin-1-yl)-2-azabicyclo[2.2.1]heptan-2-yl)prop-2-en-1-one,
33) 1-(6-(4-amino-3-(4-(phenylthio)phenyl)-1H-pyrazolo[3,4-d]pyrimidin-1-yl)-2-azabicyclo[2.2.1]heptan-2-yl)prop-2-en-1-one,
34) 1-(6-(4-amino-3-(4-(3-fluorophenoxy)phenyl)-1H-pyrazolo[3,4-d]pyrimidin-1-yl)-2-azabicyclo[2.2.1]heptan-2-yl)prop-2-en-1-one,
35) 1-(6-(4-amino-3-(2-fluoro-4-phenoxyphenyl)-1H-pyrazolo[3,4-d]pyrimidin-1-yl)-2-azabicyclo[2.2.1]heptan-2-yl)prop-2-en-1-one,
36) 1-(6-(4-amino-3-(4-(pyridin-4-yloxy)phenyl)-1H-pyrazolo[3,4-d]pyrimidin-1-yl)-2-azabicyclo[2.2.1]heptan-2-yl)prop-2-en-1-one,
37) N-(4-(1-(2-acryloyl-2-azabicyclo[2.2.1]heptan-6-yl)-4-amino-1H-pyrazolo[3,4-d]pyrimidin-3-yl)phenyl)benzamide,
38) N-(4-(1-(2-acryloyl-2-azabicyclo[2.2.1]heptan-6-yl)-4-amino-1H-pyrazolo[3,4-d]pyrimidin-3-yl)phenyl)picolinamide,
39) 1-(4-(1-(2-acryloyl-2-azabicyclo[2.2.1]heptan-6-yl)-4-amino-1H-pyrazolo[3,4-d]pyrimidin-3-yl)phenyl)-3-phenylurea,
40) 1-(6-(4-amino-3-(4-(m-tolyloxy)phenyl)-1H-pyrazolo[3,4-d]pyrimidin-1-yl)-2-azabicyclo[2.2.1]heptan-2-yl)prop-2-en-1-one,
41) 1-(6-(4-amino-3-(4-(3-methoxyphenoxy)phenyl)-1H-pyrazolo[3,4-d]pyrimidin-1-yl)-2-azabicyclo[2.2.1]heptan-2-yl)prop-2-en-1-one,
42) 1-(6-(4-amino-3-(4-(3-(dimethylamino)phenoxy)phenyl)-1H-pyrazolo[3,4-d]pyrimidin-1-yl)-2-azabicyclo[2.2.1]heptan-2-yl)prop-2-en-1-one,
43) 1-(6-(4-amino-3-(4-(3-(trifluoromethyl)phenoxy)phenyl)-1H-pyrazolo[3,4-d]pyrimidin-1-yl)-2-azabicyclo[2.2.1]heptan-2-yl)prop-2-en-1-one,
44) (E)-1-(6-(4-amino-3-(4-phenoxyphenyl)-1H-pyrazolo[3,4-d]pyrimidin-1-yl)-2-azabicyclo[2.2.1]heptan-2-yl)-4-bromobut-2-en-1-one,
45) (E)-1-(6-(4-amino-3-(4-phenoxyphenyl)-1H-pyrazolo[3,4-d]pyrimidin-1-yl)-2-azabicyclo[2.2.1]heptan-2-yl)-4-(dimethylamino)but-2-en-1-one,
46) 4-(1-(2-acryloyl-2-azabicyclo[2.2.1]heptan-6-yl)-4-amino-1H-pyrazolo[3,4-d]pyrimidin-3-yl)-N-(3-ethylphenyl)benzamide,
47) 4-(1-(2-acryloyl-2-azabicyclo[2.2.1]heptan-6-yl)-4-amino-1H-pyrazolo[3,4-d]pyrimidin-3-yl)-N-(3-isopropylphenyl)benzamide,
48) 4-(1-(2-acryloyl-2-azabicyclo[2.2.1]heptan-6-yl)-4-amino-1H-pyrazolo[3,4-d]pyrimidin-3-yl)-N-(3-chlorophenyl)benzamide,
49) 4-(1-(2-acryloyl-2-azabicyclo[2.2.1]heptan-6-yl)-4-amino-1H-pyrazolo[3,4-d]pyrimidin-3-yl)-N-(pyridin-2-yl)benzamide, 50) N-(4-(1-(2-acryloyl-2-azabicyclo[2.2.1]heptan-6-yl)-4-amino-1H-pyrazolo[3,4-d]pyrimidin-3-yl)phenyl)-3-(dimethylamino)benzamide, 51) 1-(6-(4-amino-3-(4-(3-aminophenoxy)phenyl)-1H-pyrazolo[3,4-d]pyrimidin-1-yl)-2-azabicyclo[2.2.1]heptan-2-yl)prop-2-en-1-one hydrochloride, 52) 4-(1-(2-acryloyl-2-azabicyclo[2.2.1]heptan-6-yl)-4-amino-1H-pyrazolo[3,4-d]pyrimidin-3-yl)-3-fluoro-N-phenylbenzamide, 53) 4-(1-(2-acryloyl-2-azabicyclo[2.2.1]heptan-6-yl)-4-amino-1H-pyrazolo[3,4-d]pyrimidin-3-yl)-N-(pyrazin-2-yl)benzamide, 54) 4-(1-(2-acryloyl-2-azabicyclo[2.2.1]heptan-6-yl)-4-amino-1H-pyrazolo[3,4-d]pyrimidin-3-yl)-N-phenylbenzenesulfonamide, 55) 4-(1-(2-acryloyl-2-azabicyclo[2.2.1]heptan-6-yl)-4-amino-1H-pyrazolo[3,4-d]pyrimidin-3-yl)-N-(2-(dimethylamino)phenyl)benzamide, 56) 4-(1-(2-acryloyl-2-azabicyclo[2.2.1]heptan-6-yl)-4-amino-1H-pyrazolo[3,4-d]pyrimidin-3-yl)-N-(1-methyl-1H-pyrazol-4-yl)benzamide, 57) N-(4-(1-(2-acryloyl-2-azabicyclo[2.2.1]heptan-6-yl)-4-amino-1H-pyrazolo[3,4-d]pyrimidin-3-yl)phenyl)-2-(dimethylamino)benzamide, 58) (E)-1-(6-(4-amino-3-(4-phenoxyphenyl)-1H-pyrazolo[3,4-d]pyrimidin-1-yl)-2-azabicyclo[2.2.1]heptan-2-yl)-4-morpholinobut-2-en-1-one, 59) 1-(6-(4-amino-3-(4-phenoxyphenyl)-1H-pyrazolo[3,4-d]pyrimidin-1-yl)-2-azabicyclo[2.2.2]octan-2-yl)prop-2-en-1-one, 60) (E)-4-(4-amino-1-(2-(4-(dimethylamino)but-2-enoyl)-2-azabicyclo[2.2.1]heptan-6-yl)-1H-pyrazolo[3,4-d]pyrimidin-3-yl)-N-(pyridin-2-yl)benzamide, 61) (E)-4-(4-amino-1-(2-(4-(4-methylpiperazin-1-yl)but-2-enoyl)-2-azabicyclo[2.2.1]heptan-6-yl)-1H-pyrazolo[3,4-d]pyrimidin-3-yl)-N-(pyridin-2-yl)benzamide, 62) (E)-1-(6-(4-amino-3-(4-phenoxyphenyl)-1H-pyrazolo[3,4-d]pyrimidin-1-yl)-2-azabicyclo[2.2.1]heptan-2-yl)-4-(4-methylpiperazin-1-yl)but-2-en-1-one, 63) (E)-1-(6-(4-amino-3-(4-phenoxyphenyl)-1H-pyrazolo[3,4-d]pyrimidin-1-yl)-2-azabicyclo[2.2.1]heptan-2-yl)-4-(piperidin-1-yl)but-2-en-1-one, 64) 4-(1-(2-acryloyl-2-azabicyclo[2.2.1]heptan-6-yl)-4-amino-1H-pyrazolo[3,4-d]pyrimidin-3-yl)-3-fluoro-N-(pyridin-2-yl)benzamide, 65) (E)-1-(5-(4-amino-3-(4-phenoxyphenyl)-1H-pyrazolo[3,4-d]pyrimidin-1-yl)-2-azabicyclo[2.2.1]heptan-2-yl)-4-bromobut-2-en-1-one, 66) (E)-1-(5-(4-amino-3-(4-phenoxyphenyl)-1H-pyrazolo[3,4-d]pyrimidin-1-yl)-2-azabicyclo[2.2.1]heptan-2-yl)-4-(piperidin-1-yl)but-2-en-1-one, 67) 4-(1-(2-acryloyl-2-azabicyclo[2.2.1]heptan-6-yl)-4-amino-1H-pyrazolo[3,4-d]pyrimidin-3-yl)-N-(4-fluoropyridin-2-yl)benzamide, 68) 4-(1-(2-acryloyl-2-azabicyclo[2.2.1]heptan-6-yl)-4-amino-1H-pyrazolo[3,4-d]pyrimidin-3-yl)-N-(4-methylpyridin-2-yl)benzamide, 69) 4-(1-((1R,4R,6S)-2-acryloyl-2-azabicyclo[2.2.1]heptan-6-yl)-4-amino-1H-pyrazolo[3,4-d]pyrimidin-3-yl)-N-(pyridin-2-yl)benzamide, 70) 4-(1-(2-acryloyl-2-azabicyclo[2.2.1]heptan-6-yl)-4-amino-1H-pyrazolo[3,4-d]pyrimidin-3-yl)-N-(6-(trifluoromethyl)pyridin-2-yl)benzamide, 71) 4-(1-(2-acryloyl-2-azabicyclo[2.2.1]heptan-6-yl)-4-amino-1H-pyrazolo[3,4-d]pyrimidin-3-yl)-N-(4-cyanopyridin-2-yl)benzamide, 72) 4-(1-((1S,4R,6S)-2-acryloyl-2-azabicyclo[2.2.1]heptan-6-yl)-4-amino-1H-pyrazolo[3,4-d]pyrimidin-3-yl)-N-(4-fluoropyridin-2-yl)benzamide, 73) 4-(1-((1S,4R,6S)-2-acryloyl-2-azabicyclo[2.2.1]heptan-6-yl)-4-amino-1H-pyrazolo[3,4-d]pyrimidin-3-yl)-3-fluoro-N-(4-fluoropyridin-2-yl)benzamide, 74) 4-(4-amino-1-((1R,4R,6S)-2-(2-cyanoacetyl)-2-azabicyclo[2.2.1]heptan-6-yl)-1H-pyrazolo[3,4-d]pyrimidin-3-yl)-N-(pyridin-2-yl)benzamide, 75) 4-(4-amino-1-((1R,4R)-2-(2-cyano-3-cyclopropylacryloyl)-2-azabicyclo[2.2.1]heptan-6-yl)-1H-pyrazolo[3,4-d]pyrimidin-3-yl)-N-(pyridin-2-yl)benzamide, 76) 4-(4-amino-1-((1R,4R)-2-(2-cyano-4-methylpent-2-enoyl)-2-azabicyclo[2.2.1]heptan-6-yl)-1H-pyrazolo[3,4-d]pyrimidin-3-yl)-N-(pyridin-2-yl)benzamide, 77) 4-(1-((1S,4R,6S)-2-acryloyl-2-azabicyclo[2.2.1]heptan-6-yl)-4-amino-1H-pyrazolo[3,4-d]pyrimidin-3-yl)-N-(3-methylpyridin-2-yl)benzamide, 78) 4-(1-((1S,4R,6S)-2-acryloyl-2-azabicyclo[2.2.1]heptan-6-yl)-4-amino-1H-pyrazolo[3,4-d]pyrimidin-3-yl)-N-(3-(trifluoromethyl)pyridin-2-yl)benzamide, 79) 4-(1-((1S,4R,6S)-2-acryloyl-2-azabicyclo[2.2.1]heptan-6-yl)-4-amino-1H-pyrazolo[3,4-d]pyrimidin-3-yl)-3-fluoro-N-methylbenzamide, 80) 4-(1-((1S,4R,6S)-2-acryloyl-2-azabicyclo[2.2.1]heptan-6-yl)-4-amino-1H-pyrazolo[3,4-d]pyrimidin-3-yl)-3-chloro-N-(pyridin-2-yl)benzamide, 81) 4-(1-((1S,4R,6S)-2-acryloyl-2-azabicyclo[2.2.1]heptan-6-yl)-4-amino-1H-pyrazolo[3,4-d]pyrimidin-3-yl)-3-methoxy-N-(pyridin-2-yl)benzamide, 82) 4-(4-amino-1-((1R,4R,6S)-2-(2-cyano-3-cyclopropylacryloyl)-2-azabicyclo[2.2.1]heptan-6-yl)-1H-pyrazolo[3,4-d]pyrimidin-3-yl)-3-fluoro-N-(pyridin-2-yl)benzamide, 83) 4-(4-amino-1-((1R,4R,6S)-2-(2-cyano-3-cyclopropylacryloyl)-2-azabicyclo[2.2.1]heptan-6-yl)-1H-pyrazolo[3,4-d]pyrimidin-3-yl)-3-fluoro-N-(4-fluoropyridin-2-yl)benzamide, 84) 4-(4-amino-1-((1R,4R,6S)-2-methacryloyl-2-azabicyclo[2.2.1]heptan-6-yl)-1H-pyrazolo[3,4-d]pyrimidin-3-yl)-N-(pyridin-2-yl)benzamide, and 85) 4-(1-((1S,4R,6S)-2-acryloyl-2-azabicyclo[2.2.1]heptan-6-yl)-4-amino-1H-pyrazolo[3,4-d]pyrimidin-3-yl)-3-fluoro-N-(pyridin-2-yl)benzamide.

16. A pharmaceutical composition for preventing or treating autoimmune diseases or cancers, comprising the compound according to claim 1 or a pharmaceutically acceptable salt thereof as an active ingredient.

\* \* \* \* \*